United States Patent
Martins et al.

(10) Patent No.: US 6,998,416 B2
(45) Date of Patent: *Feb. 14, 2006

(54) CYCLIC AMP-SPECIFIC PHOSPHODIESTERASE INHIBITORS

(75) Inventors: Timothy J. Martins, Bothell, WA (US); Kerry W. Fowler, Seattle, WA (US); Joshua Odingo, Everett, WA (US); Edward A. Kesicki, Bothell, WA (US); Amy Oliver, Bothell, WA (US); Laurence E. Burgess, Boulder, CO (US); John J. Gaudino, Longmont, CO (US); Zachary S. Jones, Westminster, CO (US); Bradley J. Newhouse, Broomfield, CO (US); Stephen T. Schlachter, Boulder, CO (US)

(73) Assignee: Icos Corporation, Bothell, WA (US)

( * ) Notice: Subject to any disclaimer, the term of this patent is extended or adjusted under 35 U.S.C. 154(b) by 4 days.

This patent is subject to a terminal disclaimer.

(21) Appl. No.: 10/758,675

(22) Filed: Jan. 15, 2004

(65) Prior Publication Data

US 2004/0152754 A1  Aug. 5, 2004

Related U.S. Application Data

(60) Division of application No. 10/151,202, filed on May 17, 2002, now Pat. No. 6,716,871, which is a division of application No. 09/717,956, filed on Nov. 21, 2000, now Pat. No. 6,423,710, which is a continuation-in-part of application No. 09/471,846, filed on Dec. 23, 1999, now Pat. No. 6,258,833.

(51) Int. Cl.
*A61K 31/40* (2006.01)
(52) U.S. Cl. ...................................... 514/408; 514/422
(58) Field of Classification Search ................ 514/408, 514/422
See application file for complete search history.

(56) References Cited

U.S. PATENT DOCUMENTS

| 5,665,754 A | 9/1997 | Feldman et al. | |
|---|---|---|---|
| 5,998,428 A | 12/1999 | Barnette et al. | |
| 6,258,833 B1 * | 7/2001 | Martins et al. | 514/395 |
| 6,716,871 B2 * | 4/2004 | Martins et al. | 514/423 |

OTHER PUBLICATIONS

Dyke et al., Expect Opinion Investigative Drugs (2002) 11(1), "Update on the Therapeutic Potentila of PDE4 Inhibitors".*

J.E. Schultz et al., *Naunyn-Schmiedeberg's Arch Pharmacol*, 333, pp. 23-30 (1986).
Z. Ma et al., *Tetrahedron: Asymmetry*, vol. 8, No. 6, pp. 883-887 (1997).
A. Robichaud et al., *Neuropharmacology*, 38, pp. 289-297 (1999).
R.A. Allen et al., *Biochemical Pharmacology*, vol. 57, pp. 1375-1382 (1999).
J. Beavo et al., "Cyclic nucleotide phosphodiesterases: Structure, regulation and drug action," Wiley and Sons, Chichester, pp. 3-14 (1990).
T.J. Torphy et al., *Drug News and Perspectives*, 6, pp. 203-214 (1993).
M.A. Giembycz et al., *Clin. Exp. Allergy*, 22, pp. 337-344 (1992).
J. Semmler et al., *Int J. Immunopharmacol.*, 15, pp. 409-413 (1993).
K.L. Molnar-Kimber et al., *Mediators of Inflammation*, 1, pp. 411-417 (1992).
M.W. Verghese et al., *J. Mol. Cell. Cardiiol.*, 21 (*Suppl.* 2), S61 (1989).
C.P. Nielson et al., *J. Allergy Immunol.*, 86, pp. 801-808 (1990).
P.T. Peachell et al., *J. Immunol.*, 148, pp. 2503-2510 (1992).
G. Dent et al., *J. Pharmacol.*, 103, pp. 1339-1346 (1991).
S.A. Robicsek et al., *Biochem. Pharmacol.*, 42, pp. 869-877 (1991).
H.S. Dhillon et al., *J. Neurotrauma*, 12, pp. 1035-1043 (1995).
N. Suttorp et al., *J. Clin. Invest.*, 91, pp. 1421-1428 (1993).
M.R. Bristow et al., *Circulation*, 97, pp. 1340-1341 (1998).
G. Poli et al., *Proc. Natl. Acad. Sci. USA*, 87, pp. 782-785 (1990).
P. Orosz et al., *J. Exp. Med.*, 177, pp. 1391-1398 (1993).
M. Mentz et al., *Blood*, 88, pp. 2172-2182 (1996).
S. Takeda et al., *Kidney Int.*, 37, p. 362 (1990).
D. Chabardea et al., *Kidney Int.*, 35, p. 494 (1989).
C.D. Nicholson, *Psychopharmacology*, 101, p. 147 (1990).

(Continued)

Primary Examiner—Cecilia J. Tsang
Assistant Examiner—Ebenezer Sackey
(74) Attorney, Agent, or Firm—Marshall, Gerstein & Borun LLP

(57) ABSTRACT

Novel pyrrolidine compounds that are potent and selective inhibitors of PDE4, as well as methods of making the same, are disclosed. Use of the compounds in the treatment of inflammatory diseases and other diseases involving elevated levels of cytokines, as well as central nervous system (CNS) disorders, also is disclosed.

2 Claims, No Drawings

OTHER PUBLICATIONS

F. Eckmann et al., *Curr. Ther. Res.*, 43, p. 291 (1988).
A. Klodzinska et al., *Neuropharmacology*, 38, p. 1831 (1991).
H. Kato et al., *Eur. J. Pharmacol.*, 272, p. 107 (1995).
G. Gardos et al., *J. Clin. Pharmocol.*, 16, p. 304 (1976).
I. Shoulson et al., *Neurology*, 25, p. 722 (1975).
T. Hayakawa et al., *Clin. Exp. Pharmacol. Physiol.*, 26, p. 421 (1999).
R.D. Porsolt et al., *Eur. J. Pharmacol.*, 47, p. 379 (1978).
R.D. Porsolt et al., *Eur. J. Pharmacol.*, 57, p. 431 (1979).
L. Steru, *Psychopharmacology*, 85, p. 376 (1985).
M. Takahashi, *J. Neuroscience*, 19, p. 610 (1999).
D. Pinsky et al., *J. Clin. Invest.*, 92, pp. 2994-3002 (1993).
*Antidepressants: neurochemical, behavioral and clinical prospectives*, Enna, Malick, and Richelson, eds. Raven Press, pp. 121-139 (1981).

* cited by examiner

CYCLIC AMP-SPECIFIC PHOSPHODIESTERASE INHIBITORS

CROSS-REFERENCE TO RELATED APPLICATIONS

This application is a divisional of application Ser. No. 10/151,202, filed May 17, 2002, now U.S. Pat. No. 6,716,871, which is a divisional of application Ser. No. 09/717,956, filed Nov. 21, 2000, now U.S. Pat. No. 6,423,710, which is a continuation-in-part application of U.S. patent application Ser. No. 09/471,846, filed Dec. 23, 1999, now U.S. Pat. No. 6,258,833.

FIELD OF INVENTION

The present invention relates to a series of compounds that are potent and selective inhibitors of cyclic adenosine 3',5'-monophosphate specific phosphodiesterase (cAMP specific PDE). In particular, the present invention relates to a series of novel pyrrolidine compounds that are useful for inhibiting the function of cAMP specific PDE, in particular, PDE4, as well as methods of making the same, pharmaceutical compositions containing the same, and their use as therapeutic agents, for example, in treating inflammatory diseases and other diseases involving elevated levels of cytokines and proinflammatory mediators.

BACKGROUND OF THE INVENTION

Chronic inflammation is a multi-factorial disease complication characterized by activation of multiple types of inflammatory cells, particularly cells of lymphoid lineage (including T lymphocytes) and myeloid lineage (including granulocytes, macrophages, and monocytes). Proinflammatory mediators, including cytokines, such as tumor necrosis factor (TNF) and interleukin-1 (IL-1), are produced by these activated cells. Accordingly, an agent that suppresses the activation of these cells, or their production of proinflammatory cytokines, would be useful in the therapeutic treatment of inflammatory diseases and other diseases involving elevated levels of cytokines.

Cyclic adenosine monophosphate (cAMP) is a second messenger that mediates the biologic responses of cells to a wide range of extracellular stimuli. When the appropriate agonist binds to specific cell surface receptors, adenylate cyclase is activated to convert adenosine triphosphate (ATP) to cAMP. It is theorized that the agonist induced actions of cAMP within the cell are mediated predominately by the action of cAMP-dependent protein kinases. The intracellular actions of cAMP are terminated by either a transport of the nucleotide to the outside of the cell, or by enzymatic cleavage by cyclic nucleotide phosphodiesterases (PDEs), which hydrolyze the 3'-phosphodiester bond to form 5'-adenosine monophosphate (5'-AMP). 5'-AMP is an inactive metabolite. The structures of cAMP and 5'-AMP are illustrated below.

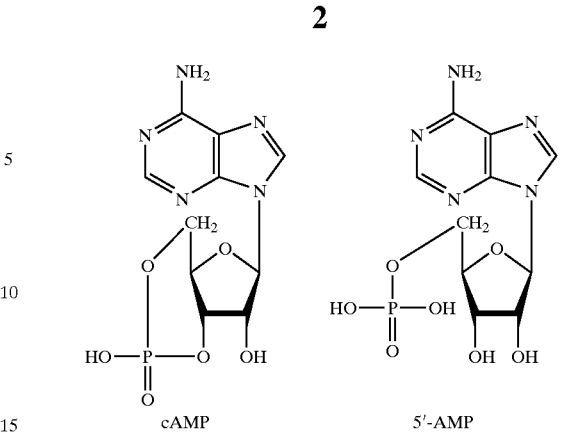

Elevated levels of cAMP in human myeloid and lymphoid lineage cells are associated with the suppression of cell activation. The intracellular enzyme family of PDEs, therefore, regulates the level of cAMP in cells. PDE4 is a predominant PDE isotype in these cells, and is a major contributor to cAMP degradation. Accordingly, the inhibition of PDE function would prevent the conversion of cAMP to the inactive metabolite 5'-AMP and, consequently, maintain higher cAMP levels, and, accordingly, suppress cell activation (see Beavo et al., "Cyclic Nucleotide Phosphodiesterases: Structure, Regulation and Drug Action," Wiley and Sons, Chichester, pp. 3–14, (1990)); Torphy et al., *Drug News and Perspectives*, 6, pp. 203–214 (1993); Giembycz et al., *Clin. Exp. Allergy*, 22, pp. 337–344 (1992)).

In particular, PDE4 inhibitors, such as rolipram, have been shown to inhibit production of TNFα and partially inhibit IL-1β release by monocytes (see Semmler et al., *Int. J. Immunopharmacol.*, 15, pp. 409–413, (1993); Molnar-Kimber et al., *Mediators of Inflammation*, 1, pp. 411–417, (1992)). PDE4 inhibitors also have been shown to inhibit the production of superoxide radicals from human polymorphonuclear leukocytes (see Verghese et al., *J. Mol. Cell. Cardiol.*, 21 (Suppl. 2), S61 (1989); Nielson et al., *J. Allergy Immunol.*, 86, pp. 801–808, (1990)); to inhibit the release of vasoactive amines and prostanoids from human basophils (see Peachell et al., *J. Immunol.*, 148, pp. 2503–2510, (1992)); to inhibit respiratory bursts in eosinophils (see Dent et al., *J. Pharmacol.*, 103, pp. 1339–1346, (1991)); and to inhibit the activation of human T-lymphocytes (see Robicsek et al., *Biochem. Pharmacol.*, 42, pp. 869–877, (1991)).

Inflammatory cell activation and excessive or unregulated cytokine (e.g., TNFα and IL-1β) production are implicated in allergic, autoimmune, and inflammatory diseases and disorders, such as rheumatoid arthritis, osteoarthritis, gouty arthritis, spondylitis, thyroid associated ophthalmopathy, Behcet's disease, sepsis, septic shock, endotoxic shock, gram negative sepsis, gram positive sepsis, toxic shock syndrome, asthma, chronic bronchitis, adult respiratory distress syndrome, chronic pulmonary inflammatory disease, such as chronic obstructive pulmonary disease, silicosis, pulmonary sarcoidosis, reperfusion injury of the myocardium, brain, and extremities, fibrosis, cystic fibrosis, keloid formation, scar formation, atherosclerosis, transplant rejection disorders, such as graft vs. host reaction and allograft rejection, chronic glomerulonephritis, lupus, inflammatory bowel disease, such as Crohn's disease and ulcerative colitis, proliferative lymphocyte diseases, such as leukemia, and inflammatory dermatoses, such as atopic dermatitis, psoriasis, and urticaria.

Other conditions characterized by elevated cytokine levels include brain injury due to moderate trauma (see Dhillon et al., *J. Neurotrauma*, 12, pp. 1035–1043 (1995); Suttorp et al., *J. Clin. Invest.*, 91, pp. 1421–1428 (1993)), cardiomyopathies, such as congestive heart failure (see Bristow et al., *Circulation*, 97, pp. 1340–1341 (1998)), cachexia, cachexia secondary to infection or malignancy, cachexia secondary to acquired immune deficiency syndrome (AIDS), ARC (AIDS related complex), fever myalgias due to infection, cerebral malaria, osteoporosis and bone resorption diseases, keloid formation, scar tissue formation, and pyrexia.

In particular, TNFα has been identified as having a role with respect to human acquired immune deficiency syndrome (AIDS). AIDS results from the infection of T-lymphocytes with Human Immunodeficiency Virus (HIV). Although HIV also infects and is maintained in myeloid lineage cells, TNF has been shown to upregulate HIV infection in T-lymphocytic and monocytic cells (see Poli et al., *Proc. Natl. Acad. Sci. USA*, 87, pp. 782–785, (1990)).

Several properties of TNFα, such as stimulation of collagenases, stimulation of angiogenesis in vivo, stimulation of bone resorption, and an ability to increase the adherence of tumor cells to endothelium, are consistent with a role for TNF in the development and metastatic spread of cancer in the host. TNFα recently has been directly implicated in the promotion of growth and metastasis of tumor cells (see Orosz et al., *J. Exp. Med.*, 177, pp. 1391–1398, (1993)).

PDE4 has a wide tissue distribution. There are at least four genes for PDE4 of which multiple transcripts from any given gene can yield several different proteins that share identical catalytic sites. The amino acid identity between the four possible catalytic sites is greater than 85%. Their shared sensitivity to inhibitors and their kinetic similarity reflect the functional aspect of this level of amino acid identity. It is theorized that the role of these alternatively expressed PDE4 proteins allows a mechanism by which a cell can differentially localize these enzymes intracellularly and/or regulate the catalytic efficiency via post translational modification. Any given cell type that expresses the PDE4 enzyme typically expresses more than one of the four possible genes encoding these proteins.

Investigators have shown considerable interest in the use of PDE4 inhibitors as anti-inflammatory agents. Early evidence indicates that PDE4 inhibition has beneficial effects on a variety of inflammatory cells such as monocytes, macrophages, T-cells of the Th-1 lineage, and granulocytes. The synthesis and/or release of many proinflammatory mediators, such as cytokines, lipid mediators, superoxide, and biogenic amines, such as histamine, have been attenuated in these cells by the action of PDE4 inhibitors. The PDE4 inhibitors also affect other cellular functions including T-cell proliferation, granulocyte transmigration in response to chemotoxic substances, and integrity of endothelial cell junctions within the vasculature.

The design, synthesis, and screening of various PDE4 inhibitors have been reported. Methyl-xanthines, such as caffeine and theophylline, were the first PDE inhibitors discovered, but these compounds are nonselective with respect to which PDE is inhibited. The drug rolipram, an antidepressant agent, was one of the first reported specific PDE4 inhibitors. Rolipram, having the following structural formula, has a reported 50% Inhibitory Concentration ($IC_{50}$) of about 200 nM (nanomolar) with respect to inhibiting recombinant human PDE4.

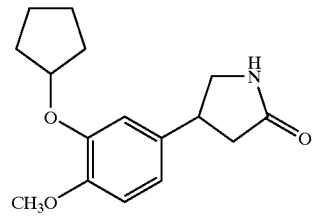

Rolipram

Investigators have continued to search for PDE4 inhibitors that are more selective with respect to inhibiting PDE4, that have a lower $IC_{50}$ than rolipram, and that avoid the undesirable central nervous system (CNS) side effects, such as retching, vomiting, and sedation, associated with the administration of rolipram. One class of compounds is disclosed in Feldman et al. U.S. Pat. No. 5,665,754. The compounds disclosed therein are substituted pyrrolidines having a structure similar to rolipram. One particular compound, having structural formula (I), has an $IC_{50}$ with respect to human recombinant PDE4 of about 2 nM. Inasmuch as a favorable separation of emetic side effect from efficacy was observed, these compounds did not exhibit a reduction in undesirable CNS effects.

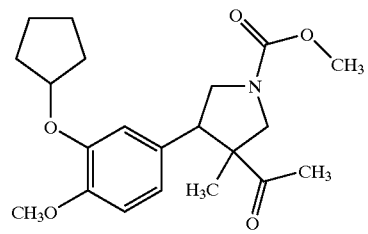

(I)

In addition, several companies are now undertaking clinical trials of other PDE4 inhibitors. However, problems relating to efficacy and adverse side effects, such as emesis and central nervous system disturbances, remain unsolved.

Accordingly, compounds that selectively inhibit PDE4, and that reduce or eliminate the adverse CNS side effects associated with prior PDE4 inhibitors, would be useful in the treatment of allergic and inflammatory diseases, and other diseases associated with excessive or unregulated production of cytokines, such as TNF. In addition, selective PDE4 inhibitors would be useful in the treatment of diseases that are associated with elevated cAMP levels or PDE4 function in a particular target tissue.

SUMMARY OF THE INVENTION

The present invention is directed to potent and selective PDE4 inhibitors useful in treatment of diseases and conditions where inhibition of PDE4 activity is considered beneficial. The present PDE4 inhibitors unexpectedly reduce or eliminate the adverse CNS side effects associated with prior PDE4 inhibitors.

In particular, the present invention is directed to pyrrolidine compounds having the structural formula (II):

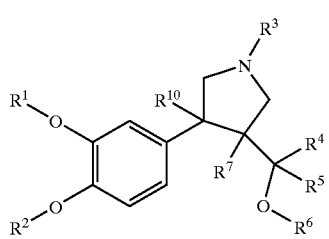

(II)

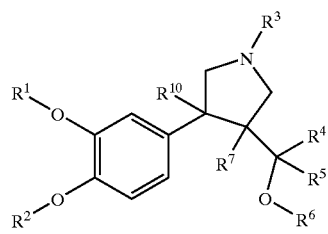

(IIa)

wherein $R^1$ is selected from the group consisting of hydrogen, lower alkyl, bridged alkyl (e.g., norbornyl), aryl, cycloalkyl (e.g., indanyl), a 4-, 5-, or 6-membered saturated heterocycle (e.g., 3-tetrahydrofuryl), heteroaryl, $C_{1-4}$alkylenearyl, $C_{1-4}$alkyleneOaryl, $C_{1-4}$alkyleneheteroaryl, $C_{1-4}$alkyleneHet, $C_{2-4}$alkylenearylOaryl, $C_{1-4}$alkylene bridged alkyl, $C_{1-4}$alkylenecycloalkyl (e.g., cyclopentylmethyl), substituted or unsubstituted propargyl (e.g., —$CH_2C\equiv C$—$C_6H_5$), substituted or unsubstituted allyl (e.g., —$CH_2CH=CH$—$C_6H_5$), and halocycloalkyl (e.g., fluorocyclopentyl);

$R^2$ is selected from the group consisting of hydrogen, methyl, and halo-substituted methyl, e.g., $CHF_2$;

$R^3$ is selected from the group consisting of $C(=O)OR^7$, $C(=O)R^7$, $NHC(=O)OR^7$, $C_{1-3}$alkyleneC$(=O)OR^8$, $C_{1-3}$alkyleneC$(=O)R^8$, $C(=NH)NR^8R^9$, $C(=O)NR^8R^9$, $C(=O)$— $C(=O)NR^8R^9$, $C(=O)C(=O)OR^8$, $C_{1-4}$-alkyleneOR$^8$, aryl, $C_{1-3}$alkylenearyl, $C_{1-3}$alkyleneheteroaryl, $SO_2$heteroaryl, Het, and heteroaryl;

$R^4$ is selected from the group consisting of hydrogen, lower alkyl, haloalkyl, cycloalkyl, and aryl;

$R^5$ is selected from the group consisting of hydrogen, lower alkyl, alkynyl, haloalkyl, hydroxyalkyl, cycloalkyl, and aryl;

$R^6$ is selected from the group consisting of hydrogen, lower alkyl, and $C(=O)R^7$;

$R^7$ is selected from the group consisting of lower alkyl, branched or unbranched, $C_{1-4}$alkylenearyl, cycloalkyl, Het, $C_{1-4}$alkylenecycloalkyl, heteroaryl, and aryl, each optionally substituted with one or more of $OC(=O)R^8$, $C(=O)OR^8$, $OR^8$, $NR^8R^9$, or $SR^8$;

$R^8$ and $R^9$, same or different, are selected from the group consisting of hydrogen, lower alkyl, cycloalkyl, aryl, heteroaryl, $C(=O)$Oalkyl, $C(=O)$—Oaryl, $C(=O)$alkyl, alkylSO$_2$, haloalkylSO$_2$, $C(=O)$—$C_{1-3}$alkylenearyl, $C(=O)OC_{1-4}$alkylenearyl, $C_{1-4}$alkylenearyl, and Het, or $R^8$ and $R^9$ together form a 4-membered to 7-membered ring;

$R^{10}$ is selected from the group consisting of hydrogen, alkyl, haloalkyl, cycloalkyl, aryl, $C(=O)$alkyl, $C(=O)$cycloalkyl, $C(=O)$aryl, $C(=O)$Oalkyl, $C(=O)$Ocycloalkyl, $C(=O)$aryl, $CH_2OH$, $CH_2$Oalkyl, CHO, CN, NO$_2$, and $SO_2R^{11}$;

$R^{11}$ is selected from the group consisting of alkyl, cycloalkyl, trifluoromethyl, aryl, aralkyl, and $NR^8R^9$; and salts and solvates (e.g., hydrates) thereof.

In another embodiment, the present invention is directed to pyrrolidine compounds having a structural formula (IIa):

wherein $R^1$ is selected from the group consisting of hydrogen, lower alkyl, bridged alkyl, aryl, cycloalkyl, a 4-, 5-, or 6-membered saturated heterocycle, heteroaryl, $C_{1-4}$alkylenearyl, $C_{1-4}$alkyleneOaryl, $C_{1-4}$alkyleneheteroaryl, $C_{1-4}$alkyleneHet, $C_{2-4}$alkylenearylOaryl, $C_{1-4}$alkylene bridged alkyl, $C_{1-4}$alkylenecycloalkyl, substituted or unsubstituted propargyl, substituted or unsubstituted allyl, and halocycloalkyl;

$R^2$ is selected from the group consisting of hydrogen, methyl, and halo-substituted methyl;

$R^3$ is selected from the group consisting of hydrogen, $C_{1-4}$alkylenearyl, and $C(=O)C_{1-3}$alkyleneO—$C_{1-3}$alkylenearyl;

$R^4$ is selected from the group consisting of hydrogen, lower alkyl, haloalkyl, cycloalkyl, and aryl;

$R^5$ is selected from the group consisting of hydrogen, lower alkyl, alkynyl, haloalkyl, hydroxyalkyl, cycloalkyl, and aryl;

$R^6$ is selected from the group consisting of hydrogen, lower alkyl, and $C(=O)R^7$;

$R^7$ is selected from the group consisting of lower alkyl, branched or unbranched, $C_{1-4}$alkylenearyl, cycloalkyl, Het, $C_{1-4}$alkylenecycloalkyl, heteroaryl, and aryl, each optionally substituted with one or more of $OC(=O)R^8$, $C(=O)OR^8$, $OR^8$, $NR^8R^9$, and $SR^8$; and $R^8$ and $R^9$, same or different, are selected from the group consisting of hydrogen, lower alkyl, cycloalkyl, aryl, heteroaryl, $C(=O)$Oalkyl, $C(=O)$-alkyl, $C(=O)$Oaryl, alkylSO$_2$, haloalkylSO$_2$, $C(=O)$—$C_{1-3}$alkylenearyl, $C(=O)OC_{1-4}$alkylenearyl, $C_{1-4}$alkylenearyl, and Het, or $R^8$ and $R^9$ together form a 4-membered to 7-membered ring;

$R^{10}$ is selected from the group consisting of hydrogen, alkyl, haloalkyl, cycloalkyl, aryl, $C(=O)$alkyl, $C(=O)$cycloalkyl, $C(=O)$aryl, $C(=O)$Oalkyl, $C(=O)$Ocycloalkyl, $C(=O)$aryl, $CH_2OH$, $CH_2$Oalkyl, CHO, CN, NO$_2$, and $SO_2R^{11}$; and $R^{11}$ is selected from the group consisting of alkyl, cycloalkyl, trifluoromethyl, aryl, aralkyl, and $NR^8R^9$; and salts and solvates (e.g., hydrates) thereof.

The present invention also is directed to pharmaceutical compositions containing one or more of the compounds of structural formula (II), to use of the compounds and compositions containing the compounds in the treatment of a disease or disorder, and to methods of preparing compounds and intermediates involved in the synthesis of the compounds of structural formula (II).

The present invention also is directed to methods of (a) treating a mammal having a condition where inhibition of PDE4 provides a benefit, (b) modulating cAMP levels in a mammal, (c) reducing TNFα levels in a mammal, (d) suppressing inflammatory cell activation in a mammal, and (e) inhibiting PDE4 function in a mammal by administering to the mammal a therapeutically effective amount of a compound of structural formula (II) or a composition containing a composition of structural formula (II).

DETAILED DESCRIPTION OF THE PREFERRED EMBODIMENTS

The present invention is directed to compounds having the structural formula (II):

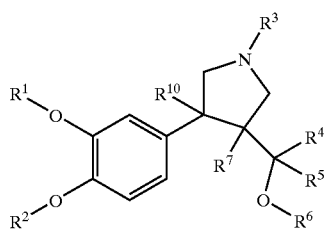

(II)

wherein $R^1$ is selected from the group consisting of hydrogen, lower alkyl, bridged alkyl (e.g., norbornyl), aryl, cycloalkyl (e.g., indanyl), a 4-, 5-, or 6-membered saturated heterocycle (e.g., 3-tetrahydrofuryl), heteroaryl, $C_{1-4}$alkylenearyl, $C_{1-4}$alkyleneOaryl, $C_{1-4}$alkyleneheteroaryl, $C_{1-4}$alkyleneHet, $C_{2-4}$alkylenearylOaryl, $C_{1-4}$alkylene bridged alkyl, $C_{1-4}$alkylenecycloalkyl (e.g., cyclopentylmethyl), substituted or unsubstituted propargyl (e.g., $-CH_2C{\equiv}C-C_6H_5$), substituted or unsubstituted allyl (e.g., $-CH_2CH{=}CH-C_6H_5$), and halocycloalkyl (e.g., fluorocyclopentyl);

$R^2$ is selected from the group consisting of hydrogen, methyl, and halo-substituted methyl, e.g., $CHF_2$;

$R^3$ is selected from the group consisting of $C({=}O)OR^7$, $C({=}O)R^7$, $NHC({=}O)OR^7$, $C_{1-3}$alkyleneC({=}O)OR^8$, $C_{1-3}$alkyleneC({=}O)R^8$, $C({=}NH)NR^8R^9$, $C({=}O)NR^8R^9$, $C({=}O)-C({=}O)NR^8R^9$, $C({=}O)C({=}O)OR^8$, $C_{1-4}$alkyleneOR$^8$, aryl, $C_{1-3}$alkylenearyl, $C_{1-3}$alkyleneheteroaryl, $SO_2$heteroaryl, Het, and heteroaryl;

$R^4$ is selected from the group consisting of hydrogen, lower alkyl, haloalkyl, cycloalkyl, and aryl;

$R^5$ is selected from the group consisting of hydrogen, lower alkyl, alkynyl, haloalkyl, hydroxyalkyl, cycloalkyl, and aryl;

$R^6$ is selected from the group consisting of hydrogen, lower alkyl, and $C({=}O)R^7$;

$R^7$ is selected from the group consisting of lower alkyl, branched or unbranched, $C_{1-4}$alkylenearyl, cycloalkyl, Het, $C_{1-4}$alkylenecycloalkyl, heteroaryl, and aryl, each optionally substituted with one or more of $OC({=}O)R^8$, $C({=}O)OR^8$, $OR^8$, $NR^8R^9$, or $SR^8$;

$R^8$ and $R^9$, same or different, are selected from the group consisting of hydrogen, lower alkyl, cycloalkyl, aryl, heteroaryl, $C({=}O)Oalkyl$, $C({=}O)-$ $Oaryl$, $C({=}O)alkyl$, alkylSO$_2$, haloalkylSO$_2$, $C({=}O)-C_{1-3}$alkylenearyl, $C({=}O)OC_{1-4}$alkylenearyl, $C_{1-4}$alkylenearyl, and Het, or $R^8$ and $R^9$ together form a 4-membered to 7-membered ring;

$R^{10}$ is selected from the group consisting of hydrogen, alkyl, haloalkyl, cycloalkyl, aryl, $C({=}O)$alkyl, $C({=}O)$cycloalkyl, $C({=}O)$aryl, $C({=}O)$Oalkyl, $C({=}O)$Ocycloalkyl, $C({=}O)$aryl, $CH_2OH$, $CH_2Oalkyl$, $CHO$, $CN$, $NO_2$, and $SO_2R^{11}$;

$R^{11}$ is selected from the group consisting of alkyl, cycloalkyl, trifluoromethyl, aryl, aralkyl, and $NR^8R^9$; and salts and solvates (e.g., hydrates) thereof.

In another embodiment, the present invention is directed to pyrrolidine compounds having a structural formula (IIa):

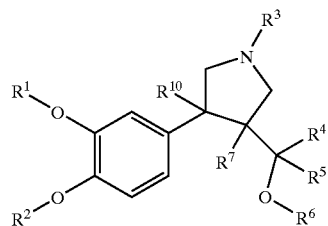

(IIa)

wherein $R^1$ is selected from the group consisting of hydrogen, lower alkyl, bridged alkyl, aryl, cycloalkyl, a 4-, 5-, or 6-membered saturated heterocycle, heteroaryl, $C_{1-4}$alkylenearyl, $C_{1-4}$alkyleneOaryl, $C_{1-4}$alkyleneheteroaryl, $C_{1-4}$alkyleneHet, $C_{2-4}$alkylenearylOaryl, $C_{1-4}$alkylene bridged alkyl, $C_{1-4}$alkylenecycloalkyl, substituted or unsubstituted propargyl, substituted or unsubstituted allyl, and halocycloalkyl;

$R^2$ is selected from the group consisting of hydrogen, methyl, and halo-substituted methyl;

$R^3$ is selected from the group consisting of hydrogen, $C_{1-4}$alkylenearyl, and $C({=}O)C_{1-3}$alkyleneOC$_{1-3}$-alkylenearyl;

$R^4$ is selected from the group consisting of hydrogen, lower alkyl, haloalkyl, cycloalkyl, and aryl;

$R^5$ is selected from the group consisting of hydrogen, lower alkyl, alkynyl, haloalkyl, hydroxyalkyl, cycloalkyl, and aryl;

$R^6$ is selected from the group consisting of hydrogen, lower alkyl, and $C({=}O)R^7$;

$R^7$ is selected from the group consisting of lower alkyl, branched or unbranched, $C_{1-4}$alkylenearyl, cycloalkyl, Het, $C_{1-4}$alkylenecycloalkyl, heteroaryl, and aryl, each optionally substituted with one or more of $OC({=}O)R^8$, $C({=}O)OR^8$, $OR^8$, $NR^8R^9$, and $SR^8$; and $R^8$ and $R^9$, same or different, are selected from the group consisting of hydrogen, lower alkyl, cycloalkyl, aryl, heteroaryl, $C({=}O)Oalkyl$, $C({=}O)$-alkyl, $C({=}O)Oaryl$, alkylSO$_2$, haloalkylSO$_2$, $C({=}O)-C_{1-3}$alkylenearyl, $C({=}O)OC_{1-4}$alkylenearyl, $C_{1-4}$-alkylenearyl, and Het, or $R^8$ and $R^9$ together form a 4-membered to 7-membered ring;

$R^{10}$ is selected from the group consisting of hydrogen, alkyl, haloalkyl, cycloalkyl, aryl, $C({=}O)$alkyl, $C({=}O)$cycloalkyl, $C({=}O)$aryl, $C({=}O)Oalkyl$, $C({=}O)Ocycloalkyl$, $C({=}O)$aryl, $CH_2OH$, $CH_2Oalkyl$, $CHO$, $CN$, $NO_2$, and $SO_2R^{11}$; and $R^{11}$ is selected from the group consisting of alkyl, cycloalkyl, trifluoromethyl, aryl, aralkyl, and $NR^8R^9$; and salts and solvates (e.g., hydrates) thereof.

As used herein, the term "alkyl," alone or in combination, is defined to include straight chain and branched chain saturated hydrocarbon groups containing one to 16 carbon atoms, either substituted or unsubstituted. The term "lower alkyl" is defined herein as an alkyl group having one through six carbon atoms ($C_1$–$C_6$). Examples of lower alkyl groups include, but are not limited to, methyl, ethyl, n-propyl, isopropyl, isobutyl, tertiary butyl, isopentyl, n-butyl, neopentyl, n-hexyl, and the like. The term "alkynyl" refers to an unsaturated alkyl group that contains a carbon-carbon triple bond.

The term "bridged alkyl" is defined herein as a $C_6$–$C_{16}$ bicyclic or polycyclic hydrocarbon group, for example, norboryl, adamantyl, bicyclo[2.2.2]octyl, bicyclo[2.2.1]heptyl, bicyclo[3.2.1]octyl, bicyclo[4.1.0]heptyl, bicyclo[3.1.0]hexyl, and decahydronaphthyl, substituted or unsubstituted.

The term "cycloalkyl" is defined herein to include monocyclic or fused polycyclic $C_3$–$C_{10}$ aliphatic hydrocarbon groups. Examples of cycloalkyl groups include, but are not limited to, cyclopropyl, cyclobutyl, cyclohexyl, decahydronaphthlene, and cyclopentyl. As used herein, "cycloalkyl" also encompasses cyclic $C_3$–$C_7$ aliphatic hydrocarbon groups fused to an aryl ring. For example, indanyl and tetrahydronaphthalenyl are cycloalkyl groups as defined herein.

An alkyl, bridged alkyl, or cycloalkyl group optionally can be substituted with one or more, typically one to three, substituents, for example, lower alkyl, cycloalkyl, haloalkyl, e.g., $CF_3$—, halo, hydroxy, alkoxy, aryl, heteroaryl, and Het.

The term "alkylene" refers to an alkyl group having a substituent. For example, the term "$C_{1-3}$alkylenecycloalkyl" refers to an alkyl group containing one to three carbon atoms, and substituted with a cycloalkyl group. An example of "$C_{1-3}$alkylenearyl" is benzyl.

The term "haloalkyl" is defined herein as an alkyl group substituted with one or more halo substituents, either fluoro, chloro, bromo, iodo, or combinations thereof. Similarly, "halocycloalkyl" and "haloaryl" are defined as a cycloalkyl or an aryl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, phenyl, substituted phenyl, hydroxy, hydroxyalkyl, alkoxy, aryloxy, alkoxyalkyl, haloalkyl, nitro, amino, alkylamino, acylamino, alkylthio, alkylsulfinyl, and alkylsulfonyl. Exemplary aryl groups include phenyl, naphthyl, biphenyl, tetrahydronaphthyl, indanyl, 2-chlorophenyl, 3-chlorophenyl, 4-chlorophenyl, 4-fluorophenyl, 2-methylphenyl, 4-methoxyphenyl, 4-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, aryl, haloaryl, nitro, amino, alkylamino, acylamino, alkylthio, alkylsulfinyl, and alkylsulfonyl. Examples of heteroaryl groups include thienyl, furyl, pyridyl, oxazolyl, 1,2,4-oxadiazol-3-yl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The terms "heterocycle" and "Het" are defined as a 4-, 5-, or 6-membered nonaromatic ring having one or more, typically one to three, heteroatoms selected from oxygen, nitrogen, and sulfur present in the ring, and optionally substituted with alkyl, halo, aryl, alkoxy, $C_{1-3}$alkyleneHet, $C_{1-3}$alkyleneamino, $C_{1-3}$alkylenealkylamino, and haloaryl. Nonlimiting examples include tetrahydrofuran, tetrahydropyran, piperidine, piperazine, sulfolane, morpholine, 1,3-dioxolane, tetrahydropyran, dioxane, trimethyleneoxide, and the like.

The term "halogen" or "halo" is defined herein to include fluorine, chlorine, bromine, and iodine.

The term "alkoxy" and "aryloxy" are defined as —OR, wherein R is alkyl or aryl, respectively.

The term "alkoxyalkyl" is defined as an alkoxy group appended to an alkyl group.

The term "propargyl" is defined as R—C≡C—$CH_2$—, wherein R is hydrogen, lower alkyl, haloalkyl, cycloalkyl, substituted or unsubstituted aryl, or substituted or unsubstituted heteroaryl.

The term "allyl" is defined as R—CH=CH$CH_2$—, wherein R is hydrogen, lower alkyl, haloalkyl, cycloalkyl, substituted or unsubstituted aryl, or substituted or unsubstituted heteroaryl.

The term "hydroxy" is defined as —OH.

The term "hydroxyalkyl" is defined as a hydroxy group appended to an alkyl group.

The term "amino" is defined as —$NH_2$.

The term "alkylamino" is defined as —$NR_2$ wherein at least one R is alkyl and the second R is alkyl or hydrogen.

The term "acylamino" is defined as RC(=O)NH, wherein R is alkyl or aryl.

The term "nitro" is defined as —$NO_2$.

The term "alkylthio" is defined as —SR, where R is alkyl.

The term "alkylsulfinyl" is defined as R—$S(O)_2$, where R is alkyl.

The term "alkylsulfonyl" is defined as R—S ($O_3$), where R is alkyl.

In preferred embodiments, $R^5$ is methyl, $R^7$ is methyl or benzyl, $R^2$ is methyl or difluoromethyl, $R^4$ is selected from the group consisting of hydrogen, methyl, trifluoromethyl, cyclopropyl, benzyl, and phenyl, and $R^6$ is selected from the group consisting of hydrogen, acetyl, and benzoyl. Preferably, $R^1$ is selected from the group consisting of

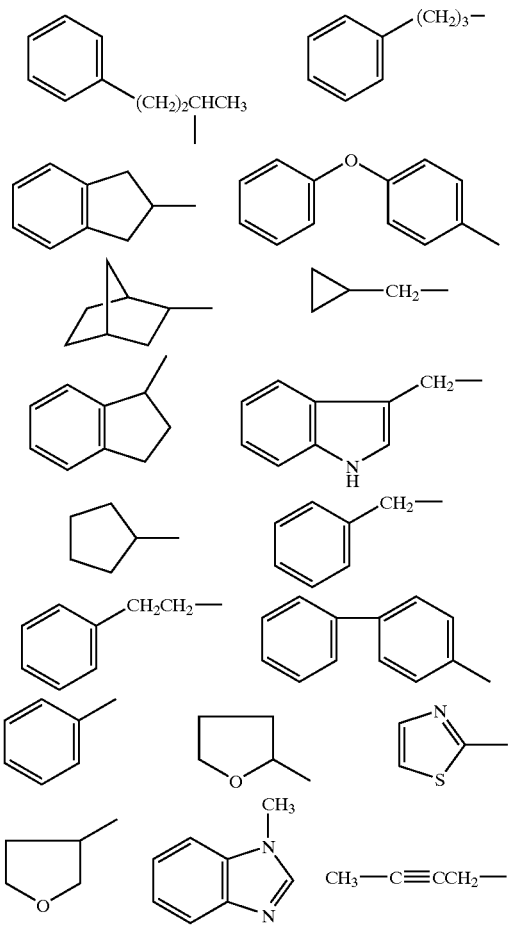

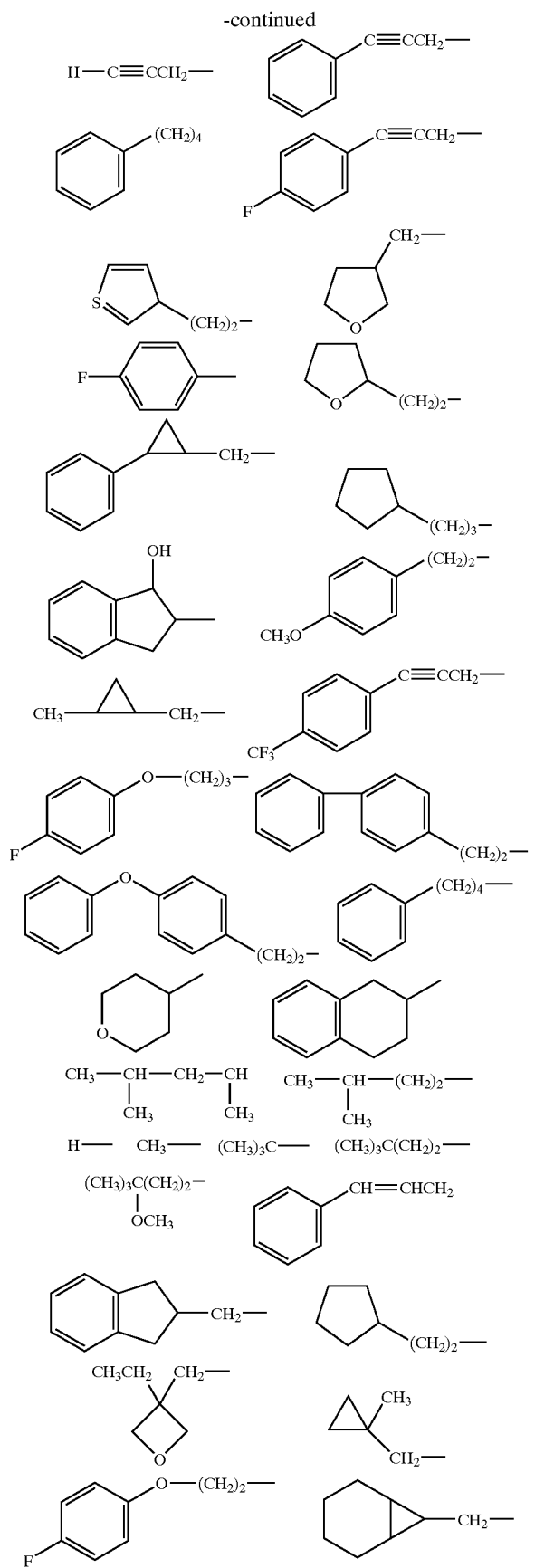
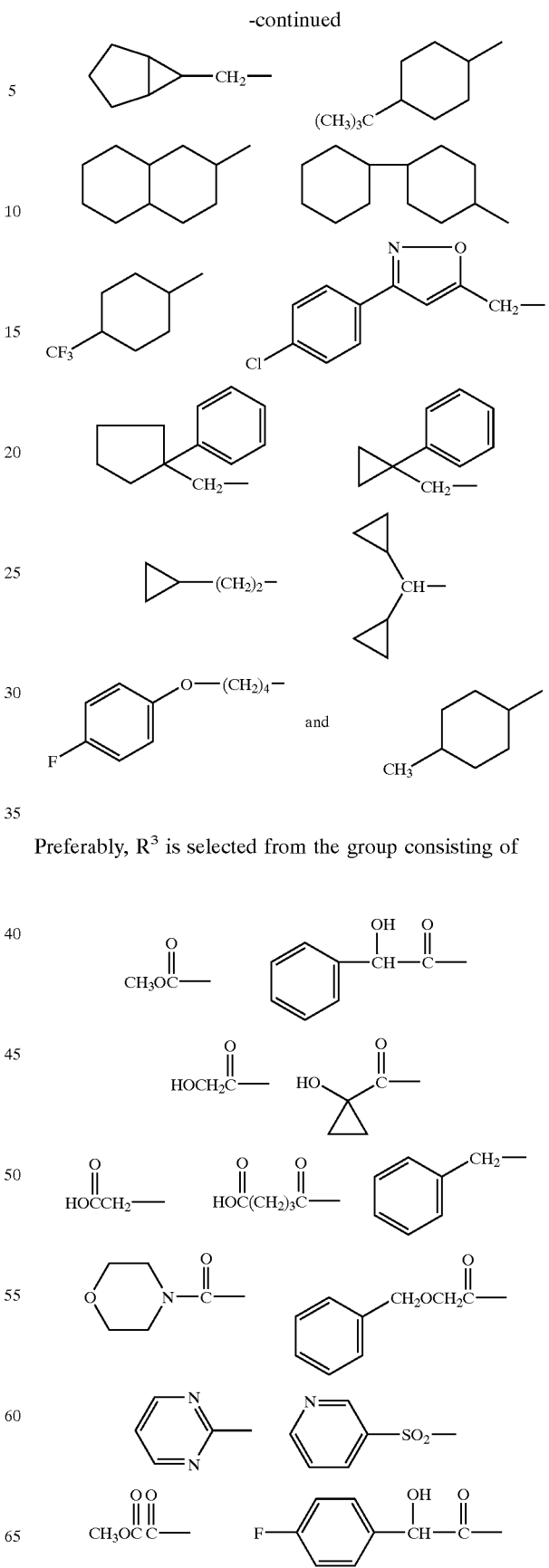
Preferably, $R^3$ is selected from the group consisting of

-continued
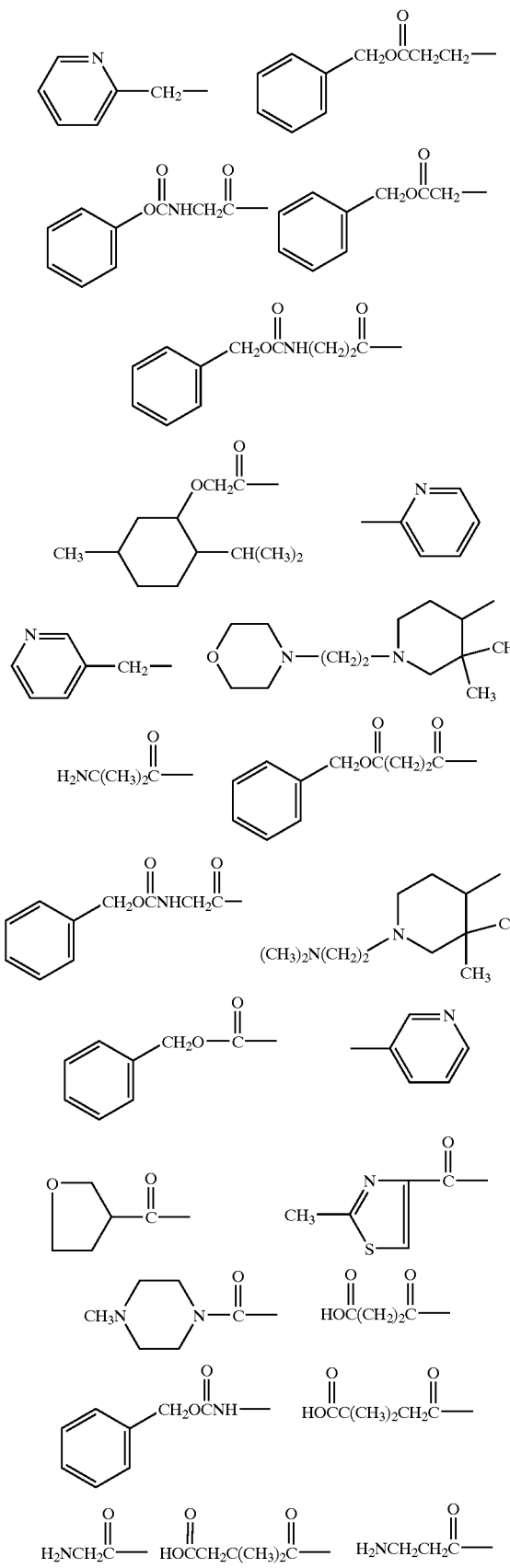
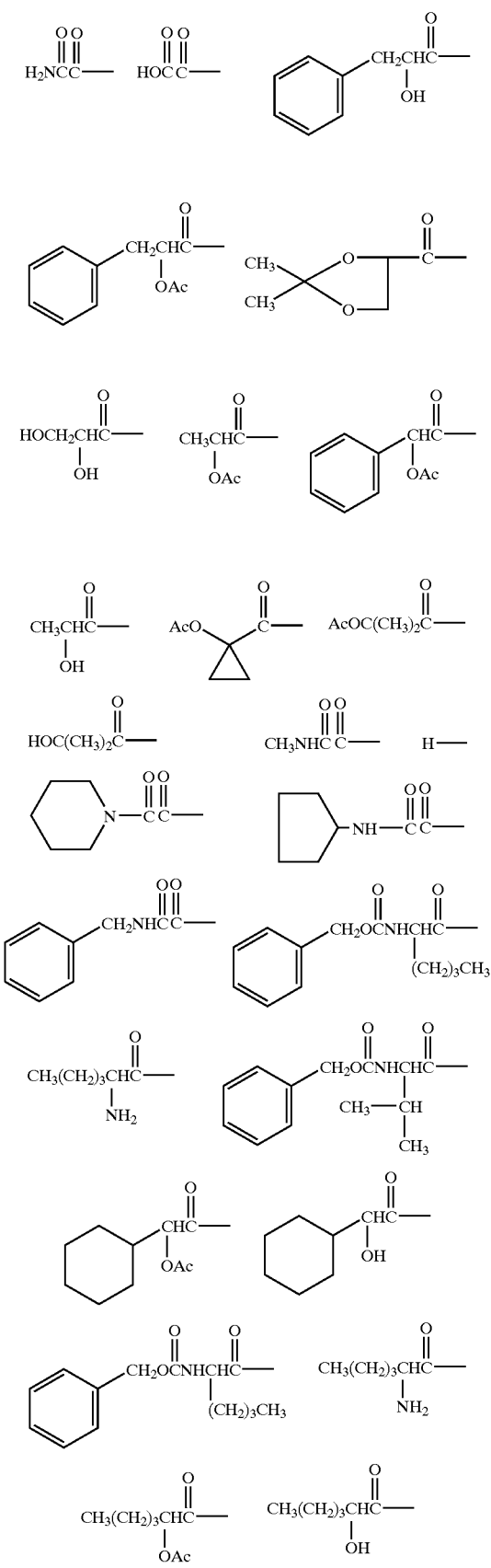

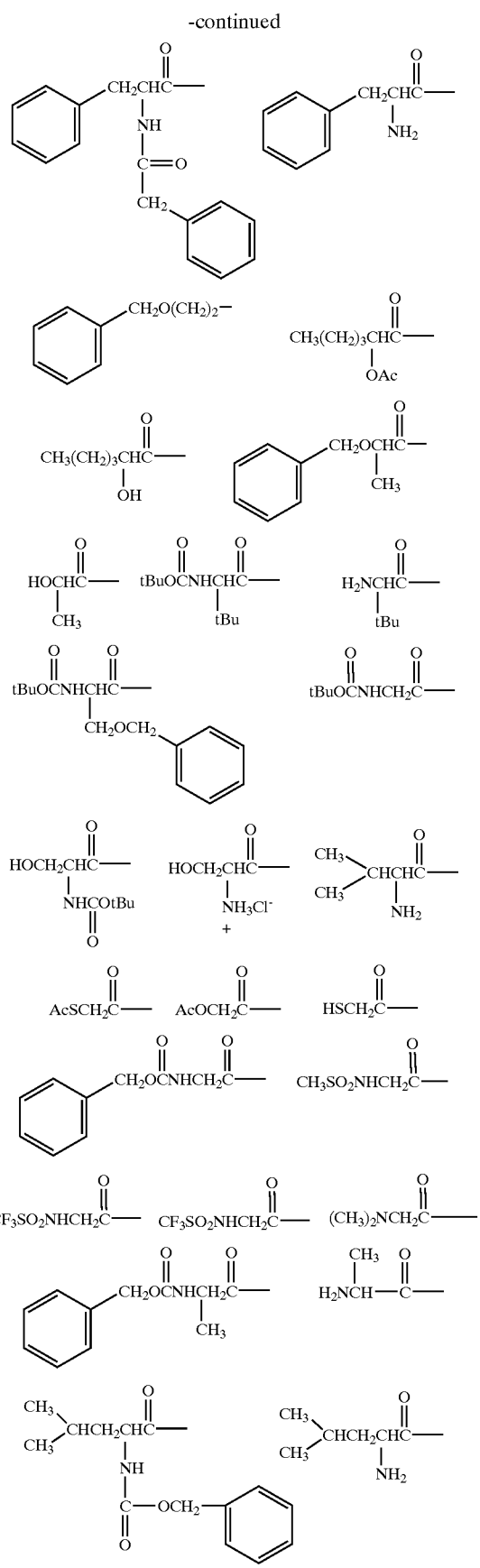
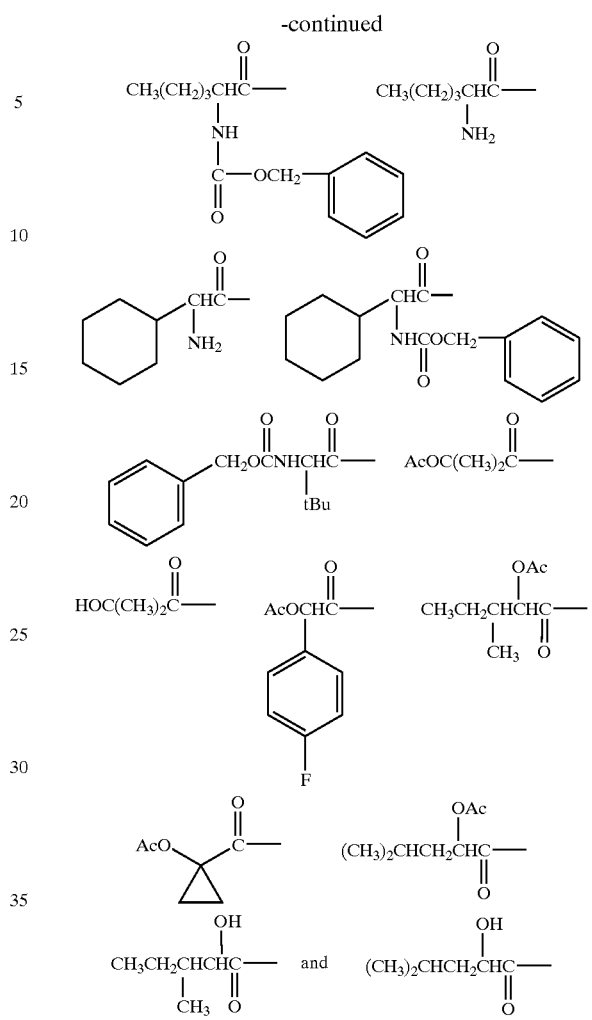

wherein Ac is $CH_3C(=O)$ and tBu is $C(CH_3)_3$.

In most preferred embodiments, $R^1$ is selected from the group consisting of cyclopentyl, benzyl, tetrahydrofuryl, indanyl, norbornyl, phenethyl, phenylbutyl, methylenecyclopropyl, methylenetetrahydrofuryl, ethylenethienyl, $C_{1-4}$alkylenecyclopentyl, methyleneindanyl, $C_{1-4}$alkylenephenyl, phenylpropargyl, phenylallyl, 3-(4-chlorophenyl)-(1,2,4-oxadiazol-5-yl)methyl, $C_{1-4}$ alkylenephenoxy, $C_{1-4}$alkylenebiphenyl, $C_{1-4}$alkylenecyclohexyl, pyranyl, methylene bridged alkyl, tetrahydronaphtyl, decahydronaphthyl, and $C_{1-6}$alkyl, wherein $R^1$ is optionally substituted with one or more phenyl, hydroxy, methoxy, methyl, ethyl, trifluoromethyl, fluoro, phenoxy, t-butyl, methoxy, cyclopropyl, and halophenyl; $R^2$ is selected from the group consisting of methyl and difluoromethyl; $R^3$ is selected from the group consisting of $CO_2CH_3$, $C(=O)CH_2OH$, $C(=O)CH(CH_3)$—OH, $C(=O)C(CH_3)_2OH$, $C(=O)C(=O)NH_2$, $C(=O)C(=O)OH$, $C(=O)CH_2NH_2$, $C(=O)CH(OH)CH_2OH$, $C(=O)CH(OH)CH_2CH_2CH_3$, $$C(=O)CHCH_2OH, \quad C(=O)CHCH_2C_6H_5,$$
$$\underset{NH_2}{|} \qquad \underset{NH_2}{|}$$

-continued

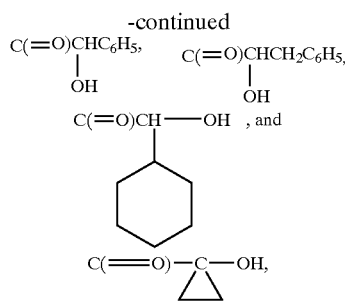

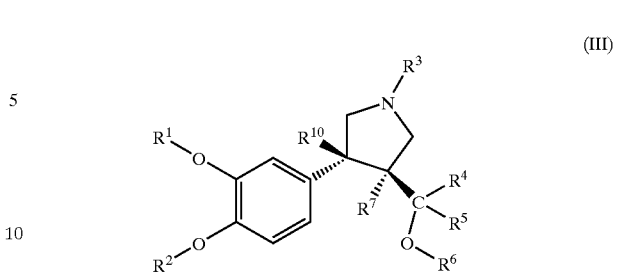

$R^4$ is hydrogen; $R^5$ is methyl; $R^6$ is hydrogen; and $R^8$ and $R^9$, independently, are selected from the group consisting of hydrogen and lower alkyl, or form a 5-membered or 6-membered ring.

The present invention includes all possible stereoisomers and geometric isomers of compounds of structural formula (II), and includes not only racemic compounds but also the optically active isomers as well. When a compound of structural formula (II) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883–888 (1997). Resolution of the final product, an intermediate, or a starting material can be achieved by any suitable method known in the art. Additionally, in situations where tautomers of the compounds of structural formula (II) are possible, the present invention is intended to include all tautomeric forms of the compounds. As demonstrated hereafter, specific stereoisomers exhibit an exceptional ability to inhibit PDE4 without manifesting the adverse CNS side effects typically associated with PDE4 inhibitors.

In particular, it is generally accepted that biological systems can exhibit very sensitive activities with respect to the absolute stereochemical nature of compounds. (See, E. J. Ariens, *Medicinal Research Reviews*, 6:451–466 (1986); E. J. Ariens, *Medicinal Research Reviews*, 7:367–387 (1987); K. W. Fowler, Handbook of Stereoisomers: Therapeutic Drugs, CRC Press, edited by Donald P. Smith, pp. 35–63 (1989); and S. C. Stinson, *Chemical and Engineering News*, 75:38–70 (1997).)

For example, rolipram is a stereospecific PDE4 inhibitor that contains one chiral center. The (−)-enantiomer of rolipram has a higher pharmacological potency than the (+)-enantiomer, which could be related to its potential antidepressant action. Schultz et al., *Naunyn-Schmiedeberg's Arch Pharmacol*, 333:23–30 (1986). Furthermore, the metabolism of rolipram appears stereospecific with the (+)-enantiomer exhibiting a faster clearance rate than the (−)-enantiomer. Krause et al., *Xenobiotica*, 18:561–571 (1988). Finally, a recent observation indicated that the (−)-enantiomer of rolipram (R-rolipram) is about ten-fold more emetic than the (+)-enantiomer (S-rolipram). A. Robichaud et al.; *Neuropharmacology*, 38:289–297 (1999). This observation is not easily reconciled with differences in test animal disposition to rolipram isomers and the ability of rolipram to inhibit the PDE4 enzyme. The compounds of the present invention can have three or more chiral centers. As shown below, compounds of a specific stereochemical orientation exhibit similar PDE4 inhibitory activity and pharmacological activity, but altered CNS toxicity and emetic potential.

Accordingly, preferred compounds of the present invention have the structural formula (III):

The compounds of structural formula (III) are potent and selective PDE4 inhibitors, and do not manifest the adverse CNS effects and emetic potential demonstrated by stereoisomers of a compound of structural formula (III).

Compounds of structural formula (II) which contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the compounds of structural formula (II), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulphonate, and p-toluenesulphonate salts. In light of the foregoing, any reference to compounds of the present invention appearing herein is intended to include compounds of structural formula (II), as well as pharmaceutically acceptable salts and solvates thereof.

The compounds of the present invention can be therapeutically administered as the neat chemical, but it is preferable to administer compounds of structural formula (II) as a pharmaceutical composition or formulation. Accordingly, the present invention further provides for pharmaceutical formulations comprising a compound of structural formula (II), together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

In particular, a selective PDE4 inhibitor of the present invention is useful alone or in combination with a second antiinflammatory therapeutic agent, for example, a therapeutic agent targeting TNFα, such as ENBREL® or REMICADE®, which have utility in treating rheumatoid arthritis. Likewise, therapeutic utility of IL-1 antagonism has also been shown in animal models for rheumatoid arthritis. Thus, it is envisioned that IL-1 antagonism, in combination with PDE4 inhibition, which attenuates TNFα, would be efficacious.

The present PDE4 inhibitors are useful in the treatment of a variety of allergic, autoimmune, and inflammatory diseases.

The term "treatment" includes preventing, lowering, stopping, or reversing the progression of severity of the condition or symptoms being treated. As such, the term "treatment" includes both medical therapeutic and/or prophylactic administration, as appropriate.

In particular, inflammation is a localized, protective response elicited by injury or destruction of tissues, which serves to destroy, dilute or wall off (i.e., sequester) both the injurious agent and the injured tissue. The term "inflammatory disease," as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

The present invention also provides a method of modulating cAMP levels in a mammal, as well as a method of treating diseases characterized by elevated cytokine levels.

The term "cytokine," as used herein, means any secreted polypeptide that affects the functions of other cells, and that modulates interactions between cells in the immune or inflammatory response. Cytokines include, but are not limited to monokines, lymphokines, and chemokines regardless of which cells produce them. For instance, a monokine is generally referred to as being produced and secreted by a monocyte, however, many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines include, but are not limited to, interleukin-1 (IL-1), interleukin-6 (IL-6), Tumor Necrosis Factor alpha (TNFα), and Tumor Necrosis Factor beta (TNFβ).

The present invention further provides a method of reducing TNF levels in a mammal, which comprises administering an effective amount of a compound of structural formula (II) to the mammal. The term "reducing TNF levels,"as used herein, means either:

a) decreasing excessive in vivo TNF levels in a mammal to normal levels or below normal levels by inhibition of the in vivo release of TNF by all cells, including but not limited to monocytes or macrophages; or b) inducing a down-regulation, at the translational or transcription level, of excessive in vivo TNF levels in a mammal to normal levels or below normal levels; or c) inducing a down-regulation, by inhibition of the direct synthesis of TNF as a postranslational event.

Moreover, the compounds of the present invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

The compounds of the present-invention also are useful in causing airway smooth muscle relaxation, bronchodilation, and prevention of bronchoconstriction.

The compounds of the present invention, therefore, are useful in treating such diseases as arthritic diseases (such as rheumatoid arthritis), osteoarthritis, gouty arthritis, spondylitis, thyroid-associated ophthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Mentz et al., *Blood* 88, pp. 2172–2182 (1996)), and inflammatory dermatoses, such as atopic dermatitis, psoriasis, or urticaria.

The compounds of the present invention also are useful in the treatment of obesity, alone or in combination with a PDE3 inhibitor, and in the treatment and prevention of nephropathy in Type 2 diabetes (see Mora et al., *New England Journal of Medicine*, 342, p. 441 (2000)). PDE3 inhibitors are known to persons skilled in the art.

Other examples of such diseases or related conditions include cardiomyopathies, such as congestive heart failure, pyrexia, cachexia, cachexia secondary to infection or malignancy, cachexia secondary to acquired immune deficiency syndrome (AIDS), ARC (AIDS-related complex), cerebral malaria, osteoporosis and bone resorption diseases, and fever and myalgias due to infection. In addition, the compounds of the present invention are useful in the treatment of erectile dysfunction, especially vasculogenic impotence (Doherty, Jr. et al. U.S. Pat. No. 6,127,363), diabetes insipidus and central nervous system disorders, such as depression and multi-infarct dementia.

Compounds of the present invention also have utility outside of that typically known as therapeutic. For example, the present compounds can function as organ transplant preservatives (see Pinsky et al., *J. Clin. Invest.*, 92, pp. 2994–3002 (1993)) as well.

Selective PDE4 inhibitors also can be useful in the treatment of erectile dysfunction, especially vasculogenic impotence (Doherty, Jr. et al. U.S. Pat. No. 6,127,363), diabetes insipidus (*Kidney Int.*, 37, p. 362, (1990); *Kidney Int.*, 35, p. 494, (1989)), and central nervous system disorders, such as multiinfarct dementia (Nicholson, *Psychopharmacology*, 101, p. 147 (1990)), depression (Eckman et al., *Curr. Ther. Res.*, 43, p. 291 (1988)), anxiety and stress responses (*Neuropharmacology*, 38, p. 1831 (1991)), cerebral ischemia (*Eur. J. Pharmacol.*, 272, p. 107 (1995)), tardive dyskinesia (*J. Clin. Pharmocol.*, 16, p. 304 (1976)), Parkinson's disease (see *Neurology*, 25, p. 722 (1975); *Clin.*

*Exp. Pharmacol, Physiol.*, 26, p. 421 (1999)), and premenstrual syndrome. With respect to depression, PDE4-selective inhibitors show efficacy in a variety of animal models of depression such as the "behavioral despair" or Porsolt tests (*Eur. J. Pharmacol.*, 47, p. 379 (1978); *Eur. J. Pharmacol.*, 57, p. 431 (1979); *Antidepressants: neurochemical, behavioral and clinical prospectives*, Enna, Malick, and Richelson, eds., Raven Press, p. 121 (1981)), and the "tail suspension test" (*Psychopharmacology*, 85, p. 367 (1985)). Recent research findings show that chronic in vivo treatment by a variety of antidepressants increase the brain-derived expression of PDE4 (*J. Neuroscience*, 19, p. 610 (1999)). Therefore, a selective PDE4 inhibitor can be used alone or in conjunction with a second therapeutic agent in a treatment for the four major classes of antidepressants: electroconvulsive procedures, monoamine oxidase inhibitors, and selective reuptake inhibitors of serotonin or norepinephrine. Selective PDE4 inhibitors also can be useful in applications that modulate bronchodilatory activity via direct action on bronchial smooth muscle cells for the treatment of asthma.

The selective PDE4 inhibitors of the present invention also can be used in the treatment of infertility in both females and males. The present PDE4 inhibitors elevate cAMP levels within granulosa cells, and thereby enhance gonadotropin induction of ovulation and oocyte maturation (Tsafriri et al., *Dev. Biol.*, 178, pp. 393–402 (1996)). Furthermore, the present PDE4 inhibitors can be used in treatments for infertile couples having abnormal semen parameters by enhancing sperm motility without affecting the acrosome reaction (see Fosch et al., *Hum. Reprod.*, 13, pp. 1248–1254 (1998)).

Compounds and pharmaceutical compositions suitable for use in the present invention include those wherein the active ingredient is administered to a mammal in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

The term "mammal" as used herein includes males and females, and encompasses humans, domestic animals (e.g., cats, dogs), livestock (e.g., cattle, horses, swine), and wildlife (e.g., primates, large cats, zoo specimens).

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 mg/kg to about 100 mg/kg per day. The desired dose can be conveniently administered in a single dose, or as multiple doses administered at appropriate intervals, for example as two, three, four or more subdoses per day. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of the present invention.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For buccal administration, the composition can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline, cellulose, maize-starch, calcium phosphate or sorbitol), lubricants (for example, magnesium, stearate, stearic acid, talc, polyethylene glycol or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, methyl cellulose, glucose/sugar syrup, gelatin, hydroxyethylcellulose, hydroxypropylmethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

For veterinary use, a compound of formula (II), or nontoxic salts thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (II), together with a pharmaceutically acceptable diluent or carrier therefor. There is further provided by the present invention a process of preparing a pharmaceutical composition comprising a compound of formula (II), which process comprises mixing a compound of formula (II), together with a pharmaceutically acceptable diluent or carrier therefor.

Specific, nonlimiting examples of compounds of structural formula (II) are provided below, the synthesis of which were performed in accordance with the procedures set forth below.

Generally, compounds of structural formula. (II) can be prepared according to the following synthetic schemes. In each scheme described below, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of structural formula (II) not specifically set forth herein can be accomplished by methods analogous to the schemes set forth below.

Unless otherwise noted, all starting materials were obtained from commercial suppliers and used without further purification. All reactions and chromatography fractions were analyzed by thinlayer chromatography on 250-mm silica gel plates, visualized with UV (ultraviolet) light $I_2$ (iodine) stain. Products and intermediates were purified by flash chromatography, or reverse-phase HPLC.

The compounds of general structural formula (II) can be prepared, for example, by first reacting a disubstituted benzaldehyde (1) with 2-butanone, then following the reaction scheme illustrated below. Other synthetic routes also are known and available to persons skilled in the art. For example, see Feldman et al. U.S. Pat. No. 5,665,754, incorporated herein by reference, for various individual reactions, and the synthetic methods disclosed in the Intermediates and Examples presented hereafter.

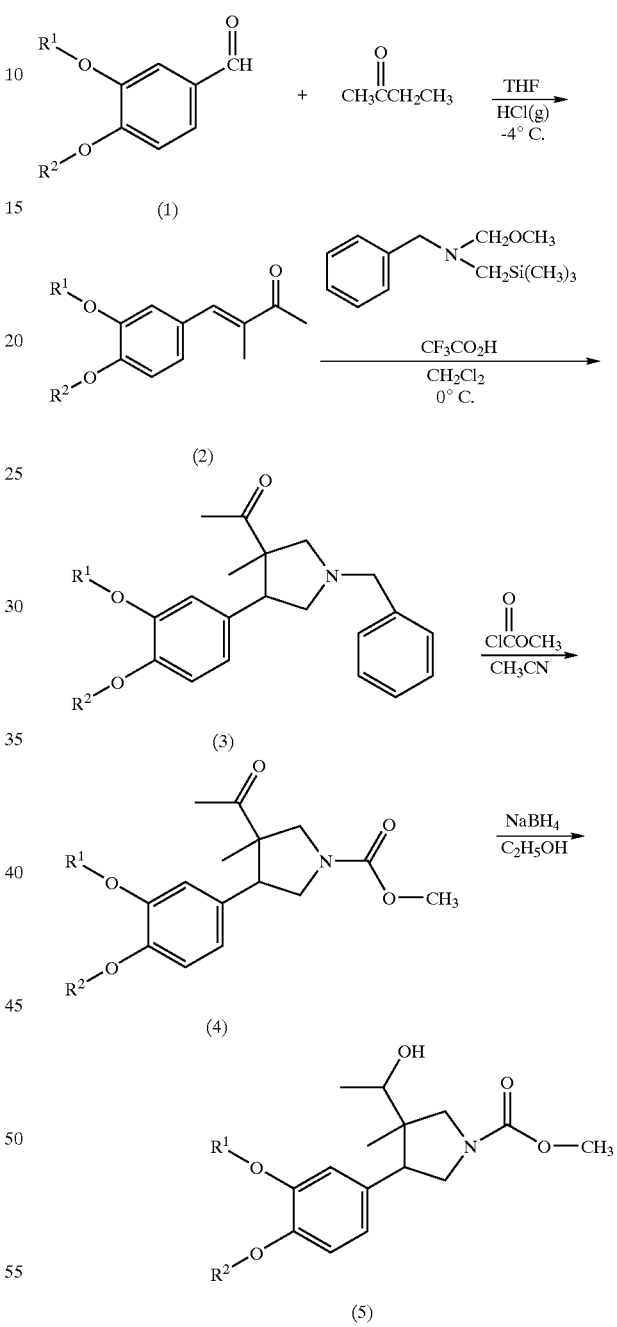

The above reaction scheme provides a compound (5) of structural formula (II), wherein $R^1$ and $R^2$ are determined by the starting benzaldehyde, $R^3$ is C(=O)OCH$_3$, $R^4$ is hydrogen, $R^5$ is methyl, $R^6$ is hydrogen, and $R^7$ is methyl, and $R^{10}$ is hydrogen. Proper selection of starting materials, or performing conversion reactions on compound (5), provide compounds of general structural formula (II) having other recited $R^1$ through $R^7$ and $R^{10}$ substituents.

The following illustrates the synthesis of various intermediates and compounds of structural formula (II). The following examples are provided for illustration and should not be construed as limiting.

In the structures herein, for a bond lacking a substituent, the substituent is methyl, for example:

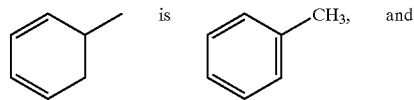

and

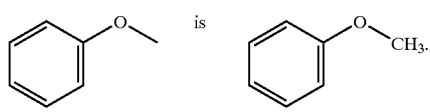

Where no substituent is indicated as attached to a carbon or a nitrogen atom, it is understood that the carbon atom contains the appropriate number of hydrogen atoms.

Abbreviations which are well known to one of ordinary skill in the art also are used, e.g., "Me" for methyl, "OMs" for mesylate, "Ph" for phenyl, "$CH_2Cl_2$" for methylene chloride, "NaOH" for sodium hydroxide, "EtOAc" for ethyl acetate, "$NH_4OH$" for ammonium hydroxide, "MeOH" for methanol, "LiOH" for lithium hydroxide, "$CsCO_3$" for cesium carbonate, "$H_2$" for hydrogen gas, "TFA" for trifluoroacetic acid, "OAc" for acetate, "Ac" for acetyl, "t-Bu" for tertiary butyl, "sat." for saturated, "h" for hour, "gm" for gram", "mmol" for millimole, "eq" for equivalent, "M" for molar, and "N" for normal.

General Synthesis for Cyclopentyl Series

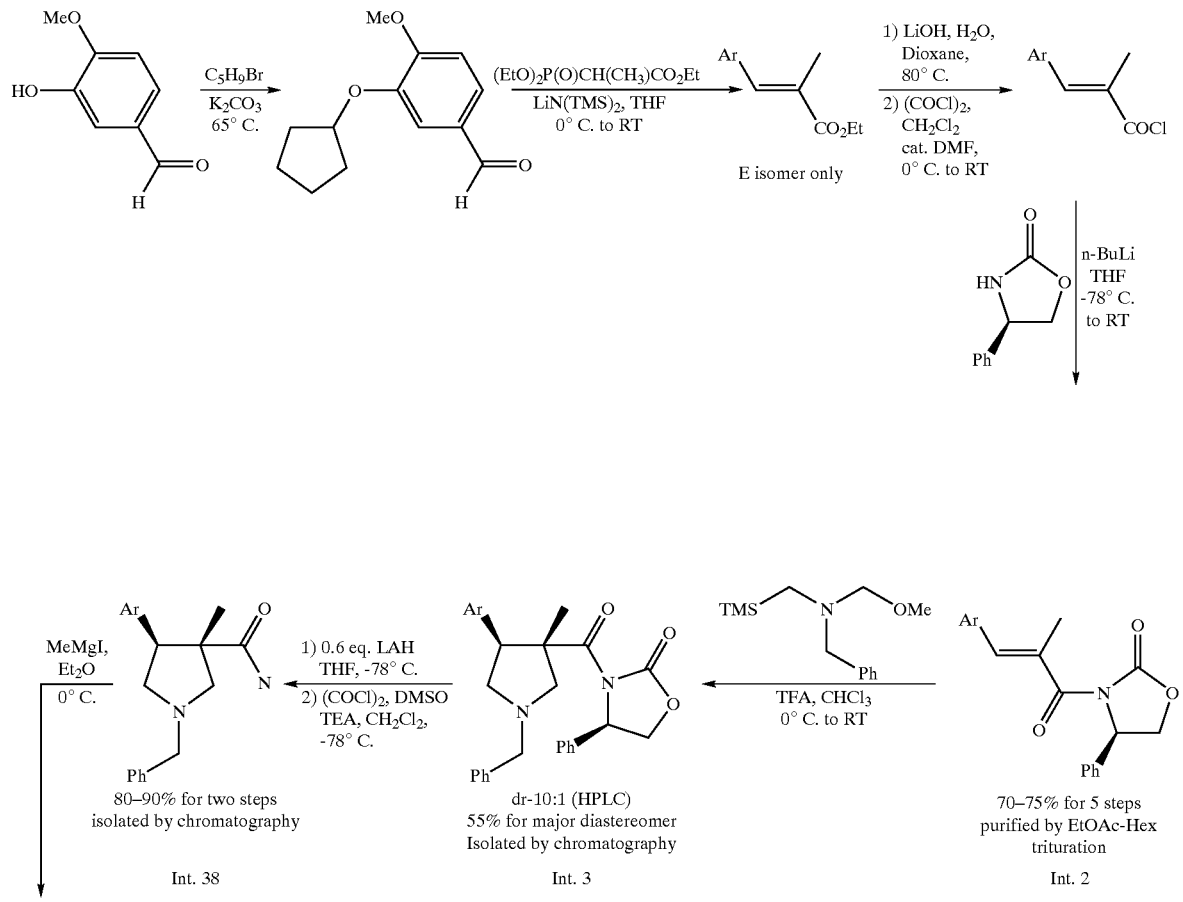

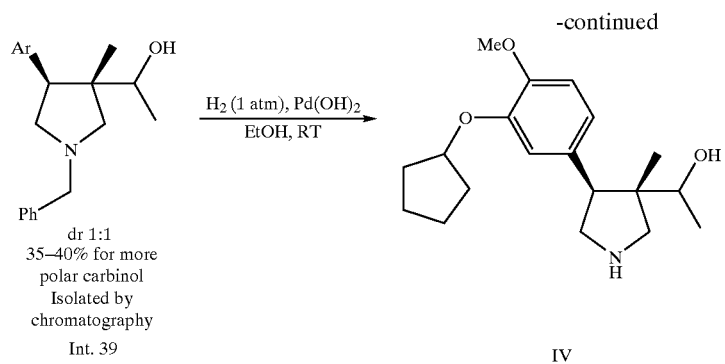
Int. 39
IV
General Synthesis for Indanyl Series
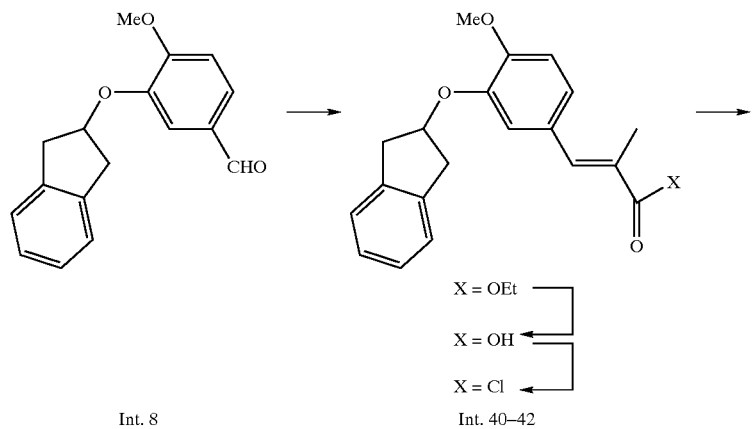
Int. 8
X = OEt
X = OH
X = Cl
Int. 40–42
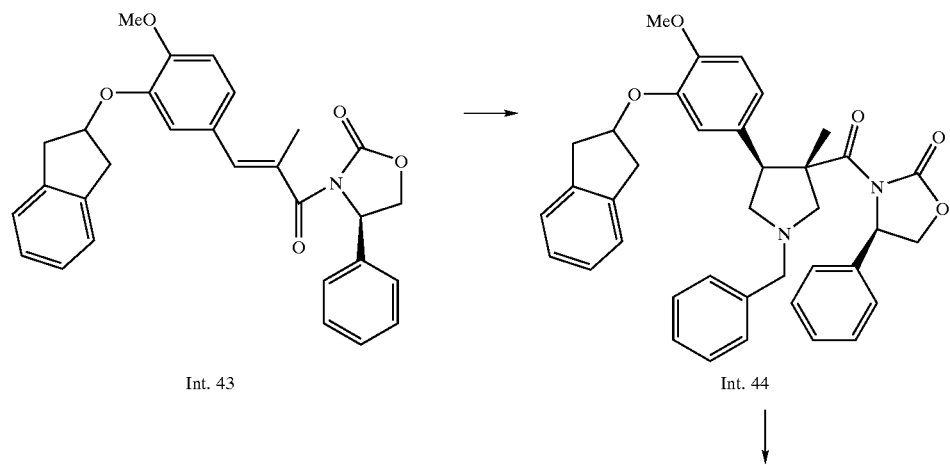
Int. 43
Int. 44

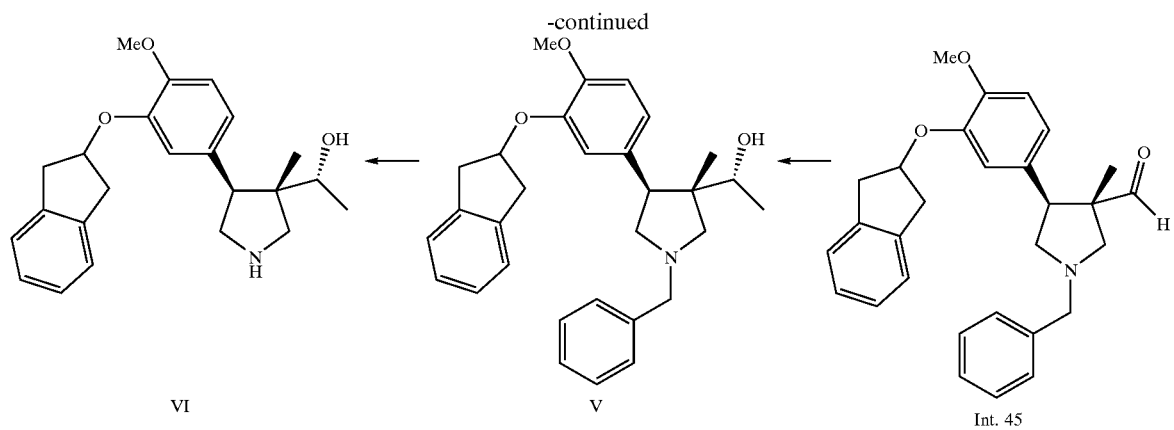
General Synthesis Varying R[1] Substituents
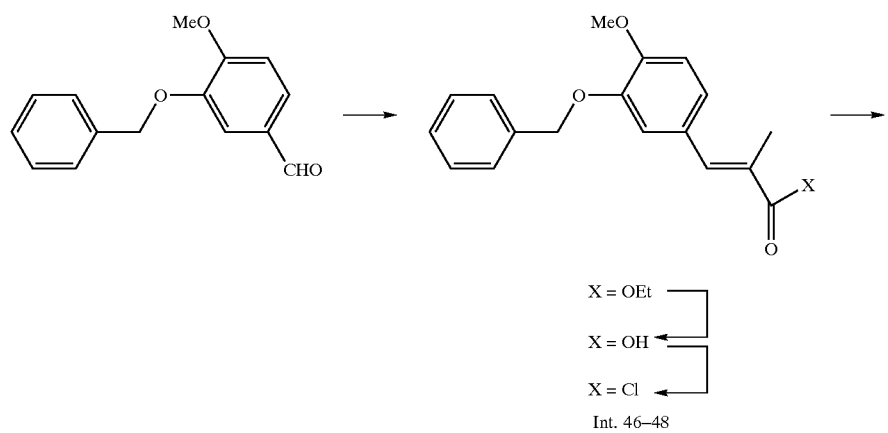
Int. 46–48
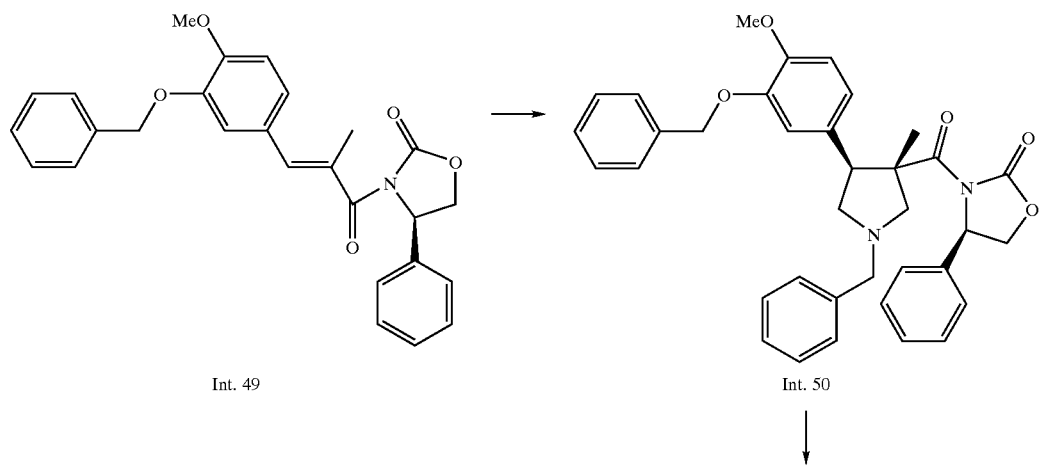

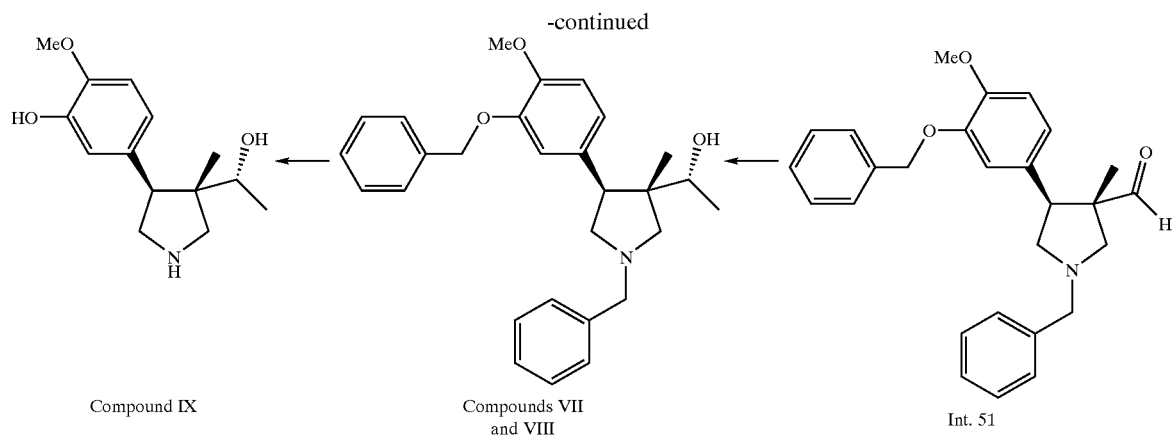

Compound IX     Compounds VII and VIII     Int. 51

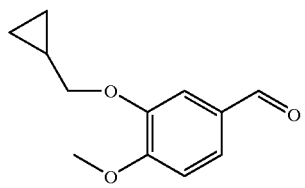

Intermediate 1

3-Cyclopropylmethoxy-4-methoxybenzaldehyde

A solution of 3-hydroxy-4-methoxybenzaldehyde (400 g, 2.63 mole) and bromomethylcyclopropane (426 g, 3.2 mole) in 1 L dimethylformamide (DMF) was stirred with potassium carbonate ($K_2CO_3$) (483 g, 3.5 mole) at 55° C. for 3.5 h. Then, 1 L of water was added, the mixture chilled on ice, and Intermediate 1 filtered as a white solid, (535 g, 99%). m/z 207 (MH$^+$).

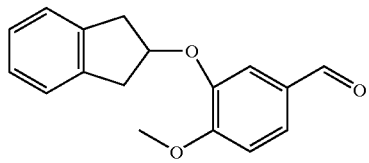

Intermediate 2

3-(Indan-2-yloxy)-4-methoxybenzaldehyde

Mitsunobu Procedure

A solution of 3-hydroxy-4-methoxybenzaldehyde (15.2 g, 100 mmol, 1 eq), 2-indanol (12.1 g, 90 mmol, 0.9 eq), and triphenylphosphine (26.2 g, 100 mmol, 1 eq) in dry THF (300 mL) was treated dropwise with diisopropylazodicarboxylate (DIAC) (19.6 mL, 100 mmol, 1 eq). The reaction mixture was stirred at reflux for 16 h, then cooled and diluted with diethyl ether (500 mL). The solution was washed with water (2×150 mL), 1 M NaOH (4×125 mL), and saturated sodium chloride (NaCl) (2×100 mL), dried with sodium sulfate ($Na_2SO_4$), and concentrated to a syrup that solidified upon standing. The solid was suspended in $Et_2O$ (350 mL) and stirred overnight to provide small particles. The solid was collected by vacuum filtration and recrystallized from ethanol/water (21.4 g). The ethereal filtrate was concentrated and purified by flash chromatography (silica gel, 7.5×36 cm Biotage KP-Sil column, eluted with 25% EtOAc in heptane) to yield an additional 5 g of Intermediate 2.

$^1$H NMR (300 MHz, CDCl$_3$) δ: 9.86 (s, 1H), 7.49–7.44 (m, 2H), 7.25–7.16 (m, 4H), 6.97 (d, J=8.7 Hz, 1H), 5.29–5.22 (m, 1H), 3.89 (s, 1H), 3.45 (dd, J=16.7, 6.6 Hz, 2H), 3.24 (dd, J=16.7, 3.6 Hz, 2H). $^{13C}$NMR (75 MHz, CDCl$_3$) δ: 190.9, 155.5, 147.9, 140.4, 130.0, 126.9, 126.8, 124.7, 112.1, 111.0, 78.9, 56.1, 39.7.

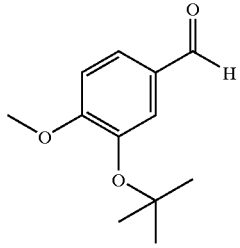

Intermediate 3

3-(tert-Butoxy)-4-methoxybenzaldehyde

To a stirred solution of isovanillin (30.4 gm, 200 mmol) in CH$_2$Cl$_2$ (200 mL) at room temperature under a nitrogen blanket was added (2-aza-1-(tert-butoxy)-3-methylbut-1-enyl)(methylethyl)amine (crude 40 mL, about 200 mmol) as an alkylating agent. Every 2 hours, another molar equivalent of the alkylating agent was added until 5 equivalents total were added. The reaction was allowed to stir another 16 hours. TLC in 3/7 EtOAc/hexane indicated the reaction was approximately 80% to complete. The mixture was diluted with CH$_2$Cl$_2$ (500 mL) and washed with 3M NaOH (4×300 mL) to remove unreacted isovanillin. The organics were dried over magnesium sulfate (MgSO$_4$), filtered, and concentrated in vacuo to a crude brown oil, which was flash chromatographed in 3/1 hexane/EtOAc and dried in vacuo to provide pure Intermediate 3 (22.6 gm, 54%).

¹H-NMR (CDCl₃, 400 MHz) δ: 9.84 (s, 1H), 7.60 (d, 1H), 7.55 (s, 1H), 7.00 (d, 1H), 3.86 (s, 3H), 1.39 (s, 9H).

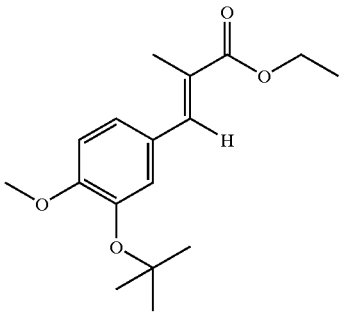

Intermediate 4

(2E)-3-(3-tert-Butoxy-4-methoxyphenyl)-2-methyl-acrylic acid ethyl ester

Horner-Emmons Procedure

To a stirred solution of triethyl 2-phosphonopropionate (25.6 mL, 119.4 mmol) in THF (120 mL) at 0° C. under a nitrogen blanket was added lithium hexamethyldisilylamide (1M in THF, 114 mL, 114 mmol) dropwise by syringe. After 30 minutes, a solution of Intermediate 3 (22.6 gm, 108 mmol) in THF (40 mL) was added by cannulation. After 2 hours at 0° C., TLC in 4/1 hexane/EtOAc showed complete reaction. The reaction was partially concentrated by rotary evaporator and partitioned between EtOAc (500 mL) and water (500 mL). The organics were washed with saturated NaCl (500 mL), dried (MgSO₄), filtered, and concentrated in vacuo. The crude product was flash chromatographed in 9/1 hexane/EtOAc to provide, after concentration in vacuo, Intermediate 4 (34.1 gm, 98%).

¹H-NMR (CDCl₃, 400 MHz) δ: 7.60 (s,. 1H), 7.16 (d, 1H), 7.12 (s, 1H), 6.91 (d, 1H), 3.83 (s, 3H), 2.13 (s, 3H), 1.37 (s, 9H).

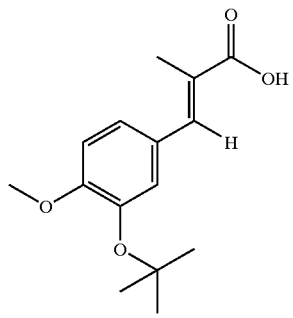

Intermediate 5

(2E)-3-(3-tert-Butoxy-4-methoxyphenyl)-2-methyl-acrylic acid

Lithium Hydroxide Hydrolysis Procedure

To a stirred solution of Intermediate 4 (34.1 gm, 116 mmol) in dioxane (116 mL) at room temperature under a nitrogen blanket was added a solution of LiOH monohydrate (5.87 gm, 140 mmol) in water (116 mL). The reaction was heated at 80° C. for 2 hours, then allowed to cool to room temperature. The reaction then was partitioned between EtOAc (400 mL) and 1M phosphoric acid (H₃PO₄) (400 mL). The organics were isolated, washed with H₂O (400 mL) and saturated NaCl (400 mL), dried (MgSO₄), filtered, and concentrated in vacuo to provide Intermediate 5 as a white solid (28.2 gm, 92%).

¹H-NMR (CDCl₃, 400 MHz) δ: 7.66 (s, 1H), 7.20 (d, 1H), 7.18 (s, 1H), 6.92 (d, 1H), 3.83 (s, 3H), 2.16 (s, 3H), 1.38 (s, 9H).

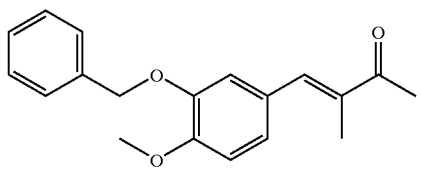

Intermediate 6

(E)-4-(3-Benzyloxy-4-methoxyphenyl)-3-methylbut-3-en-2-one

Acid-Catalyzed Aldol Condensation Procedure

A solution of commercially available 3-benzyloxy-4-methoxybenzaldehyde (34 g, 0.14 mol, 1 eq) and 2-butanone (50 mL, 0.56 mol, 4 eq) in dry THF (50 mL) was cooled to −4° C. Hydrogen chloride gas was passed through the well-stirred solution for several minutes, and the reaction mixture was capped and stored at −4° C. for 16 h. The mixture was poured into a well stirred solution of ice-cold saturated sodium bicarbonate (NaHCO₃) (about 2 L). If necessary, the pH was adjusted to >7 with sat. NaHCO₃, and the mixture was extracted with EtOAc (3×300 mL).

The EtOAc layer was washed with NaHCO₃ (2×200 mL), water (2×200 mL), and saturated NaCl (2×200 mL), dried with Na₂SO₄, and concentrated to a syrup. Crude mixture was purified by flash chromatography (silica gel, 7.5×36 cm Biotage KP-Sil column, eluted with 25% EtOAc in heptane) to yield Intermediate 6 (29.1 g, 70%).

¹H NMR (300 MHz, CDCl₃) δ: 7.46–7.27 (m, 6H), 7.06–6.91 (m, 3H), 3.93 (s, 3H), 2.41 (s, 3H), 1.92 (d, J=1.1 Hz, 3H).

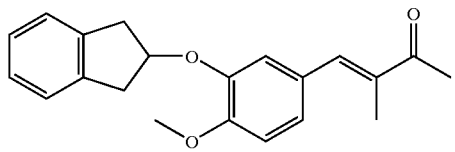

Intermediate 7

(E)-4-[3-(Indan-2-yloxy)-4-methoxyphenyl]-3-methyl-but-3-en-2-one

Prepared from Intermediate 2 by the acid-catalyzed aldol condensation procedure of Intermediate 6. LRMS (Electrospray, positive): Da/e 323.4 (m+1).

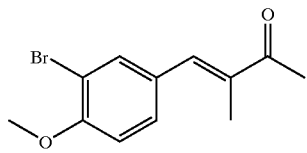

Intermediate 8

(E)-4-(3-Bromo-4-methoxyphenyl)-3-methylbut-3-en-2-one

Prepared from 3-bromo-4-methoxybenzaldehyde by the acid-catalyzed aldol condensation procedure of Intermediate 6.

$^1$H NMR (300 MHz, CDCl$_3$) δ: 7.66 (d, J=2.0 Hz, 1H), 7.36–7.41 (m, 2H), 6.94 (d, J=8.6 Hz, 1H), 3.94 (s, 3H), 2.45 (s, 3H), 2.06 (d, J=1.1 Hz, 3H).

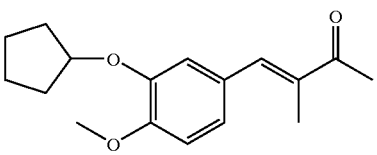

Intermediate 9

(E)-4-(3-Cyclopentyloxy-4-methoxyphenyl)-3-methyl-but-3-en-2-one

Prepared from Intermediate 1 by the acid-catalyzed aldol condensation procedure of Intermediate 6.

$^1$H NMR (300 MHz, CDCl$_3$) δ: 7.45 (br s, 1H), 7.05–6.99 (m, 2H), 6.90 (d, J=8.26 Hz, 1H), 4.81–4.75, m, 1H), 3.89 (s, 3H), 2.46 (s, 3H), 2.09 (d, J=1.1 Hz, 3H), 1.98–1.79 (m, 6H), 1.66–1.60 (m, 2H).

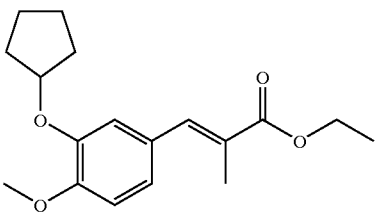

Intermediate 10

Ethyl (2E)-3-(3-cyclopentyloxy-4-methoxyphenyl)-2-methylprop-2-enoate

Prepared from commercially available 3-cyclopentyloxy-4-methoxybenzaldehyde by the Horner-Emmons procedure of Intermediate 4 to yield a brown liquid (68.4 g, 100%).

$^1$H NMR (400 MHz, CDCl$_3$) δ: 7.64 (s, 1H), 7.01–6.96 (c, 2H), 6.87 (m, 1H), 4.77 (m, 1H), 4.26 (q, 2H), 3.87 (s, 3H), 2.14 (s, 3H), 1.81–1.96 (c, 6H), 1.59–1.63 (c, 2H), 1.34 (t, 3H). LRMS (Electrospray, positive): Da/e 305.3 (m+1).

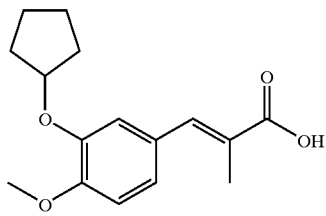

Intermediate 11

(2E)-3-(3-Cyclopentyloxy-4-methoxyphenyl)-2-methyl-prop-2-enoic acid

Intermediate 10 (68.4 g; 225 mmol)was hydrolyzed by the LiOH hydrolysis procedure of Intermediate 5 to provide Intermediate 11 as an orange solid (55 g, 88%).

$^1$H NMR (400 MHz, CDCl$_3$) δ: 7.76 (s, 1H), 7.06–7.00 (c, 2H), 6.89 (m, 1H), 4.78 (m, 1H), 3.88 (s, 3H), 2.17 (s, 3H), 1.97–1.83 (c, 6H), 1.64–1.61 (c, 2H). LRMS (Electrospray, negative): Da/e 275.3 (M−1).

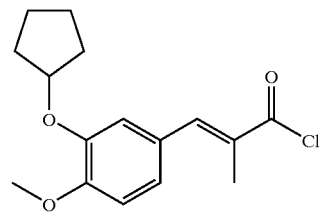

Intermediate 12

(2E)-3-(3-Cyclopentyloxy-4-methoxyphenyl)-2-methyl-prop-2-enoyl chloride

Acid Chloride Procedure

To a cooled (0° C.), stirred slurry of Intermediate 11 (55 g, 199 mmol) in anhydrous CH$_2$Cl$_2$ (400 mL) was added a solution of oxalyl chloride in CH$_2$Cl$_2$ (109 mL of 2.0 M, 218 mmol, 1.1 eq.) via syringe under a calcium chloride-dried atmosphere over 10 minutes. Vigorous bubbling was observed. The resulting dark solution was allowed to stir at 0° C. for 15 minutes, then a catalytic amount of DMF was added via syringe (0.3 mL). The resulting solution was stirred at 0° C. for 0.5 hours while the bubbling subsided, then allowed to warm to room temperature and stir overnight (17 hours). The reaction was diluted with EtOAc (500 mL) and was carefully quenched with water (250 mL). After vigorously stirring for 1 hour, the layers were separated and the organic layer was washed with water (400 mL) and brine (400 mL), then dried (MgSO$_4$), filtered, and concentrated in vacuo to provide Intermediate 12 as a brown solid (57.5 g, 98%).

$^1$H NMR (400 MHz, CDCl$_3$) δ: 7.98 (s, 1H), 7.11–7.02 (c, 2H), 6.92 (m, 1H), 4.79 (m, 1H), 3.90 (s, 3H), 2.22 (s, 3H), 2.01–1.82 (c, 6H), 1.68–1.62 (c, 2H).

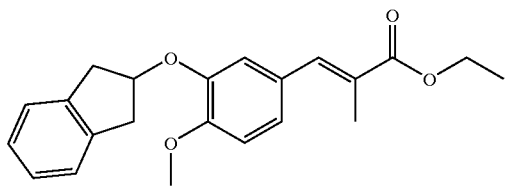

Intermediate 13

Ethyl (2E)-3-(3-indan-2-yloxy-4-methoxyphenyl)-2-methylprop-2-enoate

Prepared via the Horner Emmons procedure of Intermediate 4 from Intermediate 2.

¹H NMR (400 MHz, CDCl₃) δ: 7.64 (d, 1H), 7.28–7.17 (m, 4H), 7.06 (dd, 1H), 7.03 (d, 1H), 6.90 (d, 1H), 5.20 (c, 1H), 4.28 (q, 2H), 3.85 (s, 3H), 3.39 (dd, 2H), 3.26 (dd, 2H), 2.16 (d, 3H), 1.36 (t, 3H).

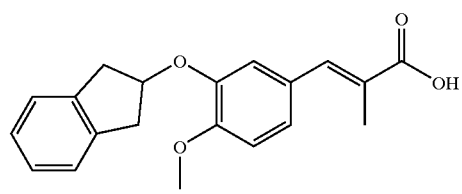

Intermediate 14

(2E)-3-(3-Indan-2-yloxy-4-methoxyphenyl)-2-methyl-prop-2-enoic acid

Prepared from Intermediate 13 via the LiOH hydrolysis procedure of Intermediate 5.

¹H NMR (D₆ DMSO, 400 MHz) δ: 7.56 (s, 1H), 7.25–7.11 (m, 5H), 7.06 (d, 1H), 6.99 (d, 1H), 5.22 (c, 1H), 3.71 (s, 3H), 3.34 (dd, 2H), 3.03 (d, 2H), 2.06 (s, 3H).

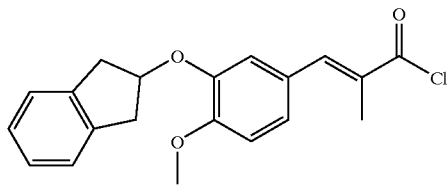

Intermediate 15

(2E)-3-(3-Indan-2-yloxy-4-methoxyphenyl)-2-methyl-prop-2-enoyl chloride

Prepared from Intermediate 14 via the acid chloride procedure of Intermediate 12.

¹H NMR (400 MHz, CDCl₃) δ: 8.01 (s, 1H), 7.29–6.93 (m, 7H), 5.23 (c, 1H), 3.89 (s, 3H), 3.42 (dd, 2H), 3.28 (dd, 2H), 2.26 (s, 3H).

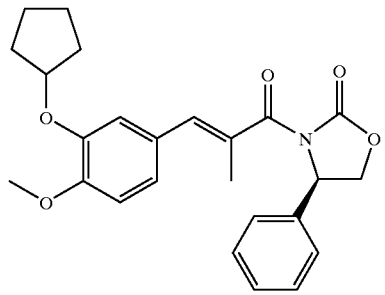

Intermediate 16

3-[(2E)-3-(3-Cyclopentyloxy-4-methoxyphenyl)-2-methylprop-2-enoyl](4R)-4-phenyl-1,3-oxazolidin-2-one Oxazolidinone Acylation Procedure To a cooled (−78° C.), overhead, mechanically stirred solution of R-phenyl oxazolidinone (10.0 g, 61.3 mmol) in dry tetrahydrofuran (400 mL) was added a solution of n-butyllithium in hexanes (27 mL of 2.5 M, 1.1 eq.) via syringe under a nitrogen atmosphere. The resulting solution was allowed to stir at −78° C. for 0.8 hours, then a solution of Intermediate 12 (19.9 g, 67.4 mmol, 1.1 eq.) in THF (100 mL) was added via cannula. After stirring at −78° C. for 15 minutes, the reaction was allowed to slowly warm to 0° C. over 40 minutes during which time the reaction became a thick slurry. After stirring at 0° C. for 2.5 hours, the reaction was quenched with saturated, aqueous ammonium chloride (NH₄Cl) (300 mL) and the bulk of the THF was removed at reduced pressure. The residue then was extracted with chloroform (CHCl₃) (3×700 mL) and the combined organic layers were washed with water (300 mL) and brine (300 mL), then dried (MgSO₄), filtered, and concentrated in vacuo to provide about 33 g of a light orange solid. The material was suspended in 10% EtOAc in hexane (1.2 L) and vigorously stirred overnight. The resulting fine powdery solids were collected on a Buchner funnel with suction, then dried in vacuo to provide Intermediate 16 as a tan powder (21.8 g, 88%).

¹H NMR (400 MHz, CDCl₃) δ: 7.41–7.37 (c, 5H), 7.06 (s, 1H), 7.01–6.97 (c, 2H), 6.86 (m, 1H), 5.54 (t, 1H), 4.77–4.73 (c, 2H), 4.29 (t, 1H), 3.87 (s, 3H), 2.17 (s, 3H), 1.97–1.82 (c, 6H), 1.62–1.56 (c, 2H).

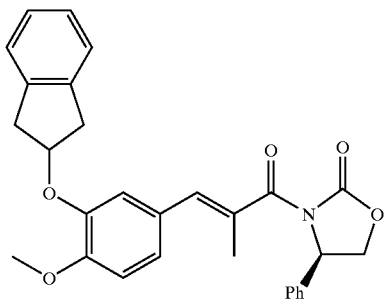

Intermediate 17

3-[(2E)-3-(3-Indan-2-yloxy-4-methoxyphenyl)-2-methylprop-2-enoyl](4R)-4-phenyl-1,3-oxazolidin-2-one Prepared from Intermediate 15 via the oxazolidinone acylation procedure of Intermediate 16.

$^1$H NMR (400 MHz, CDCl$_3$) δ: 7.43–7.33 (m, 5H), 7.25–7.16 (m, 4H), 7.07–7.03 (m, 2H), 6.89 (d, 1H), 5.54 (dd, 1H), 5.19 (c, 1H), 4.74 (t, 1H), 4.28 (dd, 1H), 3.84 (s, 3H), 3.38 (dd, 2H), 3.24 (ddd, 2H), 2.19 (d, 3H).

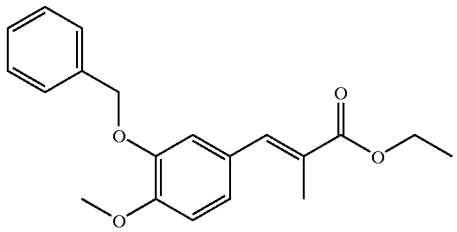

Intermediate 18

Ethyl (2E)-3-[4-methoxy-3-(phenylmethoxy)phenyl]-2-methylprop-2-enoate

Prepared from 3-benzyloxy-4-methoxybenzaldehyde via the Horner Emmons procedure of Intermediate 4.

$^1$H NMR (400 MHz, CDCl$_3$) δ: 7.56 (s, 1H), 7.44 (t, 2H), 7.36 (t, 2H), 7.30 (t, 1H), 7.01 (dd, 1H), 6.95 (d, 1H), 6.90 (d, 1H), 5.18 (s, 2H), 4.24 (q, 2H), 3.92 (s, 3H), 1.98 (d, 3H), 1.33 (t, 3H).

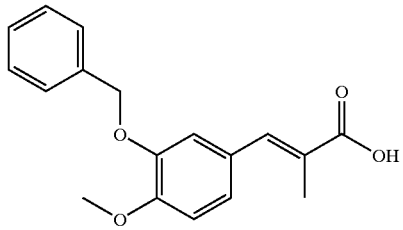

Intermediate 19

(2E)-3-[4-Methoxy-3-(phenylmethoxy)phenyl]-2-methylprop-2-enoic acid

Prepared from Intermediate 18 via the LiOH hydrolysis procedure of Intermediate 5 and used without characterization.

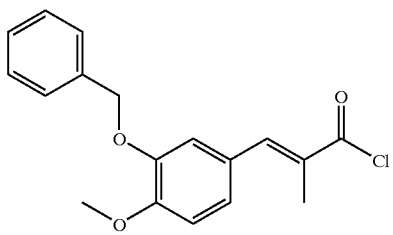

Intermediate 20

(2E)-3-[4-Methoxy-3-(phenylmethoxy)phenyl]-2-methyl-prop-2-enoyl chloride

Prepared from Intermediate 19 via the acid chloride procedure of Intermediate 12.

$^1$H NMR (400 MHz, CDCl$_3$) δ: 7.91 (s, 1H), 7.47–7.29 (m, 5H), 7.10 (dd, 1H), 7.00 (d, 1H), 6.95 (d, 1H), 5.20 (s, 2H), 3.95 (s, 3H), 2.04 (s, 3H).

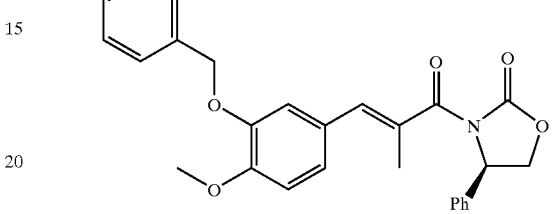

Intermediate 21

3-{(2E)-3-[4-Methoxy-3-(phenylmethoxy)phenyl]-2-methylprop-2-enoyl}(4R)-4-phenyl-1,3-oxazolidin-2-one Prepared from Intermediate 19 via the oxazolidinone acylation procedure of Intermediate 16.

$^1$H NMR (400 MHz, CDCl$_3$) δ: 7.44–7.29 (m, 11H), 7.03–6.89 (m, 3H), 5.52 (dd, 1H), 5.17 (s, 2H), 4.73 (dt, 1H), 4.27 (dd, 1H), 3.91 (s, 3H), 2.00 (s, 3H).

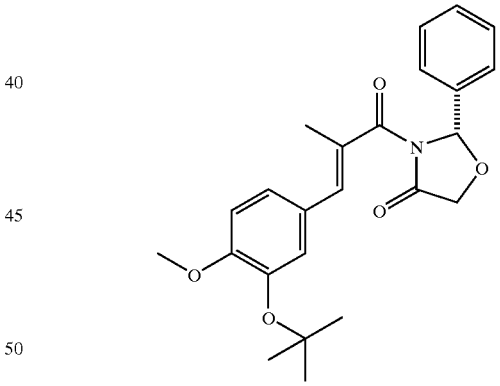

Intermediate 22

(2E)-3-[3-(3-tert-Butoxy-4-methoxyphenyl)-2-methyl-acryloyl]-4-R-phenyloxazolidin-2-one Prepared from Intermediate 5 (25.7 gm, 97.2 mmol) via the oxazolidinone acylation procedure of Intermediate 16 to provide Intermediate 22 as an off-white solid (39.8 gm, quantitative yield).

$^1$H-NMR (CDCl$_3$, 400 MHz) δ: 7.42–7–33 (m, 5H), 7.16 (d, 1H), 7.02 (s, 1H), 6.87 (d, 1H), 5.55 (dd, 1H), 4.73 (dd, 1H), 4.26 (dd, 1H), 3.81 (s, 3H), 2.16 (s, 3H), 1.38 (s, 9H).

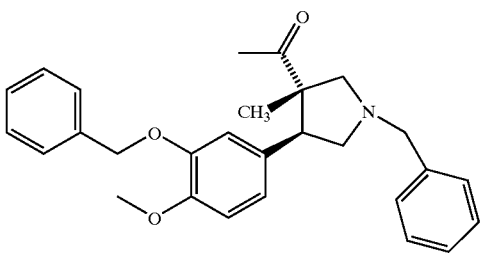

Intermediate 23 trans-(±)-1-[1-Benzyl-4-(3-benzyloxy-4-methoxyphenyl)-3-methylpyrrolidin-3-yl]ethanone Azomethine Ylide Cyclization A solution of Intermediate 6 (15 g, 50.6 mmol, 1 eq) and N-(methoxymethyl)-N-(trimethysilylmethyl)benzyl-amine (11.9 g, 50.6 mmol, 1 eq) in CH$_2$Cl$_2$ (85 mL) at 0° C. was treated dropwise with a solution of TFA (1 M in CH$_2$Cl$_2$, 5 mL, 5.1 mmol, 0.1 eq). After stirring at the 0° C. for 30 min., the reaction mixture was stirred at room temperature for 16 h. The solution was treated with additional N-(methoxymethyl)-N-(trimethysilylmethyl)benzylamine (6 g, 25.3 mmol, 0.5 eq), stirred 1 h at room temperature, and treated for a third time with N-(methoxymethyl)-N-(trimethysilylmethyl)benzylamine (6 g, 25.3 mmol, 0.5 eq). The reaction mixture was concentrated, and the residue was dissolved in EtOAc (500 mL). The solution was washed with 1 N HCl (2×60 mL with 10 mL sat. NaCl added), water (250 mL), 1 M NaOH (250 mL), water (250 mL), sat. NaCl (2×100 mL), dried with Na$_2$SO$_4$, and concentrated in vacuo. The residue was purified by flash chromatography (silica gel, 7.5×36 cm Biotage KP-Sil column, eluted with 5–10% diethyl ether in dichloromethane) to yield Intermediate 23 as a light yellow syrup (17.4 g, 80%).

$^1$H NMR (300 MHz, CDCl$_3$) δ: 7.44–7.22 (m, 10 H), 6.81–6.72 (m, 3H), 5.14 (s, 2H), 3.86 (s, 3H), 3.72–3.67 (m, 2H), 3,58 (d, J=13.0 Hz, 1H), 3.08 (d, J=9.7 Hz, 1H), 2.99 (dd, J=8.9, 7.8 Hz, 1H), 2.74 (dd, J=9.1, 7.4 Hz, 1H), 2.33 (d, J=9.7 Hz, 1H), 2.15 (s, 3H), 0.68 (s, 3H). $^{13}$C NMR (75 MHz, CDCl$_3$) δ: 211.3, 148.4, 147.4, 139.2, 137.2, 132.7, 128.51, 128.50, 128.3, 127.8, 127.4, 127.0, 121.6, 115.5, 111.2, 71.0, 63.8, 60.0, 59.5, 57.9, 56.0, 47.7, 25.6, 20.6.

Intermediate 24 trans-(±)-1-{1-Benzyl-4-[3-(indan-2-yloxy)-4-methoxyphenyl]-3-methylpyrrolidin-3-yl}ethanone Prepared from Intermediate 7 by the azomethine cyclization procedure of Intermediate 23.

$^1$H NMR (300 MHz, CDCl$_3$) δ: 7.38–7.16 (m, 9 H), 6.88 (br s, 1H), 6.78 (br s, 2H), 5.18–5.13 (m, 1H), 3.82–3.73 (m, 2H), 3.79 (s, 3H), 3.60 (d, J=13.0 Hz, 1H), 3.41–3.17 (m, 4H), 3.14 (d, J=9.7 Hz, 1H), 3.05 (t, J=8.3 Hz, 1H), 2.84 (t, J=8.3 Hz, 1H), 2.44 (d, J=9.7 Hz, 1H), 2.24 (s, 3H), 0.86 (s, 3H).

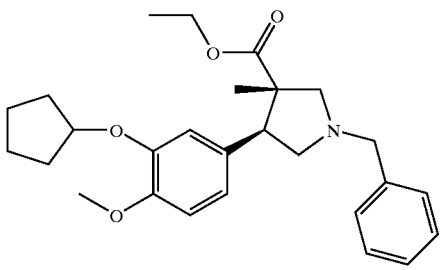

Intermediate 25

(±)-1-Benzyl-4-(3-cyclopentyloxy-4-methoxyphenyl)-3-methylpyrrolidine-3-carboxylic acid ethyl ester Prepared from Intermediate 10 by the azomethine ylide cyclization reaction of Intermediate 23 to yield an amber oil (16.7 g, 61% yield).

$^1$H NMR (300 MHz, CDCl$_3$) δ: 7.39–7.23 (m, 5H, aromatic), 6.91 (s, 1H, aromatic), 6.78 (m, 2H, aromatic), 4.75 (m, 1H), 4.18 (q, 2H, OEt), 3.86 (m, 1H), 3.81 (s, 3H,OCH$_3$), 3.75 (d, 1H, J=13.2 Hz), 3.62 (d, 1H, J=13.2 Hz) 3.20 (d, 1H, J=9.5 Hz) 3.01 (m, 1H), 2.91 (m, 1H), 2.51 (d, 1H, J=9.5 Hz), 1.93–1.58 (m, 8H, cyclopentyl), 1.28 (t, 3H, OEt), 0.9 (s, 3H, CH$_3$).

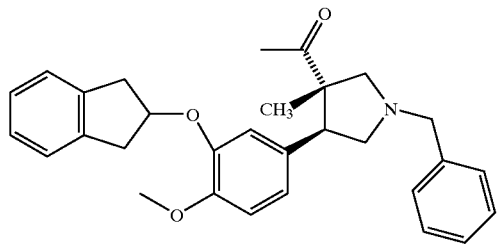
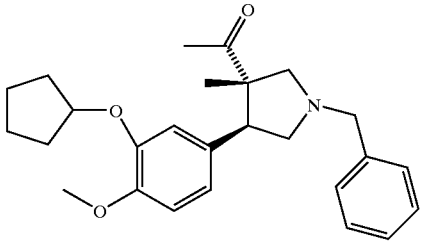

Intermediate 26 trans-(±)-1-[1-Benzyl-4-(3-cyclopentyloxy-4-methoxyphenyl)-3-methylpyrrolidin-3-yl]ethanone Prepared according to procedure set forth in U.S. Pat. No. 5,665,754.

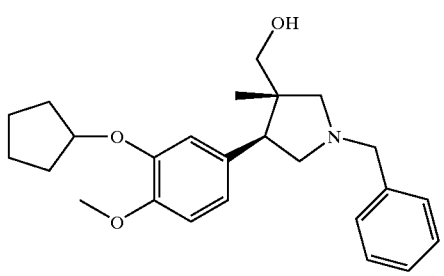

Intermediate 27

(±)-[1-Benzyl-4-(3-cyclopentyloxy-4-methoxyphenyl)-3-methylpyrrolidin-3-yl]methanol To a magnetically stirred solution of Intermediate 25 (9.32g, 21.3 mmol) in dry toluene (10 mL) at 0° C. was added diisobutylaluminum hydride (64 mL, 1.0M in $CH_2Cl_2$, 63.9 mmol). The mixture was stirred for 30 minutes at 0° C., then at room temperature for 1 hour, and finally quenched with MeOH (20 mL). A 1.0 N hydrochloric acid (HCl) solution (100 mL) then was added, and the mixture stirred another 30 minutes. The phases were separated and the aqueous phase extracted with $CH_2Cl_2$ (2×20 mL). The organic phases were washed with a saturated $NH_4Cl$ solution, dried over anhydrous $Na_2SO_4$, then concentrated to afford a light yellow oil product (8.28 g, 98% yield).

$^1$H NMR (300 MHz, $CDCl_3$) δ: 7.31–7.14 (m, 5H, aromatic), 6.78–6.71 (m, 3H, aromatic), 4.76–4.73 (br. m, 1H), 3.79 (s, 3H, $OCH_3$), 3.71–3.55 (m, 3H), 3.47–3.10 (m, 3H), 2.92 (d, 1H, J=9.2 Hz), 2.62 (m, 1H), 3.35–2.33 (m, 2H), 1.89–1.58 (m, 8H, cyclopentyl), 0.52 (s, 3H, $CH_3$).

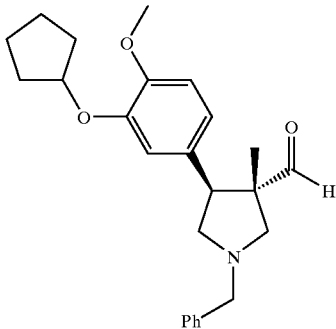

Intermediate 28

(±)-1-Benzyl-4-(3-cyclopentyloxy-4-methoxyphenyl)-3-methylpyrrolidine-3-carboxaldehyde A solution of oxalyl chloride (4.87 mL, 9.73 mmol) in dry $CH_2Cl_2$ (20 mL) was chilled to −78° C. under a nitrogen blanket, and stirred while being treated with a solution of dimethyl sulfoxide (DMSO, 1.38 mL, 19.5 mmol) in $CH_2Cl_2$ (5 mL). Gas evolution was observed. When the addition was complete, the solution was stirred for 5 minutes, then a solution of Intermediate 27 (3.5 g, 8.85 mmol) in $CH_2Cl_2$ (10 mL) was added over a period of 10 minutes. The mixture was stirred for 30 minutes, treated with triethylamine ($Et_3N$) (6.7 mL, 44.3 mmol), and allowed to warm to room temperature. Water was added to the mixture, and the resulting phases separated. The aqueous phase was extracted with $CH_2Cl_2$ (2×50 mL). The combined organic phases were washed with brine, dried ($Na_2SO_4$) and concentrated to give an oily product (3.2 g, 92%).

$^1$H NMR (300 MHz, $CDCl_3$) δ: 9.63 (s, 1H, CHO), 7.34–7.21 (m, 5H, aromatic), 6.78–6.68 (m, 3H, aromatic), 4.73 (br. m, 1H), 3.80 (s, 3H, $OCH_3$), 3.78–3.61 (m, 3H), 3.18–3.11 (m, 2H), 2.86–2.81 (m, 1H), 2.58–2.52 (m, 1H), 2.43–2.34 (m, 2H), 1.87–1.59 (m, 8H, cyclopentyl), 0.74 (s, 3H, $CH_3$).

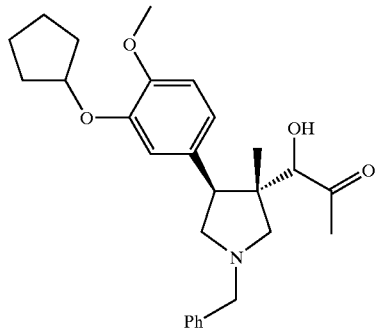

Intermediate 29

(±)-1-[1-Benzyl-4-(3-cyclopentyloxy-4-methoxyphenyl)-3-methylpyrrolidin-3-yl]-1-hydroxypropan-2-one To a solution of ethyl vinyl ether (0.95 mL, 9.91 mmol) in dry THF (4 mL) at −78° C. was added 1.7M t-butyllithium in pentane (5.25 mL, 8.93 mmol), and the resulting solution was warmed to 0° C. The color of the solution changed from yellow to colorless. The resulting vinyl anion then was cooled to −78° C., and a solution of Intermediate 28 (1.95 g, 4.96 mmol) in THF (1.0 mL) was added dropwise. The resulting mixture was stirred for 45 minutes, quenched with saturated $NH_4Cl$ (15 mL), and extracted with $Et_2O$ (3×30 mL). The combined organic extracts were dried over $Na_2SO_4$ and concentrated. The crude product was dissolved in $Et_2O$ and treated with concentrated sulfuric acid ($H_2SO_4$) in a separatory funnel while shaking vigorously. The $Et_2O$ solution was washed with water (30 mL), with saturated $NaHCO_3$ (30 mL) solution, dried over $Na_2SO_4$, and concentrated. The residue was purified by flash chromatography (silica gel, 20% EtOAc-hexanes) to provide Intermediate 29 as an orange oil (1.36 g, 62% yield).-

¹H NMR (300 MHz, CDCl₃) δ: 7.34–7.27 (m, 5H, aromatic), 6.77–6.68 (m, 3H, aromatic), 4.75–4.72 (br. m, 1H), 4.13–4.08 (m, 1H), 3.81 (s, 3H, OCH₃), 3.79–3.57 (m, 3H), 3.26 (m, 1H), 2.99 (d, 1H, J=9.2 Hz), 2.69–2.64 (m, 1H), 2.39 (d, 1H, J=9.2 Hz) 2.25 (s, 3H, OCH₃), 1.94–1.59 (m, 8H, cyclopentyl), 0.69 (s, 3H, CH₃).

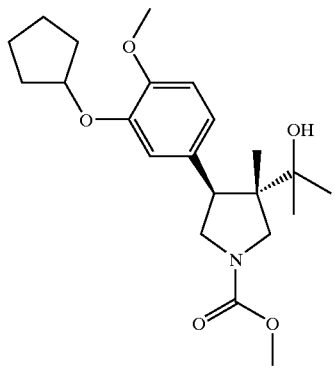

EXAMPLE 1

(±)-4-(3-Cyclopentyloxy-4-methoxyphenyl)-3-(1-hydroxy-1-methylethyl)-3-methylpyrrolidine-1-carboxylic acid methyl ester To a 3.0 M solution of methylmagnesium bromide (0.6 mL, 1.8 mmol) in Et₂O at 0° C. was added a solution of Intermediate 36 (0.65 g, 1.73 mmol) in dry THF (5 mL), dropwise via a syringe pump. The resulting mixture was stirred at 0° C. for 30 minutes, then at room temperature for 1 hour. The reaction mixture then was quenched with saturated NH₄Cl (15 mL) and extracted with Et₂O (2×10 mL). The combined organic extracts were dried over Na₂SO₄ and concentrated. The residue was purified by flash chromatography (silica gel, 20% EtOAc-hexanes, then 50%) to provide Example 1 as an orange oil (0.37 g, 55%).

¹H NMR (300 MHz, CDCl₃) δ: 6.83–6.77 (m, 3H, aromatic), 4.75–4.74 (br. m, 1H), 3.83 (s, 3H, OCH₃), 3.96–3.50 (m,4H), 3.73 (s, 3H, OCH₃), 3.37–3.25 (m, 1H), 1.96–1.59 (m, 8H, cyclopentyl), 1.22 (s, 3H, CH₃), 1.07 (s, 6H, CH₃).

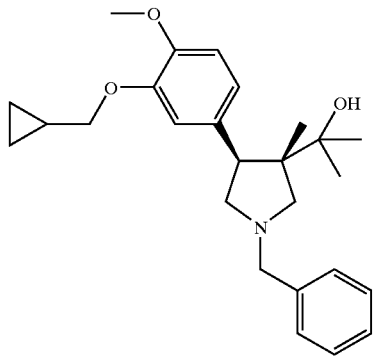

Intermediate 30

2-[1-Benzyl-4-(S)-(3-cyclopropylmethoxy-4-methoxyphenyl)-3-(S)-methylpyrrolidin-3-yl]propan-2-ol Intermediate 33 (0.992 g, 2.52 mmol) was dissolved in THF (7.5 mL) and the solution was cooled to 0° C. Methylmagnesium iodide (3.0 M in ether, 2.52 mL, 7.6 mmol) was added and the reaction mixture was stirred at 0° C. for 1.5 hours. Saturated NH₄Cl was added and the reaction mixture was concentrated in vacuo. The residue was diluted with EtOAc and the organic layer was washed three times with saturated NaHCO₃, saturated NaCl, then dried over Na₂SO₄ and concentrated in vacuo (0.96 g, 93%).

¹H NMR (CDCl₃, 400 MHz) δ: 7.33–7.24 (m, 5H), 6.83–6.77 (m, 3H), 3.86–3.74 (m, 7H), 3.68–3.59 (dd, 2H), 3.32 (dd, 1H), 3.24 (d, 1H), 2.48 (dd, 1H), 2.16 (d, 1H), 1.35–1.28 (m, 1H), 1.21–1.18 (m, 5H), 0.66–0.60 (m, 2H), 0.56 (s, 3H), 0.38–0.33 (m, 2H). LRMS (Electrospray, positive): Da/e 410.5 (m+1).

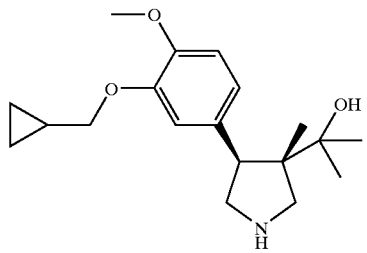

Intermediate 31

2-[4-(S)-(3-Cyclopropylmethoxy-4-methoxyphenyl)-3-(S)-methylpyrrolidin-3-yl]propan-2-ol Intermediate 30 (0.96 g, 2.3 mmol) was dissolved in methanol (10 mL) and the solution was treated with Pearlman's catalyst (20% Pd(OH)₂ on carbon, 200 mg) and ammonium formate (1.0 g, 15.8 mmol). The solution was heated to reflux for 6 hours. The catalyst was removed by filtration and the solution was concentrated in vacuo. The residue was dissolved in EtOAc and washed three times with water, saturated NaCl, dried over Na₂SO₄ and concentrated in vacuo, (384 mg, 52%).

¹H NMR (CDCl₃, 400 MHz) δ: (6.83–6.79(m, 3H), 3.86–3.80 (m, 5H), 3.75–3.66 (m, 2H), 3.57–3.51 (m, 2H), 3.22–3.17 (m, 1H), 2.78–2.67 (m, 1H), 1.34–1.21 (m, 7H), 0.69 (s, 3H), 0.66–0.60 (m, 2H), 0.37–0.33 (m, 2H). LRMS (Electrospray, positive): Da/e 320.3(m+1).

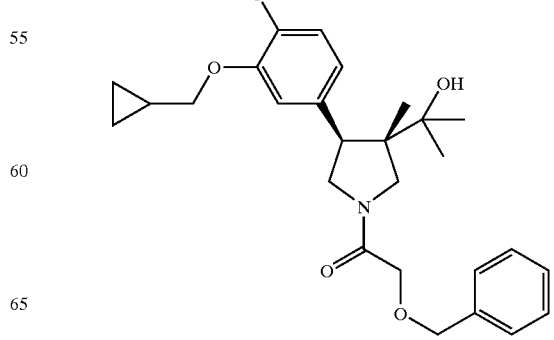

Intermediate 32

2-Benzyloxy-1-[4-(S)-(3-cyclopropylmethoxy-4-methoxyphenyl)-3-(1-hydroxy-1-methylethyl)-3-(S)-methylpyrrolidin-1-yl]ethanone Intermediate 31 (75 mg, 0.23 mmol) was dissolved in CH$_2$Cl$_2$ (1 mL) and the solution was treated with N,N-diisopropylethylamine (DIEA) (61 μL, 0.35 mmol), then cooled to 0° C. Benzyloxyacetyl chloride (55.6 μL, 0.23 mmol) was added, and the solution was stirred at 0° C. for 3 hours. The reaction mixture was diluted with CH$_2$Cl$_2$ and washed three times with 1N HCl, once with water, three times with 6% NaHCO$_3$, then dried with Na$_2$SO$_4$ and concentrated in vacuo. The crude product (103 mg) was chromatographed with EtOAc/hexane (1:1) to provide Intermediate 32 (21 mg, 19%).

$^1$H NMR (CDCl$_3$, 400 MHz) δ: 7.41–7.27 (m, 5H), 6.85–6.76 (m, 3H), 4.66–4.61 (m, 2H), 4.13–4.07 (m, 2H), 3.94–3.59 (m, 7H), 3.53–3.47 (m, 1H), 3.28–3.22 (m, 1H), 1.34–1.24 (m, 2H), 1.24–1.19 (m, 2H), 1.14–1.11 (m, 2H), 1.07–0.98 (m, 6H), 0.66–0.59 (m, 2H), 0.36–0.31 (m, 2H). LRMS (Electrospray, positive): Da/e 468.3 (m+1).

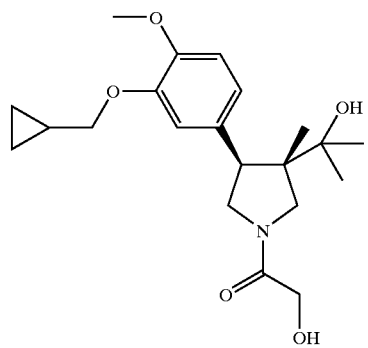

EXAMPLE 2

1-[4-(S)-(3-Cyclopropylmethoxy-4-methoxyphenyl)-3-(1-hydroxy-1-methylethyl)-3-(S)-methylpyrrolidin-1-yl]-2-hydroxyethanone Intermediate 32 (21 mg, 45 μmol) was dissolved in ethanol (95%, 2 mL) and treated with Pearlman's catalyst (20% Pd(OH)$_2$ on carbon, 20 mg). The solution was subjected to 1 atmosphere of H$_2$ for 20 hours. The catalyst was removed by filtration and concentrated in vacuo, to afford Example 2 (15 mg, 88%).

$^1$H NMR (CDCl$_3$, 400 MHz) δ: 6.87–6.80 (m, 3H), 4.20–4.09 (m, 2H), 3.89–3.62 (m, 9H), 3.58–3.51 (m, 1H), 3.13–2.87 (m, 2H), 1.35–1.01 (m, 10H), 0.67–0.61 (m, 2H), 0.39–0.33 (2H). LRMS (Electrospray, positive): Da/e 378.4 (m+1).

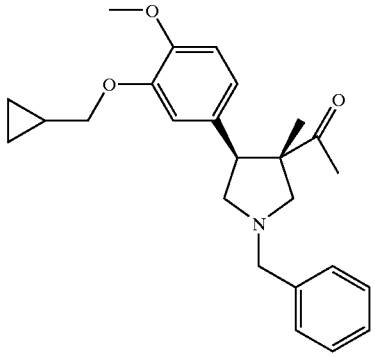

Intermediate 33

1-[1-Benzyl-4-(S)-(3-cyclopropylmethoxy-4-methoxyphenyl)-3-(S)-methylpyrrolidin-3-yl]ethanone Oxalyl chloride (2.0M in CH$_2$Cl$_2$, 1.35 mL, 2.7 mmol) was added to CH$_2$Cl$_2$ (4 mL) and the solution was cooled to −60° C. A solution of DMSO (0.36 mL, 5.0 mmol) in CH$_2$Cl$_2$ (1.5 mL) was added slowly. This solution was stirred for 5 minutes, then Intermediate 66 (1.06 g, 2.7 mmol) dissolved in CH$_2$Cl$_2$ (7.5 mL) was added to the solution. The reaction was stirred for 30 minutes at −60° C., then quenched with Et$_3$N (1.9 mL). The mixture was allowed to warm to room temperature, diluted with water, and after stirring vigorously for several minutes, the layers were separated. The organic layer was washed three times with 1 N HCl, three times with 6% NaHCO$_3$ then dried over Na$_2$SO$_4$, and concentrated in vacuo. Intermediate 33 was recovered and used without purification, (0.992 g, 93%)

LRMS (Electrospray, positive): Da/e 392.4 (m+1).

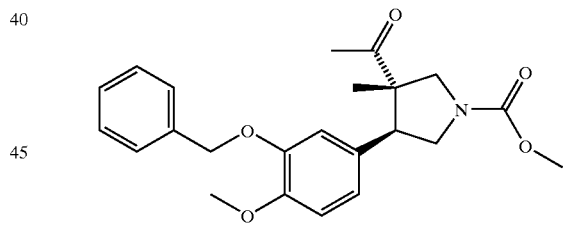

Intermediate 34 trans-(±)-[3-Acetyl-4-(3-benzyloxy-4-methoxyphenyl)-3-methyl]pyrrolidine-1-carboxylic acid methyl ester A solution of Intermediate 23 (17.4 g, 40.5 mmol, 1 eq) in acetonitrile (150 mL) was treated with methyl chloroformate (15.6 mL, 202.5 mmol, 5 eq), then stirred at reflux 1 hour. The reaction mixture was concentrated, and the residue was purified by flash chromatography (silica gel, 7.5×36 cm Biotage KP-Sil column, eluted with 50–60% EtOAc in heptane) to afford Intermediate 34 as a colorless syrup (13.7 g, 85%).

$^1$H NMR (300 MHz, CDCl$_3$) δ: 7.42–7.27 (m, 5H), 6.82 (d, J=8.8 Hz, 1H), 6.69 (br d, J=8.3 Hz, 1H), 6.63 (d, J=1.8 Hz, 1H), 5.15 (s, 2H), 3.88 (s, 3H), 3.84 (dd, J=16.3, 11.0 Hz, 1H), 3.73 (br s, 3H), 3.24/3.12 (2 d, J=11.31/11.0 Hz, 1H), 2.09/2.01 (2 s, 3H), 0.84 (s, 3H). $^{13}$C NMR (75 MHz,

CDCl$_3$) δ: 210.0/209.8, 155.2, 149.0, 147.5, 137.0, 130.5/ 130.0, 128.5, 127.8, 127.2/127.1, 121.2/121.0, 114.9/114.8, 111.5, 70.9, 58.1/57.2, 55.9, 54.4/54.0, 52.5, 50.2/50.0, 48.4/48.0, 26.3, 17.5.

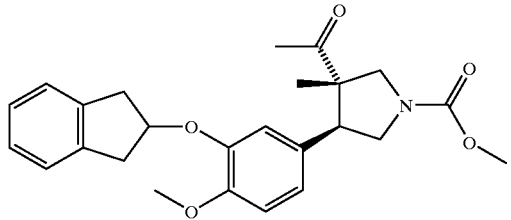

Intermediate 35 trans-(±)-3-Acetyl-4-[3-(indan-2-yloxy)-4-methoxyphenyl]-3-methylpyrrolidine-1-carboxylic acid methyl ester Prepared from Intermediate 24 by the methyl chloroformate procedure of Intermediate 34.

$^1$H NMR (300 MHz, CDCl$_3$) δ: 7.24–7.16 (m, 4H), 6.82 (d, J=8.8 Hz, 1H), 6.75–6.72 (m, 2H), 5.18–5.10 (m, 1H), 3.91 (t, J=11.2 Hz, 1H), 3.80 (s, 3H), 3.77–3.65 (m, 3H), 3.74 (s, 3H), 3.42–3.16 (m, 5H), 2.17 (d, J=6.8 Hz, 3H), 1.04 (s, 3H). $^{13}$C NMR (75 MHz, CDCl$_3$) δ: 210.1/209.9, 155.3, 149.4, 146.9/146.8, 140.5/140.4, 130.5/130.0, 126.7, 124.7, 121.3/121.1, 116.1/115.8, 111.9, 79.2, 58.2/57.4, 55.9, 54.7/54.2, 52.6, 50.2/50.0, 48.5/48.1, 39.7, 26.6/26.5, 17.8.

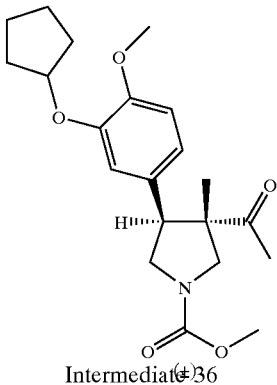

Intermediate 36 trans-(±)-3-Acetyl-4-(3-cyclopentyloxy-4-methoxyphenyl)-3-methylpyrrolidine-1-carboxylic acid methyl ester Prepared according to procedure set forth in U.S. Pat. No. 5,665,754. Racemic form of Intermediate 46.

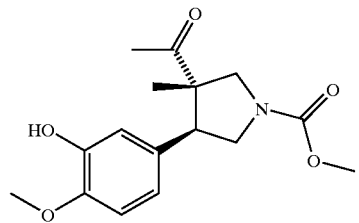

Intermediate 37 trans-(±)-[3-Acetyl-4-(3-hydroxy-4-methoxyphenyl)-3-methyl]pyrrolidine-1-carboxylic acid methyl ester A solution of Intermediate 34 (8.7 g, 21.9 mmol) in ethanol (50 mL) was shaken for 16 hours under H$_2$ (50 psi) in the presence of palladium on carbon catalyst (0.5 g, 10% Pd/C). The catalyst was filtered off through a pad of diatomaceous earth followed by a 0.22 um membrane filter. The filtrate was concentrated in vacuo to give Intermediate 37 as a clear syrup (6.5 g, 97%).

$^1$H NMR (300 MHz, CDCl$_3$) δ: 6.79 (d, J=8.3 Hz, 1H), 6.74 (d, J=1.8 Hz, 1H), 6.63 (br d, J=8.3 Hz, 1H), 6.04 (br s, 1H), 3.96–3.85 (m, 1H), 3.87 (s, 3H), 3.75/3.73 (2 s, 3H), 3.74–3.59 (m, 3H), 3.36/3.26 (2 d, J=11.2/11.0 Hz, 1H), 2.17/2.15 (2 s, 3H), 1.01 (s, 3H). $^{13}$C NMR (75 MHz, CDCl$_3$) δ: 210.0/209.8, 155.3, 145.9/145.8, 145.5, 131.2/130.8, 119.9, 114.5, 110.6, 58.1/57.2, 55.8, 54.4/53.9, 52.5, 50.3/50.1, 48.4/48.0, 26.3, 17.6.

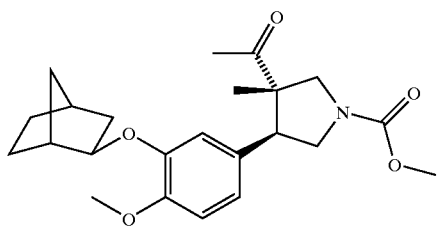

Intermediate 38 trans-3-Acetyl-4-[exo-3-(bicyclo[2.2.1]hept-2-yloxy)-4-methoxyphenyl]-3-methylpyrrolidine-1-carboxylic acid methyl ester Prepared by the Mitsunobu procedure of Intermediate 2 from Intermediate 37 and endo-norborneol (36% yield).

$^1$H NMR (300 MHz, CDCl$_3$) δ: 6.80 (d, J=8.2 Hz, 1H), 6.66 (d, J=9.0 Hz, 1H), 6.62 (s, 1H), 4.15–4.08 (m, 1H), 3.95–3.86 (m, 1H), 3.83 (s, 3H), 3.74 (s, 3H), 3.73–3.60 (m, 3H), 3.37/3.28 (2 d, J=11.2/10.8 Hz, 1H), 2.47 (br s, 1H), 2.32 (br s, 1H), 2.17/2.15 (2 s, 3H), 1.76–1.66 (m, 2H), 1.63–1.45 (m, 3H), 1.28–1.08 (m, 3H), 1.02/1.01 (2 s, 3H). $^{13}$C NMR (75 MHz, CDCl$_3$) δ: 210.5/210.3, 155.7, 149.6, 147.4, 130.8/130.76, 130.3, 120.9/120.7/120.5, 115.6/115.4/115.3/115.2, 112.2, 81.5, 58.6/57.8, 56.4, 54.9/54.6, 52.9, 50.6/50.5, 49.1/49.0/48.7, 41.5, 40.4, 35.8/35.7, 28.8, 26.9/26.8, 24.7/24.6, 18.2.

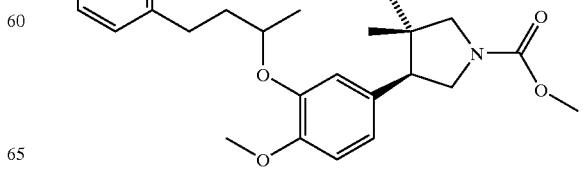

Intermediate 39 trans-[3-Acetyl-4-[4-methoxy-3-(1-methyl-3-phenyl-propoxy)phenyl]-3-methylpyrrolidine-1-carboxylic acid methyl ester Prepared by the Mitsunobu procedure of Intermediate 2 from Intermediate 37 and 4-phenyl-2-butanol.

$^1$H NMR (300 MHz, CDCl$_3$) δ: 7.29–7.15 (m, 5H), 6.82 (d, J=8.3 Hz), 6.72–6.63 (m, 2H), 4.33–4.25 (m, 1H), 3.94–3.59 (m, 4H), 3.84 (s, 3H), 3.74 (br s, 3H), 3.36/3.27 (2 dd, J=11.2, 3.0/10.9, 3.9 Hz, 1H), 2.88–2.69 (m, 2H), 2.18–2.06 (m, 4H), 1.95–1.82 (m, 1H), 1.33/1.31 (2 d, J=2.3/2.3 Hx, 3H), 1.01/0.99 (2 s, 3H). $^{13}$C NMR (75 MHz, CDCl$_3$) δ: 209.9, 155.4, 149.8, 147.1, 141.9, 130.4/129.9, 128.5, 128.4, 125.8, 121.2, 116.9, 111.9, 74.8, 58.1/57.3, 55.9, 54.6/54.3, 52.6, 50.2/50.1, 48.6/48.2, 38.1, 31.8, 26.6, 19.9, 17.7.

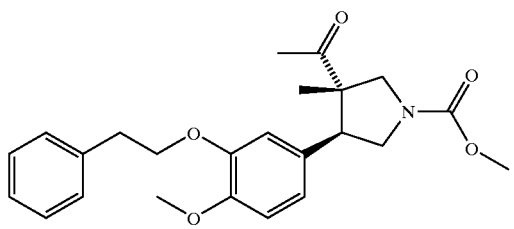

Intermediate 40 trans-(±)-3-Acetyl-4-(4-methoxy-3-phenethyloxyphenyl)-3-methylpyrrolidine-1-carboxylic acid methyl ester Prepared by the Mitsunobu procedure of Intermediate 2 from Intermediate 37 and 2-phenylethanol.

$^1$H NMR (300 MHz, CDCl$_3$) δ: 7.36–7.23 (m, 5H), 6.82 (d, J=8.2 Hz, 1H), 6.70 (d, J=8.4 Hz, 1H), 6.66 (s, 1H), 4.18 (t, J=7.5 Hz, 2H), 3.92–3.81 (m, 1H), 3.86 (s, 3H), 3.76–3.61 (m, 3H), 3.73 (s, 3H), 3.40/3.27 (2 d, J=11.2/10.9 Hz, 1H), 3.15 (t, J=7.5 Hz, 2H) 2.16/2.12 (2 s, 3H), 1.00 (s, 3H).

Intermediate 41 trans-3-Acetyl-4-[4-methoxy-3-(tetrahydrofuran-3-yloxy)phenyl]-3-methylpyrrolidine-1-carboxylic acid methyl ester Prepared by the Mitsunobu procedure of Intermediate 2 from Intermediate 37 and 3-hydroxytetrahydrofuran.

$^1$H NMR (300 MHz, CDCl$_3$) δ: 6.85–6.63 (m, 3H), 4.92–4.88 (m, 1H), 4.07–3.62 (m, 8H), 3.84 (s, 3H), 3.75 (s, 3H), 3.39/3.29 (2 d, J=11.2/10.2 Hz, 1H), 2.19–2.14 (m, 5H), 1.02 (br s, 3H). $^{13}$C NMR (75 MHz, CDCl$_3$) δ: 210.0/209.9, 155.4, 149.5, 146.5, 130.0, 121.6/121.5, 116.5/116.4/116.3, 112.0, 111.0, 78.9, 73.0, 67.2, 58.1/57.3, 55.9, 54.7/54.3, 52.6, 50.1/50.0, 48.4/48.0, 33.0, 26.6, 17.8.

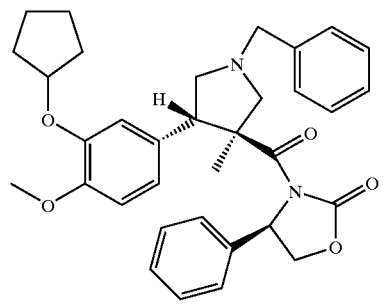

Intermediate 42

(4R)-3-{[(3S,4S)-4-(3-Cyclopentyloxy-4-methoxyphenyl)-3-methyl-1-benzylpyrrolidin-3-yl]carbonyl}-4-phenyl-1,3-oxazolidin-2-one To a cooled (−4° C.), stirred slurry of acyl oxazolidinone (9.30 g, 22.8 mmol) and N-(methoxymethyl)-N-(trimethylsilylmethyl)benzylamine (11.7 mL, 45.6 mmol, 2 eq.) in CHCl$_3$ (65 mL) was added a solution of TFA in CHCl$_3$ (4.6 mL of 1.0 M, 4.6 mmol, 0.2 eq.) via syringe under a nitrogen atmosphere. The resulting slurry was stirred at about 0° C. for 4 hours, then at about 15° C. overnight (water bath). The resulting cloudy solution then was recooled to −4° C., treated with an additional portion of N-(methoxymethyl)-N-(trimethylsilylmethyl)benzylamine (5.9 mL, 22.8 mmol, 1 eq.) via syringe, and allowed to stir for 5 hours more during which time the reaction became homogenous. TLC (5% Et$_2$O in CH$_2$Cl$_2$) showed the reaction was complete. The bulk of the CHCl$_3$ was removed at reduced pressure, and the residue was diluted with EtOAc (250 mL) and washed successively with 1 N aqueous HCl (2×50 mL), 1 N aqueous NaOH (50 mL) and brine (50 mL). The organic layer then was dried (MgSO$_4$), filtered and concentrated in vacuo to give an orange semi-solid (13.9 g). Purification via flash chromatography on silica gel (2% ether in CH$_2$Cl$_2$) provided the major diastereomer as a white foam (8.25 g, 65%).

Diastereomeric selectivity about 10:1 (HPLC).

$^1$H NMR (400 MHz, CDCl$_3$) δ: 7.42–7.21 (c, 10H), 6.95 (s, 1H), 6.81 (s, 2H), 5.55 (dd, 1H), 4.74 (t, 1H), 4.68 (m, 1H), 4.10 (dd, 1H), 3.93 (t, 1H), 3.70 (d, 1H), 3.68 (s, 3H), 3.56 (d, 1H), 3.42 (d, 1H), 2.72 (m, 2H), 2.64 (d, 1H), 2.48 (m, 1H), 1.85–1.78 (c, 2H), 1.75–1.61 (c, 4H), 1.57–1.53 (c, 2H), 0.96 (s, 3H). LRMS (Electrospray, positive): Da/e 555.2 (m+1).

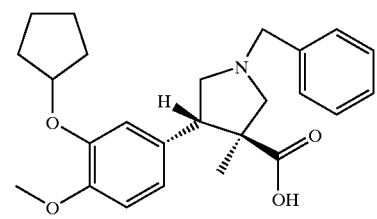

Intermediate 43

(3S,4S)-1-Benzyl-4-(3-cyclopentyloxy-4-methoxyphenyl)-3-methylpyrrolidine-3-carboxylic acid A suspension of lithium peroxide (0.5 g, 10.8 mmol) in water-THF (1:1, 6 mL) was added to a solution of Intermediate 42 (3.0 g, 5.4 mmol) in water-THF (3:1, 30 mL) at 0° C. under a nitrogen blanket. The suspension solubilized immediately. After 1 hour of stirring at 0° C., an aqueous sodium sulfite ($Na_2SO_3$) solution (1.5 N, 12 mL) was added to quench excess peroxide, and THF was removed under reduced pressure. The basic residue was extracted with three 30 mL portions of $CH_2Cl_2$. The aqueous phase was acidified to pH 1 with aqueous 1.0 N HCl solution, and extracted with three 30 mL portions of $Et_2O$. The ether extracts were dried ($Na_2SO_4$), concentrated under reduced pressure and used without further purification.

$^1$H NMR (300 MHz, $CDCl_3$) δ: 10.73 (br. s, 1H, COOH), 7.69 (br. s, 2H, aromatic), 7.38–7.36 (m, 3H, aromatic), 6.78 (s, 1H, aromatic), 6.69 (m, 2H, aromatic), 4.71 (br. s, 1H), 4.51–4.48 (m, 2H), 4.24–4.11 (br. s, 2H), 4.08–3.88 (br. s, 1H), 3.76 (s, 3H, $OCH_3$), 3.54 (br. s, 1H), 3.1 (br. s, 1H), 1.83–1.52 (m, 8H, cyclopentyl), 1.05 (br. s, 3H, $CH_3$).

Intermediate 44

(3S,4S)-1-Benzyl-4-(3-cyclopentyloxy-4-methoxyphenyl)-3-methylpyrrolidine-3-carboxylic acid methoxy methyl amide Intermediate 44 was prepared from Intermediate 43 (2.1 g, 4.98 mmol), 1,1'-carbonyldiimidazole (0.89 g, 5.47 mmol), and N,O-dimethylhydroxylamine hydrochloride (0.73 g, 7.47 mmol) to provide Intermediate 44 (0.9 g, 40%) as a white crystalline powder.

$^1$H NMR (300 MHz, $CDCl_3$) δ: 7.4–7.3 (m, 5H, aromatic), 7.06 (d, 1H, J=1.7 Hz, aromatic), 6.89 (dd, 1H, J=8.3 Hz, aromatic), 6.73 (d, 1H, J=8.3 Hz, aromatic), 4.77–4.75 (m, 1H), 4.16–4.06(m, 1H), 3.81 (s, 3H, $OCH_3$), 3.81–3.71 (m, 2H), 3.60 (s, 3H, $OCH_3$) 3.21 (s, 3H, $NCH_3$), 2.96 (d, 1H, J=9.6 Hz,), 2.91 (m, 1H), 2.78 (d, 1H, J=9.6 Hz,), 2.77 (m, 1H), 2.04 (s, 3H, $CH_3$), 1.92–1.59 (m, 8H, cyclopentyl), 0.94 (s, 3H, $CH_3$).

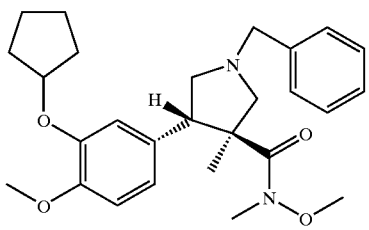

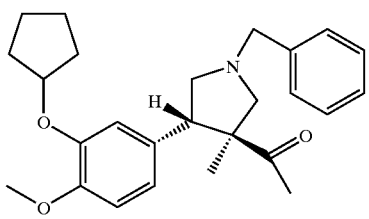

Intermediate 45

1-[(3S,4S)-1-Benzyl-4-(3-cyclopentyloxy-4-methoxyphenyl)-3-methylpyrrolidin-3-yl]ethanone A solution of Intermediate 44 (0.17 g, 0.43 mmol) in THF (8 mL) was cooled to −78° C. and treated with methyllithium (1.5 M in THF, 0.315 mL, 0.47 mmol) under a nitrogen blanket. The solution was stirred for 40 minutes at −78° C., then quenched with a cold saturated aqueous $NH_4Cl$ solution (8 mL). A mixture of hexanes/$CH_2Cl_2$ (3:1, 8 mL) was added with vigorous stirring. After a further dilution with more hexanes/$CH_2Cl_2$ (3:1, 10 mL), brine (10 mL) was added and the two layers separated. The aqueous layer was washed with $CH_2Cl_2$ (8 mL) and the combined organic extracts washed with brine, dried ($Na_2SO_4$), filtered, and concentrated under reduced pressure into an oil product (154 mg, 89%).

$^1$H NMR (300 MHz, $CDCl_3$) δ: 7.39–7.24 (m, 5H, aromatic), 6.82–6.70 (m, 3H, aromatic), 4.74 (br. s, 1H), 3.81 (s, 3H, $OCH_3$), 3.78–3.58 (m, 3H), 3.14 (d, 1H, J=9.7 Hz ), 3.05 (m, 1H), 2.84 (m, 1H), 2.40 (d, 1H, J=9.7 Hz,), 2.23 (s, 3H, $CH_3$), 1.92–1.59 (m, 8H, cyclopentyl), 0.83 (s, 3H, $CH_3$).

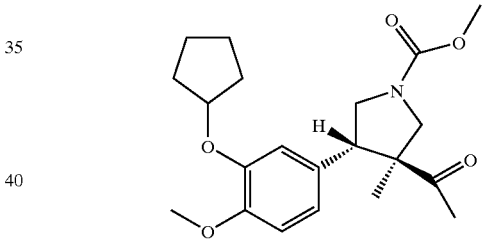

Intermediate 46

(3S,4S)-3-Acetyl-4-(3-cyclopentyloxy-4-methoxyphenyl)-3-methylpyrrolidine-1-carboxylic acid methyl ester To a stirred solution of Intermediate 45 (0.154 g, 0.38 mmol) in anhydrous acetonitrile (10 mL) was added methyl chloroformate (0.146 mL, 1.89 mmol). The solution was heated to 80° C. and refluxed for 3 hours. The solution then was cooled to room temperature, and concentrated under reduced pressure. Purification by reversed-phase HPLC provided Intermediate 46 as an oil (93 mg, 65%). Specific rotation: $[\alpha]_{259}^{23}$=+2.5 (c=1.0, EtOH).

$^1$H NMR (300 MHz, $CDCl_3$) δ: 6.8 (d, 1H, J=8.0 Hz, aromatic), 6.66. (d, 1H, J=8.0 Hz, aromatic), 6.66 (s, 1H, aromatic), 4.73(s, 1H), 3.95–3.64(m, 4H), 3.83 (s, 3H, $OCH_3$), 3.74 (s, 3H, $OCH_3$), 3.37 and 3.27(s, 3H, $CH_3$), 2.17 and 2.14 (s, 3H, $CH_3$), 1.92–1.59 (m, 8H, cyclopentyl), 1.03 and 1.02 (s, 3H, $CH_3$).

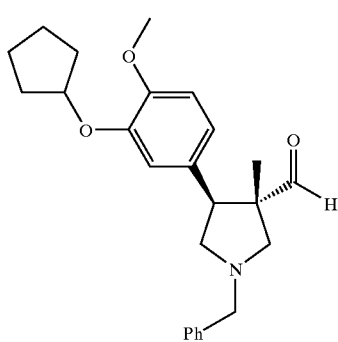

Intermediate 47

(3S,4S)-4-(3-Cyclopentyloxy-4-methoxyphenyl)-3-methyl-1-benzylpyrrolidine-3-carbaldehyde General Oxazolidinone Reduction/Oxidation Procedure To a cooled (−78° C.), stirred solution of Intermediate 42 (15.09 g, 27.2 mmol) in toluene (250 mL) was added a solution of lithium aluminum hydride in tetrahydrofuran (16.3 mL of 1.0 M, 16.3 mmol, 0.6 eq.) via syringe under a nitrogen atmosphere. Vigorous bubbling was observed. The resulting solution was allowed to stir at −78° C. for 2 hours, after which time the cooling bath was removed. The reaction was quenched with the successive addition of water (0.62 mL), 15% aqueous NaOH (0.62 mL), and water (1.9 mL). The resulting mixture was allowed to warm to room temperature, stirred for 30 minutes, then diluted with $Et_2O$ (500 mL) and dried ($MgSO_4$) Filtration and concentration in vacuo provided the alcohol (with some aldehyde present) as a semi-solid (14.8 g). This material was used immediately without further purification.

To a cooled (−78° C.), stirred solution of oxalyl chloride in $CH_2Cl_2$ (10.9 mL of 2.0 M, 21.8 mmol, 0.8 eq.) in more $CH_2Cl_2$ (75 mL) was added DMSO (3.1 mL, 43.5 mmol, 1.6 eq.) via syringe under nitrogen atmosphere. After stirring at −78° C. for 20 minutes, a solution of the crude alcohol in $CH_2Cl_2$ (75 mL) was added by cannula. The resulting yellow solution was allowed to stir at −78° C. for 20 minutes, then $Et_3N$ (15.2 mL, 109 mmol, 4 eq.) was added by syringe. The reaction was allowed to stir at −78° C. for 20 minutes, then warmed to room temperature and stirred for an additional 1 hour. The reaction was quenched with the addition of brine (150 mL), then extracted with $CH_2Cl_2$ (2×100 mL). Combined organic layers were dried ($MgSO_4$), filtered and concentrated in vacuo to provide the crude aldehyde. Purification by flash silica gel chromatography (25% EtOAc in hexanes) provided the aldehyde as a clear, colorless oil (9.8 g, 92%).

$^1$H NMR (400 MHz, $CDCl_3$) δ: 9.64 (s, 1H), 7.37–7.26 (c, 5H), 6.78–6.76 (c, 2H), 6.70 (m, 1H), 4.74 (m, 1H), 3.82 (s, 3H), 3.70 (m, 1H), 3.64–3.62 (c, 2H), 3.18–3.13 (c, 2H), 2.84 (t, 1H), 2.41 (d, 1H), 1.94–1.83 (c, 6H), 1.63–1.59 (c, 2H), 0.74 (s, 3H) LRMS (Electrospray, positive): Da/e 394.3 (m+1).

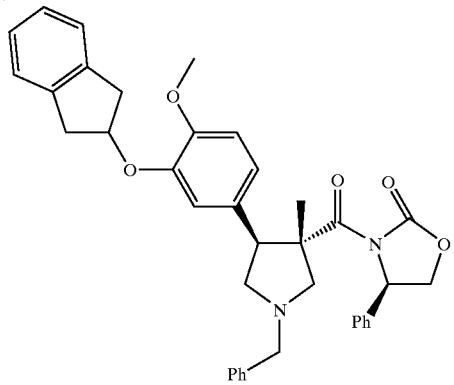

Intermediate 48

(4R)-3-{[(3S,4S)-4-(3-Indan-2-yloxy-4-methoxyphenyl)-3-methyl-1-benzylpyrrolidin-3-yl]carbonyl}-4-phenyl-1,3-oxazolidin-2-one Prepared via the azomethine cycloaddition procedure of Intermediate 23 from Intermediate 17.

$^1$H NMR (400 MHz, $CDCl_3$) δ: 7.45–7.12 (m, 15H), 6.95 (d, 1H), 6.78 (d, 1H), 5.54 (dd, 1H), 5.17 (c, 1H), 4.69 (t, 1H), 4.22 (dd, 1H), 4.11 (t, 1H), 3.84–3.60 (m, 5H), 3.51 (d, 1H), 3.37 (dt, 2H), 3.21 (dd, 2H), 2.90 (d, 1H), 2.85 (dd, 1H), 2.76 (dd, 1H), 1.12 (s, 3H).

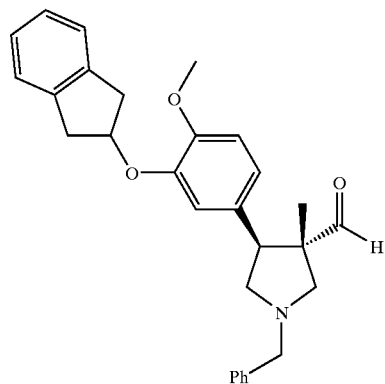

Intermediate 49

(3S,4S)-4-(3-Indan-2-yloxy-4-methoxyphenyl)-3-methyl-1-benzylpyrrolidine-3-carbaldehyde Prepared from Intermediate 48 via the reduction/oxidation procedure of Intermediate 47.

$^1$H NMR (400 MHz, $CDCl_3$) δ: 9.65 (s, 1H), 7.36–7.17 (m, 9H), 6.84 (d, 1H), 6.79 (d, 1H), 6.76 (dd, 1H), 5.16 (c, 1H), 3.79 (s, 3H), 3.76 (d, 1H), 3.68–3.63 (c, 1H), 3.40–3.31 (m, 2H), 3.24–3.13 (m, 2H), 2.85 (dd, 1H), 2.43 (d, 1H) 0.77 (s, 3H).

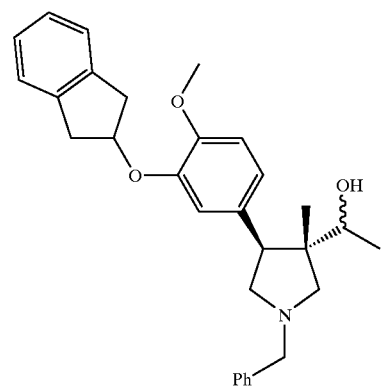

Intermediate 50

(1R)-1-[(3S,4S)-4-(3-Indan-2-yloxy-4-methoxyphenyl)-3-methyl-1-benzylpyrrolidin-3-yl]ethan-1-ol Desired, more polar diastereomer. Prepared via the Grignard addition procedure of Intermediate 56 from Intermediate 49.

$^1$H NMR (400 MHz, CDCl$_3$) δ: 7.39–7.17 (m, 9H), 6.84–6.77 (m, 3H), 5.17 (c, 1H), 3.80 (s, 3H), 3.72–3.57 (m, 4H), 3.38–3.19 (m, 5H), 3.11 (d, 1H), 2.57 (t, 1H), 2.12 (d, 1H), 1.15 (d, 3H), 0.51 (s, 3H).

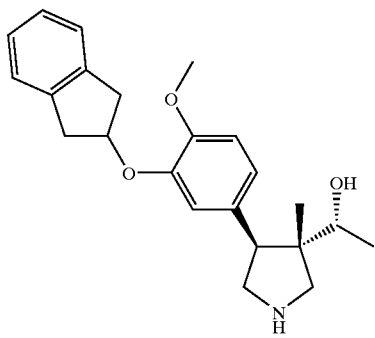

Intermediate 51

(1R)-1-[(3S,4S)-4-(3-Indan-2-yloxy-4-methoxyphenyl)-3-methylpyrrolidin-3-yl]ethan-1-ol Prepared via the debenzylation procedure of Intermediate 31 from Intermediate 50.

$^1$H NMR (400 MHz, CDCl$_3$) δ: 7.26–7.16 (m, 4H), 6.81 (s, 3H), 5.19 (c, 1H), 3.80 (s, 3H), 3.74–3.68 (m, 2H), 3.44–3.17 (m, 8H), 2.66 (d, 1H), 2.51 (br s, 1H), 1.18 (d, 3H), 0.63 (s, 3H).

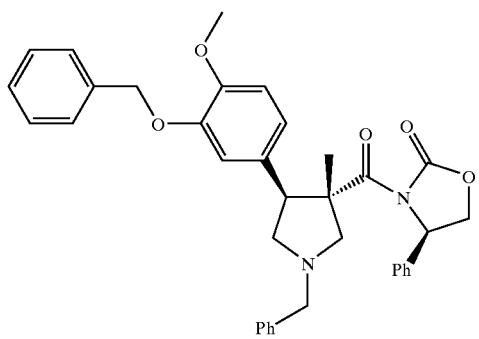

Intermediate 52

(4R)-3-({(3S,4S)-4-[4-Methoxy-3-(phenylmethoxy)phenyl]-3-methyl-1-benzylpyrrolidin-3-yl}carbonyl)-4-phenyl-1,3-oxazolidin-2-one (Major Diastereomer)

Prepared via the cycloaddition procedure of Intermediate 23 from Intermediate 21.

$^1$H NMR (400 MHz, CDCl$_3$) δ: 7.49–7.23 (m, 15H), 7.09 (d, 1H), 6.94 (dd, 1H), 6.80 (d, 1H), 5.49 (dd, 1H), 5.17 (s, 2H), 4.66 (t, 1H), 4.19 (dd, 1H), 4.09 (t, 1H), 3.87 (s, 3H), 3.68 (q, 2H), 3.51 (d, 1H), 2.85–2.79 (m, 2H), 2.69 (dd, 1H), 0.99 (s, 3H).

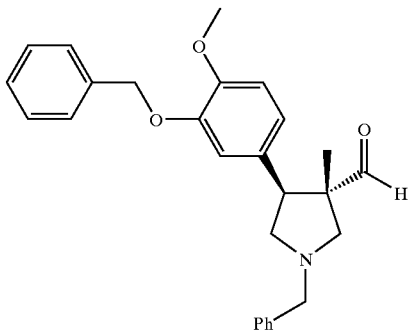

Intermediate 53

(3S,4S)-4-(4-Methoxy-3-(phenylmethoxy)phenyl)-3-methyl-1-benzylpyrrolidine-3-carbaldehyde Prepared via the reduction/oxidation procedure of Intermediate 47 from Intermediate 52.

$^1$H NMR (400 MHz, CDCl$_3$) δ: 9.56 (s, 1H), 7.43–7.22 (m, 10H), 6.79 (d, 1H), 6.77 (d, 1H), 6.71 (dd, 1H), 5.14 (dd, 2H), 3.86 (s, 3H), 3.71 (d, 1H), 3.62 (d, 1H), 3.57 (d, 1H), 3.13–3.08 (m, 2H), 2.73 (dd, 1H) 2.30 (d, 1H), 0.58 (s, 3H) LRMS (Electrospray, positive): m/z 416.3 (m+1).

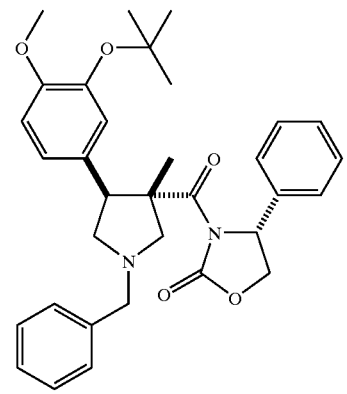

Intermediate 54

3-[1-Benzyl-4-S-(3-tert-butoxy-4-methoxyphenyl)-3-S-methylpyrrolidine-3-carbonyl]-4-R-phenyl-oxazolidin-2-one To a stirred solution of Intermediate 22 (39.8 gm, 97 mmol) in CHCl$_3$ (292 mL) at 0° C. under a nitrogen blanket was added N-(methoxymethyl)-N-(trimethyl-silylmethyl)benzylamine (49.5 mL, 194 mmol) followed by TFA acid (1M in CHCl$_3$, 9.7 mL, 9.7 mmol). The slurry was allowed to warm to room temperature overnight. TLC in 2/3 EtOAc/hexane indicated partial conversion of starting material to a slightly higher R$_f$ product. The resultant solution was treated with more N-(methoxymethyl)-N-(trimethylsilylmethyl)-benzylamine (25 mL, 97 mmol) to consume residual starting material. After 3 hours at room temperature, the reaction appeared complete by TLC. The solution was concentrated by rotory evaporator, then redissolved in EtOAc (500 mL). The organics were washed with 2N HCl (2×500 mL), 1N NaOH (2×500 mL), and saturated NaCl (1×500 mL). The organics were dried (MgSO$_4$), filtered, and concentrated in vacuo to give Intermediate 54 as an approximately 12:1 ratio of diastereomers. Chromatography on a 110 mm×8" column with 1/3 EtOAc/hexane provided, after concentration in vacuo of pooled fractions, Intermediate 54 (40 gm, 76%) as a yellow foam.

$^1$H-NMR (CDCl$_3$, 400 MHz) δ: 7.42–7.20 (m, 10H), 7.11 (s, 1H), 7.05 (d, 1H), 6.76 (d, 1H), 5.53 (dd, 1H), 4.65 (dd, 1H), 4.20 (dd, 1H), 4.08 (dd, 1H), 3.77 (s, 3H), 3.65 (dd, 2H), 3.51 (d, 1H), 2.82 (dd, 1H), 2.81 (d, 1H), 2.71 (dd, 1H), 1.34 (s, 9H), 1.06 (s, 3H).

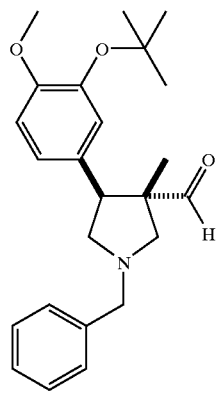

Intermediate 55

(3R)-4-[3-(tert-Butoxy)-4-methoxyphenyl]-3-methyl-1-benzylpyrrolidine-3-carbaldehyde To a stirred solution of Intermediate 54 (21.5 gm, 39.7 mmol) in toluene (400 mL) at −78° C. under a nitrogen blanket was added lithium aluminum hydride (1M in THF, 24 mL, 24 mmol) dropwise by syringe over 10 minutes. After 15 minutes, TLC in 4/1 CH$_2$Cl$_2$/Et$_2$O showed complete consumption of starting material and appearance of a lower R$_f$ material. Methanol (4 mL) in toluene (40 mL) was added carefully by syringe at −78° C. with gas evolution. When gas evolution ceased, the reaction was allowed to warm to room temperature, then treated with water (1 mL), 3N NaOH (2 mL), and water (1 mL) sequentially. After 10 minutes, the reaction was diluted with Et$_2$O (300 mL) and stirred for 15 minutes. Magnesium sulfate was added and the mixture filtered through GF/F. filter paper with Et$_2$O. The crude product was concentrated in vacuo and appeared by $^1$H-NMR to be an approximately 4:1 mixture of desired aldehyde over reduced alcohol. The crude product was dissolved in CH$_2$Cl$_2$ (40 mL). Separately, oxalyl chloride (2M in CH$_2$Cl$_2$, 11.2 mL, 22.4 mmol) was stirred at −60° C. under a nitrogen blanket and treated with DMSO (3.1 mL, 44 mmol) in CH$_2$Cl$_2$ (15 mL) dropwise by syringe. After 5 minutes, the aldehyde/alcohol mixture solution was added to the oxalyl chloride/DMSO solution by cannula. The reaction was stirred at −60° C. for 45 minutes, then treated with Et$_3$N (13.8 mL, 100 mmol) and allowed to warm to room temperature. The solution was diluted to 200 mL with CH$_2$Cl$_2$ and washed with water (1×200 mL), 2N HCl (2×200 mL), saturated NaHCO$_3$ (2×200 mL), and saturated NaCl (1×200 mL). The organic layers were dried (MgSO$_4$), filtered, and concentrated in vacuo to a yellow oil which was dissolved in 3/1 hexane/EtOAc. After dissolution, the cleaved phenyl oxazolidinone precipitated and was removed by filtration. The filtrate was chromatographed on a 70 mm×8" column with 3/1 hexane/EtOAc to provide (after concentration of product containing fractions in vacuo) pure Intermediate 55 as a yellow oil (13.7 gm, 90%)

$^1$H-NMR (400 MHz, CDCl$_3$) δ: 9.62 (s, 1H), 7.37–7.22 (m, 5H), 6.92 (s, 1H), 6.84 (d, 1H), 6.79 (d, 1H), 3.79 (s, 3H), 3.71 (dd, 2H), 3.62 (dd, 1H), 3.17 (dd, 1H), 2.80 (dd, 1H), 2.38 (d, 1H), 1.35 (s, 9H), 0.73 (s, 3H).

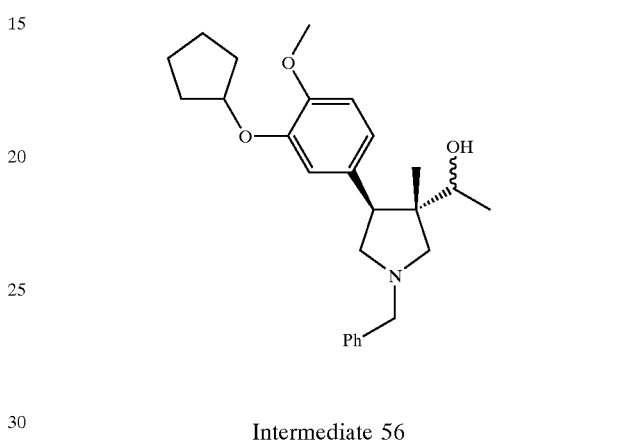

Intermediate 56

(1R)-1-[(3S,4S)-4-(3-Cyclopentyloxy-4-methoxyphenyl)-3-methyl-1-benzylpyrrolidin-3-yl]ethan-1-ol Grignard Addition Procedure To a cooled (0° C.), stirred solution of Intermediate 47 (0.96 mg, 2.45 mmol) in dry Et$_2$O (10 mL) was added a solution of methylmagnesium iodide (or other Grignard reagent) in ether (2.45 mL of 3.0 M, 7.35 mmol, 3 eq.) via syringe under a nitrogen atmosphere. After stirring at 0° C. for 15 minutes, the reaction was allowed to warm to room temperature and stirred for 2 hours. The reaction then was carefully quenched with saturated aqueous NH$_4$Cl (40 mL), and extracted with EtOAc (3×50 mL). Combined organic layers were washed with brine, dried (Na$_2$SO$_4$) filtered, and concentrated in vacuo to give 990 mg of an orange oil. Purification via flash silica gel chromatography (CH$_2$Cl$_2$ to 5% methanol in CH$_2$Cl$_2$) afforded the less polar diastereomer (419 mg, 42%) and the more polar diastereomer (375 mg, 37%) as colorless, viscous oils.

Less Polar Diastereomer:

(1S)-1-[(3S,4S)-4-(3-cyclopentyloxy-4-methoxyphenyl)-3-methyl-1-benzylpyrrolidin-3-yl]ethan-1-ol $^1$H NMR (400 MHz, CDCl$_3$) δ: 7.34–7.28 (c, 5H), 6.79–6.73 (c, 3H), 4.74 (m, 1H), 3.82 (s, 3H), 3.74 (q, 1H), 3.65 (q, 2H), 3.53 (t, 1H), 3.40 (t, 1H), 2.99 (d, 1H), 2.50 (t, 1H), 2.35 (d, 1H), 1.94–1.81 (c, 6H), 1.63–1.59 (c, 2H), 1.10 (d, 3H), 0.52 (s, 3H). LRMS (Electrospray, positive): Da/e 410.3 (m+1).

More Polar Diastereomer:

(1R)-1-[(3S,4S)-4-(3-cyclopentyloxy-4-methoxyphenyl)-3-methyl-1-benzylpyrrolidin-3-yl]ethan-1-ol $^1$H NMR (400 MHz, CDCl$_3$) δ: 7.33–7.31 (c, 5H), 6.79–6.72 (c, 3H), 4.74 (m, 1H), 3.82 (s, 3H), 3.69–3.56 (c, 4H), 3.29 (t, 1H), 3.10 (d, 1H), 2.56 (t, 1H), 2.09 (d, 1H), 2.04 (s, 3H), 1.92–1.81 (c, 6H), 1.62–1.59 (c, 2H), 1.13 (d, 3H), 0.47 (s, 3H). LRMS (Electrospray, positive): Da/e 410.3 (m+1).

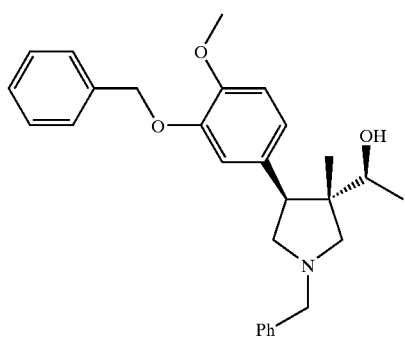

Intermediate 57

(1S)-1-{(3S,4S)-4-[4-Methoxy-3-(phenylmethoxy)phenyl]-3-methyl-1-benzylpyrrolidin-3-yl}ethan-1-ol Less polar diastereomer. Prepared via the Grignard procedure of Intermediate 56 from Intermediate 53.

$^1$H NMR (400 MHz, CDCl$_3$) δ: 7.44–7.22 (m, 10H), 6.80 (d, 1H), 6.75 (dd, 1H), 6.67 (d, 1H), 5.17 (s, 2H), 3.88 (s, 3H), 3.66 (q, 1H), 3.60 (d, 2H), 3.43 (t, 1H), 2.92 (d, 1H), 2.38 (t, 1H), 2.22 (d, 1H), 0.98 (d, 3H), 0.32 (s, 3H) LRMS (Electrospray, positive): m/z 432.5 (m+1).

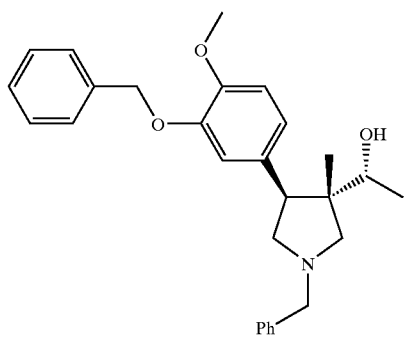

Intermediate 58

(1R)-1-{(3S,4S)-4-[4-Methoxy-3-(phenylmethoxy)phenyl]-3-methyl-1-benzylpyrrolidin-3-yl}ethan-1-ol More polar, desired diastereomer. Prepared via the Grignard procedure of Intermediate 56 from Intermediate 53.

$^1$H NMR (400 MHz, CDCl$_3$) δ: 7.43–7.21 (m, 10H), 6.79 (d, 1H), 6.75–6.70 (m, 2H), 5.16 (dd, 2H), 3.87 (s, 3H), 3.64–3.49 (m, 4H), 3.23 (t, 1H), 3.06 (d, 1H), 2.46 (t, 1H), 1.99 (d, 1H), 1.07 (d, 3H), 0.28 (s, 3H). LRMS (Electrospray, positive): m/z 432.5 (m+1).

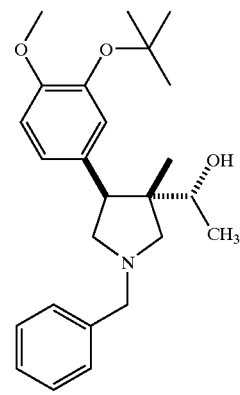

Intermediate 59

1-R-[1-Benzyl-4-S-(3-tert-butoxy-4-methoxyphenyl)-3-S-methylpyrrolidin-3-yl]ethanol To a stirred solution of trimethylaluminum (2M in toluene, 59.4 mL, 119 mmol) at 0° C. under a nitrogen blanket was added methylmagnesium iodide (3M in Et$_2$O, 36 mL, 108 mmol). After 30 minutes at 0° C., the organometallic solution was added via cannulation to a solution of Intermediate 55 (13.7 gm, 36 mmol) in CH$_2$Cl$_2$ (360 mL) at –78° C. under a nitrogen blanket. After complete addition, the reaction was stirred at –78° C. for 6 hours. The reaction then was warmed to 0° C. and carefully poured into ice cold 1M potassium sodium tartrate (1500 mL) with rapid stirring, and diluted with EtOAc (1500 mL). After stirring for 15 minutes, the layers were separated and the organics washed with 1M potassium sodium tartrate (1×1000 mL) and saturated NaCl (1×1000 mL). The organics were dried (MgSO$_4$), filtered, and concentrated in vacuo to provide a 2.5:1 mixture of diastereomers plus approximately 10% residual starting aldehyde by crude $^1$H-NMR. The crude product was chromatographed on a 110 mm×8" column with 3/7/0.4 EtOAc/hexane/MeOH to provide, after pooling and concentration in vacuo of the desired lower R$_f$ diastereomer containing fractions, Intermediate 59 (8.1 gm, 57%) as an orange oil.

$^1$H-NMR (CDCl$_3$, 400 MHz) δ: 7.34–7.23 (m, 5H), 6.86 (m, 3H), 6.79 (d, 1H), 3.79 (s, 3H), 3.65 (dd, 1H), 3.62 (s, 2H), 3.58 (dd, 1H), 3.29 (dd, 1H), 3.10 (d, 1H), 2.53 (dd, 1H), 2.07 (d, 1H), 1.35 (s, 9H), 1.12 (d, 3H), 0.45 (s, 3H).

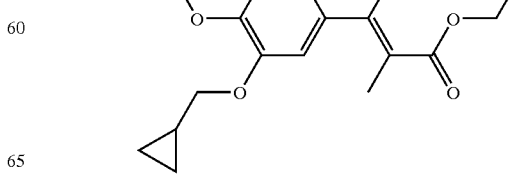

Intermediate 60

3-(3-Cyclopropylmethoxy-4-methoxyphenyl)-2-methyl-E-acrylic acid ethyl ester A round-bottomed flash was charged with THF (850 mL) and triethyl 2-phosphonopropionate (97.2 g, 0.408 mol) and the resulting mixture was cooled to 0° C. Lithium hexamethyldisilazide (1.0 M in THF, 489 mL, 0.489 mol) then was added dropwise. The mixture was stirred for 30 minutes at 0° C., then a solution of Intermediate 1 (70 g, 0.34 mol) in THF (100 mL) was added. After the dropwise addition, the reaction mixture was maintained at 22° C. for 62 hours. The reaction was quenched with saturated NaCl and diluted with EtOAc. After separation, the organic layer was washed with saturated NaCl, dried over $Na_2SO_4$, and concentrated in vacuo. The green oil was purified by chromatography through a pad of SiO2 (650 g) using EtOAc/hexanes (1:10) as eluant, (40.8 g).

$^1$H NMR (400 MHz, $CDCl_3$) δ: 7.67–7.61 (m, 1H), 7.07–7.02 (m, 1H), 6.98–6.95 (m, 1H), 6.92–6.89 (m, 1H), 4.32–4.25 (m, 2H), 3.92 (s, 3H), 3.90–3.85 (m, 2H), 2.15 (s, 3H), 1.38–1.32 (m, 4H), 0.70–0.63 (m, 2H), 0.41–0.37 (m, 2H).

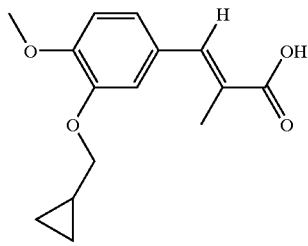

Intermediate 61

3-(3-Cyclopropylmethoxy-4-methoxyphenyl)-2-methyl-E-acrylic acid

Intermediate 60 (26.9 g, 93 mmol) was dissolved in 1,4-dioxane (95 mL) and treated with a solution of LiOH monohydrate (4.6 g, 111 mmol) dissolved in water (95 mL). The resulting solution was heated at 80° C. for 3 hours, then stirred overnight at room temperature. The reaction mixture was poured into water (350 mL) and extracted twice with $Et_2O$ (500 mL total). The aqueous layer was diluted with EtOAc (350 mL) and the pH was adjusted with concentrated $H_3PO_4$ (24 mL) The layers were separated, the EtOAc layer was washed with water and saturated NaCl, dried over $MgSO_4$, and concentrated in vacuo (20.4 9).

$^1$H NMR (400 MHz, $CDCl_3$) δ: 7.77 (s, 1H), 7.11–7.07 (dd, 1H), 7.02–6.98 (d, 1H), 6.93–6.90 (d, 1H), 3.93 (s, 3H), 3.86 (d, 2H), 2.18 (s, 3H), 1.39–1.31 (m, 1H), 0.69–0.63 (m, 2H), 0.39–0.35 (m, 2H).

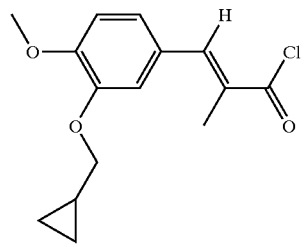

Intermediate 62

3-(3-Cyclopropylmethoxy-4-methoxyphenyl)-2-methyl-E-acryloyl chloride

Intermediate 61 (55.8 g, 0.213 mol) was dissolved in $CH_2Cl_2$ (300 mL) and cooled to 0° C. with a drying tube attached. Oxalyl chloride (2.0 M in $CH_2Cl_2$, 117 mL, 0.234 mol) was added followed by addition of DMF (1.0 mL). The reaction mixture was maintained at 22° C. for several hours. The mixture was diluted with $CH_2Cl_2$ and washed with water, saturated NaCl, then dried over $Na_2SO_4$, and concentrated in vacuo (65.1 g yellow solid).

$^1$H NMR (400 MHz, $CDCl_3$) δ: 7.97 (s, 1H), 7.16–7.11 (dd, 1H), 7.03–7.00 (d, 1H), 6.95–6.91 (dd, 1H), 3.93 (s, 3H), 3.87 (d, 2H), 2.23 (s, 3H), 1.39–1.31 (m, 1H), 0.69–0.64 (m, 2H), 0.40–0.37 (m, 2H).

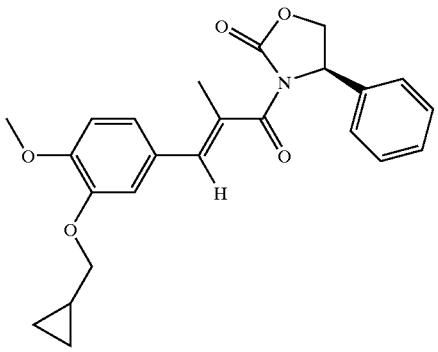

Intermediate 63

3-[3-(3-Cyclopropylmethoxy-4-methoxyphenyl)-2-methyl-E-acryloyl]-4-(R)-phenyloxazolidin-2-one 4-(R)-Phenyloxazolidin-2-one (33.0 g, 0.202 mol) was dissolved in THF (1 L) and cooled to −78° C. n-Butyl lithium (2.5 M in hexanes, 79.5 mL, 0.198 mol) was added, and the resulting reaction mixture was stirred for 20 minutes. A solution of Intermediate 62 (65.1 g, 0.213 mol) in THF (200 mL) was added dropwise over 15 minutes. The reaction mixture was stirred for 1 hour at −78° C., then warmed to 0° C., slowly. The reaction mixture became thick with beige solids. The mixture was neutralized at 0° C. with saturated $NH_4Cl$ (600 mL) and water (300 mL) The solution was warmed to 22° C. quickly and poured into $CHCl_3$ (2400 mL). After shaking and separation, the organic layer was washed with water (1 L), saturated NaCl (1 L), dried over $Na_2SO_4$, and concentrated in vacuo to a pale orange solid (94.4 g).

$^1$H NMR (400 MHz, $CDCl_3$) δ: 7.41–7.32 (m, 5H), 7.07–6.98 (m, 2H), 6.95–6.93 (d, 1H), 6.90–6.86 (d, 1H), 5.55–5.51 (dd, 1H), 4.77–4.71 (dd, 1H), 4.30–4.26 (dd, 1H), 3.91 (s, 3H), 3.85 (d, 2H), 2.17 (s, 3H), 1.38–1.29 (m, 1H), 0.66–0.62 (m, 2H), 0.39–0.34 (m, 2H).

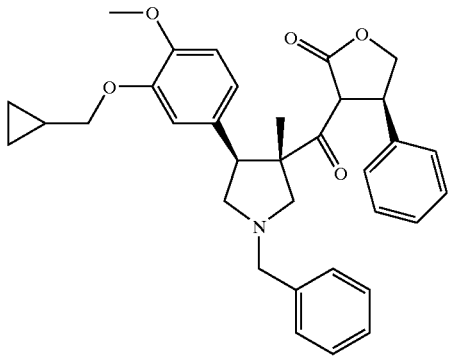

Intermediate 64

3-[1-Benzyl-4-(S)-(3-cyclopropylmethoxy-4-methoxyphenyl)-3-(S)-methylpyrrolidine-3-carbonyl]-4-(R)-phenyloxazolidin-2-one Intermediate 63 (94.4 g, 0.21 mol) was dissolved in CHCl$_3$ (640 mL), then cooled to 0° C. Benzyl methoxymethyltrimethylsilanylmethylamine (95 g, 0.40 mol) was added, and the reaction mixture was treated dropwise with a solution of TFA (3.08 mL) in CHCl$_3$ (40 mL). The reaction was stirred overnight while warming to 22° C. Additional benzyl methoxymethyl-trimethylsilanylmethylamine (71.2 g, 0.3 mol) was added, then the mixture was stirred for an additional 68 hours. The reaction was quenched with saturated NH$_4$Cl (600 mL) and separated. The organic layer was washed twice with 1 N HCl (500 mL), once with water, once with 1 N NaOH (500 mL), once with water, once with 6% NaHCO3, once with saturated NaCl, dried over Na$_2$SO$_4$, and concentrated in vacuo. The crude material was chromatographed on SiO$_2$ (1.2 kg) in two portions using hexanes/EtOAc (2:1) as eluant (62.3 g).

$^1$H NMR (400 MHz, CDCl$_3$) δ: 7.44–7.20 (m, 10H), 7.07 (d, 1H), 6.94–6.91 (dd, 1H), 6.78–6.76 (d, 1H), 5.56–5.50 (dd, 1H), 4.69–4.63 (dd, 1H), 4.21–4.16 (dd, 1H), 3.83–3.80 (m, 2H), 3.82 (s, 3H), 3.74–3.70 (d, 1H), 3.64–3.59 (d, 1H), 3.50–3.46 (d, 1H), 2.90–2.86 (d, 1H), 2.83–2.71 (m, 2H), 1.36–1.29 (m, 1H), 0.64–0.60 (m, 2H), 0.38–0.32 (m, 2H).

Intermediate 65

1-Benzyl-4-(S)-(3-cyclopropylmethoxy-4-methoxyphenyl)-3-(S)-methylpyrrolidine-3-carbaldehyde Intermediate 64 (62.3 g, 0.115 mol) was dissolved in toluene (1 L), then cooled to –78° C. The solution was treated with lithium aluminum hydride (1.0 M in THF, 69 mL, 69 mmol) by slow addition. The reaction was stirred for 0.5 hours, then quenched at –78° C. with a dropwise addition of MeOH (13 mL). The reaction was stirred for 5 minutes at –78° C., warmed to 0° C., followed by an addition of water (2.62 mL), 15% NaOH (2.62.mL), and water (7.85 mL). The solution was stirred for 10 minutes, then Et$_2$O was added (1.5 L) and the resulting mixture was stirred overnight at 22° C. Magnesium sulfate was added and after stirring for 15 minutes, the solution was filtered through MgSO$_4$ and concentrated in vacuo. NMR showed that the products of this reaction were a mixture of the desired aldehyde and the primary alcohol (about 4:1). This material was used without further purification in the following Swern oxidation below. Oxalyl chloride (2.0 M in CH$_2$Cl$_2$, 25 mL, 50 mmol) was added to CH$_2$Cl$_2$ (75 mL) and cooled to –60° C. Dimethylsulfoxide (7.1 mL, 100 mmol) was added as a solution in CH$_2$Cl$_2$ (30 mL) in a dropwise manner. After 5 minutes, a solution of aldehyde/alcohol mixture (4:1, ~0.115 mol, (ca. 0.05 mol alcohol)) dissolved in CH$_2$Cl$_2$ was added dropwise. The mixture was stirred for 30 minutes, then Et$_3$N (31 mL, 222 mmol) was added, and the solution was warmed to 22° C. and stirred overnight. The reaction was quenched with water and stirred vigorously for 20 minutes, then separated. The aqueous layer was washed with CH$_2$Cl$_2$. The combined organic layers were washed with saturated NaCl, dried over Na$_2$SO$_4$, and concentrated in vacuo. Intermediate 65 was purified by filter chromatography using hexanes/EtOAc (4:1) as eluant (42 g).

$^1$H NMR (400 MHz, CDCl$_3$) δ: 9.64 (s, 1H), 7.39–7.23 (m, 5H), 6.81–6.71 (m, 3H), 3.83 (s, 3H), 3.83–3.81 (m, 2H), 3.80–3.75 (d, 1H), 3.67–3.61 (m, 2H), 3.19–3.11 (m, 2H), 2.86–2.81 (m, 1H), 2.43–2.40 (m, 1H), 1.38–1.29 (m, 1H), 0.76 (s, 3H), 0.68–0.62 (m, 2H), 0.30–0.37 (m, 2H).

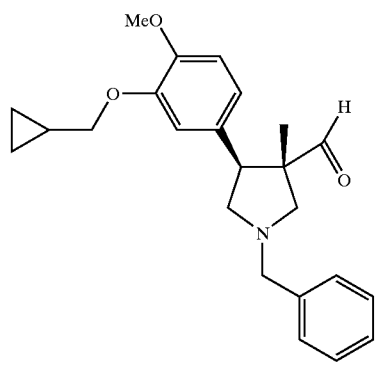

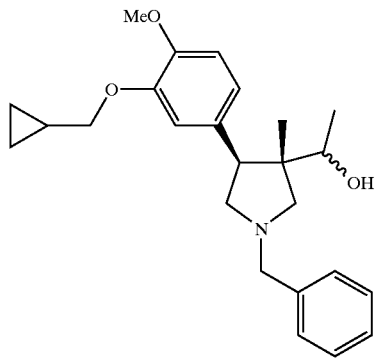

Intermediate 66

1-[1-Benzyl-4-(S)-(3-cyclopropylmethoxy-4-methoxyphenyl)-3-(S)-methylpyrrolidin-3-yl]ethanol Trimethylaluminum (2.0 M in toluene, 2.1 mL, 4.2 mmol) was cooled to 0° C. and methylmagnesium iodide (3.0 M in ethyl ether, 1.3 mL, 3.95 mmol) was added dropwise. This grey suspension was stirred at 0° C. for 30 minutes then it was added through a cannula to a solution of Intermediate 65 (0.5 g, 1.3 mmol) dissolved in $CH_2Cl_2$ (6.6 mL), which was cooled to −78° C. The reaction mixture was stirred at −78° C. for 6 hours. The mixture then was poured directly into a separatory funnel containing Rochelle's salt (1 M, 150 mL). The residue was rinsed into the funnel with EtOAc. The mixture was diluted with EtOAc and separated. The organic layer was washed a second time with Rochell's salt, followed by saturated NaCl, dried over $MgSO_4$, and concentrated in vacuo. The crude product was a mixture (1:1) of the two diasteromeric alcohols plus a small amount of aldehyde. These materials were separable by chromatography on $SiO_4$ with EtOAc/hexanes (1:1).

Desired more polar carbinol:

$^1$H NMR (400 MHz, $CDCl_3$) δ: 7.36–7.30 (m, 3H), 7.28–7.24 (m, 2H), 6.81–6.74 (m, 3H), 3.85 (s, 3H), 3.84–3.79 (m, 2H), 3.71–3.56 (m, 4H), 3.33–3.25 (dd, 1H), 3.12–3.09 (d, 1H), 2.59–2.53 (dd, 1H), 2.16–2.08 (d, 1H), 1.38–1.25 (m, 1H), 1.16 (d, 3H), 0.69–0.61 (m, 2H), 0.49 (s, 3H), 0.39–0.35 (m, 2H).

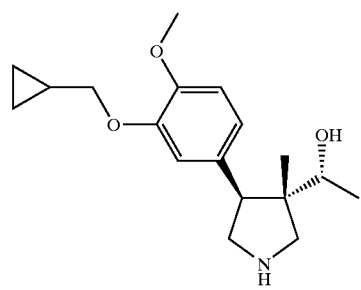

Intermediate 67

(1R)-1-{(3S,4S)-4-[3-(Cyclopropylmethoxy)-4-methoxyphenyl]-3-methylpyrrolidin-3-yl}ethan-1-ol Prepared from Intermediate 66 by the debenzylation procedure of Intermediate 31.

$^1$H NMR (400 MHz, $CDCl_3$) δ: 6.88–6.71 (m, 3H), 3.92–3.56 (c, 11H), 3.14–3.05 (m, 1H), 1.37–1.25 (m, 1H), 1.20 (d, 2H), 0.72 (s, 3H), 0.63 (d, 2H), 0.37 (d, 2H). LRMS (Electrospray, positive): Da/e 306.2 (m+1).

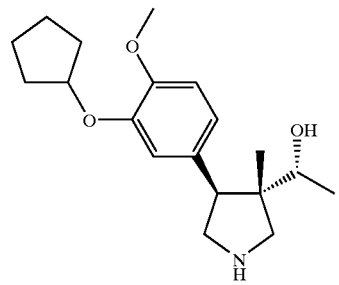

Intermediate 68

(1R)-1-[(3S,4S)-4-(3-Cyclopentyloxy-4-methoxyphenyl)-3-methylpyrrolidin-3-yl]ethan-1-ol Prepared by the debenzylation procedure of Intermediate 31 from the 1-(R) carbinol isomer (more polar diastereomer) of Intermediate 56.

$^1$H NMR (400 MHz, $CDCl_3$) δ: 6.81 (d, 1H), 6.75–6.73 (m, 2H), 4.80 (c, 1H), 3.82 (s, 3H), 3.79–3.68 (m, 5H), 3.61 (t, 1H), 3.10 (d, 1H), 1.96–1.80 (m, 6H), 1.63–1.57 (m, 2H), 1.21 (d, 3H), 0.72 (s, 3H). LRMS (Electrospray, positive): Da/e 320.4 (m+1).

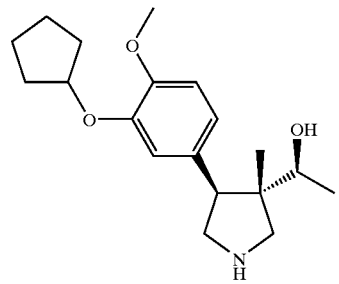

Intermediate 69

(1S)-1-[(3S,4S)-4-(3-Cyclopentyloxy-4-methoxyphenyl)-3-methylpyrrolidin-3-yl]ethan-1-ol Prepared by the debenzylation procedure of Intermediate 31 from the 1-(S) isomer (less polar intermediate) of Intermediate 56.

LRMS (Electrospray, positive): Da/e 320.4 (m+1).

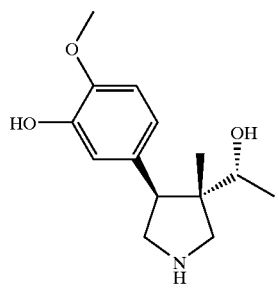

Intermediate 70

5-[4-((1R)-1-Hydroxyethyl)(3S,4S)-4-methylpyrrolidin-3-yl]-2-methoxyphenol

Prepared from Intermediate 58 via the debenzylation procedure of Intermediate 31 (10% palladium on carbon used in place of palladium acetate).

$^1$H NMR (400 MHz, CDCl$_3$) δ: 6.72 (d, 1H), 6.67 (d, 1H), 6.59 (dd, 1H), 3.80 (s, 3H), 3.60 (qd, 1H), 3.29–3.17 (m, 6H), 3.10 (t, 1H), 2.55 (d, 1H), 1.06 (d, 3H), 0.56 (s, 3H). LRMS (Electrospray, positive): m/z 252.1 (m+1).

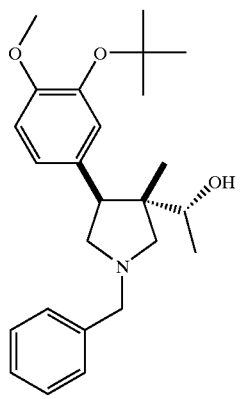

Intermediate 71

1-R-[1-Benzyl-4-S-(3-tert-butoxy-4-methoxyphenyl)-3-S-methylpyrrolidin-3-yl]-ethanol To a stirred solution of trimethylaluminum (2M in toluene, 59.4 mL, 119 mmol) at 0° C. under a nitrogen blanket was added methylmagnesium iodide (3M in Et$_2$O, 36 mL, 108 mmol). After 30 minutes at 0° C., the organometallic solution was added via cannula to a solution of Intermediate 55 (13.7 gm, 36 mmol) in CH$_2$Cl$_2$ (360 mL) at −78° C. under a nitrogen blanket. After complete addition, the reaction was stirred at −78° C. for 6 hours. The reaction then was warmed to 0° C. and carefully poured into ice cold 1M potassium sodium tartrate (1500 mL) with rapid stirring, and diluted with EtOAc (1500 mL). After stirring for 15 minutes, the layers were separated, and the organic layers washed with 1M potassium sodium tartrate (1×1000 mL) and saturated NaCl (1×1000 mL). The organic layers were dried (MgSO$_4$), filtered, and concentrated in vacuo to provide a 2.5:1 mixture of diastereomers plus approximately 10% residual starting aldehyde by crude $^1$H-NMR. The crude product was chromatographed on a 110 mm×8" column with 3/7/0.4 EtOAc/hexane/MeOH to provide, after pooling and concentration in vacuo of the desired lower R$_f$ diastereomer containing fractions, Intermediate 71 (8.1 gm, 57%) as an orange oil.

$^1$H-NMR (400 MHz, CDCl$_3$) δ: 7.34–7.23 (m, 5H), 6.86 (m, 3H), 6.79 (d, 1H), 3.79 (s, 3H), 3.65 (dd, 1H), 3.62 (s, 2H), 3.58 (dd, 1H), 3.29 (dd, 1H), 3.10 (d, 1H), 2.53 (dd, 1H), 2.07 (d, 1H), 1.35 (s, 9H), 1.12 (d, 3H), 0.45 (s, 3H).

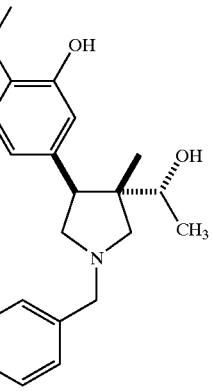

Intermediate 72

5-[(4R)-4-((1S)-1-Hydroxyethyl)-4-methyl-1-benzyl-pyrrolidin-3-yl]-2-methoxyphenol To a stirred solution of Intermediate 71 (2.3 gm, 5.8 mmol) in CH$_2$Cl$_2$ (18 mL) at 0° C. under a drying tube was added trifluoroacetic acid (2.7 mL, 35 mmol). The cooling bath was removed and the reaction allowed to warm to room temperature, then stirred for 3.5 hours. The reaction was concentrated by rotary evaporator to remove excess trifluoroacetic acid, redissolved in CH$_2$Cl$_2$ (50 mL), then washed with 10% Na$_2$CO$_3$ (2×50 mL) and saturated NaCl (1×50 mL). The organic layers were dried (MgSO$_4$), filtered, and concentrated in vacuo to provide Intermediate 72 as a white foam (1.9 gm, 96%).

$^1$H-NMR (400 MHz, CDCl$_3$) δ: 7.36–7.20 (m, 5H), 6.82 (s, 1H), 6.77 (d, 1H), 6.66 (d, 1H), 5.57 (s, 1H), 3.83 (s, 3H), 3.70–3.56 (m, 4H), 3.30 (dd, 1H), 3.13 (d, 1H), 2.55 (dd, 1H), 2.04 (d, 1H), 1.12 (d, 3H), 0.45 (s, 3H).

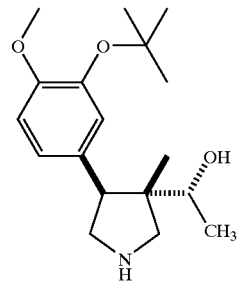

Intermediate 73

(1R)-1-{(3R)-4-(3-(tert-Butoxy)-4-methoxyphenyl]-3-methylpyrrolidin-3-yl}ethan-1-ol Prepared from Intermediate 71 (1 gm, 2.53 mmol) by the debenzylation procedure of Intermediate 31 to give 775 mg of Intermediate 73.

$^1$H-NMR (400 MHz, CDCl$_3$) δ: 6.92–6.79 (m, 3H), 3.78 (s, 3H), 3.51–3.42 (m, 4H), 3.29 (dd, 1H), 2.77 (d, 1H), 1.35 (s, 9H), 1.17 (d, 3H), 0.62 (s, 3H).

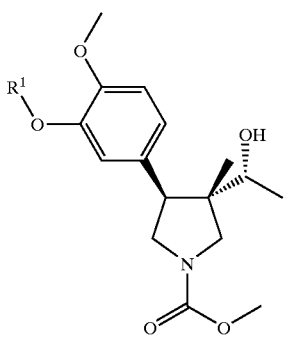

Intermediate 74

R¹=H

Methyl 3-((1R)-1-hydroxyethyl)(3S,4S)-4-(3-hydroxy-4-methoxyphenyl)-3-methylpyrrolidinecarboxylate Hunig's Base Mediated Acylation Procedure To a cooled (0° C.), stirred solution of Intermediate 70 (670 mg, 2.67 mmol) and Hunig's base (1.4 mL, 8.0 mmol) in dry CH$_2$Cl$_2$ (10 mL), 1,4-dioxane (5 mL), and MeOH (1 mL) was added methyl chloroformate (0.41 mL, 5.3 mmol) via syringe under a nitrogen atmosphere. The resulting solution was allowed to stir at 0° C. for 1 hour, then diluted with CH$_2$Cl$_2$ (90 mL), washed successively with 1 N aqueous HCl (2×20 mL) and brine (20 mL), and dried (Na$_2$SO$_4$), filtered, and concentrated in vacuo. The residue (737 mg) was dissolved in THF (3 mL) and water (2 mL), then treated with a solution of LiOH (112 mg, 2.67 mmol in 2 mL water) at room temperature. After stirring for 4 hours, the reaction was diluted with EtOAc (100 mL) and washed successively with 1 N aqueous HCl (2×50 mL), saturated aqueous NaHCO$_3$ (30 mL) and brine (30 mL), then dried (Na$_2$SO$_4$), filtered, and concentrated in vacuo. The residue was purified via radial chromatography (4 mm plate with 3% MeOH in CH$_2$Cl$_2$) to provide Intermediate 74 as a light tan foam (250 mg, 30%).

$_1$H NMR (400 MHz, CDCl$_3$, mixture of rotomers) δ: 6.84 (d, 1H), 6.78 (d, 1H), 6.72 (dd, 1H), 5.57 (d, 1H), 3.90–3.54 (m, 1H), 3.30 (d, 0.5H), 3.20 (d, 0.5H), 1.35 (br d, 1H), 1.14 (t, 3H), 0.75 (s, 3H). LRMS (Electrospray, negative): m/z 308.6 (m−1). LRMS (Electrospray, positive): m/z 310.5 (m+1).

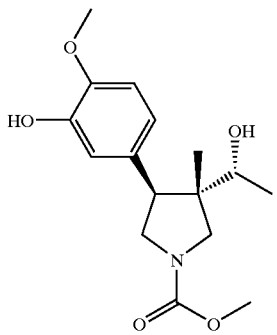

Intermediate 75

From Intermediate 57 via debenzylation procedure of Intermediate 31 and Hunig's Base Mediated Acylation procedure of Intermediate 74.

LRMS (Electrospray, negative): m/z 308.6 (m−1). LRMS (Electrospray, positive): m/z 310.5 (m+1).

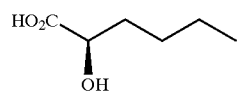

Intermediate 76

(2R)-2-Hydroxyhexanoic acid

To a cooled (0° C.), stirred solution of D-norleucine (500 mg, 3.81 mmol) in 10 mL of 1N aqueous sulfuric acid was added sodium nitrite (421 mg, 6.10 mmol) in 3 mL of water dropwise over a 20-minute period. The reaction mixture was allowed to slowly warm to room temperature over a 16-hour period. The mixture then was extracted with EtOAc (2×25 mL), dried (Na$_2$SO$_4$), and concentrated to yield 200 mg (40%) of a white waxy solid.

$^1$H NMR (400 MHz, CDCl$_3$) δ: 4.28 (dd, 1H), 1.92–1.81 (m, 1H), 1.76–1.64 (m, 1H), 1.51–1.29 (m, 4H), 0.92 (t, 3H). LRMS (Electrospray, negative): Da/e 131.1 (m−1).

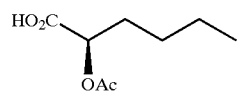

Intermediate 77

(1R)-1-(Chlorocarbonyl)pentyl acetate

Acylation/Hydrolysis/Acid Chloride Formation Procedure

To a cooled (0° C.) solution of Intermediate 76 (200 mg, 1.51 mmol) and Hunig's base (657 mL, 3.78 mmol) in CH$_2$Cl$_2$ (6 mL) was added acetyl chloride (215 μL, 3.03 mmol) by syringe. The resulting mixture was allowed to slowly warm to room temperature over a 16 hour period. The reaction mixture then was washed with 1N HCl (2×20 mL), dried (Na$_2$SO$_4$), and concentrated to an orange brown oil, which by NMR was shown to be the bis-acylated material. To this material was added 5 mL of 4:1 THF:water, and the mixture stirred for 16 hours at room temperature, extracted with EtOAc, dried (Na$_2$SO$_4$), and concentrated to 186 mg (71%) of an orange oil. NMR and mass spectrometry confirmed the acetoxy acid. To this material in 5 mL of CH$_2$Cl$_2$ was added oxalyl chloride (1.07 mL, 2.14 mmol, 2M solution in CH$_2$Cl$_2$) and a drop of DMF. The mixture was stirred at room temperature for 4 hours, then concentrated under reduced pressure to afford Intermediate 77.

$^1$H NMR (400 MHz, CDCl$_3$) δ: 5.17 (dd, 1H), 2.18 (s, 3H), 2.04–1.86 (m, 2H), 1.50–1.30 (m, 4H), 0.93 (t, 3H).

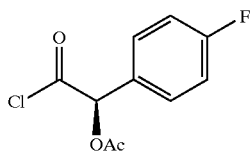

Intermediate 78

(Chlorocarbonyl)(4-fluorophenyl)methyl acetate
Prepared via the acylation/hydrolysis/acid chloride formation procedure of Intermediate 77 from 2-(4-fluorophenyl)-2-hydroxyacetic acid.

$^1$H NMR (400 MHz, CDCl$_3$) δ: 7.48 (q, 2H), 7.14 (t, 2H), 6.06 (s, 1H), 2.21 (s, 3H).

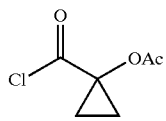

Intermediate 79

(Chlorocarbonyl)cyclopropyl acetate

Prepared via the acylation/hydrolysis/acid chloride formation procedure of Intermediate 77 from 1-hydroxycyclopropanecarboxylic acid.

$^1$H NMR (400 MHz, CDCl$_3$) δ: 2.13 (s, 3H), 1.89–1.84 (m, 2H), 1.46–1.42 (m, 2H).

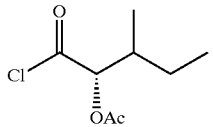

Intermediate 80

(1S)-1-(Chlorocarbonyl)-2-methylbutyl acetate

Prepared via the acylation/hydrolysis/acid chloride formation procedure of Intermediate 77 from (2S)-2-hydroxy-3-methylpentanoic acid.

$^1$H NMR (400 MHz, CDCl$_3$) δ: 5.01 (d, 1H), 2.24–2.17 (m, 1H), 2.17 (s, 3H), 1.57–1.47 (m, 1H), 1.39–1.28 (m, 1H), 1.03 (d, 3H), 0.94 (t, 3H).

Intermediate 81

(1S)-1-(Chlorocarbonyl)-3-methylbutyl acetate

Prepared via the acylation/hydrolysis/acid chloride formation procedure of Intermediate 77 from (2S)-2-hydroxy-4-methylpentanoic acid.

$^1$H NMR (400 MHz, CDCl$_3$) δ: 5.12 (d, 1H), 2.16 (s, 3H), 1.88–1.75 (m, 3H), 0.97 (dd, 6H).

Intermediate 82

(1R)-1-(Chlorocarbonyl)-2-phenylethyl acetate

Prepared via the acylation/hydrolysis/acid chloride formation procedure of Intermediate 77 from (2R)-2-hydroxy-3-phenylpropanoic acid.

$^1$H NMR (400 MHz, CDCl$_3$) δ: 7.38–7.21 (m, 5H), 5.33 (dd, 1H), 3.33 (dd, 1H), 3.18 (dd, 1H), 2.11 (s, 3H).

Intermediate 83

(1S)-1-(Chlorocarbonyl)-2-phenylethyl acetate

Prepared via the acylation/hydrolysis/acid chloride formation procedure of Intermediate 77 from (2S)-2-hydroxy-3-phenylpropanoic acid.

$^1$H NMR (400 MHz, CDCl$_3$) δ: 7.38–7.21 (m, 5H), 5.33 (dd, 1H), 3.33 (dd, 1H), 3.18 (dd, 1H), 2.11 (s, 3H).

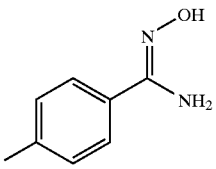

Intermediate 84

(4-Chlorophenyl)(hydroxyimino)methylamine

A solution of 4-chlorobenzonitrile (10 g, 0.073 mole), hydroxylamine hydrochloride, and NaOH (3.5 g, 0.087 mole) in ethanol (300 mL) and water (80 mL) was refluxed for 10 hours, then concentrated under reduced pressure. The resulting off-white solid was taken up in water/4:1 EtOAc:CH$_2$Cl$_2$. The organic layers were isolated, washed once with water, dried (Na$_2$SO$_4$), and concentrated to 10.4 g of a white solid (84%).

$^1$H NMR (DMSO-d$_6$, 400 MHz) δ: 9.71 (s, 1H), 7.66 (d, 2H), 7.41 (d, 2H), 5.85 (br s, 2H).

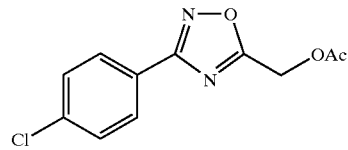

Intermediate 85

[3-(4-Chlorophenyl)-1,2,4-oxadiazol-5-yl]methyl acetate

To a chilled (0° C.) solution of Intermediate 84 (4.5 g, 0.026 mole) in dry pyridine (20 mL) was added acetoxyacetyl chloride (6 mL, 0.056 mole) dropwise over a one-hour period. After the addition was complete, the mixture was heated at 90° C. for three hours, then allowed to cool to room temperature. The pyridine was removed under reduced pressure, and the resulting dark oily material was taken up in CH$_2$Cl$_2$ and filtered through GF/F filter paper. The filtrate was washed with brine (2×100 mL), dried (Na$_2$SO$_4$), and concentrated. Biotage purification (40M cartridge, 20% EtOAc/hexane) afforded 1.93 g of Intermediate 85 as a white solid (29%).

$^1$H NMR (400 MHz, CDCl$_3$) δ: 8.01 (d, 2H), 7.46 (d, 2H), 5.35 (s, 2H), 2.21 (s, 3H).

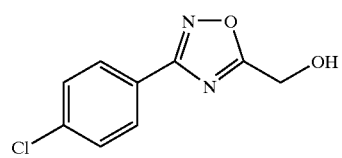

Intermediate 86

[3-(4-Chlorophenyl)-1,2,4-oxadiazol-5-yl]methan-1-ol

To a solution of Intermediate 85 (1 g, 3.96 mmol) in MeOH (50 mL) was added aqueous K$_2$CO$_3$ (0.56 M, 7 mL, 3.96 mmol) and the mixture stirred at room temperature for two hours. The solvents then were removed under reduced pressure, and the residue taken up in EtOAc (75 mL), washed with water (2×75 mL), dried (Na$_2$SO$_4$), and concentrated to 820 mg (98%) of Intermediate 86 as a white solid.

$^1$H NMR (400 MHz, CDCl$_3$) δ: 8.02 (d, 2H), 7.47 (d, 2H), 4.97 (s, 2H), 2.52 (br s, 1H).

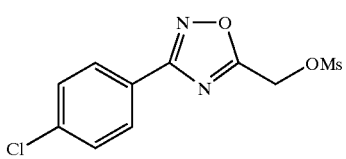

Intermediate 87

[3-(4-Chlorophenyl)-1,2,4-oxadiazol-5-yl]methyl methylsulfonate

Prepared via the mesylation procedure of Intermediate 90.

$^1$H NMR (400 MHz, CDCl$_3$) δ: 8.02 (d, 2H), 7.47 (d, 2H), 5.49 (s, 2H), 3.24 (s, 3H).

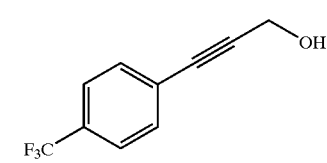

Intermediate 88

3-[4-(Trifluoromethyl)phenyl]prop-2-yn-1-ol

Palladium Catalyzed Coupling Procedure

A solution of 4-iodobenzotrifluoride (5 g, 0.018 mole), propargyl alcohol (1.07 ml, 0.018 mole), copper(I) iodide (17.5 mg, 0.092 mmol), and bis-triphenylphosphinepalladium(II) chloride (129 mg, 0.184 mmol) in 50 mL of diethylamine was stirred at room temperature for several hours. The diethylamine then was removed under reduced pressure and the residue taken up in CH$_2$Cl$_2$ (150 mL). This was washed with 1N HCl (3×150 mL), dried (Na$_2$SO$_4$), and concentrated to 3.1 g of Intermediate 88 as an orange/brown oil (84%).

$^1$H NMR (400 MHz, CDCl$_3$) δ: 7.55 (q, 4H), 4.52 (d, 2H), 1.74 (br s, 1H).

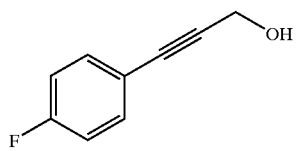

Intermediate 89

3-(4-Florophenyl)prop-2-yn-1-ol

Prepared via the procedure of Intermediate 88.

$^1$H NMR (400 MHz, CDCl$_3$) δ: 7.42 (q, 2H), 7.01 (t, 2H), 1.70 (t, 1H).

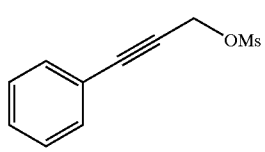

Intermediate 90

3-Phenylprop-2-ynyl methylsulfonate

Mesylation Procedure

To a solution of 3-phenyl-2-propyn-1-ol (100 g, 0.757 mole) and Et$_3$N (158 mL, 1.13 mole) in 3 liters of dry CH$_2$Cl$_2$ chilled to 5° C. was added methanesulfonyl chloride (59 mL, 0.757 mole) via an addition funnel, maintaining the internal temperature about 5° C. (addition complete after approximately 45 minutes). After one hour at 5° C., TLC indicated most of starting material was consumed. One mL of methanesulfonyl chloride was added, and the reaction mixture stirred for an additional 30 minutes at 5° C. TLC indicated complete consumption of starting material. The mixture then was washed with 1N HCl (3×250 mL), dried (Na$_2$SO$_4$), and concentrated to yield 113 g of Intermediate 90 as a yellow liquid (71%).

$^1$H NMR (400 MHz, CDCl$_3$) δ: 7.48–7.45 (m, 2H), 7.39–7.34 (m, 3H), 5.09 (s, 2H), 3.16 (s, 3H).

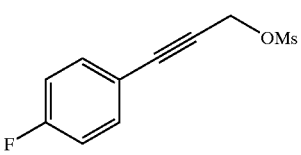

Intermediate 91

3-(4-Fluorophenyl)prop-2-ynyl methylsulfonate

Prepared from Intermediate 89 via the mesylation method of Intermediate 90.

$^1$H NMR (400 MHz, CDCl$_3$) δ: 7.47–7.44 (q, 2H), 7.04 (t, 2H), 5.07 (s, 2H), 3.15 (s, 3H).

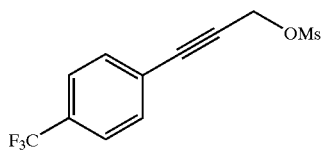

Intermediate 92

3-[4-(Trifluoromethyl)phenyl]prop-2-ynyl methyl-sulfonate

Prepared from Intermediate 88 via the mesylation method of Intermediate 90.

$^1$H NMR (400 MHz, CDCl$_3$) δ: 7.62–7.56 (m, 4H), 5.09 (s, 2H), 3.16 (s, 3H).

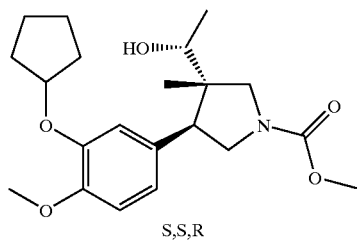

S,S,R

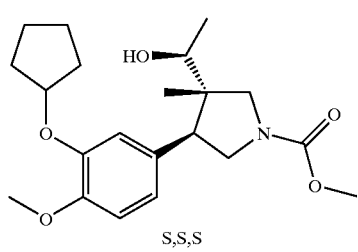

S,S,S

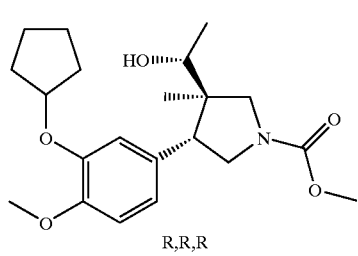

R,R,R

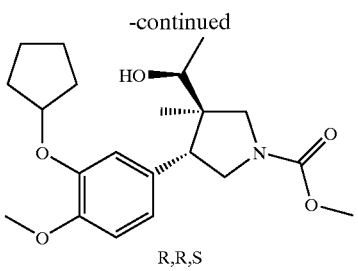

R,R,S

EXAMPLE 3

Preparation of four stereoisomers from reduction of Intermediate 36. Sodium borohydride (2.0 mmol, 0.075 g) was added to Intermediate 36 (1.3 mmol, 0.50 g) dissolved in 10 mL of ethanol. The complete reaction was dried in vacuo after 1 hour. The resulting oil was extracted three times with EtOAc from water, then the combined extracts were washed with brine and dried over MgSO$_4$. The mixture of two racemates was obtained as an oil.

$^1$H NMR δ: 6.80 (d, 1H); 6.67 (d, 2H); 4.72 (bd, 1H); 3.86–3.95 (bm, 1H); 3.83 (s, 3H); 3.64–3.78 (bm, 1H); 3.74 (s, 3H); 3.33 (dd, 1H); 2.16 (d, 3H); 1.79–1.92 (bm, 4H); 1.59–1.63 (bm, 2H); 1.01 (sd, 3H).

The mixture of racemates was dissolved in 50% acetonitrile and 50% water at a concentration of 50 mg/mL and purified in portions on a C-18 column (250×10 mm) using a water/acetonitrile/0.5% TFA gradient. Appropriate fractions were collected, combined, and dried to oils.

$^1$H NMR for minor racemate δ: 6.75–6.82 (bm, 3H); 4.75 (bd, 1H); 3.83 (s, 3H); 3.64–3.81 (bm, 1H); 3.74 (s, 3H); 3.54–3.61 (bm, 2H); 3.28 (dd, 1H); 1.81–1.94 (bm, 5H); 1.58–1.65 (bm, 4H); 1.15 (dd, 3H); 0.75 (s, 3H). $^1$H NMR for the major racemate δ: 6.76–6.83 (bm, 3H); 4.74 (bd, 1H); 3.77–3.89 (bm, 1H); 3.83 (s, 3H); 3.73 (s, 3H); 3.65 (quin, 1H); 3.25–3.32 (bm, 3H); 1.77–1.96 (bm, 7H); 1.58–1.61 (bm, 2H); 1.13 (d, 3H); 0.92 (s, 3H)

Chiral Separation of the Alcohols

Two columns were required to separate the four diastereomers by HPLC. The first dextrose-based column (8×30 cm) was used to separate the R,R,S isomer from the others. Ten mL (7.1 mg/mL stock solution) of crude mixture in column buffer was introduced then eluted at 1 mL/min with isocratic hexanes (85%) and isopropanol (15%), collecting the appropriate fractions. The remaining diastereomers were purified on a different dextrose-based column (10×50 cm). Again, 10 mL (7.1 mg/mL stock solution) was injected, then eluted at 1 mL/min with isocratic hexanes (95%) and isopropanol (5%). The appropriate fractions were collected, combined and dried to oils.

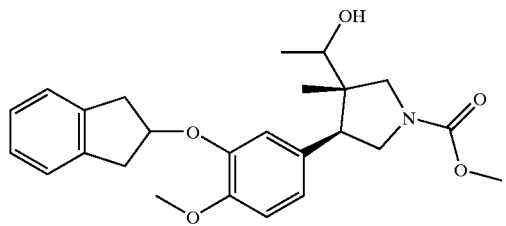

EXAMPLE 4

R$^1$=2-indanyl; R$^3$=CO$_2$CH$_3$ trans-(±)-3-(1-Hydroxyethyl)-4-[3-(indan-2-yloxy)-4-methoxyphenyl]-3-methylpyrrolidine-1-carboxylic acid methyl ester (2 carbinol diastereomers)

A solution of Intermediate 35 (racemic) (300 mg, 0.71 mmol, 1 eq) in ethanol (10 mL) was treated with sodium borohydride (54 mg, 1.42 mmol, 2 eq). The mixture was stirred 10 min at room temperature, treated with 1 N HCl (50 mL), and extracted with EtOAc (3×25 mL). The combined organic extracts were washed with 1 N HCl (25 mL), water, sat. NaHCO$_3$ (25 mL), water (25 mL), and brine (25 mL), dried over Na$_2$SO$_4$, and concentrated in vacuo. A portion of the crude residue was purified by HPLC (Vydac 20×250 mm C18 "Protein and Peptide" column, 8 min. gradient of 50–75% acetonitrile in water with each solvent containing 0.05% TFA, flow rate of 20 mL/min) to yield the separated diastereomers in a 2:1 ratio as colorless syrups (75 and 37 mg respectively, in order of elution from column).

Isomer 1: $^1$H NMR (300 MHz, CDCl$_3$) δ: 7.24–7.15 (m, 4H), 6.83 (br s, 3H), 5.21–5.12 (m, 1H), 3.91–3.59 (m, 3H), 3.81 (s, 3H), 3.73 (s, 3H), 3.40–3.18 (m, 7H), 1.14 (d, J=6.3 Hz, 3H), 0.94 (s, 3H).

Isomer 2: $^1$H NMR (300 MHz, CDCl$_3$) δ: 7.23–7.15 (m, 4H), 6.85–6.82 (m, 3H), 5.22–5.10 (m, 1H), 3.89–3.67 (m, 3H), 3,81 (s, 3H), 3,75 (s, 3H), 3,64–3.52 (m, 2H), 3.40–3.15 (m, 5H), 1.20–1.13 (m, 3H), 0.78 (s, 3H).

The compounds of Examples 5 and 6 were prepared in the same manner as Example 4:

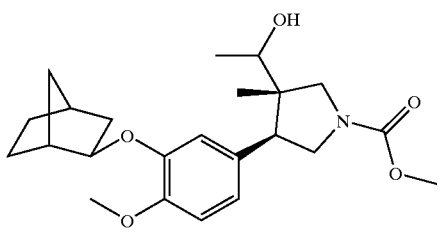

EXAMPLE 5

R$^1$=2-norbornyl; R$^3$=CO$_2$CH$_3$ trans 4-[3-Exo-(Bicyclo[2.2.1]hept-2-yloxy)-4-methoxyphenyl]-3-(1-hydroxyethyl)-3-methylpyrrolidine-1-carboxylic acid methyl ester (2 carbinol diastereomers)

Intermediate 38 was reduced and separated as above to give two isomers:

Isomer 1: $^1$H NMR (300 MHz, CDCl$_3$) δ: 6.82–6.72 (m, 3H), 4.15 (br s, 1H), 3.88–3.59 (m, 3H), 3.87 (s, 3H), 3.73 (s, 3H), 3.32–3.24 (m, 3H), 2.50–2.47 (m, 1H), 2.34–2.28 (m, 1H), 1.77–1.50 (m, 5H), 1.21–1.12 (m, 6H), 0.92 (s, 3H).

Isomer 2: $^1$H NMR (300 MHz, CDCl$_3$) δ: 6.82–6.72 (m, 3H), 4.19–4.15 (m, 1H), 3.85–3.54 (m, 5H), 3.83 (s, 3H), 3.74 (s, 3H), 3.30/3.23 (2 d, J=10.4/10.4 Hz, 1H), 2.49–2.46 (m, 1H), 2.32 (br s, 1H), 1.76–1.70 (m, 2H), 1.65–1.44 (m, 3H), 1.21–1.14 (m, 6H), 0.75 (s, 3H).

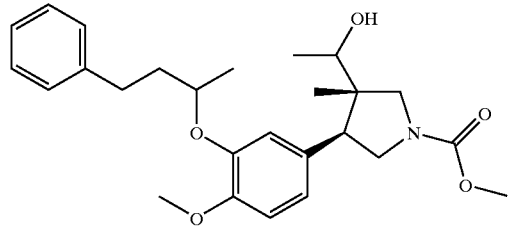

EXAMPLE 6

R$^1$=PhCH$_2$CH$_2$CH(CH$_3$); R$^3$=CO$_2$CH$_3$ trans-3-(1-Hydroxyethyl)-4-[4-methoxy-3-(1-methyl-3-phenylpropoxy)phenyl]-3-methylpyrrolidine-1-carboxylic acid methyl ester (2 carbinol diastereomers)

Intermediate 39 was reduced and separated as above to give two isomers:

Isomer 1: $^1$H NMR (300 MHz, CDCl$_3$) δ: 7.30–7.25 (m, 3H), 7.22–7.15 (m, 3H), 6.85–6.69 (m, 3H), 4.34–4.27 (m, 1H), 3.87–3.54 (m, 3H), 3.84 (s, 3H), 3.73/3.72 (2 s, 3H), 3.31–3.20 (m, 3H), 2.83–2.75 (m, 2H) 2.18/2.08 (m, 1H), 1.95–1.84 (m, 1H), 1.34/1.31 (2 s, 3H), 1.12 (d, J=6.3 Hz, 3H), 0.89 (br s, 3H). $^{13}$C NMR (75 MHz, CDCl$_3$) δ: 156.0, 150.3, 147.8, 142.2, 131.3/131.1, 128.9, 128.8, 126.2, 121.7, 117.1, 112.5, 77.6, 75.3/75.1, 74.1/74.0, 56.3, 56.2/55.8, 52.9, 52.0/51.5/51.2, 49.9/49.1, 38.5/38.4, 32.2, 20.3, 19.0/18.9, 14.6/14.5.

Isomer 2: $^1$H NMR (300 MHz, CDCl$_3$) δ: 7.29–7.24 (m, 2H), 7.20–7.14 (m, 3H), 6.84–6.69 (m, 3H), 4.35–4.24 (m, 1H), 3.85/3.84 (2 s, 3H) 3.83–3.45 (m, 5H) 3.75 (s, 3H), 3.31–3.23 (m, 1H), 2.88–2.76 (m, 2H), 2.21–2.07 (m, 1H), 1.95–1.83 (m, 1H), 1.34/1.32 (2 s, 3H), 1.15–1.11 (m, 3H), 0.73 (br s, 3H). $^{13}$C NMR (75 MHz, CDCl$_3$) δ: 156.1, 149.9, 147.4, 142.3, 129.5/129.4, 128.9, 128.7, 126.2, 122.1/121.8, 117.9/117.7/117.4, 112.0, 77.6, 75.3/75.0/74.9, 69.4/69.3, 56.3, 53.2, 53.1, 49.5/49.3/49.1/48.6, 46.5/46.0, 38.5/38.4/38.3, 32.1, 20.3, 20.0, 17.7.

The following compounds were prepared from chiral free pyrrolidine Intermediate 68.

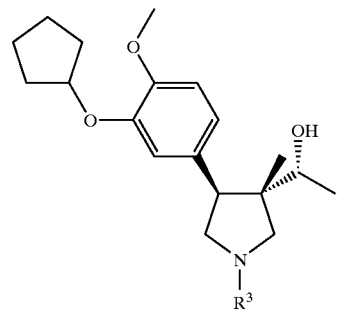

EXAMPLE 7

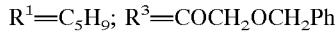

1-[3-((1R)-1-Hydroxyethyl)(3S,4S)-4-(3-cyclopentyloxy-4-methoxyphenyl)-3-methylpyrrolidinyl]-2-(phenylmethoxy)ethan-1-one N-Acylation Procedure To a stirred solution Intermediate 68 (42.6 mg, 0.13 mmol) in 1,4-dioxane (0.4 mL) was added, successively, aqueous $K_2CO_3$ (0.8 mL of 0.65 M, 4 eq.) and a solution of the acid chloride ($R_3$—Cl) (21 μL, 0.13 mmol) in 1,4-dioxane (0.4 mL) at room temperature. The resulting solution was allowed to stir at room temperature for 4 hours. The reaction was diluted with EtOAc (30 mL), then washed successively with water (20 mL) and brine (20 mL), dried ($MgSO_4$), filtered, and concentrated in vacuo to provide Example 7 as a slightly tan foam (46.5 mg, 99%).

$^1$H NMR (400 MHz, $CDCl_3$) δ: mixture of rotomers): 7.40–7.31 (m, 5H), 6.80–6.72 (m, 3H), 4.73 (c, 1H), 4.67 (s, 2H), 4.14 (s, 2H), 3.82 (s, 3H), 3.79–3.45 (m, 5H), 3.22 (d, 1H), 1.92–1.80 (c, 6H), 1.61–1.55 (c, 2H), 1.14 (dd, 3H), 0.73 (d, 3H). LRMS (Electrospray, positive): Da/e 468.4 (m+1).

EXAMPLE 8

$R^1=C_5H_9$; $R^3=COCH_2OH$

1-[3-((1R)-1-Hydroxyethyl)(3S,4S)-4-(3-cyclopentyloxy-4-methoxyphenyl)-3-methylpyrrolidinyl]-2-hydroxyethan-1-one Example 7 (35 mg, 75 μmol) was subjected to the debenzylation procedure of Intermediate 31 to give Example 8 (24 mg, 84%).

$^1$H NMR ($CD_3OD$, 400 MHz, mixture of rotomers) δ: 6.91–6.82 (m, 3H), 4.83 (c, 1H), 4.22 (c, 1H), 3.87–3.22 (m, 11H), 1.93–1.73 (m, 6H), 1.69–1.59 (m, 2H), 1.11 (dd, 3H), 0.75 (br s, 3H). LRMS (Electrospray, positive): Da/e 378.4 (m+1).

EXAMPLE 9

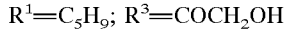N-{3-[3-((1R)-1-Hydroxyethyl)(3S,4S)-4-(3-cyclopentyloxy-4-methoxyphenyl)-3-methylpyrrolidinyl]-3-oxopropyl}(phenylmethoxy)carboxamide Prepared from Intermediate 68 via the acylation procedure of Example 7. The p-nitrophenylester of N-Cbz-beta-alanine was used in place of the acid chloride.

$^1$H NMR (400 MHz, $CDCl_3$, mixture of rotomers) δ: 7.38–7.28 (m, 5H), 6.92–6.83 (m, 3H), 5.06 (c, 2H), 4.86 (s, 2H), 4.84 (c, 1H), 3.81–3.27 (m, 10H), 2.59 (c, 2H), 1.98–1.69 (c, 6H), 1.64–1.57 (c, 2H), 1.09 (d, 3H), 0.73 (d, 3H). LRMS (Electrospray, positive): Da/e 525.3 (m+1).

EXAMPLE 10

$R^1=C_5H_9$; $R^3=COCH_2CH_2NH_2$
1-[3-((1R)-1-Hydroxyethyl)(3S,4S)-4-(3-cyclopentyloxy-4-methoxyphenyl)-3-methylpyrrolidinyl]-3-amino-propan-1-one Prepared from Example 9 via the debenzylation procedure of Intermediate 31.

$^1$H NMR ($CD_3OD$, 400 MHz, mixture of rotomers) δ: 6.91–6.79 (m, 3H), 4.81 (c, 1H), 3.92–3.29 (m, 11H), 3.01 (br s, 2H), 2.61–2.58 (m, 2H), 1.95–1.73 (m, 6H), 1.68–1.58 (m, 2H), 1.10 (dd, 3H), 0.76 (d, 3H). LRMS (Electrospray, positive): Da/e 391.4 (m+1).

EXAMPLE 11

Phenylmethyl 4-[3-((1R)-1-hydroxyethyl)(3S,4S)-4-(3-cyclopentyloxy-4-methoxyphenyl)-3-methylpyrrolidinyl]-4-oxobutanoate Prepared from Intermediate 68 via the acylation procedure of Example 7.

$^1$H NMR (400 MHz, $CDCl_3$, mixture of rotomers) δ: 7.41–7.31 (m, 5H), 6.84–6.75 (m, 3H), 5.14 (d, 2H), 4.74 (c, 1H), 3.94–3.44 (m, 8H), 3.27 (d, 1H), 2.80–2.73 (m, 2H), 2.67–2.58 (m, 2H), 1.96–1.81 (m, 6H), 1.68–1.56 (m, 2H), 1.15 (dd, 3H), 0.75 (d, 3H). LRMS (Electrospray, positive): Da/e 510.3 (m+1).

EXAMPLE 12

$R^1=C_5H_9$; $R^3=COCH_2CH_2CO_2H$

4-[3-((1R)-1-Hydroxyethyl)(3S,4S)-4-(3-cyclopentyloxy-4-methoxyphenyl)-3-methylpyrrolidinyl]-4-oxo-butanoic acid Prepared from Example 11 via the debenzylation procedure of Intermediate 31.

$^1$H NMR (400 MHz, $CDCl_3$, mixture of rotomers) δ: 6.80–6.72 (m, 3H), 4.74 (c, 1H), 3.98–3.54 (m, 10H), 3.40 (d, 1H), 3.24 (d, 1H), 2.69 (c, 2H), 1.95–1.74 (m, 6H), 1.69–1.51 (m, 2H), 1.14 (dd, 3H), 0.74 (d, 3H). LRMS (Electrospray, positive): Da/e 420.3 (m+1).

EXAMPLE 13

N-{2-[3-((1R)-1-Hydroxyethyl)(3S,4S)-4-(3-cyclopentyloxy-4-methoxyphenyl)-3-methylpyrrolidinyl]-2-oxoethyl}(phenylmethoxy)carboxamide Prepared from Intermediate 68 via the acylation procedure of Example 7. The p-nitrophenylester of N-Cbz-glycine was used in place of the acid chloride.

$^1$H NMR (400 MHz, $CDCl_3$, mixture of rotomers) δ: 7.40–7.25 (m, 5H), 6.92–6.81 (m, 3H), 5.11 (s, 2H), 4.87 (s, 2H), 4.82 (c, 1H), 4.11–3.28 (m, 9H), 1.95–1.70 (m, 6H), 1.65–1.55 (m, 2H), 1.10 (br s, 3H), 0.76 (br s, 3H). LRMS (Electrospray, positive): Da/e 511.6 (m+1).

EXAMPLE 14

$R^1=C_5H_9$; $R^3=COCH_2NH_2$

1-[3-((1R)-1-Hydroxyethyl)(3S,4S)-4-(3-cyclopentyloxy-4-methoxyphenyl)-3-methylpyrrolidinyl]-2-amino-ethan-1-one Prepared from Example 13 via the debenzylation procedure of Intermediate 31.

$^1$H NMR (CD$_3$OD, 400 MHz, mixture of rotomers) δ: 6.91–6.82 (m, 3H), 4.80 (c, 1H), 3.91–3.28 (m, 11H), 1.90–1.75 (m, 6H), 1.66–1.57 (m, 2H), 1.09 (dd, 3H), 0.74 (d, 3H). LRMS (Electrospray, positive): Da/e 377.2 (m+1).

EXAMPLE 15

$R^1=C_5H_9$; $R^3=CO$-4-Methyl-piperazine 3-((1R)-1-Hydroxyethyl)(3S,4S)-4-(3-cyclopentyloxy-4-methoxyphenyl)-3-methylpyrrolidinyl-4-methyl-piperazinyl ketone Intermediate 68 (30.2 mg, 94 mmol) was dissolved in 1,2-dichloroethane (400 μL) and cooled to 0° C., then carbonyl diimidazole (16 mg, 94 μmol) was added. The reaction was stirred at 0° C. for 1.5 hours, followed by the addition of 1-methylpiperazine (21 μL, 180 μmol). The solution was heated to 80° C. for 60 hours. After cooling, the reaction mixture was diluted with CH$_2$Cl$_2$ and washed three times with 6% NaHCO$_3$, dried over Na$_2$SO$_4$ and concentrated in vacuo. The residue was chromatographed on SiO$_2$ with EtOAc (15.5 mg).

$^1$H NMR (400 MHz, CDCl$_3$, mixture of rotomers) δ: 6.83–6.78 (m, 3H), 4.76 (c, 1H), 4.06–3.77 (m, 18H), 3.61 (q, 1H), 3.39 (br s, 1H), 1.93–1.78 (m, 6H), 1.63–1.57 (m, 2H), 1.15 (br s, 3H), 0.81 (br s, 3H). LRMS (Electrospray, positive): Da/e 446.4 (m+1).

EXAMPLE 16

$R^1=C_5H_9$; $R^3=CO$—N-morpholine 3-((1R)-1-Hydroxyethyl)(3S,4S)-4-(3-cyclopentyloxy-4-methoxyphenyl)-3-methylpyrrolidinyl morpholin-4-yl ketone Prepared from Intermediate 68 using morpholine and carbonyldiimidazole as a coupling reagent by the procedure set forth in Example 15.

$^1$H NMR (400 MHz, CDCl$_3$, mixture of rotomers) δ: 6.84–6.77 (m, 3H), 4.76 (c, 1H), 3.88–3.52 (m, 12H), 3.41 (dd, 1H), 3.38 (dd, 1H), 3.28 (dd, 1H), 3.25 (dd, 1H), 3.10 (d, 1H), 1.95–1.81 (m, 6H), 1.62–1.54 (m, 2H), 1.15 (d, 3H), 0.75 (s, 3H). LRMS (Electrospray, positive): Da/e 433.3 (m+1).

EXAMPLE 17

$R^1=C_5H_9$; $R^3=COCH_2O$-Menthol; (1S)-carbinol isomer

1-[3-((1S)-1-Hydroxyethyl)(3S,4S)-4-(3-cyclopentyloxy-4-methoxyphenyl)-3-methylpyrrolidinyl]-2-[(2S,1R,5R)-5-methyl-2-(methylethyl)cyclohexyloxy]-ethan-1-one Prepared from the S-carbinol isomer Intermediate 69 by the Hunig's base mediated acylation procedure of Intermediate 69.

$^1$H NMR (400 MHz, CDCl$_3$, mixture of rotomers) δ: 6.82–6.75 (m, 3H), 4.74 (c, 1H), 4.19 (dd, 1H), 4.04 (dd, 1H), 3.92–3.76 (m, 5H), 3.47–3.19 (m, 5H), 2.26 (c, 1H), 2.13 (c, 1H), 1.94–1.80 (m, 6H), 1.65–1.53 (m, 4H), 1.51–1.19 (m, 4H), 1.14 (d, 3H), 0.95–0.84 (m, 9H), 0.79 (d, 3H). LRMS (Electrospray, positive): Da/e 516.3 (m+1).

EXAMPLE 18

$R^1=C_5H_9$; $R^3=CO$-4-(2-methylthiazole)

3-((1R)-1-Hydroxyethyl)(3S,4S)-4-(3-cyclopentyloxy-4-methoxyphenyl)-3-methylpyrrolidinyl 2-methyl-(1,3-thiazol-4-yl)ketone Prepared from Intermediate 68 via the EDCI coupling procedure of Example 27 from 2-methyl-1,3-thiazole-4-carboxylic acid.

$^1$H NMR (CD$_3$OD, 400 MHz, mixture of rotomers) δ: 7.98 (dd, 1H), 6.92–6.82 (m, 3H), 4.84 (c, 1H), 4.27 (t, 0.5H), 4.16 (t, 0.5H), 4.08 (t, 0.5H), 3.96 (d, 0.5H), 3.85–3.4 (m, 7H), 2.72 (dd, 3H), 1.88–1.72 (m, 6H), 1.68–1.56 (m, 2H), 1.14 (dd, 1.5H), 1.08 (dd, 1.5H), 0.82 (d, 1.5H), 0.73 (d, 1.5H). LRMS (Electrospray, positive): Da/e 445.4 (m+1).

EXAMPLE 19

$R^1=C_5H_9$; $R^3=SO_2$-3-pyridyl

3-{[3-((1R)-1-Hydroxyethyl)(3S,4S)-4-(3-cyclopentyloxy-4-methoxyphenyl)-3-methylpyrrolidinyl]sulfonyl}-pyridine To a stirred solution of Intermediate 68 (32 mg, 0.1 mmol) in dioxane (0.3 mL) were added, successively, aqueous K$_2$CO$_3$ (0.6 mL of 0.65 M, 4 eq.) and a solution of the R$^3$-sulfonyl chloride (26 mg, 0.12 mmol) in dioxane (0.3 mL) at room temperature. The resulting solution was allowed to stir at room temperature for 2 hours. The reaction was diluted with 1:1 hexanes:EtOAc (30 mL) and washed successively with water (20 mL) and brine (20 mL), then dried (MgSO$_4$), filtered, and concentrated in vacuo to provide Example 19 as a slightly orange foam (36 mg, 78%).

$^1$H NMR (400 MHz, CDCl$_3$) δ: 9.11 (d, 1H, J=2.2 Hz), 8.83 (dd, 1H, J=1.6, 4.8 Hz), 8.17 (ddd, 1H, J=1.5, 2.4, 8.1 Hz), 7.50 (ddd, 1H, J=0.8, 4.9, 8.0 Hz), 6.74 (d, 1H, J=8.5 Hz), 6.68 (d, 1H, J=2.1 Hz), 6.62 (dd, 1H, J=2.1, 8.3 Hz), 4.70 (c, 1H), 3.80 (s, 3H), 3.66–3.62 (m, 2H), 3.51–3.43 (m, 3H), 3.24 (d, 1H, J=13.3 Hz), 1.91–1.62 (m, 6H), 1.60–1.55 (m, 2H), 1.08 (d, 3H, J=6.4 Hz), 0.62 (s, 3H). LRMS (Electrospray, positive): Da/e 461.2 (m+1).

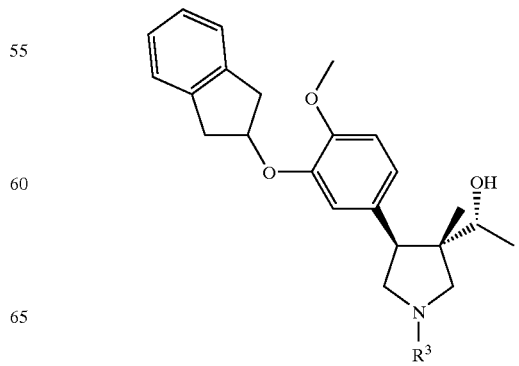

EXAMPLE 20

R¹=2-indanyl; R³=COCH$_2$OCH$_2$Ph

1-[3-((1R)-1-Hydroxyethyl)(3S,4S)-4-(3-indan-2-yl-oxy-4-methoxyphenyl)-3-methylpyrrolidinyl]-2-(phenylmethoxy)ethan-1-one Prepared from Intermediate 51 (50 mg, 0.14 mmol) by the Hunig's base acylation procedure of Intermediate 74 using benzyloxyacetyl chloride (22.5 µL, 0.14 mmol) to provide Example 20 as a clear oil (48 mg, 68%).

$^1$H NMR (400 MHz, CDCl$_3$, mixture of rotomers) δ: 7.41–7.16 (m, 9H), 6.84–6.79 (m, 3H), 5.17 (c, 1H), 4.66 (d, 2H), 4.19–4.11 (m, 2H), 3.96 (dd, 0.5H), 3.83–3.54 (m, 7H), 3.47 (d, 0.5H), 3.38–3.29 (m, 2H), 3.24–3.17 (m, 3H), 1.57 (br t, 1H), 1.15 (dd, 3H), 0.75 (s, 3H). LRMS (Electrospray, positive): Da/e 516.8 (m+1).

EXAMPLE 21

R¹=2-indanyl; R³=COCH$_2$OH

1-[3-((1R)-1-Hydroxyethyl)(3S,4S)-4-(3-indan-2-yl-oxy-4-methoxyphenyl)-3-methylpyrrolidinyl]-2-hydroxyethan-1-one Prepared from Example 20 via the debenzylation procedure of Intermediate 31.

$^1$H NMR (CD$_3$OD, 400 MHz, mixture of rotomers) δ: 7.24–7.18 (m, 2H), 7.14–7.12 (m, 2H), 6.92–6.86 (m, 3H), 5.20 (c, 1H), 4.27–4.14 (m, 2H), 3.90–3.50 (m, 6H), 3.41 (d, 1H), 3.34–3.24 (m, 4H), 3.13–3.08 (m, 2H), 1.12 (dd, 3H), 0.77 (br s, 3H). LRMS (Electrospray, positive): Da/e 426.5 (m+1).

EXAMPLE 22

R¹=2-indanyl; R³=COCO$_2$CH$_3$

Methyl 2-[3-((1R)-1-hydroxyethyl)(3S,4S)-4-(3-indan-2-yloxy-4-methoxyphenyl)-3-methylpyrrolidinyl]-2-oxoacetate Prepared from Intermediate 51 and methyl oxalyl chloride via the Hunig's base coupling procedure of Intermediate 74.

$^1$H NMR (400 MHz, CDCl$_3$, mixture of rotomers) δ: 6.82–6.75 (m, 3H), 4.74 (c, 1H), 4.01 (d, 1H), 3.98–3.56 (m, 10H), 3.50 (dd, 1H), 1.93–1.84 (m, 6H), 1.64–1.56 (m, 2H), 1.45 (dd, 1H), 1.16 (dd, 3H), 0.79 (s, 1.5H), 0.75 (s, 1.5H). LRMS (Electrospray, positive): Da/e 406.2 (m+1).

EXAMPLE 23

R¹=2-indanyl; R³=COC(CH$_3$)2N(H)CO$_2$CH$_2$Ph

N-{2-[3-((1R)-1-Hydroxyethyl)(3S,4S)-4-(3-indan-2-yloxy-4-methoxyphenyl)-3-methylpyrrolidinyl]-1,1-dimethyl-2-oxoethyl}(phenylmethoxy)carboxamide PyBrOP Coupling Procedure To a stirred solution of bromo-tris-pyrrolidino-phosphonium hexafluorophosphate (PyBrOP, 70 mg, 0.15 mmol), N-carbobenzyloxy-2-methylalanine (35.5 mg, 0.15 mmol), and Hunig's base (78 µL, 0.45 mmol) in dry dimethylformamide (1 mL) was added Intermediate 51 (50 mg, 0.14 mmol) at room temperature under a nitrogen atmosphere. The resulting solution was allowed to stir at room temperature for 16 hours, then heated to 70° C. for 5 hours. The reaction was allowed to cool to room temperature, then concentrated in vacuo. The residue was purified via radial chromatography (1 mm plate with 3% MeOH in CH$_2$Cl$_2$) to provide Example 23 as a white foam (20 mg, 24%).

$^1$H NMR (400 MHz, CDCl$_3$, mixture of rotomers) δ: 7.43–7.15 (m, 9H), 6.82–6.62 (m, 3H), 5.64 (br s, 0.5H), 5.51 (br s, 0.5H), 5.15–5.08 (m, 3H), 3.97–3.15 (m, 13H), 1.58 (br s, 6H), 1.13 (br d, 3H), 0.68 (br s, 3H). LRMS (Electrospray, positive): Da/e 604.9 (m+18).

EXAMPLE 24

R¹=2-indanyl; R³=COC(CH$_3$)$_2$NH$_2$

1-[3-((1R)-1-Hydroxyethyl)(3S,4S)-4-(3-indan-2-yl-oxy-4-methoxyphenyl)-3-methylpyrrolidinyl]-2-amino-2-methylpropan-1-one Prepared from Example 23 via the debenzylation procedure of Intermediate 31.

$^1$H NMR (CD$_3$OD, 400 MHz, mixture of rotomers) δ: 7.21–7.16 (m, 2H), 7.15–7.12 (m, 2H), 6.94–6.87 (m, 3H), 5.22 (c, 1H), 4.05 (d, 1H), 3.88 (c, 1H), 3.77–3.69 (m, 4H), 3.60–3.52 (c, 2H), 3.40–3.29 (c, 2H), 3.22 (q, 1H), 3.13–3.09 (c, 2H), 1.37 (d, 6H), 1.13 (br s, 3H), 0.80 (s, 3H). LRMS (Electrospray, positive): Da/e 453.5 (m+1).

EXAMPLE 25

R¹=2-indanyl; R³=CO$_2$CH$_3$

Methyl 3-((1R)-1-hydroxyethyl)(3S,4S)-4-(3-indan-2-yloxy-4-methoxyphenyl)-3-methylpyrrolidinecarboxylate Prepared from Intermediate 51 via the Hunig's base mediated acylation procedure of Intermediate 74 using methyl chloroformate.

$^1$H NMR (400 MHz, CDCl$_3$, mixture of rotomers) δ: 7.24–7.16 (m, 4H), 6.86–6.82 (m, 3H), 5.18 (c, 1H), 3.85–3.56 (m, 8H), 3.38–3.30 (m, 3H), 3.25–3.19 (m, 3H), 1.51 (d, 0.5H), 1.47 (d, 0.5H), 1.16 (t, 3H), 0.77 (s, 3H). LRMS (Electrospray, positive): Da/e 426.5 (m+1), 443.3 (m+18).

EXAMPLE 26

R¹=2-indanyl; R³=COCH$_2$C(CH$_3$)$_2$CO$_2$H

4-[3-((1R)-1-Hydroxyethyl)(3S,4S)-4-(3-indan-2-yloxy-4-methoxyphenyl)-3-methylpyrrolidinyl]-2,2-dimethyl-4-oxobutanoic acid A thick walled glass tube fitted with a threaded cap was charged with Intermediate 51 (20 mg, 0.05 mmol) and 2,2-dimethylsuccinic anhydride (25.8 mg, 0.05 mmol). The tube was sealed, then heated at 150° C. for 30 minutes. The reaction mixture was allowed to cool to room temperature to provide Example 26 (containing about 15–20% of the other regioisomer) as a brown solid (22 mg, 82%).

$^{1}$H NMR (CD$_{3}$OD, 400 MHz, mixture of rotomers) δ: 7.22–7.20 (m, 2H), 7.15–7.12 (m, 2H), 6.96–6.85 (m, 3H), 5.23 (c, 1H), 3.92–3.49 (m, 7H), 3.37–3.28 (m, 4H), 3.13–3.09 (m, 2H), 2.73–2.55 (m, 2H), 1.30 (br s, 6H), 1.12 (t, 3H), 0.76 (d, 3H). LRMS (Electrospray, negative): Da/e 494.5 (m−1).

EXAMPLE 27

R$^{1}$=2-indanyl; R$^{3}$=CO-4-(2-methylthiazole)

3-((1R)-1-Hydroxyethyl)(3S,4S)-4-(3-indan-2-yloxy-4-methoxyphenyl)-3-methylpyrrolidinyl 2-methyl(1,3-thiazol-4-yl) ketone EDCI Coupling Procedure To a stirred solution of 1-(3-dimethylaminopropyl)-3-ethylcarbodiimide hydrochloride (42.3 mg, 0.214 mmol) in dry CH$_{2}$Cl$_{2}$ (1 mL) was added 2-methyl-1,3-thiazole-4-carboxylic acid (30.7 mg, 0.214 mmol) at room temperature under a nitrogen atmosphere. The resulting bright red mixture was allowed to stir for 1 hour, then Intermediate 51 (75 mg, 0.204 mmol) was added in one portion. After stirring at room temperature overnight, the reaction was concentrated at reduced pressure and the residue purified via radial chromatography (1 mm plate with 3% MeOH in CH$_{2}$Cl$_{2}$) to provide Example 27 as a clear film (21 mg, 20%).

$^{1}$H NMR (400 MHz, CDCl$_{3}$; mixture of rotomers) δ: 7.91 (s, 0.5H), 7.88 (s, 0.5H), 7.25–7.20 (m, 2H), 7.18–7.16 (m, 2H), 6.90–6.82 (m, 3H), 5.19 (c, 1H), 4.33 (dd, 0.5H), 4.23 (t, 0.5H), 4.15 (d, 0.5H), 4.10 (dd, 0.5H), 3.99 (t, 0.5H), 3.85 (d, 0.5H), 3.81 (s, 3H), 3.77–3.58 (m, 3H), 3.38–3.31 (m, 2H), 3.24–3.20 (m, 2H), 2.74 (s, 1.5H), 2.71 (s, 1.5H), 1.93 (s, 0.5H), 1.61 (d, 0.5H), 1.22 (d, 1.5H), 1.18 (d, 1.5H), 0.86 (s, 1.5H), 0.75 (s, 1.5H). LRMS (Electrospray, positive): Da/e 493.6 (m+1).

EXAMPLE 28

R$^{1}$=2-indanyl; R$^{3}$=CO-3-tetrahydrofuranyl 3-((1R)-1-Hydroxyethyl)(4S,3R)-4-(3-indan-2-yloxy-4-methoxyphenyl)-3-methylcyclopentyl oxolan-3-yl ketone (mixture of 2 diastereomers at the tetrahydrofuranyl point of attachment)

Prepared from Intermediate 51 via the Hunig's base coupling procedure of Intermediate 74 using tetrahydrofuran-3-carbonyl chloride.

$^{1}$H NMR (400 MHz, CDCl$_{3}$, mixture of rotomers) δ: 7.40–7.20 (m, 2H), 7.19–7.16 (m, 2H), 6.86–6.83 (m, 3H), 5.18 (c, 1H), 4.15–4.04 (m, 1H), 3.98–3.15 (m, 13H), 2.31–2.09 (m, 2H), 1.75 (br s, 1H), 1.26 (t, 1.5H), 1.17 (t, 1.5H), 0.80 (d, 1.5H), 0.78 (s, 1.5H). LRMS (Electrospray, positive): Da/e 466.3 (m+1).

EXAMPLE 29

R$^{1}$=2-indanyl; R$^{3}$=COCH$_{2}$N(H)CO$_{2}$CH$_{2}$Ph

N-{2-[3-((1R)-1-Hydroxyethyl)(3S,4S)-4-(3-indan-2-yloxy-4-methoxyphenyl)-3-methylpyrrolidinyl]-2-oxoethyl}(phenylmethoxy)carboxamide Prepared from Intermediate 51 via the PyBrOP coupling procedure of Example 23 using N-benzyloxycarbonyl glycine.

$^{1}$H NMR (CD$_{3}$OD, 400 MHz, mixture of rotomers) δ: 7.35–7.20 (m, 9H), 6.91–6.88 (m, 3H), 5.22 (br s, 1H), 5.10 (s, 2H), 4.07–3.09 (m, 15H), 1.13 (t, 3H), 0.78 (s, 3H).

EXAMPLE 30

R$^{1}$=2-indanyl; R$^{3}$=COCH$_{2}$NH$_{2}$

1-[3-((1R)-1-Hydroxyethyl)(3S,4S)-4-(3-indan-2-yloxy-4-methoxyphenyl)-3-methylpyrrolidinyl]-2-aminoethan-1-one Prepared from Example 29 via the debenzylation procedure of Intermediate 31.

$^{1}$H NMR (400 MHz, CDCl$_{3}$, mixture of rotomers) δ: 7.22–7.19 (m, 2H), 7.18–7.15 (m, 2H), 6.84 (d, 1H), 6.81 (d, 2H), 5.17 (c, 1H), 3.96 (dd, 0.5H), 3.81–3.43 (m, 9H), 3.37–3.30 (m, 1.5H), 3.23–3.13 (m, 2H), 2.99 (br s, 2H), 1.15 (t, 3H), 0.75 (d, 3H). LRMS (Electrospray, positive): Da/e 425.5(m+1).

EXAMPLE 31

R$^{1}$=2-indanyl; R$^{3}$=2-pyridyl (1R)-1-[(3S,4S)-4-(3-Indan-2-yloxy-4-methoxyphenyl)-3-methyl-1-(2-pyridyl)pyrrolidin-3-yl]ethan-1-ol Aryl Bromide Coupling Procedure To a stirred mixture of Intermediate 51 (115 mg, 0.31 mmol) and K$_{2}$CO$_{3}$ (173 mg, 1.2 mmol) in dry DMF (2 mL) was added 2-bromopyridine (0.12 mL, 1.2 mmol) via syringe at room temperature under a nitrogen atmosphere. The resulting mixture was heated at 90° C. for 22 hours, then allowed to cool to room temperature. The reaction was diluted with water (60 mL), and extracted with EtOAc (3×30 mL). The combined organic extracts were washed with brine, dried (Na$_{2}$SO$_{4}$), filtered, and concentrated in vacuo. The residue was purified via flash chromatography on silica gel (100% EtOAc) to provide Example 31 (73.4 mg, 53%).

$^{1}$H NMR (400 MHz, CDCl$_{3}$) δ: 8.18 (ddd, 1H), 7.45 (ddd, 1H), 7.26–7.21 (m, 2H), 7.19–7.16 (m, 2H), 6.92–6.88 (m, 2H), 6.83 (d, 1H), 6.54 (ddd, 1H), 6.40 (d, 1H), 5.17 (c, 1H), 3.86–3.78 (m, 5H), 3.70 (d, 1H), 3.67 (d, 1H), 3.38–3.30 (m, 3H). LRMS (Electrospray, positive): Da/e 445.4 (m+1).

EXAMPLE 32

R$^{1}$=2-indanyl; R$^{3}$=3-pyridyl (1R)-1-[(3S,4S)-4-(3-Indan-2-yloxy-4-methoxyphenyl)-3-methyl-1-(3-pyridyl)pyrrolidin-3-yl]ethan-1-ol Palladium-Catalyzed Coupling Procedure To a stirred solution of Intermediate 51 (79.3 mg, 0.22 mmol) and sodium t-butoxide (29 mg, 0.31 mmol) in dry toluene (3 mL) was added, sequentially, 3-bromopyridine (22.9 mL, 0.24 mmol), tris(dibenzylideneacetone)dipalladium(0) (3.9 mg, cat.), and (R)-(+)-1,1'-bi-2-naphthol (5.4 mg, cat.) at room temperature under a nitrogen atmosphere.

89

The resulting mixture was heated at 80° C. for 3 hours, then allowed to cool to room temperature. The reaction then was diluted with EtOAc (40 mL), washed with brine, dried (Na$_2$SO$_4$), filtered, and concentrated in vacuo. The residue was purified via flash chromatography on silica gel (40% EtOAc in hexanes) to provide Example 32 (72.1 mg, 75%).

$^1$H NMR (400 MHz, CDCl$_3$) δ: 7.98 (d, 1H), 7.91 (d, 1H), 7.24–7.15 (m, 4H), 7.11 (dd, 1H), 6.90–6.82 (m, 4H), 5.15 (c, 1H), 3.81–3.72 (m, 4H), 3.70–3.62 (m, 4H), 3.35–3.11 (m, 5H), 1.24 (d, 3H), 0.84 (s, 3H). LRMS (Electrospray, positive): Da/e 445.3 (m+1).

EXAMPLE 33

R$^1$=2-indanyl; R$^3$=2-pyrimidyl (1R)-1-[(3S,4S)-4-(3-Indan-2-yloxy-4-methoxyphenyl)-3-methyl-1-pyrimidin-2-ylpyrrolidin-3-yl] ethan-1-ol Prepared from Intermediate 51 via the aryl bromide coupling procedure of Example 31.

$^1$H NMR (400 MHz, CDCl$_3$) δ: 8.34 (dd, 2H), 7.24–7.18 (m, 2H), 7.16 (dd, 2H), 6.94–6.84 (m, 2H), 6.82 (c, 1H), 6.48 (t, 1H), 5.16 (c, 1H), 4.12–3.75 (m, 7H), 3.64 (br d, 1H), 3.52 (d, 1H), 3.36 (d, 1H), 3.32 (d, 1H), 3.24 (t, 1H), 3.20 (t, 1H), 1.23 (d, 3H), 0.83 (s, 3H). LRMS (Electrospray, positive): Da/e 446.4 (m+1).

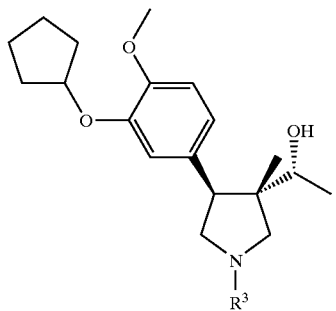

EXAMPLE 34

R$^1$=C$_5$H$_9$; R$^3$=2-pyridyl (1R)-1-[(3S,4S)-4-(3-Cyclopentyloxy-4-methoxyphenyl)-3-methyl-1-(2-pyridyl)pyrrolidin-3-yl] ethan-1-ol Prepared from Intermediate 68 via the aryl bromide coupling procedure of Example 31.

$^1$H NMR (400 MHz, CDCl$_3$) δ: 8.18 (ddd, 1H), 7.46 (ddd, 1H), 6.89–6.82 (m, 3H), 6.54 (ddd, 1H), 6.40 (d, 1H), 4.75 (c, 1H), 3.92–3.65 (m, 8H), 3.36 (d, 1H), 1.94–1.80 (m, 6H), 1.66–1.55 (m, 2H). LRMS (Electrospray, positive): Da/e 397.4 (m+1).

EXAMPLE 35

R$^1$=C$_5$H$_9$; R$^3$=3-pyridyl (1R)-1-[(3S,4S)-4-(3-Cyclopentyloxy-4-methoxyphenyl)-3-methyl-1-(3-pyridyl)pyrrolidin-3-yl] ethan-1-ol Prepared from Intermediate 68 via the palladium catalyzed coupling procedure of Example 32.

$^1$H NMR (400 MHz, CDCl$_3$) δ: 8.00 (d, 1H), 7.93 (d, 1H), 7.12 (dd, 1H), 6.86–6.78 (m, 4H), 4.73 (c, 1H) 3.85–3.59 (m, 8H) 3.12 (d, 1H), 1.90–1.79 (m, 6H) 1.60–1.54 (m, 2H), 1.22 (d, 3H), 0.82 (s, 3H). LRMS (Electrospray, positive): Da/e 397.2 (m+1).

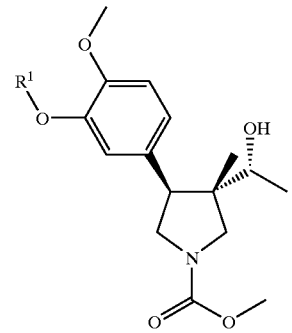

EXAMPLE 36

R$^1$=(4-PhO)-Ph; R$^3$=CO$_2$CH$_3$

Methyl 3-((1R)-1-hydroxyethyl)(3S,4S)-4-[4-methoxy-3-(4-phenoxyphenoxy)phenyl]-3-methylpyrrolidinecarboxylate Cryptand Etherification Procedure To a stirred suspension of sodium hydride (16 mg of a 60% dispersion in mineral oil, 0.40 mmol) in dry anisole (2 mL) was added Intermediate 74 (100 mg, 0.32 mmol), portionwise, over 5 minutes with H$_2$ evolution, at room temperature under a nitrogen atmosphere. After stirring for 30 minutes, tris[2-(2-methoxyethoxy)ethyl]amine (10 mL, 0.03 mmol), copper (I) chloride (10 mg, 0.10 mmol), and 4-bromobiphenyl ether were added, and the resulting mixture heated at reflux for 20 hours. The anisole then was removed via vacuum distillation. The residue dissolved in EtOAc (25 mL), and filtered through GF/F filter paper. The filtrate was washed with 1N aq. HCl (20 mL), dried (Na$_2$SO$_4$), filtered, and concentrated in vacuo. The residue was purified via radial chromatography (2 mm silica plate with 1:1 hexanes:EtOAc) to provide Example 36 as a tan oil (40 mg, 26%).

$^1$H NMR (400 MHz, CDCl$_3$; mixture of rotomers) δ: 7.30 (dd, 2H), 7.09–6.86 (m, 10H), 3.88–3.49 (m, 11H), 3.28 (d, 0.5H), 3.19 (d, 0.5H), 1.93 (br s, 0.5H) 1.83 (br s, 0.5H), 1.12 (dd, 3H), 0.71 (br s, 3H). LRMS (Electrospray, positive): Da/e 478.2 (m+1).

EXAMPLE 37

R$^1$=(4-PhO)-Ph; R$^3$=CO$_2$CH$_3$: Other Carbinol Diastereomer

Methyl 3-((1S)-1-hydroxyethyl)(3S,4S)-4-[4-methoxy-3-(4-phenoxyphenoxy)phenyl]-3-methylpyrrolidinecarboxylate Prepared from the (1S)-carbinol isomer Intermediate 75 via the cryptand etherification procedure of Example 36.

$^1$H NMR (400 MHz, CDCl$_3$, mixture of rotomers) δ: 7.32 (t, 2H), 7.07 (dt, 1H), 7.03–6.74 (m, 9H), 3.91–3.55 (m, 9H), 3.35–3.17 (m, 3H), 2.16 (d, 0.5H), 1.38 (br s, 0.5H), 1.12 (d, 3H), 0.85 (s, 3H). LRMS (Electrospray, positive): Da/e 478.2 (m+1).

EXAMPLE 38

R$^1$=(4-Ph)-Ph; R$^3$=CO$_2$CH$_3$

Methyl 3-((1R)-1-hydroxyethyl)(3S,4S)-4-[4-methoxy-3-(4-phenylphenoxy)phenyl]-3-methylpyrrolidinecarboxylate Prepared from Intermediate 74 via the cryptand etherification procedure of Example 36.

$^1$H NMR (400 MHz, CDCl$_3$; mixture of rotomers) δ: 7.55 (d, 2H), 7.51 (d, 2H), 7.42 (t, 2H), 7.31 (t, 1H), 7.05 (dt, 1H), 6.98–6.92 (m, 4H), 3.87–3.54 (m, 11H), 3.29 (d, 0.5H), 3.19 (d, 0.5H), 1.64 (br s, 0.5H), 1.57 (br s, 0.5H), 1.14 (dd, 3H), 0.74 (s, 3H). LRMS (Electrospray, positive): Da/e 462.2 (m+1).

EXAMPLE 39

R$^1$=(4-Ph)-Ph; R$^3$=CO$_2$CH$_3$: Other Carbinol Diastereomer

Methyl 3-((1S)-1-hydroxyethyl)(3S,4S)-4-[4-methoxy-3-(4-phenylphenoxy)phenyl]-3-methylpyrrolidinecarboxylate Prepared from the (1S)-carbinol isomer Intermediate. 75 via the cryptand etherification procedure of EXAMPLE 36.

$^1$H NMR (400 MHz, CDCl$_3$, mixture of rotomers) δ: 7.56 (d, 2H), 7.52 (dt, 2H), 7.42 (t, 2H), 7.32 (t, 1H), 7.10–6.94 (m, 5H), 3.93–3.58 (m, 9H), 3.38–3.18 (m, 3H), 1.13 (d, 3H), 0.88 (s, 3H) LRMS (Electrospray, positive): Da/e 462.2 (m+1).

EXAMPLE 40

R$^1$=Ph; R$^3$=CO$_2$CH$_3$

Methyl 3-((1R)-1-hydroxyethyl)(3S,4S)-4-(4-methoxy-3-phenoxyphenyl)-3-methylpyrrolidinecarboxylate Prepared from Intermediate 74 via the cryptand etherification procedure of Example 36.

$^1$H NMR (400 MHz, CDCl$_3$, mixture of rotomers) δ: 7.32–7.26 (m, 3H), 7.02 (t, 2H), 6.94–6.88 (m, 3H), 3.85–3.49 (m, 11H), 3.27 (d, 0.5H), 3.18 (d, 0.5H), 1.12 (t, 3H), 0.71 (s, 3H). LRMS (Electrospray, positive): Da/e 386.3 (m+1).

EXAMPLE 41

R$^1$=Ph; R$^3$=CO$_2$CH$_3$: Other Carbinol Diastereomer

Methyl 3-((1S)-1-hydroxyethyl)(3S,4S)-4-(4-methoxy-3-phenoxyphenyl)-3-methylpyrrolidinecarboxylate Prepared from the (1S)-carbinol isomer Intermediate 75 via the cryptand etherification procedure of Example 36.

$^1$H NMR (400 MHz, CDCl$_3$, mixture of rotomers) δ: 7.29 (t, 2H), 7.08–6.85 (m, 6H), 3.87–3.52 (m, 9H), 3.34–3.16 (m, 3H), 1.11 (d, 3H), 0.85 (s, 3H). LRMS (Electrospray, positive): Da/e 386.3 (m+1).

EXAMPLE 42

R$^1$=4-fluorophenyl; R$^3$=CO$_2$CH$_3$

Methyl 3-((1R)-1-hydroxyethyl)(3S,4S)-4-[3-(4-fluorophenoxy)-4-methoxyphenyl]-3-methylpyrrolidinecarboxylate Prepared from Intermediate 74 via the cryptand etherification procedure of Example 36.

$^1$H NMR (400 MHz, CDCl$_3$, mixture of rotomers) δ: 7.05–6.84 (m, 7H), 3.89–3.45 (m, 11H), 3.28 (d, 0.5H), 3.18 (d, 0.5H), 1.13 (t, 3H), 0.71 (br s, 3H) LRMS (Electrospray, positive): Da/e 404.4 (m+1).

EXAMPLE 43

R$^1$=CH$_2$C$_3$H$_5$; R$^3$=CO$_2$CH$_3$

Methyl 3-((1R)-1-hydroxyethyl)(3S,4S)-4-[3-(cyclopropylmethoxy)-4-methoxyphenyl]-3-methyl pyrrolidinecarboxylate K$_2$CO$_3$ Etherification Procedure To a stirred mixture of Intermediate 74 (50 mg, 0.16 mmol) and powdered K$_2$CO$_3$ (24.6 mg, 0.18 mmol) in dry DMF (1 mL) was added bromomethylcyclopropane (16.5 µL, 0.17 mmol) via syringe at room temperature under a nitrogen atmosphere. The resulting mixture was heated at 65° C. for 24 hours, then allowed to cool to room temperature. The reaction then was diluted with water (5 mL) and extracted with Et$_2$O (3×20 mL). The combined organic layers were dried (MgSO$_4$), filtered, and concentrated in vacuo. The residue was purified via radial chromatography (1 mm silica plate with 30% EtOAc in hexanes) to provide Example 43 as a clear oil (30 mg, 51%).

$^1$H NMR (400 MHz, CDCl$_3$; mixture of rotomers) δ: 6.84–6.75 (m, 3H), 3.94–3.54 (m, 13H), 3.29 (d, 0.5H), 3.21 (d, 0.5H), 1.72 (br s, 0.5H), 1.65 (br s, 0.5H), 1.30 (c, 1H), 1.13 (t, 3H), 0.73 (s, 3H), 0.61 (c, 2H), 0.34 (c, 2H) LRMS (Electrospray, positive): Da/e 364.3 (m+1).

EXAMPLE 44

R$^1$=CH$_2$C$_3$H$_5$; R$^3$=CO$_2$CH$_3$ Diastereomer

Methyl 3-((1S)-1-hydroxyethyl)(3S,4S)-4-[3-(cyclopropylmethoxy)-4-methoxyphenyl]-3-methylpyrrolidinecarboxylate Prepared from (1S)-carbinol isomer Intermediate 75 via the K$_2$CO$_3$ etherification procedure of Example 43 using bromomethylcyclopropane.

¹H NMR (400 MHz, CDCl₃, mixture of rotomers) δ: 6.84–6.75 (m, 3H), 3.89–3.58 (m, 11H), 3.33–3.20 (m, 3H), 1.52 (br s, 1H), 1.31 (c, 1H), 1.11 (d, 3H) 0.89 (s, 3H), 0.62 (m, 2H), 0.33 (m, 2H) LRMS (Electrospray, positive): Da/e 364.3 (m+1).

EXAMPLE 45

R¹=2-thiazole; R³=CO₂CH₃

Methyl 3-((1R)-1-hydroxyethyl)(3S,4S)-4-(4-methoxy-3-(1,3-thiazol-2-yloxy)phenyl)-3-methylpyrrolidinecarboxylate Prepared from Intermediate 74 via the K₂CO₃ etherification procedure of Example 43 using 2-bromothiazole.
¹H NMR (400 MHz, CDCl₃, mixture of rotomers) δ: 7.24–7.12 (m, 3H), 6.96 (d, 1H), 6.75 (d, 1H), 3.89–3.52 (m, 11H), 3.29 (d, 0.5H), 3.20 (d, 0.5H), 1.74 (br s, 1H), 1.14 (t, 3H), 0.74 (s, 3H). LRMS (Electrospray, positive): Da/e 393.2 (m+1).

EXAMPLE 46

R¹=2-thiazole; R³=CO₂CH₃, Diastereomer

Methyl 3-((1S)-1-hydroxyethyl)(3S,4S)-4-(4-methoxy-3-(1,3-thiazol-2-yloxy)phenyl)-3-methylpyrrolidinecarboxylate Prepared from (1S)-carbino) isomers Intermediate 75 via the K₂CO₃ etherification procedure of Example 43.
¹H NMR (400 MHz, CDCl₃, mixture of rotomers) δ: 7.17 (d, 1H), 7.16 (d, 1H), 7.11 (dd, 1H), 6.97 (d, 1H), 6.75 (d, 1H), 3.86–3.59 (m, 9H), 3.42–3.19 (m, 3H), 1.52 (br s, 1H), 1.14 (d, 3H), 0.87 (s, 3H) LRMS (Electrospray, positive): Dale 393.2 (m+1).

EXAMPLE 47

R¹=2-(N-Methyl)benzimidazole; R³=CO₂CH₃

Methyl 3-((1R)-1-hydroxyethyl)(3S,4S)-4-(3-benzimidazol-2-yloxy-4-methoxyphenyl)-3-methylpyrrolidinecarboxylate Prepared from Intermediate 74 via the K₂CO₃ etherification procedure of Example 43 with 2-chloro-N-methylbenzimidazole.
¹H NMR (400 MHz, CDCl₃, mixture of rotomers) δ: 7.50 (d, 1H), 7.29–7.10 (m, 5H), 6.95 (d, 1H), 3.80–3.66 (m, 13H), 3.57 (t, 1H), 3.29 (d, 0.5H) 3.20 (d, 0.5H), 2.04 (br s, 1H), 1.13 (t, 3H), 0.77 (s, 3H). LRMS (Electrospray, positive): Da/e 440.2 (m+1).

EXAMPLE 48

R¹=2-(N-Methyl)benzimidazole; R³=CO₂CH₃: Diastereomer

Methyl 3-((1S)-1-hydroxyethyl)(3S,4S)-4-(3-benzimidazol-2-yloxy-4-methoxyphenyl)-3-methylpyrrolidinecarboxylate Prepared from the (1S)-carbinol isomer Intermediate 75 via the K₂CO₃ etherification procedure of Example 43 using 2-chloro-1-methyl-1H-benzimidazole.

¹H NMR (400 MHz, CDCl₃, mixture of rotomers) δ: 7.50 (d, 1H), 7.50 (d, 1H), 7.30–7.09 (m, 5H), 6.96 (d, 1H), 3.87–3.63 (m, 12H), 3.40–3.21 (m, 3H), 1.15 (d, 3H), 0.91 (s, 3H) LRMS (Electrospray, positive): Da/e 440.2 (m+1).

EXAMPLE 49

R¹=CH₂CH₂CH₂Ph; R³=CO₂CH₃

Methyl 3-((1R)-1-hydroxyethyl) (3S,4S)-4-[4-methoxy-3-(3-phenylpropoxy)phenyl]-3-methylpyrrolidinecarboxylate Prepared from Intermediate 74 via the K₂CO₃ etherification procedure of Example 43 using 3-phenylpropyl chloride.
¹H NMR (400 MHz, CDCl₃, mixture of rotomers) δ: 7.35–7.17 (m, 5H), 6.85–6.77 (m, 3H), 4.02 (dt, 2H), 3.90–3.52 (m, 11H), 3.30 (d, 0.5H), 3.21 (d, 0.5H), 2.82 (t, 2H), 2.14 (p, 2H), 1.54 (br s, 0.5H), 1.49 (br s, 0.5H), 1.13 (t, 3H), 0.72 (s, 3H).

EXAMPLE 50

R¹=CH₂CH₂CH₂Ph; R³=CO₂CH₃, Other Carbinol Diastereomer

Methyl 3-((1S)-1-hydroxyethyl)(3S,4S)-4-[4-methoxy-3-(3-phenylpropoxy)phenyl]-3-methylpyrrolidinecarboxylate Prepared from the (1S)-carbinol isomer Intermediate 75 via the K₂CO₃ etherification procedure of Example 43 using the (1S)-carbinol isomer of Intermediate 75.
¹H NMR (400 MHz, CDCl₃, mixture of rotomers) δ: 7.33–7.19 (m, 5H), 6.84–6.78 (m, 2H), 6.72 (br s, 1H), 4.01 (t, 2H), 3.90–3.56 (m, 9H), 3.34–3.23 (m, 3H), 2.82 (t, 2H), 2.15 (p, 2H), 1.11 (d, 3H), 0.89 (s, 3H).

EXAMPLE 51

R¹=CH₂CH₂CH₂CH₂Ph; R³=CO₂CH₃

Methyl 3-((1R)-1-hydroxyethyl)(3S,4S)-4-[4-methoxy-3-(4-phenylbutoxy)phenyl]-3-methylpyrrolidinecaboxylate Prepared from Intermediate 74 via the K₂CO₃ etherificaiton procedure of Example 43 using 1-chloro-4-phenylbutane.
¹H NMR (400 MHz, CDCl₃, mixture of rotomers) δ: 7.32–7.15 (m, 5H), 6.84–6.74 (m, 3H), 4.00 (t, 2H), 3.89–3.51 (m, 11H), 3.30 (d, 0.5H), 3.22 (d, 0.5H), 2.69 (t, 2H), 1.90–1.79 (m, 4H), 1.41 (dd, 1H), 1.13 (t, 3H), 0.73 (s, 3H)

EXAMPLE 52

R¹=CH₂CH₂CH₂CH₂Ph; R³=CO₂CH₃, Other Carbinol Diastereomer

Methyl 3-((1S)-1-hydroxyethyl)(3S,4S)-4-[4-methoxy-3-(4-phenylbutoxy)phenyl]-3-methylpyrrolidinecarboxylate Prepared from Intermediate 74 via the K₂CO₃ etherification procedure of Example 43 using 1-chloro-5-phenylpentane.

¹H NMR (400 MHz, CDCl₃, mixture of rotamers) δ: 7.32–7.16 (m, 5H), 6.83–6.70 (m, 3H), 3.99 (t, 2H), 3.90–3.58 (m, 9H), 3.34–3.21 (m, 3H), 2.69 (t, 2H), 1.90–1.77 (m, 4H), 1.45 (br s, 1H), 1.12 (d, 3H), 0.90 (s, 3H). LRMS (Electrospray, positive): Da/e 442.4 (m+1).

EXAMPLE 53

R¹=CH₂CH₂Ph; R³=CO₂CH₃

Methyl 3-((1R)-1-hydroxyethyl)(3S,4S)-4-[4-methoxy-3-(2-phenylethoxy)phenyl]-3-methylpyrrolidinecarboxylate Prepared from Intermediate 74 via the K₂CO₃ etherification procedure of Example 43 using 2-phenethyl bromide.

¹H NMR (400 MHz, CDCl₃, mixture of rotamers) δ: 7.39–7.23 (m, 5H), 6.84–6.78 (m, 3H), 4.20 (t, 2H), 3.87–3.52 (m, 11H), 3.30 (d, 0.5H), 3.21 (d, 0.5H), 3.15 (t, 2H), 1.13 (t, 3H), 0.73 (s, 3H). LRMS (Electrospray, positive): Da/e 414.3 (m+1).

EXAMPLE 54

R¹=CH₂CH₂Ph; R³=CO₂CH₃, Other Carbinol Diastereomer

Methyl 3-((1S)-1-hydroxyethyl)(3S,4S)-4-[4-methoxy-3-(2-phenylethoxy)phenyl]-3-methylpyrrolidinecarboxylate Prepared from the (1S)-carbinol isomer Intermediate 75 via the K₂CO₃ etherification procedure of Example 43.

¹H NMR (400 MHz, CDCl₃, mixture of rotamers) δ: 7.34–7.24 (m, 5H), 6.83 (d, 1H), 6.79 (dd, 1H), 6.73 (br s, 1H), 4.18 (t, 2H), 3.89–3.56 (m, 9H), 3.31–3.20 (m, 3H), 3.15 (t, 2H), 1.11 (d, 3H), 0.89 (s, 3H).

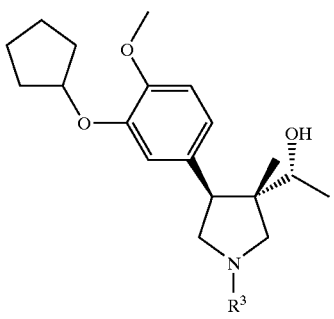

EXAMPLE 55

R¹=C₅H₉; R³=CH₂-2-pyridyl (1R)-1-[(3S,4S)-4-(3-Cyclopentyloxy-4-methoxyphenyl)-3-methyl-1-(2-pyridylmethyl)pyrrolidin-3-yl]ethan-1-ol Reductive Amination Procedure To a stirred solution of Intermediate 68 (32 mg, 0.1 mmol) and pyridine 2-carboxaldehyde (10 mL, 0.1 μmol) in dry 1,2-dichloroethane (0.3 mL) was added sodium triacetoxyborohydride (30 mg, 0.14 mmol) under a nitrogen atmosphere at room temperature. After stirring for 3 hours, the reaction was quenched with saturated aqueous NaHCO₃ (0.1 mL) and stirred for 5 minutes. The reaction was diluted with EtOAc (20 mL), washed with saturated aqueous NaHCO₃ (20 mL), and brine (20 mL), then dried (MgSO₄), filtered, and concentrated in vacuo to provide Example 55 as a yellow oil (40.4 mg, 98%).

¹H NMR (400 MHz, CDCl₃) δ: 8.54 (ddd, 1H), 7.68 (dt, 1H), 7.43 (d, 1H), 7.18 (ddd, 1H), 6.79–6.73 (m, 3H), 4.75 (c, 1H), 3.89–3.77 (m, 5H), 3.69 (q, 1H), 3.59 (t, 1H), 3.33 (t, 1H), 3.16 (d, 1H), 2.70 (t, 1H), 2.21 (d, 1H), 1.92–1.80 (m, 6H), 1.64–1.57 (m, 2H), 1.14 (d, 3H), 0.50 (s, 3H). LRMS (Electrospray, positive): Da/e 411.4 (m+1).

EXAMPLE 56

R¹=C₅H₉; R³=CH₂-3-pyridyl (1R)-1-[(3S,4S)-4-(3-Cyclopentyloxy-4-methoxyphenyl)-3-methyl-1-(3-pyridylmethyl)pyrrolidin-3-yl]ethan-1-ol Prepared from Intermediate 68 via the reductive amination procedure of Example 55 using pyridine-3-carboxaldehyde.

¹H NMR (400 MHz, CDCl₃) δ: 8.54 (d, 1H), 8.51 (dd, 1H), 7.68 (d, 1H), 7.26 (dd, 1H), 6.78–6.71 (m, 3H), 4.74 (c, 1H), 3.86–3.78 (m, 4H), 3.68 (q, 1H), 3.64 (d, 1H), 3.53 (t, 1H), 3.22 (t, 1H), 3.05 (d, 1H), 2.62 (t, 1H), 2.14 (d, 1H), 1.92–1.78 (m, 6H), 1.64–1.56 (m, 2H), 1.12 (d, 3H), 0.50 (s, 3H). LRMS (Electrospray, positive): Da/e 411.4 (m+1).

EXAMPLE 57

R¹=C₅H₉; R³=CH₂-4-pyridyl (1R)-1-[(3S,4S)-4-(3-Cyclopentyloxy-4-methoxyphenyl)-3-methyl-1-(4-pyridylmethyl)pyrrolidin-3-yl]ethan-1-ol Prepared from Intermediate 68 via the reductive amination procedure of Example 55 using pyridine-4-carboxaldehyde.

¹H NMR (400 MHz, CDCl₃) δ: 8.54 (d, 2H), 7.27 (d, 2H), 6.79–6.72 (m, 3H), 4.74 (c, 1H), 3.86–3.74 (m, 4H), 3.70 (q, 1H), 3.64 (d, 1H), 3.55 (t, 1H), 3.23 (t, 1H), 3.06 (d, 1H), 2.64 (t, 1H), 2.15 (d, 1H), 1.92–1.80 (m, 6H), 1.65–1.58 (m, 2H), 1.14 (d, 3H), 0.52 (s, 3H). LRMS (Electrospray, positive): Da/e 411.4 (m+1).

EXAMPLE 58

R¹=C₅H₉; R³=CH₂CH₂CO₂CH₂Ph

Phenylmethyl 3-[3-((1R)-1-hydroxyethyl) (3S,4S)-4-(3-cyclopentyloxy-4-methoxyphenyl)-3-methyl pyrrolidinyl]propanoate To a stirred solution of benzyl acrylate (19.4 mg, 0.12 mmol) in dry DMF (0.1 mL) was added Intermediate 68 (12.8 mg, 0.04 mmol) and powdered K₂CO₃ (26.5 mg, 0.18 mmol) under a nitrogen atmosphere. The resulting mixture was allowed to stir at 80° C. for 16 hours, then allowed to cool to room temperature. The reaction was diluted with $CH_2Cl_2$ (20 mL), washed with water, saturated aqueous $NaHCO_3$, and brine, then dried ($Na_2SO_4$), filtered, and concentrated in vacuo. The residue was purified via flash chromatography (2:1 EtOAc:hexanes on silica gel) to provide Example 58 (11.7 mg, 60%).

$^1$H NMR (400 MHz, $CDCl_3$) δ: 7.37–7.31 (m, 5H), 6.81–6.72 (m, 3H), 5.14 (q, 2H), 4.76 (c, 1H), 3.87–3.81 (m, 4H), 3.65 (q, 1H), 3.54 (t, 1H), 3.31 (t, 1H), 3.15 (d, 1H), 2.82 (dt, 2H), 2.62–2.54 (m, 3H), 2.08 (d, 1H), 1.91–1.81 (m, 6H), 1.66–1.56 (m, 2H), 1.15 (d, 3H), 0.48 (s, 3H). LRMS (Electrospray, positive): Da/e 482.3 (m+1).

EXAMPLE 59

$R^1=C_5H_9$; $R^3=CH_2CH_2CO_2H$

3-[3-((1R)-1-Hydroxyethyl)(3S,4S)-4-(3-cyclopentyloxy-4-methoxyphenyl)-3-methylpyrrolidinyl]propanoic acid Prepared from Example 58 via the debenzylation procedure of Intermediate 31.

$^1$H NMR (400 MHz, $CDCl_3$) δ: 6.82–6.71 (m, 3H), 4.80 (c, 1H), 4.06–3.15 (m, 11H), 2.73 (br s, 2H), 1.91–1.74 (m, 6H), 1.63–1.53 (m, 2H), 1.14 (d, 3H), 0.68 (s, 3H).

EXAMPLE 60

$R^1=C_5H_9$; $R^3=CH_2CO_2CH_2Ph$

Phenylmethyl 2-[3-((1R)-1-hydroxyethyl)(3S,4S)-4-(3-cyclopentyloxy-4-methoxyphenyl)-3-methylpyrrolidinyl]acetate Prepared from Intermediate 68 via the Hunig's base mediated coupling procedure of Intermediate 74 using benzyl bromoacetate.

$^1$H NMR (400 MHz, $CDCl_3$) δ: 7.41–7.32 (m, 5H), 6.82–6.73 (m, 3H), 5.18 (q, 2H), 4.77 (c, 1H), 3.82 (s, 3H), 3.68 (q, 1H), 3.59 (t, 1H), 3.52 (d, 1H), 3.36–3.30 (m, 2H), 3.24 (d, 1H), 2.88 (t, 1H), 2.31 (d, 1H), 1.93–1.80 (m, 6H), 1.65–1.56 (m, 2H), 1.16 (d, 3H), 0.53 (s, 3H) LRMS (Electrospray, positive): Da/e 468.3 (m+1).

EXAMPLE 61

$R^1=C_5H_9$; $R^3=CH_2CO_2H$

2-[3-((1R)-1-Hydroxyethyl)(3S,4S)-4-(3-cyclopentyloxy-4-methoxyphenyl)-3-methylpyrrolidinyl]acetic acid Prepared from Example 60 via debenzylation procedure of Intermediate 31.

$^1$H NMR (400 MHz, $CDCl_3$) δ: 6.77–6.68 (m, 3H), 5.56 (br s, 1H), 4.77 (c, 1H), 3.99–3.85 (m, 4H), 3.82–3.59 (m, 7H), 2.88 (br s, 1H), 1.91–1.75 (m, 6H), 1.59–1.51 (m, 2H), 11.1 (d, 3H), 0.67 (s, 3H). LRMS (Electrospray, negative): Da/e 376.2 (m–1).

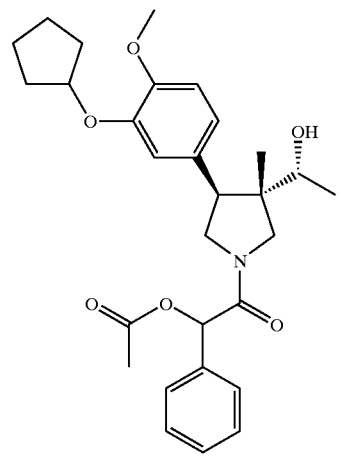

EXAMPLE 62

$R^1=C_5H_9$; $R^3=COCH(OAc)Ph$

2-[(3R)-3-((1R)-1-Hydroxyethyl)-4-(3-cyclopentyloxy-4-methoxyphenyl)-3-methylpyrrolidinyl]-2-oxo-1-phenylethyl acetate Prepared from Intermediate 68 (104 mg, 0.33 mmol) and O-acetyl mandelic acid chloride (75 μL, 0.33 mmol) by the acylation procedure of Example 7 to give Example 62 (149 mg, 100%).

1H-NMR (400 MHz, $CDCl_3$) δ: 7.60–7.37 (m, 5H), 6.82–6.70 (m, 3H), 6.08 (m, 1H), 4.76 (m, 1H), 4.05–3.32 (m, 7H), 3.81 (s, 3H), 2.20 (s, 3H), 1.95–1.53 (br m, 5H), 1.13 and 0.51 (doublets, 3H, rotomers), 0.79 and 0.41 (singlets, 3H, rotomers).

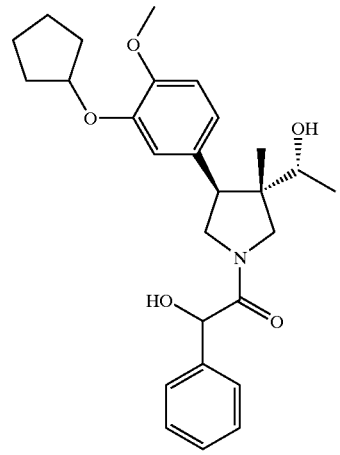

EXAMPLE 63

$R^1=C_5H_9$; $R^3=COCH(OH)Ph$

1-[(3R)-3-((1R)-1-Hydroxyethyl)-4-(3-cyclopentyloxy-4-methoxyphenyl)-3-methylpyrrolidinyl]-2-hydroxy-2-phenylethan-1-one Prepared from Example 62 by the LiOH hydrolysis procedure of Intermediate 5 to provide Example 63 as a white foam (99 mg, 66%).

1H-NMR (400 MHz, CDCl₃) δ: 7.41–7.26 (m, 5H), 6.80–6.41 (m, 3H), 5.16–5.07 (m, 1H), 4.75–4.54 (multiplets, 1H, rotomers and diastereomers), 4.06–2.80 (m, 7H), 3.81 and 3.79 and 3.78 (singlets, 3H, rotomers and diastereomers), 1.95–1.55 (br m, 5H), 1.15 and 1.02 (doublets, 3H, rotomers), 0.77 and 0.75 and 0.46 and 0.38 (singlets, 3H, rotomers and diastereomers). LRMS (Electrospray, positive): Da/e 454.5 (m+1).

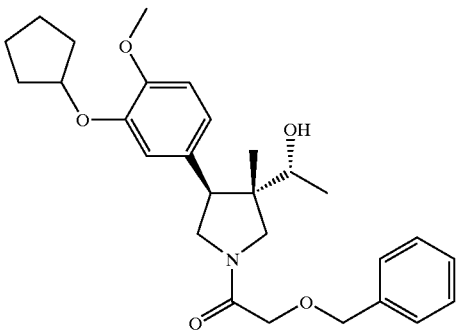

EXAMPLE 64

R¹=C₅H₉; R³=COCH₂OCH₂Ph

1-[3-((1R)-1-Hydroxyethyl)(3S,4S)-4-(3-cyclopentyloxy-4-methoxyphenyl)-3-methylpyrrolidinyl]-2-(phenylmethoxy)ethan-1-one Prepared from Intermediate 68 (176 mg, 0.574 mmol) by the Hunig's base procedure of Intermediate 74 using benzyloxyacetyl chloride (31 μL, 0.22 mmol, 2 eq), yielding a clear, colorless oil (79 mg, 29%).

¹H NMR (400 MHz, CDCl₃, mixture of rotomers) δ: 7.38–7.28 (m, 5H), 6.77–6.73 (m, 3H), 4.73–4.71 (m, 1H), 4.65–4.64 (m, 2H), 4.14–3.19 (c, 12H), 2.07–1.56 (m, 8H), 1.16–1.09 (dd, 3H), 0.72 (s, 3H).

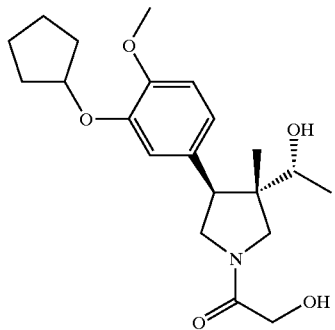

EXAMPLE 65

R¹=C₅H₉; R³=COCH₂OH

1-[3-((1R)-1-Hydroxyethyl)(3S,4S)-4-(3-cyclopentyloxy-4-methoxyphenyl)-3-methylpyrrolidinyl]-2-hydroxyethan-1-one Prepared from Example 64 by the debenzylation procedure of Intermediate 31 yielding a white solid (47 mg, 73%).

¹H NMR (400 MHz, CDCl₃, mixture of rotomers) δ: 6.82–6.76 (m, 3H), 4.75–4.73 (m, 1H), 4.15–3.04 (c, 12H), 1.92–1.61 (m, 9H), 1.27–1.24 (dd, 3H), 0.76 (s, 3H). LRMS (Electrospray, positive): Da/e 378.2 (m+1).

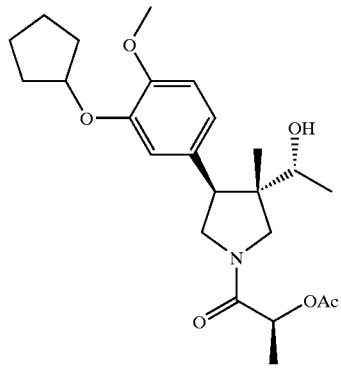

EXAMPLE 66

R¹=C₅H₉; R³=(S)—COCH(OAc)CH₃

2-[3-((1R)-1-Hydroxyethyl)(3S,4S)-4-(3-cyclopentyloxy-4-methoxyphenyl)-3-methylpyrrolidinyl](1S)-1-methyl-2-oxoethyl acetate Prepared from Intermediate 68 (106 mg, 0.330 mmol) by the acylation procedure of Example 7 using (S)-(–)-2-acetoxypropionyl chloride (84 μL, 0.66 mmol, 2 eq), yielding a clear, colorless oil that was not purified further.

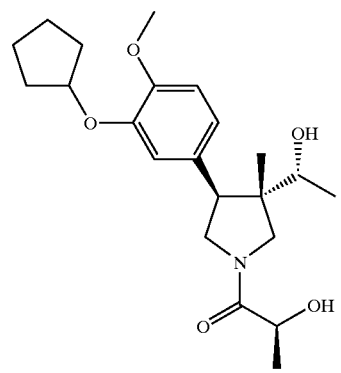

EXAMPLE 67

R¹=C₅H₉; R³=(S)—COCH(OH)CH₃

1-[3-((1R)-1-Hydroxyethyl)(3S,4S)-4-(3-cyclopentyloxy-4-methoxyphenyl)-3-methylpyrrolidinyl](2S)-2-hydroxypropan-1-one The crude compound of Example 66 was deprotected by the LiOH procedure of Intermediate 5 to give Example 67 as a white solid (22 mg, 17% for two steps).

¹H NMR (400 MHz, CDCl₃) δ: 6.82–6.76 (m, 3H), 4.75–4.73 (m, 1H), 4.38–4.35 (m, 1H), 3.88–3.55 (c, 9H), 3.39–3.25 (dd, 1H), 1.92–1.58 (m, 9H), 1.41–1.36 (dd, 3H), 1.18–1.14 (dd, 3H), 0.77–0.76 (d, 3H). LRMS (Electrospray, positive): Da/e 392.3 (m+1).

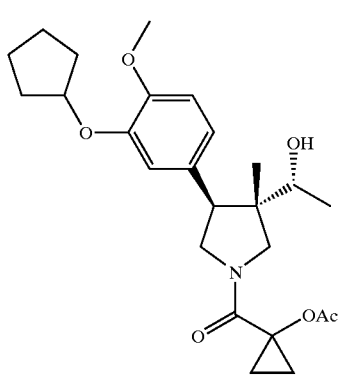

EXAMPLE 68

R$^1$=C$_5$H$_9$; R$^3$=CO(CH$_2$CH$_2$)OAc

{[3-((1R)-1-Hydroxyethyl)(3S,4S)-4-(3-cyclopentyloxy-4-methoxyphenyl)-3-methylpyrrolidinyl]carbonyl}-cyclopropyl acetate Intermediate 68 (97.6 mg, 0.306 mmol) was acylated by the acylation procedure of Example 7 using 2-acetoxy-2-cyclopropanethanoyl chloride (99 mg, 0.61 mmol, 2 eq), yielding a clear, colorless oil (77 mg, 56%).
$^1$H NMR (400 MHz, CDCl$_3$, mixture of rotomers) δ: 6.78–6.71 (m, 3H), 4.72–4.71 (m, 1H), 3.80–3.36 (c, 10H), 2.08 (s, 3H), 1.90–1.50 (m, 11H), 1.16–1.11 (d, 3H), 0.96 (br s, 1H), 1.18–1.14 (dd, 3H), 0.70 (s, 3H).

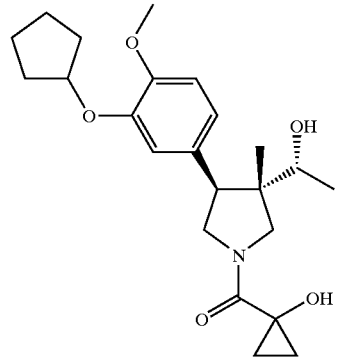

EXAMPLE 69

R$^1$=C$_5$H$_9$; R$^3$=CO(CH$_2$CH$_2$)OH 3-((1R)-1-Hydroxyethyl)(3S,4S)-4-(3-cyclopentyloxy-4-methoxyphenyl)-3-methylpyrrolidinyl hydroxycyclopropyl ketone The compound of Example 68 (77 mg) was hydrolyzed by the LiOH procedure of Intermediate 5 to give Example 69 as a white solid (34 mg, 44% for two steps).
$^1$H NMR (400 MHz, CDCl$_3$, mixture of rotomers) δ: 6.80–6.75 (m, 3H), 4.74–3.33 (c, 10H), 2.30 (br s, 1H), 1.93–1.56 (m, 8H), 1.37–0.89 (m, 8H), 0.74–0.72 (d, 3H). LRMS (Electrospray, positive): Da/e 404.4 (m+1).

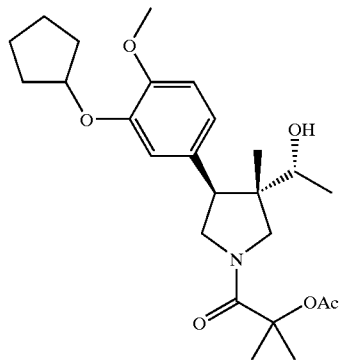

EXAMPLE 70

R$^1$=C$_5$H$_9$; R$^3$=COCH(OAc)(CH$_3$)CH$_3$

2-[3-((1R)-1-Hydroxyethyl)(3S,4S)-4-(3-cyclopentyloxy-4-methoxyphenyl)-3-methylpyrrolidinyl]-1,1-dimethyl-2-oxoethyl acetate Intermediate 68 (124 mg, 0.0.389 mmol) was acylated by the acylation procedure of Example 7 using (+)-2-acetoxy-2-methylpropionyl chloride (11 µL, 0.78 mmol, 2 eq.). The resulting oil was not purified further.

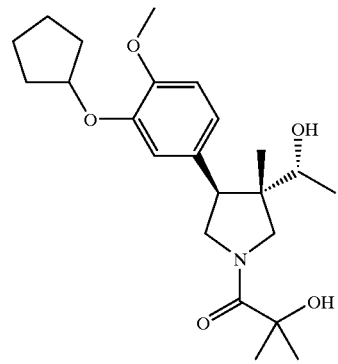

EXAMPLE 71

R$^1$=C$_5$H$_9$; R$^3$=COCH(OH)(CH$_3$)CH$_3$

1-[3-((1R)-1-Hydroxyethyl)(3S,4S)-4-(3-cyclopentyloxy-4-methoxyphenyl)-3-methylpyrrolidinyl]-2-hydroxy-2-methylpropan-1-one The crude product of Example 70 was converted by the LiOH hydrolysis procedure of Intermediate 5 to the give Example 71 as a white solid (47 mg, 30%).
$^1$H NMR (400 MHz, CDCl$_3$, mixture of rotomers) δ: 6.79–6.75 (m, 3H), 4.75 (br s, 1H), 4.49 (br s, 1H), 3.91–3.48 (c, 10H), 1.90–1.46 (m, 14H), 1.18–1.14 (dd, 3H), 0.77–0.74 (d, 3H). LRMS (Electrospray, positive): Da/e 406.3 (m+1).

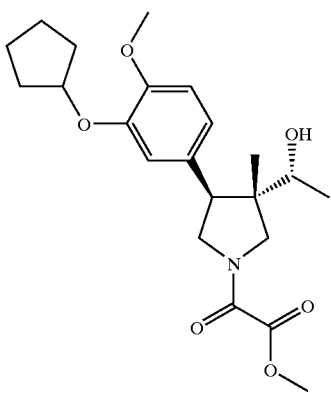

EXAMPLE 72

R$^1$=C$_5$H$_9$; R$^3$=COCO$_2$CH$_3$

Methyl 2-[3-((1R)-1-hydroxyethyl)(3S,4S)-4-(3-cyclopentyloxy-4-methoxyphenyl)-3-methylpyrrolidinyl]-2-oxoacetate Intermediate 68 (57.5 mg, 0.180 mmol) was converted by the DIEA procedure of Intermediate 32 using methyl oxalyl chloride to yield Example 72 as a clear, colorless oil (26.8 mg, 36%).

$^1$H NMR (400 MHz, CDCl$_3$) δ: 6.81–6.77 (m, 3H), 4.75–4.74 (m, 1H), 4.12–3.45 (c, 13H), 1.91–1.52 (m, 8H), 1.18–1.13 (dd, 3H), 0.78–0.75 (d, 3H). LRMS (Electrospray, positive): Da/e 406.4 (m+1).

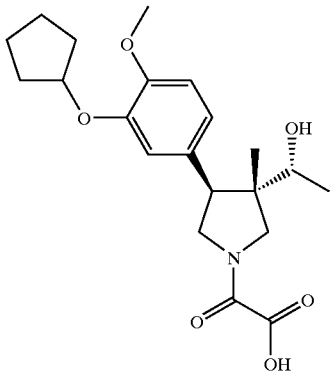

EXAMPLE 73

R$^1$=C$_5$H$_9$; R$^3$=COCO$_2$H

2-[3-((1R)-1-Hydroxyethyl)(3S,4S)-4-(3-cyclopentyloxy-4-methoxyphenyl)-3-methylpyrrolidinyl]-2-oxo-acetic acid Example 72 (46.8 mg, 0.116 mmol) was converted by the LiOH procedure of Intermediate 5 to give Example 73 as a clear, colorless film (34 mg, 76%).

$^1$H NMR (400 MHz, CDCl$_3$) δ: 6.82–6.76 (m, 3H), 4.75–4.73 (m, 1H), 4.43–3.49 (c, 10H), 1.92–1.58 (m, 8H), 1.19–1.16 (dd, 3H), 0.78–0.76 (d, 3H). LRMS (Electrospray, negative): Da/e 390.2 (m−1).

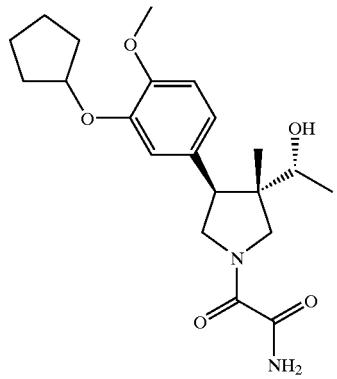

EXAMPLE 74

R$^1$=C$_5$H$_9$; R$^3$=COCONH$_2$

2-[3-((1R)-1-Hydroxyethyl)(3S,4S)-4-(3-cyclopentyloxy-4-methoxyphenyl)-3-methylpyrrolidinyl]-2-oxo-acetamide Example 72 (7.1 mg, 0.014 mmol) was dissolved in THF (0.5 mL), NH$_4$OH (0.5 mL) was added, and the apparatus was sealed and stirred for 2 hours at room temperature. TLC (1:1 EtOAc:hexanes) showed complete consumption of starting material. The reaction was diluted with EtOAc (20 mL), and the organic layers were washed with brine (2×15 mL). The organic layer was dried over Na$_2$SO$_4$ and concentrated in vacuo to give a clear, colorless oil (6.6 mg, 117%).

$^1$H NMR (400 MHz, CDCl$_3$) δ: 7.36 (br s, 1H), 6.82–6.79 (m, 3H), 5.53 (br s, 1H), 4.76–4.75 (m, 1H), 4.44–3.47 (c, 10H), 1.92–1.58 (m, 8H), 1.18–1.17 (d, 3H), 0.78–0.74 (d, 3H). LRMS (Electrospray, negative): Da/e 389.1 (m−1).

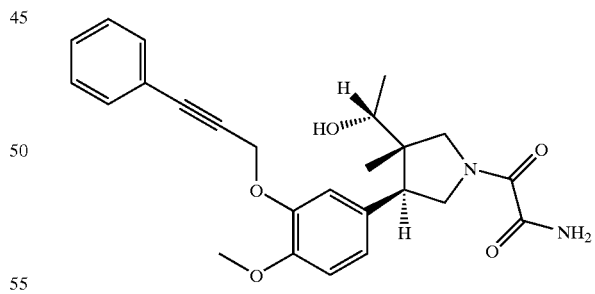

EXAMPLE 75

R$^1$=PhC≡CCH$_2$; R$^3$=COCONH$_2$

2-{(3S,4S)-3-((R)-1-Hydroxyethyl)-4-[4-methoxy-3-(3-phenylprop-2-ynyloxy)-phenyl]-3-methylpyrrolidin-1-yl}-2-oxo-acetamide Prepared by acylation of Intermediate 73 with methyl oxalyl chloride by the DIEA procedure of Intermediate 32, removal of the t-butyl group by the procedure of Intermediate 72, O-alkylation with Intermediate 90 by the $K_2CO_3$ etherification procedure of Example 43, and amidation by the procedure of Example 74.

$^1$H NMR data δ: 7.28–7.42 (m, 5H); 7.08 (sd, 1H); 6.83–6.87 (m, 2H); 5.45 (bs, 1H); 5.0 (s, 2H); 4.42–4.48 (2d, 0.5H); 4.26 (t, 0.5H); 3.72–4.01 (m, 3.5H); 3.89 (s, 3H); 3.50–3.70 (m, 1H); 3.44 (d, 0.5H); 0.96–0.99 (dd, 3H); 0.71 (d, 3H).

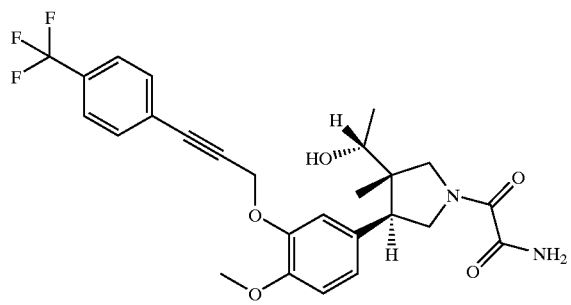

EXAMPLE 76

$R^1$=4-$CF_3$PhC≡$CCH_2$; $R^3$=$COCONH_2$ 2-((3S,4S)-3-((R)-1-Hydroxyethyl)-4-{4-methoxy-3-[3-(4-trifluoromethyl-phenyl)prop-2-ynyloxy]-phenyl}-3-methylpyrrolidin-1-yl)-2-oxo-acetamide Prepared as described in Example 75, using Intermediate 92 as the O-alkylating reagent.

$^1$H NMR data δ: 7.50–7.61 (m, 4H); 7.04 (s, 1H); 6.85–6.91 (m, 2H); 5.69 (bs, 1H); 5.00 (s, 2H); 4.42–4.49 (2d, 0.5H); 4.26 (t, 0.5H); 3.69–4.07 (m, 5H); 3.90 (s, 3H); 3.45–3.58 (m, 1H); 1.04–1.07 (dd, 3H); 0.73 (d, 3H)

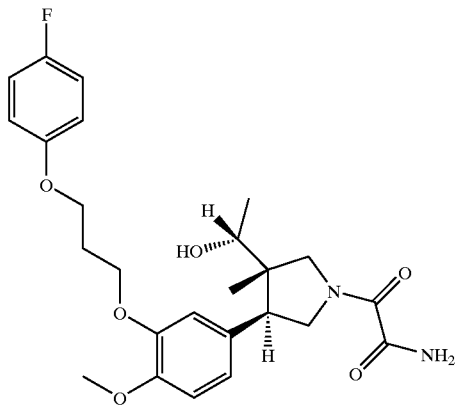

EXAMPLE 77

$R^1$=4-FPhO$CH_2CH_2CH_2$; $R^3$=$COCONH_2$

2-[(3S,4S)-4-{3-[3-(4-Fluorophenoxy)propoxy]-4-methoxyphenyl}-3-((R)-1-hydroxyethyl)-3-methylpyrrolidin-1-yl]-2-oxo-acetamide Prepared as described in Example 75, using 1-(3-chloropropoxy)-4-fluorobenzene as the alkylating reagent.

$^1$H NMR data δ: 6.93–6.99 (m, 2H); 6.82–6.88 (m, 5); 5.44 (s, 1H); 4.40 (dd, 0.5H); 4.14–4.22(m, 5H); 3.83 (s, 3H); 3.69–4.04 (m, 5H); 3.56 (d, 0.5H); 2.28 (quint, 2H); 1.16 (dd, 3H): 0.75 (d, 3H).

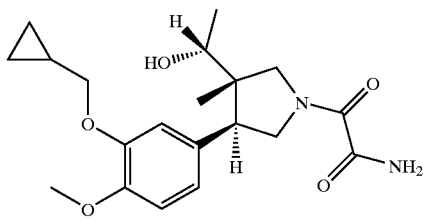

EXAMPLE 78

$R^1$=$CH_2C_3H_5$; $R^3$=$COCONH_2$

2-[(3S,4S)-4-(3-Cyclopropylmethoxy-4-methoxyphenyl)-3-((R)-1-hydroxyethyl)-3-methylpyrrolidin-1-yl]-2-oxo-acetamide Prepared as described in Example 75, using cyclopropylmethyl bromide as the alkylating reagent.

$^1$H NMR data δ: 6.80–6.81 (m, 3H); 5.50 (bs, 1H); 4.40 (2d, 0.5H); 4.23 (t, 0.5H); 3.68–4.05 (m, 7H); 3.84 (s, 3H); 1.40 (t, 1H); 1.17 (sd, 3H); 0.76 (d, 3H); 0.61–0.67 (m, 2H); 0.33–0.38 (m, 2H).

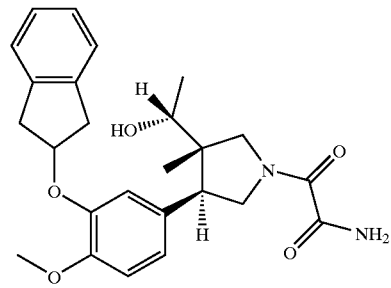

EXAMPLE 79

$R^1$=2-indanyl; $R^3$=$COCONH_2$

2-{(3S,4S)-3-((R)-1-Hydroxyethyl)-4-[3-(indan-2-yloxy)-4-methoxyphenyl]-3-methylpyrrolidin-1-yl}-2-oxo-acetamide Prepared as described in Example 75, using 2-bromoindane as the alkylating reagent.

$^1$H NMR data δ: 7.16–7.24 (m, 4H); 6.84–6.87 (m, 3H); 5.51 (s, 1H); 5.17–5.20 (m, 1H); 4.42–4.5 (2d, 0.5H); 4.24 (t, 0.5H); 3.60–4.06 (m, 6H); 3.81 (s, 3H); 3.20–3.40 (m, 4H); 1.20 (sd, 3H); 0.78 (d, 3H).

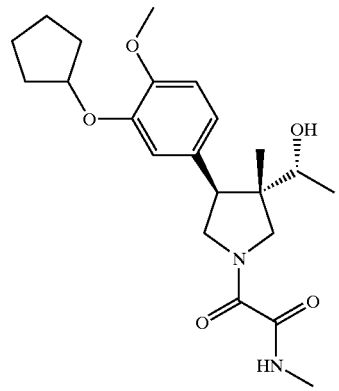

EXAMPLE 80

R¹=C₅H₉; R³=COCONHCH₃

2-[3-((1R)-1-Hydroxyethyl)(3S,4S)-4-(3-cyclopentyloxy-4-methoxyphenyl)-3-methylpyrrolidinyl]-N-methyl-2-oxoacetamide Example 72 (17.3 mg, 0.0427 mmol) was dissolved in THF (0.8 mL). Methylamine (40% in water, 0.5 mL) was added, and the apparatus was sealed and stirred for 1 hour at room temperature. TLC (3:1 EtOAc:hexanes) showed complete consumption of starting material. The reaction was diluted with EtOAc (20 mL), and the organic layers were washed with brine (2×15 mL). The organic layer was dried over Na₂SO₄ and concentrated in vacuo to give a clear, colorless oil (16.9 mg, 97%).

¹H NMR (400 MHz, CDCl₃) δ: 7.59 (br s, 1H), 6.80–6.79 (m, 3H), 4.75–4.73 (m, 1H), 4.47–3.46 (c, 10H), 2.89–2.87 (dd, 3H), 1.91–1.57 (m, 8H), 1.18–1.16 (dd, 3H), 0.76–0.73 (d, 3H). LRMS (Electrospray, positive): Da/e 405.1 (m+1).

EXAMPLE 81

R¹=C₅H₉; R³=COCO-piperidine

1-[3-((1R)-1-Hydroxyethyl)(3S,4S)-4-(3-cyclopentyloxy-4-methoxyphenyl)-3-methylpyrrolidinyl]-2-piperidylethane-1,2-dione Example 72 (25.4 mg, 0.0626 mmol) was dissolved in THF (0.8 mL). Piperidine (213 μL, 2.15 mmol, 34 eq.) was added, and the apparatus was sealed and heated at 53° C. for 12 hours. TLC (100% EtOAc) showed a small amount of product formation. The reaction was diluted with EtOAc (20 mL), the organic layers were washed with 2N HCl (2×15 mL), 1N NaOH (15 mL), and brine (2×15 mL). The organic layer was dried over Na₂SO₄ and concentrated in vacuo to give a clear, colorless oil (1.2 mg, 4%).

¹H NMR (400 MHz, CDCl₃) δ: 6.82–6.76 (m, 3H), 4.75 (m, 1H), 4.01–3.27 (c, 14H), 1.89–1.59 (m, 14H), 1.18–1.13 (dd, 3H), 0.78–0.74 (d, 3H).

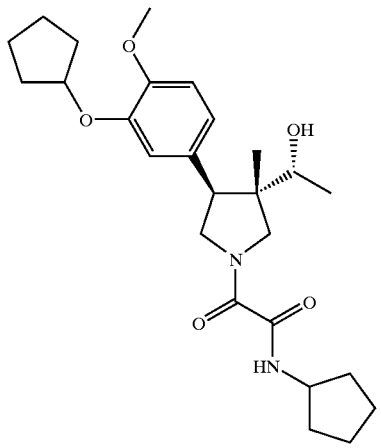

EXAMPLE 82

R¹=C₅H₉; R³=COCONHC₅H₉

2-[3-((1R)-1-Hydroxyethyl)(3S,4S)-4-(3-cyclopentyloxy-4-methoxyphenyl)-3-methylpyrrolidinyl]-N-cyclopentyl-2-oxoacetamide Example 72 (20.9 mg, 0.0515 mmol) was dissolved in THF (0.8 mL). Cyclopentylamine (211 μL, 2.13 mmol, 41 eq.) was added, and the reaction was stirred at room temperature for 42 hours. The reaction was diluted with EtOAc (20 mL), and the organic layers were washed with 2N HCl (2×15 mL), 1N NaOH (15 mL), and brine (2×15 mL). The organic layer was dried over Na₂SO₄ and concentrated in vacuo. The resulting oil was purified by silica chromatography (100% EtOAc) to give a clear, colorless oil (14.0 mg, 59%).

¹H NMR (400 MHz, CDCl₃) δ: 7.57–7.53 (br s, 1H), 6.8–6.78 (m, 3H), 4.76–4.73 (br s, 1H), 4.48–3.44 (c, 9H), 2.04–1.48 (m, 18H), 1.18–1.16 (d, 3H), 0.77–0.73 (d, 3H). LRMS (Electrospray, negative): Da/e 457.2 (m−1).

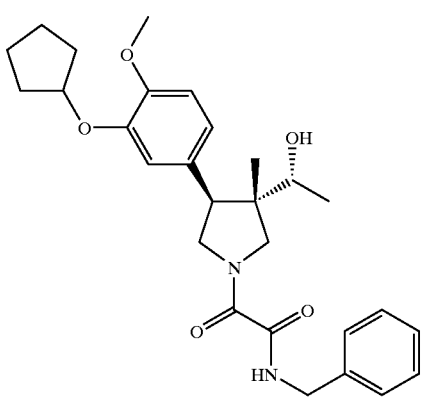

EXAMPLE 83

R$^1$=C$_5$H$_9$; R$^3$=COCONHCH$_2$Ph

2-[3-((1R)-1-Hydroxyethyl)(3S,4S)-4-(3-cyclopentyloxy-4-methoxyphenyl)-3-methylpyrrolidinyl]-2-oxo-N-benzylacetamide Example 83 was prepared by the method of Example 82 using benzylamine to give a clear, colorless oil (9.4 mg, 47%).

$^1$H NMR (400 MHz, CDCl$_3$) δ: 7.96–7.92 (br s, 1H), 7.36–7.25 (m, 3H), 4.75 (br s, 1H), 4.49–4.47 (d, 2H), 4.28–3.46 (c, 9H), 1.93–1.61 (m, 8H), 1.19–1.16 (dd, 3H), 0.78–0.74 (d, 3H). LRMS (Electrospray, positive): Da/e 481.4 (m+1).

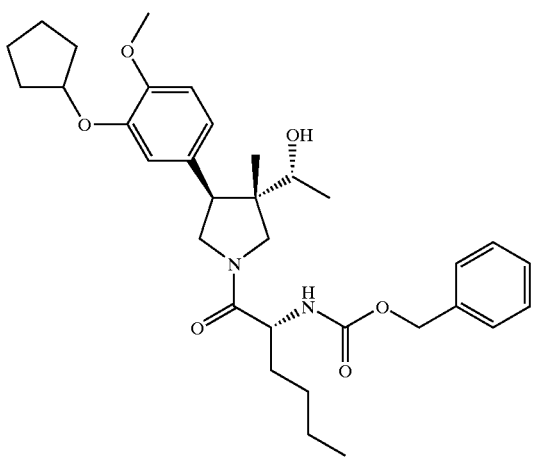

EXAMPLE 84

R$^1$=C$_5$H$_9$; R$^3$=(R)—COCH(C$_4$H$_9$)NHCO$_2$CH$_2$Ph

N-{(1R)-2-[3-((1R)-1-Hydroxyethyl)(3S,4S)-4-(3-cyclopentyloxy-4-methoxyphenyl)-3-methylpyrrolidinyl]-1-butyl-2-oxoethyl}(phenylmethoxy)carboxamide Intermediate 68 (39.5 mg, 0.129 mmol) was converted by the DIEA procedure of Intermediate 32 to yield a clear, colorless oil (59.0 mg, 80%).

$^1$H NMR (400 MHz, CDCl$_3$, mixture of rotomers) δ: 7.36–7.26(m, 5H), 6.82–6.71 (m, 3H), 5.71–5.68 (dd, 1H), 5.12–5.06 (m, 2H), 4.73 (m, 1H), 4.49–4.47 (m, 1H), 4.12–2.58 (c, 8H), 2.03–1.25 (m, 16H), 1.16–1.14 (dd, 3H), 0.92–0.84 (m, 3H), 0.73–0.72 (d, 3H).

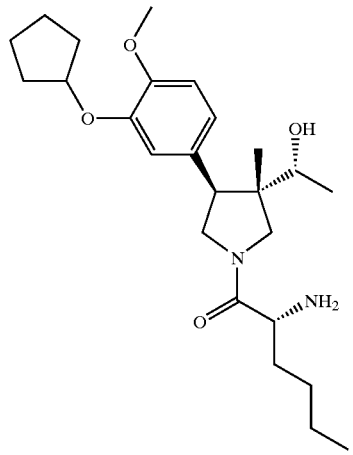

EXAMPLE 85

R$^1$=C$_5$H$_9$; R$^3$=(R)—COCH(NH$_2$)C$_4$H$_9$ (2R)-1-[3-((1R)-1-Hydroxyethyl) (3S,4S)-4-(3-cyclopentyloxy-4-methoxyphenyl)-3-methylpyrrolidinyl]-2-aminohexan-1-one Example 84 (59 mg, 0.10 mmol) was converted by the debenzylation procedure of Intermediate 31 to give Example 85 as a white powder (43 mg, 95%).

$^1$H NMR (CD$_3$OD, 400 MHz, mixture of rotomers) δ: 6.90–6.83 (m, 3H), 3.85–3.30 (c, 10H), 2.00–1.37 (m, 14H), 1.14–1.11 (dd, 3H), 1.10–0.92 (dt, 3H), 0.77 (s, 3H). LRMS (Electrospray, positive): Da/e 433.5 (m+1).

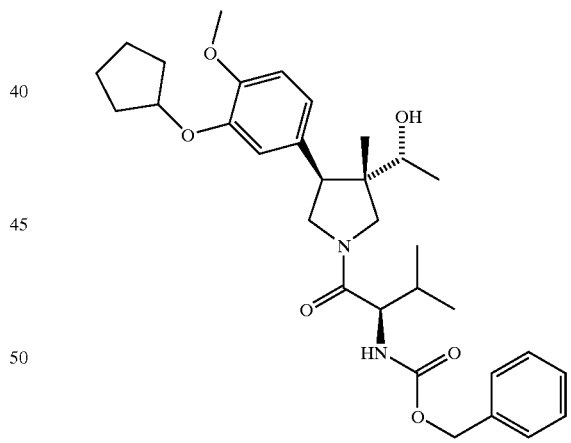

EXAMPLE 86

R$^1$=C$_5$H$_9$; R$^3$=(R)—COCH(i-Pr)NHCO$_2$CH$_2$Ph

N-{(1R)-2-[3-((1R)-1-Hydroxyethyl)(3S,4S)-4-(3-cyclopentyloxy-4-methoxyphenyl)-3-methylpyrrolidinyl]-1-(methylethyl)-2-oxoethyl}(phenylmethoxy)carboxamide Intermediate 68 (43.7 mg, 0.143 mmol) was acylated by the Hunig's base method of Intermediate 74 using Z-D-Val-OSu (54.6 mg, 0.15 mmol, 1.1 eq), yielding a clear, colorless oil (38.9 mg, 49%).

¹H NMR (400 MHz, CDCl₃, mixture of rotomers) δ: 7.36–7.33 (m, 5H), 6.80–6.71 (m, 3H), 5.62–5.59 (d, 1H), 5.10–5.06 (m, 2H), 5.84–5.72 (m, 1H), 4.12–2.68 (c, 10H), 2.03–1.52 (m, 9H), 1.18–1.14 (dd, 3H), 1.04–0.92 (m, 7H), 0.73–0.70 (d, 3H).

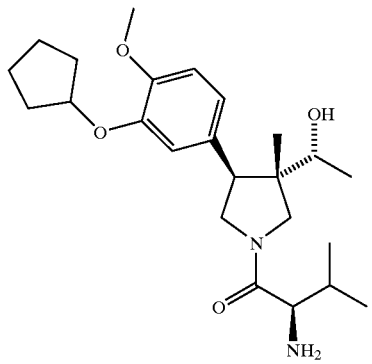

EXAMPLE 87

R¹=C₅H₉; R³=(R)—COCH(i-Pr)NH₂

(2R)-1-[3-((1R)-1-Hydroxyethyl)(3S,4S)-4-(3-cyclopentyloxy-4-methoxyphenyl)-3-methylpyrrolidinyl]-2-amino-3-methylbutan-1-one Example 86 (38.9 mg, 0.070 mmol) was converted by the debenzylation procedure of Intermediate 31 to give Example 87 as clear solid (26 mg, 88%).

¹H NMR (400 MHz, CDCl₃) δ: 6.42–6.33 (m, 3H), 4.36 (m, 1H), 3.62–2.80 (c, 10H), 2.81–2.68 (m, 1H), 1.42–1.08 (m, 9H), 0.78–0.65 (m, 9H), 0.24 (s, 3H). LRMS (Electrospray, positive): Da/e 419.5 (m+1).

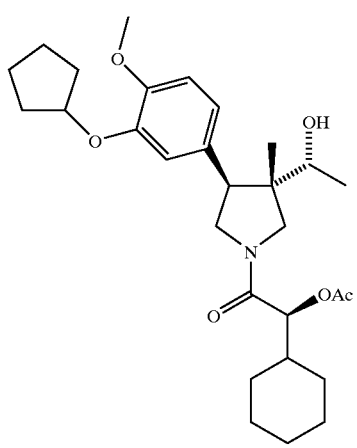

EXAMPLE 88

R¹=C₅H₉; R³=(S)—COCH(OAc)C₆H₁₁

2-[3-((1R)-1-Hydroxyethyl)(3S,4S)-4-(3-cyclopentyloxy-4-methoxyphenyl)-3-methylpyrrolidinyl](1S)-1-cyclohexyl-2-oxoethyl acetate Intermediate 68 (41.2 mg, 0.129 mmol) was acylated by the Hunig's base procedure of Intermediate 74 using (S)-(+)-acetoxyhexahydromandelic acid chloride (625 μL, 0.4121 M in CH₂Cl₂, 2 eq) to give Example 88 as a clear, colorless oil (40.5 mg, 63%).

¹H NMR (400 MHz, CDCl₃, mixture of rotomers) δ: 6.78–6.77 (m, 3H), 4.84–4.72 (m, 2H), 4.12–3.11 (m, 9H), 2.10 (d, 3H), 2.02–1.68 (m, 15H), 1.38–0.99 (m, 10H), 0.81–0.74 (d, 3H).

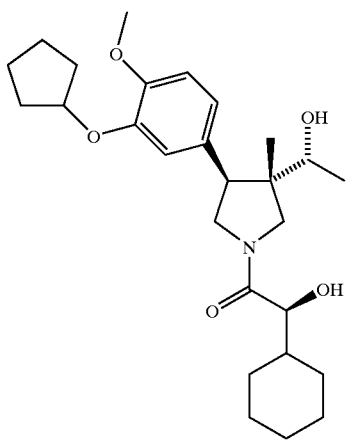

EXAMPLE 89

R¹=C₅H₉; R³=(S)—COCH(OH)C₆H₁₁

1-[3-((1R)-1-Hydroxyethyl)(3S,4S)-4-(3-cyclopentyloxy-4-methoxyphenyl)-3-methylpyrrolidinyl](2S)-2-cyclohexyl-2-hydroxyethan-1-one Example 88 (40.5 mg, 0.0807 mmol) was converted by the LiOH hydrolysis procedure of Intermediate 5 to afford Example 89 as a clear, colorless oil (26.9 mg, 72%).

¹H NMR (400 MHz, CDCl₃, mixture of rotomers) δ: 6.80–6.78(m, 3H), 4.73 (m, 1H), 4.14–4.06 (m, 1H), 3.83–2.99 (c, 9H), 1.91–1.36 (m, 17H), 1.35–1.11 (m, 7H), 0.79–0.78 (d, 3H). LRMS (Electrospray, positive): Da/e 460.3 (m+1).

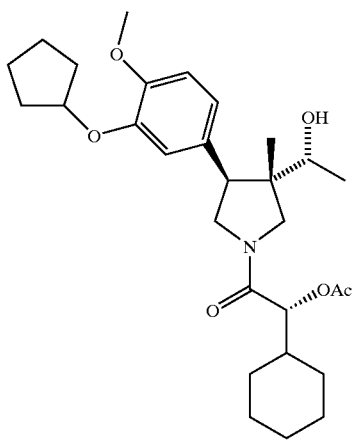

EXAMPLE 90

$R^1 = C_5H_9$; $R^3 = (R)$—COCH(OAc)$C_6H_{11}$

1-[3-((1R)-1-Hydroxyethyl)(3S,4S)-4-(3-cyclopentyloxy-4-methoxyphenyl)-3-methylpyrrolidinyl](2R)-2-cyclohexyl-2-acetoxyethan-1-one Intermediate 68 (43.1 mg, 0.135 mmol) was converted by the Hunig's base procedure of Intermediate 74 using (R)-(−)-acetoxyhexahydromandelic acid chloride (368 μL, 0.734 M in CH$_2$Cl$_2$, 2 eq) to give a clear, colorless oil (59.9 mg, 88%).

$^1$H NMR (400 MHz, CDCl$_3$, mixture of rotomers) δ: 6.84–6.64(m, 3H), 4.78–4.76 (m, 2H), 4.12–2.65 (c, 9H), 2.11 (d, 3H), 2.10–1.51 (m, 15H), 1.38–0.98 (m, 10H), 0.73–0.65 (d, 3H).

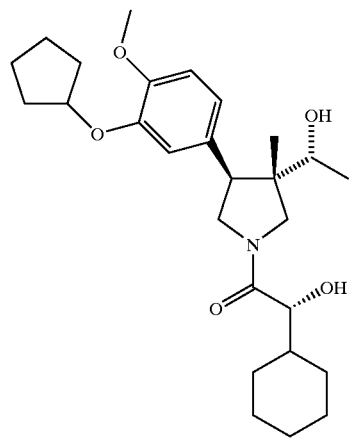

EXAMPLE 91

$R^1 = C_5H_9$; $R^3 = (R)$—COCH(OH)$C_6H_{11}$ (2R)-1-[3-((1R)-1-Hydroxyethyl)(3S,4S)-4-(3-cyclopentyloxy-4-methoxyphenyl)-3-methylpyrrolidinyl]-2-cyclohexyl-2-hydroxyethan-1-one Example 90 (59.9 mg, 0.119 mmol) was converted by the LiOH hydrolysis procedure of Intermediate 5 to give a clear, colorless film (46.6 mg, 84%).

$^1$H NMR (400 MHz, CDCl$_3$, mixture of rotomers) δ: 6.85–6.74 (m, 3H), 4.79–4.72 (m, 1H), 4.13–4.07 (m, 1H), 3.87–3.01 (c, 9H), 1.96–1.34 (m, 17H), 1.34–1.08 (m, 7H), 0.78–0.77 (d, 3H). LRMS (Electrospray, positive): Da/e 460.4 (m+1).

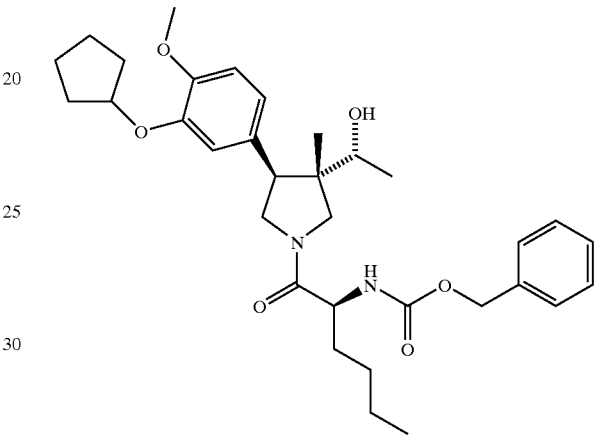

EXAMPLE 92

$R^1 = C_5H_9$; $R^3 = (S)$—COCH(C$_4$H$_9$)NHCO$_2$CH$_2$Ph

N-{2-[3-((1R)-1-Hydroxyethyl)(3S,4S)-4-(3-cyclopentyloxy-4-methoxyphenyl)-3-methylpyrrolidinyl]-(1S)-1-butyl-2-oxoethyl}(phenylmethoxy)carboxamide Intermediate 68 (40.6 mg, 0.125 mmol) was converted by the Hunig's base procedure of Intermediate 74 using Z-L-Nle-ONp (53 mg, 0.15 mmol, 1.1 eq) to give Example 92 as a clear, colorless oil (50.4 mg, 71%).

$^1$H NMR (400 MHz, CDCl$_3$, mixture of rotomers) δ: 7.36–7.25 (m, 5H), 6.80–6.75 (m, 3H), 5.74–5.72 (dd, 1H), 5.10–5.06 (m, 2H), 4.74–4.53 (m, 1H), 4.13 (m, 1H), 4.13–3.35 (c, 8H), 1.95–1.24 (m, 16H), 1.14–1.13 (d, 3H), 0.93–0.87 (m, 3H), 0.74 (s, 3H).

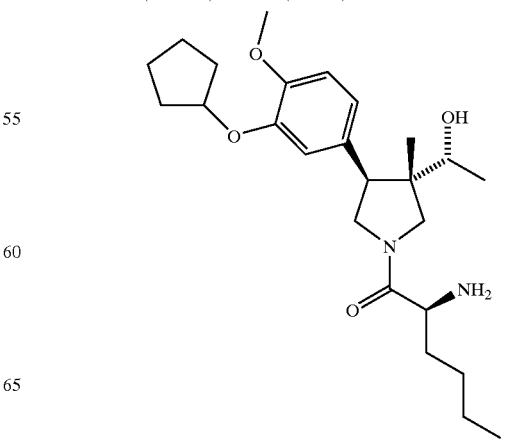

EXAMPLE 93

R$^1$=C$_5$H$_9$; R$^3$=(S)—COCH(C$_4$H$_9$)NH$_2$

1-[3-((1R)-1-Hydroxyethyl)(3S,4S)-4-(3-cyclopentyloxy-4-methoxyphenyl)-3-methylpyrrolidinyl](2S)-2-aminohexan-1-one Example 92 (50.4 mg, 0.0889 mmol) was subjected to the debenzylation procedure of Intermediate 31 to give Example 93 as a white solid (31.7 mg, 82%).
$^1$H NMR (400 MHz, CDCl$_3$, mixture of rotamers) δ: 6.89–6.74 (m, 3H), 4.83–4.75 (m, 1H), 4.40–3.32 (c, 10H), 1.99–1.68 (m, 14H), 1.14–1.12 (m, 3H), 1.04–0.95 (d, 3H), 0.91–0.88 (d, 3H). LRMS (Electrospray, positive): Da/e 433.5 (m+1).

EXAMPLE 94

R$^1$=C$_5$H$_9$; R$^3$=(R)—COCH(OAc)(CH$_2$)$_3$CH$_3$ (1R)-2-[3-((1R)-1-Hydroxyethyl)(3S,4S)-4-(3-cyclopentyloxy-4-methoxyphenyl)-3-methylpyrrolidinyl]-1-butyl-2-oxoethyl acetate Prepared from Intermediate 68 via the Hunig's base coupling procedure of Intermediate 74 using (1R)-1-(chlorocarbonyl)pentyl acetate.
$^1$H NMR (400 MHz, CDCl$_3$, mixture of rotamers) δ: 6.81 (m, 2H), 6.79–6.69 (m, 3H), 5.10–5.02 (m, 1H), 4.79–4.73 (m, 1H), 4.14–3.18 (c, 9H), 2.14 (d, 3H), 1.94–1.76 (m, 8H), 1.53–1.34 (m, 4H), 1.20 (dd, 2H), 0.96–0.86 (m, 3H), 0.74 (d, 3H).

EXAMPLE 95

R$^1$=C$_5$H$_9$; R$^3$=(R)—COCH(OH)(CH$_2$)$_3$CH$_3$ (2R)-1-[3-((1R)-1-Hydroxyethyl)(3S,4S)-4-(3-cyclopentyloxy-4-methoxyphenyl)-3-methylpyrrolidinyl]-2-hydroxyhexan-1-one Example 94 (5 mg, 0.011 mmol) was hydrolyed by LiOH to yield Example 95 (2.5 mg, 55%), as a clear film.
$^1$H NMR (Methanol-d$_4$, 400 MHz) δ: 6.91–6.80 (m, 3H), 4.34–4.28 (m, 1H), 4.04–3.35 (c, 9H), 1.90–1.77 (m, 8H), 1.74–1.62 (m, 2H), 1.55–1.23 (m, 4H), 1.12 (d, 3H), 0.97–0.87 (m, 3H), 0.74 (s, 3H). LRMS (Electrospray, positive): Da/e 434.2 (m+1).

EXAMPLE 96

R$^1$=C$_5$H$_9$; R$^3$=(S)—COCH(NHCBZ)CH$_2$Ph

N-{2-[3-((1R)-1-Hydroxyethyl)(3S,4S)-4-(3-cyclopentyloxy-4-methoxyphenyl)-3-methylpyrrolidinyl]-(1S)-2-oxo-1-benzylethyl}(phenylmethoxy)carboxamide Prepared from Intermediate 68 via the Hunig's base acylation procedure of Intermediate 74 using the p-nitrophenylester of N-CBZ-(S)-phenylalanine.
$^1$H NMR (400 MHz, CDCl$_3$, mixture of rotamers) δ: 7.41–7.26 (m, 10H), 6.78–6.42 (m, 3H), 5.78–5.74 (m, 1H), 5.14–5.05 (m, 2H), 4.76–4.70 (m, 2H), 3.81 (s, 3H), 3.75–2.66 (c, 10H), 1.94–1.80 (m, 6H), 1.65–1.57 (m, 2H), 1.08–0.99 (dd, 3H), 0.64 and 0.33 (s, 3H). LRMS (Electrospray, positive): Da/e 601.2 (m+1).

EXAMPLE 97

R$^1$=C$_5$H$_9$; R$^3$=(S)—COCH(NH$_2$)CH$_2$Ph

1-[3-((1R)-1-Hydroxyethyl)(3S,4S)-4-(3-cyclopentyloxy-4-methoxyphenyl)-3-methylpyrrolidinyl](2S)-2-amino-3-phenylpropan-1-one Prepared from Example 96 via the debenzylation procedure of Intermediate 31.
$^1$H NMR (Methanol-d$_4$, 400 MHz, mixture of rotamers) δ: 7.47–7.31 (m, 5H), 6.88–6.47 (m, 3H), 4.78–4.76 (m, 1H), 4.48–4.44 (m, 1H), 3.80–3.06 (c, 13H), 1.88–1.80 (m, 6H), 1.67–1.64 (m, 2H), 1.02 (d, 3H), 0.75 and 0.34 (s, 3H). LRMS (Electrospray, positive): Da/e 467.5 (m+1).

EXAMPLE 98

R$^1$=C$_5$H$_9$; R$^3$=(R)—COCH(NHCBZ)CH$_2$Ph

N-{(1R)-2-[3-((1R)-1-Hydroxyethyl)(3S,4S)-4-(3-cyclopentyloxy-4-methoxyphenyl)-3-methylpyrrolidinyl]-2-oxo-1-benzylethyl}(phenylmethoxy)carboxamide Prepared from Intermediate 68 via the Hunig's base acylation procedure of Intermediate 74 using the p-nitrophenylester of N-CBZ-(R)-phenylalanine.
$^1$H NMR (400 MHz, CDCl$_3$, mixture of rotamers) δ: 7.41–7.19 (m, 10H), 6.77–6.46 (m, 3H), 5.70 (d, 1H), 5.14–5.04 (m, 2H), 4.76–4.69 (m, 2H), 3.82 (s, 3H), 3.93–2.99 (c, 6H), 2,53 (d, 1H), 1.93–1.81 (m, 6H), 1.62–1.56 (m, 2H), 1.06 (dd, 3H), 0.67 and 0.28 (s, 3H). LRMS (Electrospray, positive): Da/e 602.3 (m+1).

EXAMPLE 99

R$^1$=C$_5$H$_9$; R$^3$=(R)—COCH(NH$_2$)CH$_2$Ph (2R)-1-[3-((1R)-1-Hydroxyethyl)(3S,4S)-4-(3-cyclopentyloxy-4-methoxyphenyl)-3-methylpyrrolidinyl]-2-amino-3-phenylpropan-1-one Prepared from Example 98 via the debenzylation procedure of Intermediate 31.
$^1$H NMR (Methanol-d$_4$, 400 MHz, mixture of rotamers) δ: 7.42–7.26 (m, 5H), 6.88–6.65 (m, 3H), 4.80–4.78 (m, 1H), 4.42–4.39 (m, 1H), 3.89–2.42 (c, 13H), 1.89–1.79 (m, 6H), 1.64–1.62 (m, 2H), 0.99 (dd, 3H), 0.69 and 0.21 (s, 3H). LRMS (Electrospray, positive): Da/e 467.0 (m+1).

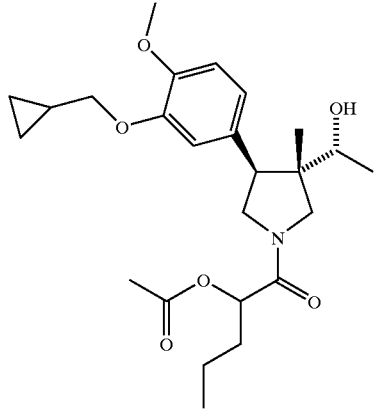

EXAMPLE 100

R$^1$=CH$_2$C$_3$H$_5$; R$^3$=COCH(OAc)C$_4$H$_9$

2-{(3S,4S)-3-((1R)-1-Hydroxyethyl)-4-[3-(cyclopropylmethoxy)-4-methoxyphenyl]-3-methylpyrrolidinyl}-2-oxo-1-propylethyl acetate Intermediate 67 (46 mg, 0.15 mmol) was converted by the Hunig's base procedure of Intermediate 74 using (±)-2-acetoxypropionyl chloride (29 mg, 0.165 mmol) to afford Example 100 (36 mg, 54%).

1H-NMR (400 MHz, CDCl$_3$) δ: 6.86–6.69 (m, 3H), 5.30–5.02 (m, 1H), 4.17–4.00 (m, 1H), 3.82 (s, 3H), 3.82–3.18 (m, 5H), 3.08 and 2.97 (singlets, 2H, rotomers), 2.13 and 2.11 (singlets, 3H, rotomers), 1.95–1.23 (m, 5H), 1.20–1.14 (m, 2H), 1.00–0.92 (m, 3H), 0.76 and 0.72 (doublets, 3H, rotomers), 0.62 (m, 2H), 0.36 (m, 2H)

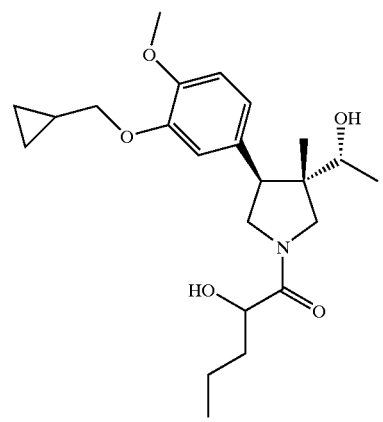

EXAMPLE 101

R$^1$=CH$_2$C$_3$H$_5$; R$^3$=COCH(OH)C$_4$H$_9$

1-{(3S,4S)-3-((1R)-1-Hydroxyethyl)-4-[3-(cyclopropylmethoxy)-4-methoxyphenyl]-3-methylpyrrolidinyl}-2-hydroxypentan-1-one Example 100 (36 mg, 80 μmol) was subjected to the LiOH hydrolysis procedure of Intermediate 5 to provide Example 101 as a clear film (30 mg, 90%).

$^1$H-NMR (400 MHz, CDCl$_3$) δ: 6.85–6.73 (m, 3H), 4.23 (m, 1H), 4.07–2.98 (m, 6H), 3.83 (s, 3H), 1.71–1.23 (m, 5H), 1.16 (m, 3H), 0.96 (m, 3H), 0.77 (s, 3H), 0.62 (m, 2H), 0.37 (m, 2H). LRMS (Electrospray, positive): Da/e 406.5 (m+1).

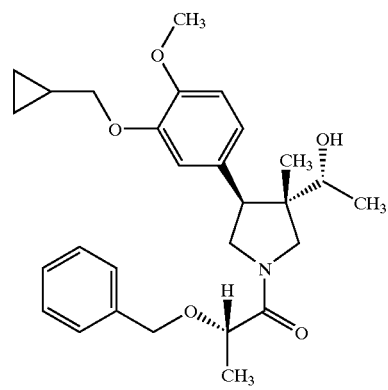

EXAMPLE 102

R$^1$=CH$_2$C$_3$H$_5$; R$^3$=(S)—COC(CH$_3$)OCH$_2$Ph

1-{(3S,4S)-3-((1R)-1-Hydroxyethyl)-4-[3-(cyclopropylmethoxy)-4-methoxyphenyl]-3-methylpyrrolidinyl}(2S)-2-(phenylmethoxy)propan-1-one Intermediate 67 (46 mg, 0.15 mmol) was converted by the Hunig's base procedure of Intermediate 74 using (2S)-2-(phenylmethoxy)propanoyl chloride (59 mg, 0.3 mmol) to give Example 102 (54 mg, 77%).

$^1$H-NMR (400 MHz, CDCl$_3$) δ: 7.40–7.25 (m, 5H), 6.82–6.77 (m, 2H), 6.72 (s, 1H), 4.63 (dd, 1H), 4.49 (dd, 1H), 4.22 (m, 1H), 3.98–3.38 (m, 8H), 3.82 (s, 3H), 3.07 and 2.96 (singlets, 1H, rotomers), 1.43 (m, 3H), 1.31 (m, 1H), 1.17 and 1.10 (doublets, 3H, rotomers), 0.72 and 0.70 (singlets, 3H, rotomers), 0.62 (m, 2H), 0.37 (m, 2H).

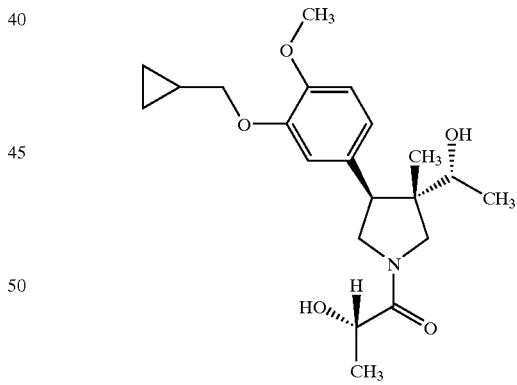

EXAMPLE 103

R$^1$=CH$_2$C$_3$H$_5$; R$^3$=(S)—COC(CH$_3$)OH

1-{(3S,4S)-3-((1R)-1-Hydroxyethyl)-4-[3-(cyclopropylmethoxy)-4-methoxyphenyl]-3-methylpyrrolidinyl}(2S)-2-(hydroxy)propan-1-one Prepared from Example 102 (54 mg, 0.12 mmol) by the debenzylation procedure of Intermediate 31 to give Example 103 as a clear oil (45 mg, 100%).

1H-NMR (400 MHz, CDCl₃) δ: 6.84–6.73 (m, 3H), 4.44 (m, 1H), 4.06–3.16 (m, 8H), 3.82 (s, 3H), 2.99 (d, 1H), 1.38 (m, 3H, rotomers), 1.30 (m, 1H), 1.18 (m, 3H, rotomers), 0.78 and 0.76 (singlets, 3H, rotomers), 0.62 (m, 2H), 0.36 (m, 2H). LRMS (Electrospray, positive): Da/e 378.7 (m+1).

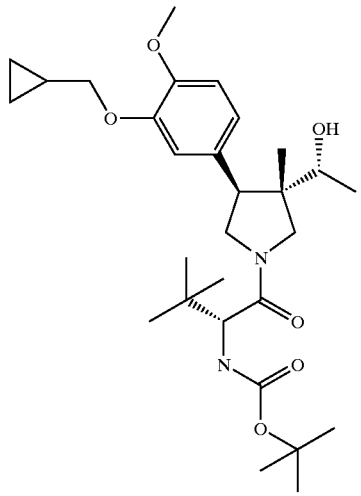

EXAMPLE 104

R¹=CH₂C₃H₅; R³=(R)—COCH(t-Bu)NHCO₂t-Bu

N-((1R)-2-{(3S,4S)-3-((1R)-1-Hydroxyethyl)-4-[3-(cyclopropylmethoxy)-4-methoxyphenyl]-3-methylpyrrolidinyl}-1-(tert-butyl)-2-oxoethyl)(tert-butoxy)carboxamide Intermediate 67 (46 mg, 0.15 mmol) was converted by the EDCI coupling procedure of Example 27 using Boc-D-t-butylglycine (35 mg, 0.15 mmol) to provide Example 104 as a white foam (62 mg, 80%).

1H-NMR (400 MHz, CDCl₃) δ: 6.85–6.79 (m, 2H), 6.72–6.64 (m, 1H), 4.36–4.00 (m, 3H, rotomers), 3.83 (s, 3H), 3.79 (d, 2H), 3.67–3.12 (m, 4H, rotomers), 1.44 and 1.41 (singlets, 9H, rotomers), 1.32 (m, 1H), 1.22–1.16 (m, 3H), 1.06 and 1.01 (singlets, 9H, rotomers), 1.02 (m, 3H), 0.73 and 0.63 (singlets, 3H, rotomers), 0.61 (m, 2H), 0.36 (m, 2H).

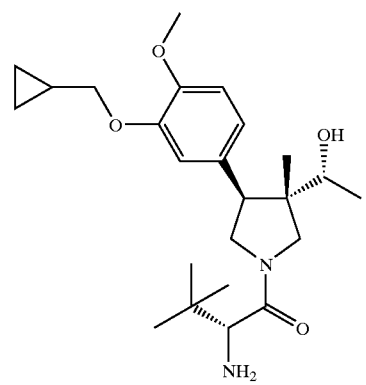

EXAMPLE 105

R¹=CH₂C₃H₅; R³=(R)—COCH(t-Bu)NH₂

(2R)-1-{(3S,4S)-3-((1R)-1-Hydroxyethyl)-4-[3-(cyclopropylmethoxy)-4-methoxyphenyl]-3-methylpyrrolidinyl}-2-amino-3,3-dimethylbutan-1-one To a stirred solution of Example 104 (62 mg, 0.12 mmol) in CH₂Cl₂ (1.5 mL) at room temperature in a capped flask was added trifluoroacetic acid (77 μL, 1 mmol). After stirring overnight, the reaction was concentrated in vacuo to provide a crude product that appeared to contain trifluoroacetate ester impurity. The crude product was dissolved in 3:2 THF:H₂O (1.5 mL) at room temperature, and stirred in a capped flask and treated with LiOH monohydrate (42 mg, 1 mmol). After 1 hour, the mixture was partitioned between EtOAc (15 mL) and water (15 mL). The organic layers were isolated, dried (MgSO₄), filtered, and concentrated in vacuo to provide Example 105 as a white foam (35 mg, 70%).

1H-NMR (400 MHz, CDCl₃) δ: 6.85–6.82 (m, 2H), 6.78–6.73 (m, 1H), 4.01–3.30 (m, 9H), 3.83 (s, 3H), 1.18 and 1.12 (doublets, 3H, rotomers), 1.06 and 1.02 (singlets, 9H, rotomers), 0.78 and 0.68 (singlets, 3H, rotomers), 0.063 (m, 2H), 0.37 (m, 2H). LRMS (Electrospray, positive): Da/e 419.4 (m+1).

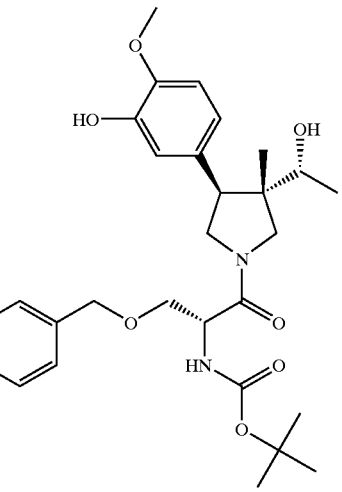

EXAMPLE 106

R¹=H; R³=(R)—COCH(CH₂OCH₂Ph)NHCO₂t-Bu

N-{2-[(3S,4S)-3-((1R)-1-Hydroxyethyl)-4-(3-hydroxy-4-methoxyphenyl)-3-methylpyrrolidinyl](1R)-2-oxo-1-[(phenylmethoxy)methyl]ethyl}(tert-butoxy)carboxamide To a stirred solution of N-Boc-O-benzyl-D-serine (2.95 gm, 10 mmol) in THF (50 mL) at −78° C. under a nitrogen blanket was added N-methyl morpholine (3.3 mL, 30 mmol) followed by isobutyl chloroformate (1.3 mL, 10 mmol). After stirring for 30 minutes, a solution/suspension of Intermediate 70 (2.51 gm, 10 mmol) in THF (50 mL) was added by cannula. The reaction was stirred for 2 hours at −78° C., then warmed to 0° C. for 2 hours. The reaction then was partially concentrated by rotary evaporator to approximately 25 mL, and partitioned between EtOAc (250 mL) and 2N HCl (250 mL). The organic layers were washed with 2N HCl (2×250 mL), saturated NaHCO₃ (3×250 mL), and saturated NaCl (1×250 mL). The organic layers were dried (MgSO₄), filtered, and concentrated in vacuo to provide Example 106 as a yellow oil (4.2 gm, 79%).

1H-NMR (400 MHz, CDCl₃) δ: 7.36–7.21 (m, 5H), 6.81–6.63 (m, 3H), 5.81 (br s, 1H), 5.47 (m, 1H), 4.73 (m, 1H), 4.51 (m, 2H), 4.00–3.40 (m, 83.83H), 3.84 and 3.82 (singlets, 3H, rotomers), 1.43 and 1.41 (singlets, 9H, rotomers), 1.13 and 1.06 (doublets, 3H, rotomers), 0.95 (m, 1H), 0.73 and 0.045 (singlets, 3H, rotomers).

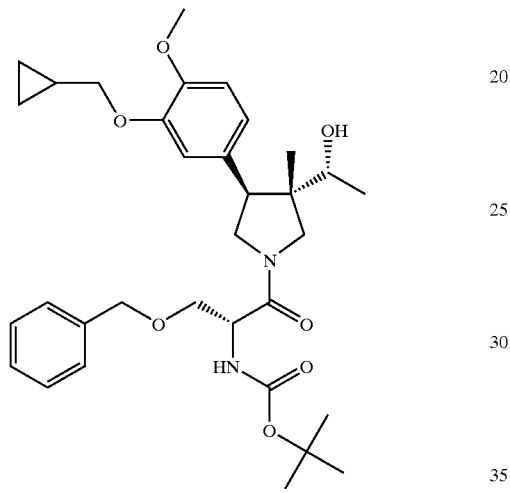

EXAMPLE 107

R¹=CH₂C₃H₅; R³=(R)—COCH(CH₂OCH₂Ph)NHCO₂t-Bu

N-(2-{(3S,4S)-3-((1R)-1-Hydroxyethyl)-4-[3-(cyclopropylmethoxy)-4-methoxyphenyl]-3-methylpyrrolidinyl}(1S)-2-oxo-1-[(phenylmethoxy)methyl]ethyl)-(tert-butoxy)carboxamide To a stirred solution of Example 106 (4.2 gm, 7.9 mmol) in DMF (24 mL) at room temperature under a nitrogen blanket was added powdered K₂CO₃ (5.45 gm, 39.5 mmol) followed by bromomethylcyclopropane (1.53 mL, 15.8 mmol). The suspension was warmed to 65° C. for 4 hours, then treated with more bromomethylcyclopropane (1.53 mL, 15.8 mmol). The reaction was stirred another 16 hours at 65° C., then cooled to room temperature and partitioned between EtOAc (500 mL) and water (500 mL). The organic layers were washed with water (3×500 mL) and saturated NaCl (1×500 mL), dried (MgSO₄), filtered, and concentrated in vacuo. The crude product was divided into two batches, and chromatographed on a Biotage 40M column with 1/1 EtOAc/hexane to provide, after pooling and concentration in vacuo of product containing fractions, Example 107 (2.11 gm, 46%). A high R_f dialkylated product was identified as a major impurity.

1H-NMR (400 MHz, CDCl₃) δ: 7.36–7.22 (m, 5H), 6.81–6.71 (m, 3H), 5.42 (m, 1H), 4.73 (m, 1H), 4.51 (m, 2H), 4.04–3.44 (m, 10H), 3.83 and 3.81 (singlets, 3H, rotomers), 1.42 and 1.43 (singlets, 9H, rotomers), 1.32 (m, 1H), 1.16 and 1.06 (doublets, 3H, rotomers), 0.76 and 0.45 (singlets, 3H, rotomers), 0.62 (m, 2H), 0.37 (m, 2H).

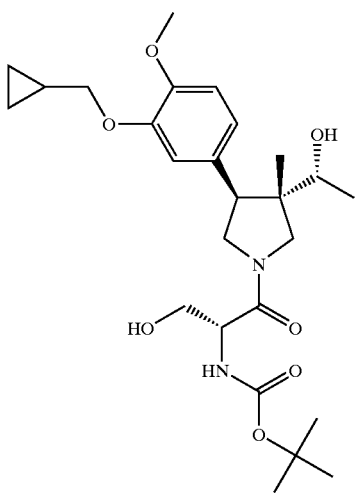

EXAMPLE 108

R¹=CH₂C₃H₅; R³=(R)—COCH(CH₂OH)NHCO₂t-Bu

N-(2-{(3S,4S)-3-((1R)-1-Hydroxyethyl)-4-[3-(cyclopropylmethoxy)-4-methoxyphenyl]-3-methylpyrrolidinyl}(1R)-1-(hydroxymethyl)-2-oxoethyl)(tert-butoxy)carboxamide Example 107 (2.1 gm, 3.6 mmol) was subjected to the debenzylation procedure of Intermediate 31 to afford Example 108 as a white foam (1.75 gm, 100%).

1H-NMR (CDCl₃/CD₃OD, 400 MHz) δ: 6.83–6.71 (m, 3H), 5.70 (br d, 1H), 4.55 (m, 1H), 4.09–3.38 (m, 10H), 3.83 (s, 3H), 1.44 (s, 9H), 1.33 (m, 1H), 1.18 (m, 3H), 0.73 (d, 3H), 0.62 (m, 2H), 0.37 (m, 2H).

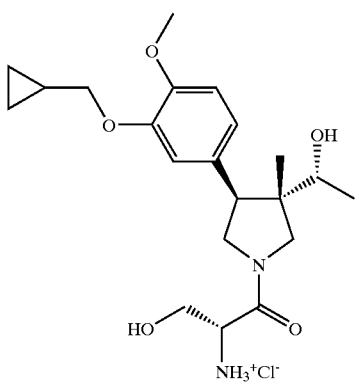

EXAMPLE 109

R¹=CH₂C₃H₅; R³=(R)—COCH(CH₂OH)NH₂

1-{(3S,4S)-((1R)-1-Hydroxyethyl)-4-[3-(cyclopropylmethoxy)-4-methoxyphenyl]-3-methylpyrrolidinyl}(2R)-2-amino-3-hydroxypropan-1-one hydrochloride To a stirred solution of Example 108 (1.75 gm, 3.6 mmol) in dioxane (16 mL) at room temperature under a drying tube was added 4N HCl in dioxane (16 mL). The clear solution was stirred for 4 hours, then concentrated in vacuo to provide Example 109 as a tan foam (1.5 gm, 97%).

1H-NMR (400 MHz, CDCl₃) δ: 6.85–6.76 (m, 3H), 4.36 (m, 1H), 4.13–3.31 (m, 10H), 3.84 (s, 3H), 1.29 (m, 1H), 1.17 and 1.12 (doublets, 3H, rotomers), 1.77 and 1.75 (singlets, 3H, rotomers), 0.62 (m, 2H), 0.36 (m, 2H). LRMS (Electrospray, positive): Da/e 393.4 (m+1).

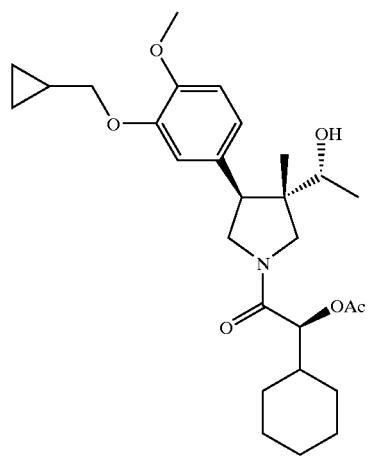

EXAMPLE 110

R¹=CH₂C₃H₅; R³=(S)—COCH(OAc)C₆H₁₁

2-{3-((1R)-1-Hydroxyethyl)(3S,4S)-4-[3-(cyclopropylmethoxy)-4-methoxyphenyl]-3-methylpyrrolidinyl}(1S)-1-cyclohexyl-2-oxoethyl acetate Intermediate 67 (91 mg, 0.6 mmol) was coupled by the Hunig's base procedure of Intermediate 74 using (S)-(+)-acetoxyhexahydromandelic acid chloride (100 μL, 4.98 M in CH₂Cl₂, 1.7 eq) to yield Example 110 as a clear, colorless oil (89 mg, 61%). LRMS (Electrospray, positive): Da/e 488.6 (m+1).

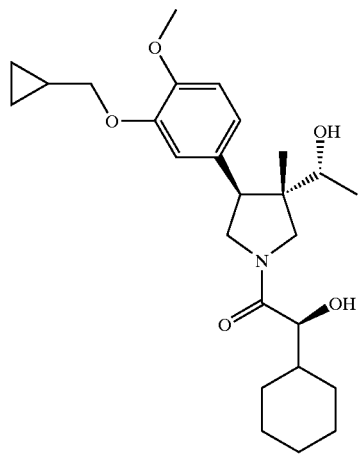

EXAMPLE 111

R¹=CH₂C₃H₅; R³=(S)—COCH(OH)C₆H₁₁

1-{3-((1R)-1-Hydroxyethyl)(3S,4S)-4-[3-(cyclopropylmethoxy)-4-methoxyphenyl]-3-methylpyrrolidinyl}(2S)-2-cyclohexyl-2-hydroxyethan-1-one Example 110 (89 mg, 0.18 mmol) was subjected to the LiOH hydrolysis procedure of Intermediate 5 to afford Example 111 as a clear, colorless film (44 mg, 54%).

¹H NMR (400 MHz, CDCl₃) δ: 6.80–6.78 (m, 3H), 3.88–3.52 (c, 10H), 3.34–3.26 (dd, 1H), 2.98 (d, 1H), 2.12 (br s, 1H), 1.77–1.10 (c, 16H), 0.75–0.73 (d, 3H), 0.62–0.59 (m, 2H), 0.34–0.31 (m, 2H). LRMS (Electrospray, positive): Da/e 446.6 (m+1).

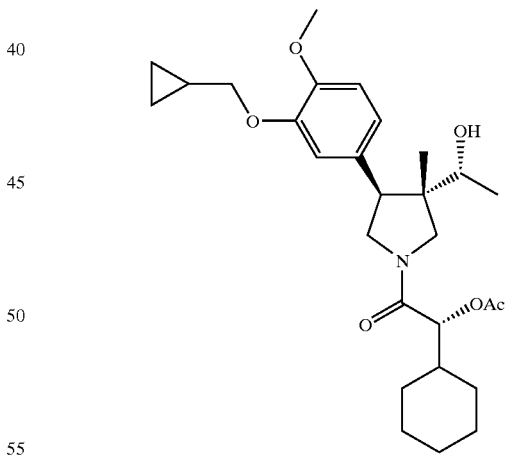

EXAMPLE 112

R¹=CH₂C₃H₅; R³=(R)—COCH(OAc)C₆H₁₁

(1R)-2-{3-((1R)-1-Hydroxyethyl)(3S,4S)-4-[3-(cyclopropylmethoxy)-4-methoxyphenyl]-3-methylpyrrolidinyl}-1-cyclohexyl-2-oxoethyl acetate Intermediate 67 (76 mg, 0.25 mmol) was coupled by the Hunig's base procedure of Intermediate 74 with (R)-(−)- acetoxyhexahydromandelic acid chloride (100 μL, 4.16 M in CH$_2$Cl$_2$, 1.7 eq) to give Example 112 as a clear, colorless oil (75 mg, 62%). LRMS (Electrospray, positive): Da/e 488.7 (m+1).

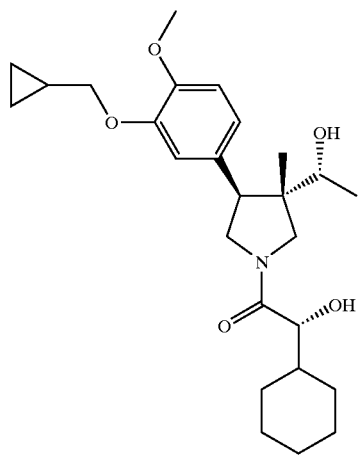

EXAMPLE 113

R$^1$=CH$_2$C$_3$H$_5$; R$^3$=(R)—COCH(OH)C$_6$H$_{11}$ (2R)-1-{3-((1R)-1-Hydroxyethyl)(3S,4S)-4-[3-(cyclopropylmethoxy)-4-methoxyphenyl]-3-methylpyrrolidinyl}-2-cyclohexyl-2-hydroxyethan-1-one Example 112 (75 mg, 0.15 mmol) was subjected to the LiOH hydrolysis procedure of Intermediate 5 to give Example 113 as a clear, colorless film (35 mg, 51%).

$^1$H NMR (400 MHz, CDCl$_3$) δ: 6.81–6.73 (m, 3H), 3.85–3.59 (c, 11H), 2.99–2.98 (d, 1H), 2.03–1.15 (c, 17H), 0.73 (s, 3H), 0.64–0.60 (m, 2H), 0.35–0.32 (m, 2H). LRMS (Electrospray, positive): Da/e 446.5 (m+1).

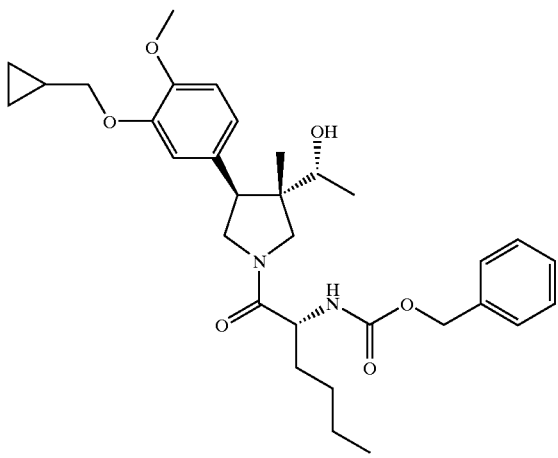

EXAMPLE 114

R$^1$=CH$_2$C$_3$H$_5$; R$^3$=(R)—COCH(C$_4$H$_9$)NHCO$_2$CH$_2$Ph

N-((1R)-2-{3-((1R)-1-Hydroxyethyl)(3S,4S)-4-[3-(cyclopropylmethoxy)-4-methoxyphenyl]-3-methylpyrrolidinyl}-1-butyl-2-oxoethyl)(phenylmethoxy)carboxamide Intermediate 67 (41 mg, 0.013 mmol) was coupled by the Hunig's base procedure of Intermediate 74 with Z-D-Nle-ONp (57 mg, 0.15 mmol, 1.1 eq) to give Example 114 as a clear, colorless oil (29.9 mg, 40%). LRMS (Electrospray, positive): Da/e 553.6 (m+1).

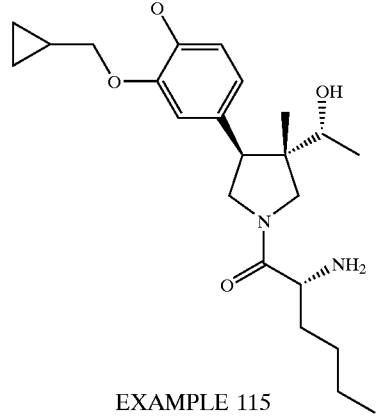

EXAMPLE 115

R$^1$=CH$_2$C$_3$H$_5$; R$^3$=(R)—COCH(C$_4$H$_9$)NH$_2$ (2R)-1-{3-((1R)-1-Hydroxyethyl)(3S,4S)-4-[3-(cyclopropylmethoxy)-4-methoxyphenyl]-3-methylpyrrolidinyl}-2-aminohexan-1-one Example 114 (29.9 mg, 0.054 mmol) was subjected to the debenzylation procedure of Intermediate 31 to give Example 115 as a white powder (18.8 mg, 83%).

$^1$H NMR (400 MHz, CDCl$_3$) δ: 6.83–6.62 (m, 3H), 4.17–4.08 (m, 2H), 3.85–3.61 (c, 9H), 3.32–3.29 (t, 1H), 3.13–3.11 (d, 1H), 2.04–1.78 (m, 3H), 1.52–1.21 (c, 10H), 0.92–0.88 (t, 3H), 0.62–0.58 (m, 5H), 0.34–0.30 (m, 2H). LRMS (Electrospray, positive): Da/e 419.4 (m+1).

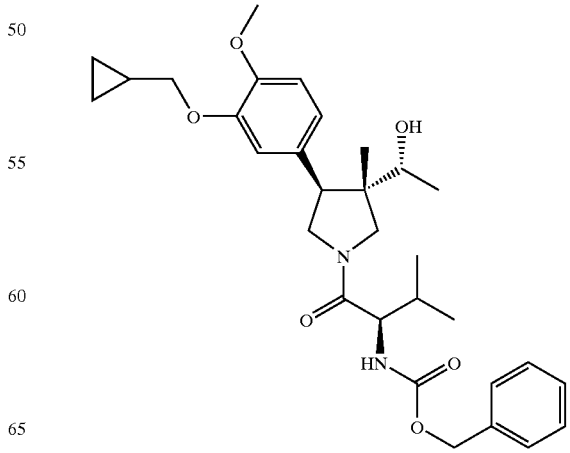

EXAMPLE 116

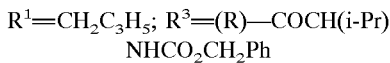

N-((1R)-2-{3-((1R)-1-Hydroxyethyl)(3S,4S)-4-[3-(cyclopropylmethoxy)-4-methoxyphenyl]-3-methylpyrrolidinyl}-1-(methylethyl)-2-oxoethyl)(phenylmethoxy)carboxamide Intermediate 67 (41 mg, 0.13 mmol) was coupled by the Hunig's base procedure of Intermediate 74 with Z-D-Val-OSu (52.2 mg, 0.15 mmol, 1.1 eq) to yield Example 116 as a clear, colorless oil (64.8 mg, 89%).

$^1$H NMR (400 MHz, CDCl$_3$) δ: 7.35–7.32 (m, 5H), 6.81–6.69 (m, 3H), 5.65–5.61 (t, 3H), 5.28–5.01 (m, 2H), 4.34–2.78 (m, 10H), 2.08–1.98 (m, 1H), 1.31–0.91 (c, 8H), 0.71–0.68 (d, 3H), 0.64–0.59 (m, 2H), 0.38–0.31 (m, 2H).

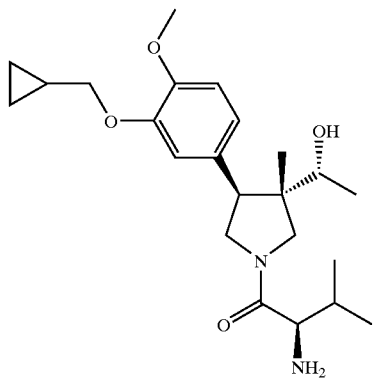

EXAMPLE 117

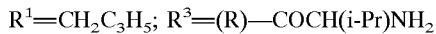

(2R)-1-{3-((1R)-1-Hydroxyethyl)(3S,4S)-4-[3-(cyclopropylmethoxy)-4-methoxyphenyl]-3-methylpyrrolidinyl}-2-amino-3-methylbutan-1-one Example 116 (64.8 mg, 0.120 mmol) was subjected to the debenzylation procedure of Intermediate 31 to give Example 117 as a clear solid (38.9 mg, 80%).

$^1$H NMR (400 MHz, CDCl$_3$, mixture of rotomers) δ: 6.77–6.59 (m, 3H), 4.41 (s, 1H), 4.23–4.12 (m, 2H), 3.85–3.60 (c, 9H), 3.24 (s, 1H), 3.15–3.13 (d, 1H), 2.40 (br s, 1H), 1.29–1.14 (m, 11H), 0.62–0.58 (m, 5H), 0.33–0.29 (m, 2H). LRMS (Electrospray, positive): Da/e 405.5 (m+1).

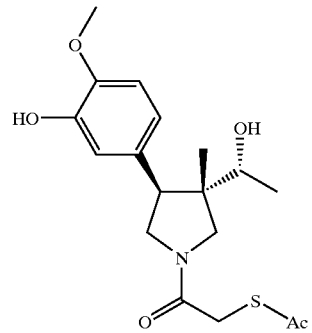

EXAMPLE 118

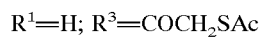

1-[3-((1R)-1-Hydroxyethyl)(3S,4S)-4-(3-hydroxy-4-methoxyphenyl)-3-methylpyrrolidinyl]-2-acetylthioethan-1-one Intermediate 70 (173 mg, 0.694 mmol) was dissolved in dioxane (2 mL), and 1 M K$_2$CO$_3$ (1 mL) was added dropwise. Acetoxymercaptoacetic acid chloride (100 μL, 13.9 M in dioxane, 2 eq) was added, and the solution was vigorously stirred for 1 hour. The solution was diluted with EtOAc (30 mL) and the organic layers were washed with 1M K$_2$CO$_3$ (20 mL), then brine (20 mL). The organic layer was dried over Na$_2$SO$_4$, and concentrated in vacuo. The resulting oil was chromatographed by silica column (1:1 EtOAc: hexanes), yielding a clear, colorless oil (34 mg, 13%).

$^1$H NMR (400 MHz, CDCl$_3$, mixture of rotomers) δ: 6.85–6.82 (m, 3H), 3.92–2.98 (c, 12H), 2.39 (s, 3H), 1.15–1.11 (t, 3H), 0.75–0.73 (d, 3H).

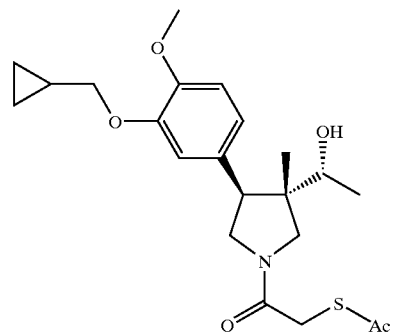

EXAMPLE 119

1-{3-((1R)-1-Hydroxyethyl)(3S,4S)-4-[3-(cyclopropylmethoxy)-4-methoxyphenyl]-3-methylpyrrolidinyl}-2-acetylthioethan-1-one To a flask containing anhydrous K$_2$CO$_3$ (52 mg, 0.37 mmol, 4.0 eq) under a nitrogen atmosphere was added a solution of Example 118 (34 mg, 0.093 mmol, 1 eq) in anhydrous DMF (1 mL). Cyclopropylmethyl bromide (40 μL, 0.37 mmol, 4.0 eq) was added via syringe to the mixture. The slurry was stirred at 65° C. overnight. The reaction was cooled to room temperature, then diluted with water (50 mL). The aqueous solution was extracted with EtOAc (3×30 mL), and the combined organic layers were washed with brine (50 mL), then dried over Na$_2$SO$_4$, filtered, and concentrated in vacuo. The resulting oil was purified by preparative TLC plate (100% EtOAc), yielding a clear, colorless oil (13.9 mg, 36%).

$^1$H NMR (400 MHz, CDCl$_3$, mixture of rotomers) δ: 7.10–6.75 (m, 3H), 3.91–3.32 (c, 11H), 2.64–2.61 (m, 2H), 2.38–2.30 (d, 3H), 1.82–1.50 (br s, 2H), 1.38–1.04 (m, 2H), 0.75 (s, 3H), 0.58–0.55 (m, 2H), 0.27–0.23 (m, 2H).

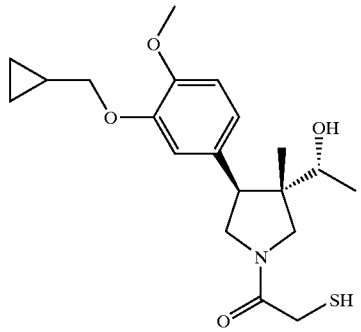

EXAMPLE 120

R$^1$=CH$_2$C$_3$H$_5$; R$^3$=COCH$_2$SH

1-{3-((1R)-1-Hydroxyethyl)(3S,4S)-4-[3-(cyclopropylmethoxy)-4-methoxyphenyl]-3-methylpyrrolidinyl}-2-sulfanylethan-1-one Example 119 (13.9 mg, 0.0329 mmol) was subjected to the LiOH hydrolysis procedure of Intermediate 5 to give a clear, colorless oil (7.2 mg, 58%).

$^1$H NMR (CD3OH, 400 MHz, mixture of rotomers) δ: 6.86–6.75 (m, 3H), 3.83–3.11 (c, 13H), 2.60–2.56 (d, 2H), 1.39–0.85 (m, 4H), 0.76–0.74 (m, 3H), 0.58–0.56 (m, 2H), 0.35–0.24 (m, 3H). LRMS (Electrospray, positive): Da/e 380.5 (m+1).

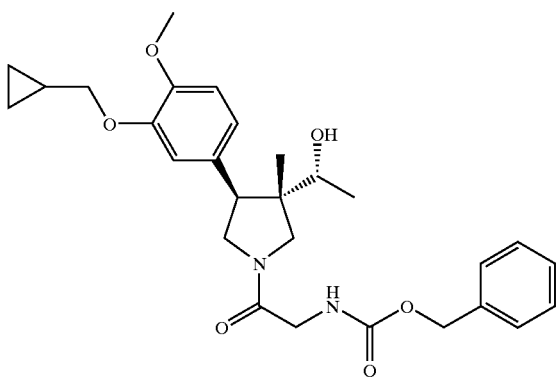

EXAMPLE 121

R$^1$=CH$_2$C$_3$H$_5$; R$^3$=COCH$_2$NHCO$_2$CH$_2$Ph

N-(2-{3-((1R)-1-Hydroxyethyl)(3S,4S)-4-[3-(cyclopropylmethoxy)-4-methoxyphenyl]-3-methylpyrrolidinyl}-2-oxoethyl)(phenylmethoxy)carboxamide Intermediate 67 was acylated by the Hunig's base procedure of Intermediate 74 with N-CBZ-glycine p-nitrophenyl ester to give Example 121.

$^1$H NMR (400 MHz, CDCl$_3$, mixture of rotomers) δ: 7.42–7.28 (m, 5H), 6.83–6.75 (m, 3H), 5.87–5.80 (m, 1H), 5.13 (s, 2H), 4.08–3.15 (c, 13H), 1.39–1.24 (m, 1H), 1.14 (t, 3H), 0.73 (d, 3H), 0.66–0.59 (m, 2H), 0.39–0.31 (m, 2H).

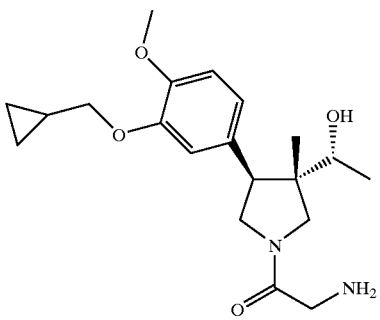

EXAMPLE 122

R$^1$=CH$_2$C$_3$H$_5$; R$^3$=COCH$_2$NH$_2$

1-{3-((1R)-1-Hydroxyethyl)(3S,4S)-4-[3-(cyclopropylmethoxy)-4-methoxyphenyl]-3-methylpyrrolidinyl}-2-aminoethan-1-one Example 121 was subjected to the debenzylation procedure of Intermediate 31 to give Example 122.

$^1$H NMR (Methanol-d$_4$, 400 MHz, mixture of rotomers) δ: 6.94–6.84 (m, 3H), 4.01–3.27 (c, 13H), 1.29–1.18 (m, 3H), 0.79–0.73 (m, 3H), 0.62–0.55 (m, 2H), 0.35–0.29 (m, 2H). LRMS (Electrospray, positive): Da/e 363.2 (m+1).

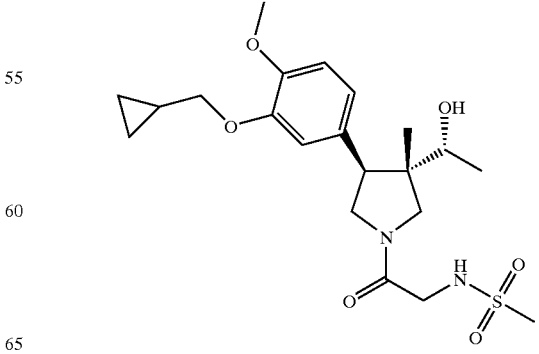

EXAMPLE 123

R$^1$=CH$_2$C$_3$H$_5$; R$^3$=COCH$_2$NHSO$_2$CH$_3$

1-{3-((1R)-1-Hydroxyethyl)(3S,4S)-4-[3-(cyclopropylmethoxy)-4-methoxyphenyl]-3-methylpyrrolidinyl}-2-[(methylsulfonyl)amino]ethan-1-one Acylation of Example 122 by the Hunig's base coupling procedure of Intermediate 74 using methanesulfonyl chloride afforded Example 123.

$^1$H NMR (400 MHz, CDCl$_3$, mixture of rotomers) δ: 6.86–6.75 (m, 3H), 5.48–5.42 (m, 1H), 4.00–3.57 (c, 11H), 3.46 and 3.15 (d and d, 1H), 3.00 (s, 3H), 1.67 (dd, 1H), 1.36–1.24 (m, 1H), 1.16 (t, 3H), 0.76 (d, 3H), 0.66–0.60 (m, 2H), 0.39–0.32 (m, 2H). LRMS (Electrospray, positive): Da/e 441.3 (m+1).

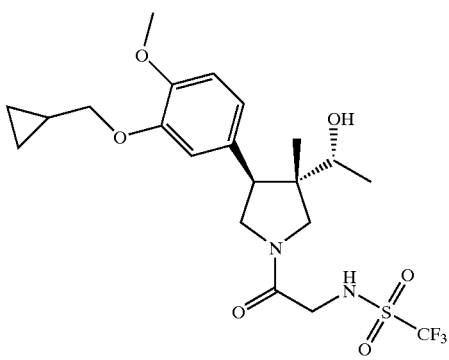

EXAMPLE 124

R$^1$=CH$_2$C$_3$H$_5$; R$^3$=COCH$_2$NHSO$_2$CF$_3$

1-{3-((1R)-1-Hydroxyethyl)(3S,4S)-4-[3-(cyclopropylmethoxy)-4-methoxyphenyl]-3-methylpyrrolidinyl}-2-{[(trifluoromethyl)sulfonyl]amino}ethan-1-one Sulfonation of Example 122 by the Hunig's base coupling procedure of Intermediate 74 using trifluoromethanesulfonyl chloride afforded Example 124.

$^1$H NMR (400 MHz, CDCl$_3$, mixture of rotomers) δ: 6.85–6.77 (m, 3H), 4.11–3.10 (c, 13H), 1.15 (t, 3H), 0.76 (d, 3H), 0.66–0.60 (m, 2H), 0.40–0.32 (m, 2H). LRMS (Electrospray, positive): Da/e 495.3 (m+1).

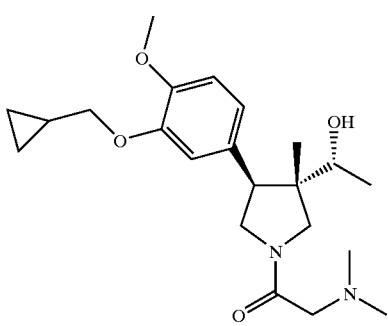

EXAMPLE 125

R$^1$=CH$_2$C$_3$H$_5$; R$^3$=COCH$_2$NMe$_2$

1-{3-((1R)-1-Hydroxyethyl)(3S,4S)-4-[3-(cyclopropylmethoxy)-4-methoxyphenyl]-3-methylpyrrolidinyl}-2-(dimethylamino)ethan-1-one Solid Phase EDCI Coupling Reaction A reaction vial equipped with a stir vane was charged with EDC resin (164 mg, 0.082 mmol, 0.5 mmol/g), NMP (2 mL), and N,N-dimethylglycine (20 mg, 0.143 mmol). The resulting mixture was allowed to stir at room temperature for one hour. Intermediate 67 then was added, and the mixture was stirred at room temperature for 20 hours, then filtered. The resin was washed with several portions of NMP. All the washings and filtrate were combined and subjected to reduced pressure to remove the solvent. Biotage purification on the residue (12S cartridge, 5% MeOH/CH$_2$Cl$_2$/0.1% NH$_4$OH) afforded 8 mg (25%) of a clear film.

$^1$H NMR (400 MHz, CDCl$_3$, mixture of rotomers) δ: 6.87–6.72 (m, 3H), 4.07–2.97 (c, 13H), 2.35 (d, 6H), 1.35–1.25 (m, 1H), 1.17 (t, 3H), 0.74 and 0.64 (s and s, 3H), 0.66–0.60 (m, 2H), 0.37–0.32 (m, 2H). LRMS (Electrospray, positive): Da/e 391.5 (m+1).

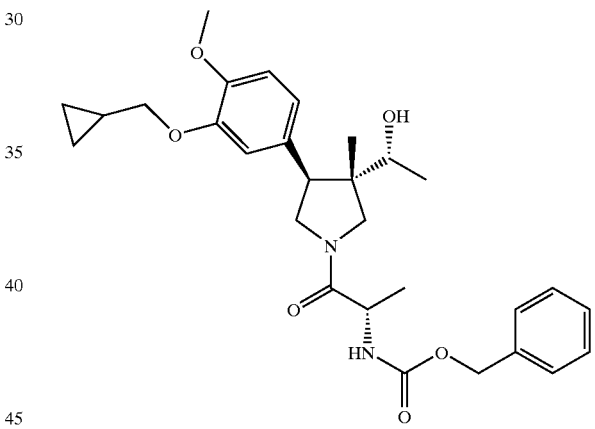

EXAMPLE 126

R$^1$=CH$_2$C$_3$H$_5$; R$^3$=(S)—COCH(Me)NHCO$_2$CH$_2$Ph

N-(2-{3-((1R)-1-Hydroxyethyl)(3S,4S)-4-[3-(cyclopropylmethoxy)-4-methoxyphenyl]-3-methylpyrrolidinyl}(1S)-1-methyl-2-oxoethyl)(phenylmethoxy)carboxamide Acylation of Intermediate 67 by the solid phase EDCI procedure of Example 125 with Z-Ala-ONp afforded Example 126.

$^1$H NMR (400 MHz, CDCl$_3$, mixture of rotomers) δ: 7.38–7.26 (m, 5H), 6.84–6.74 (m, 3H), 5.86 (dd 1H), 5.14–5.08 (m, 2H), 4.56 (quintet, 1H), 3.87–3.32 (c, 11H), 1.43–1.34 (dd, 3H), 1.33–1.24 (m, 1H), 1.13 (d, 3H), 0.74 (s, 3H), 0.66–0.59 (m, 2H), 0.37–0.32 (m, 2H). LRMS (Electrospray, positive): Da/e 511.7 (m+1).

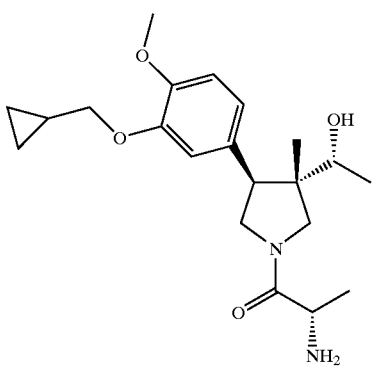

EXAMPLE 127

R$^1$=CH$_2$C$_3$H$_5$; R$^3$=(S)—COCH(CH$_3$)NH$_2$

1-{3-((1R)-1-Hydroxyethyl)(3S,4S)-4-[3-(cyclopropylmethoxy)-4-methoxyphenyl]-3-methylpyrrolidinyl}(2S)-2-aminopropan-1-one Example 126 was subjected to the procedure of Intermediate 31 to afford Example 127.

$^1$H NMR (400 MHz, CDCl$_3$, mixture of rotomers) δ: 8.44–8.16 (br s, 2H), 6.82–6.56 (m, 3H), 4.53–3.02 (c, 12H), 1.43–1.34 (dd, 3H), 1.33–1.24 (m, 1H), 1.13 (d, 3H), 0.74 (s, 3H), 0.66–0.59 (m, 2H), 0.37–0.32 (m, 2H). LRMS (Electrospray, positive): Da/e 377.3 (m+1).

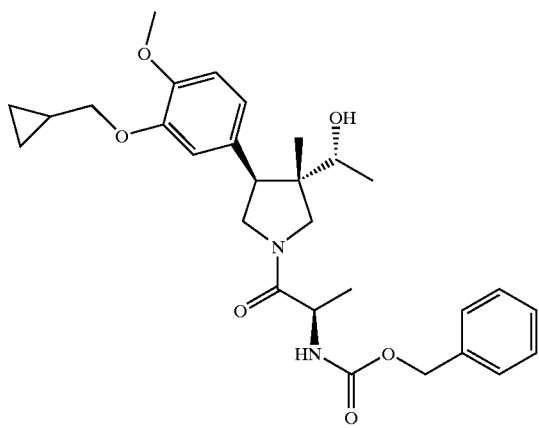

EXAMPLE 128

R$^1$=CH$_2$C$_3$H$_5$; R$^3$=(R)—COCH(CH$_3$)NHCO$_2$CH$_2$Ph

N-((1R)-2-{3-((1R)-1-Hydroxyethyl)(3S,4S)-4-[3-(cyclopropylmethoxy)-4-methoxyphenyl]-3-methylpyrrolidinyl}-1-methyl-2-oxoethyl)(phenylmethoxy)carboxamide Prepared from Intermediate 67 via the acylation procedure of Example 7 with Z-D-Ala-OSu.

$^1$H NMR (400 MHz, CDCl$_3$, mixture of rotomers) δ: 7.40–7.28 (m, 5H), 6.85–6.74 (m, 3H), 5.80 (t 1H), 5.10 (d, 2H), 4.57–4.47 (m, 1H), 3.99–3.12 (c, 11H), 1.40–1.24 (m, 4H), 1.14 (d, 3H), 0.73 (s, 3H), 0.66–0.59 (m, 2H), 0.38–0.31 (m, 2H). LRMS (Electrospray, positive): Da/e 511.6 (m+1).

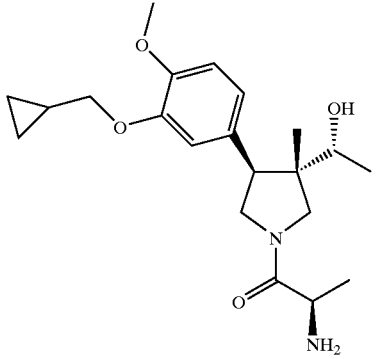

EXAMPLE 129

R$^1$=CH$_2$C$_3$H$_5$; R$^3$=(R)—COCH(CH$_3$)NH$_2$ (2R)-1-{3-((1R)-1-Hydroxyethyl)(3S,4S)-4-[3-(cyclopropylmethoxy)-4-methoxyphenyl]-3-methylpyrrolidinyl}-2-aminopropan-1-one Prepared from Example 128 via the debenzylation procedure of Intermediate 31.

$^1$H NMR (400 MHz, CDCl$_3$, mixture of rotomers) δ: 8.60–8.27 (br m, 3H), 6.87–6.58 (m, 3H), 4.75–3.10 (c, 12H), 1.74–1.59 (m, 3H), 1.33–1.05 (m, 4H), 0.66–0.55 (m, 5H), 0.35–0.27 (m, 2H). LRMS (Electrospray, positive): Da/e 377.2 (m+1).

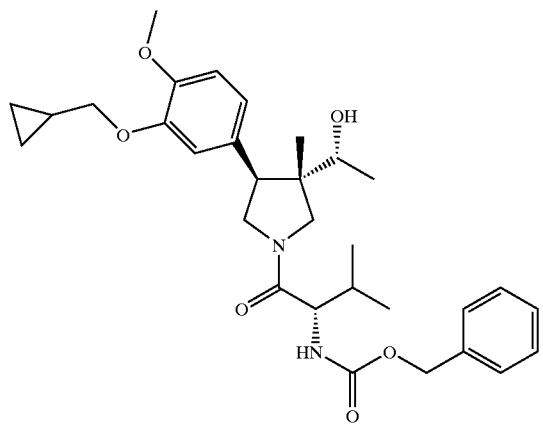

EXAMPLE 130

R$^1$=CH$_2$C$_3$H$_5$; R$^3$=(S)—COCH(i-Pr)NHCO$_2$CH$_2$Ph

N-(2-{3-((1R)-1-Hydroxyethyl)(3S,4S)-4-[3-(cyclopropylmethoxy)-4-methoxyphenyl]-3-methylpyrrolidinyl}(1S)-1-(methylethyl)-2-oxoethyl)(phenylmethoxy)carboxamide Prepared from Intermediate 67 via the acylation procedure of Example 7 using Z-Val-ONp.

$^1$H NMR (400 MHz, CDCl$_3$, mixture of rotomers) δ: 7.42–7.27 (m, 5H), 6.84–6.75 (m, 3H), 5.63 (dd 1H), 5.15–5.02 (m, 2H), 4.40–4.4.07 (dm, 1H), 3.87–3.33 (c, 12H), 2.08–1.95 (m, 1H), 1.34–1.25 (m, 1H), 1.14 (t, 3H), 1.04–0.90 (m, 6H), 0.73 (s, 3H), 0.66–0.59 (m, 2H), 0.38–0.31 (m, 2H). LRMS (Electrospray, positive): Da/e 539.5 (m+1).

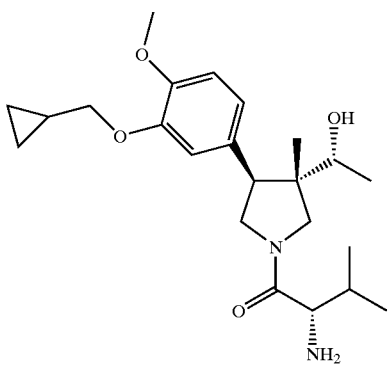

EXAMPLE 131

$R^1$=$CH_2C_3H_5$; $R^3$=(S)—COCH(i-Pr)$NH_2$

1-{3-((1R)-1-Hydroxyethyl)(3S,4S)-4-[3-(cyclopropylmethoxy)-4-methoxyphenyl]-3-methylpyrrolidinyl}(2S)-2-amino-3-methylbutan-1-one Prepared from Example 130 via the debenzylation method of Intermediate 31.

$^1$H NMR (400 MHz, CDCl$_3$, mixture of rotomers) δ: 8.37 (br s, 3H), 6.82–6.63 (m, 3H), 4.24–3.53 (c, 11H), 3.19 (d, 1H), 2.45–2.32 (m, 2H), 1.34–1.04 (m, 10H), 0.64 (s, 3H), 0.63–0.56 (m, 2H), 0.36–0.29 (m, 2H). LRMS (Electrospray, positive): Da/e 405.4 (m+1).

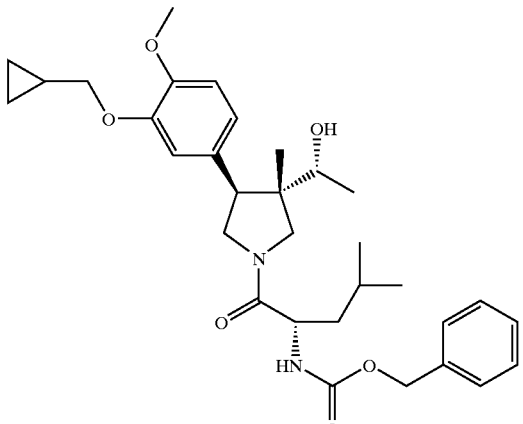

EXAMPLE 132

$R^1$=$CH_2C_3H_5$; $R^3$=(S)—COCH($CH_2$CH($CH_3$)$CH_3$)NH$CO_2CH_2$Ph

N-(2-{3-((1R)-1-Hydroxyethyl)(3S,4S)-4-[3-(cyclopropylmethoxy)-4-methoxyphenyl]-3-methylpyrrolidinyl}(1S)-1-(2-methylpropyl)-2-oxoethyl)(phenylmethoxy)carboxamide Prepared from Intermediate 67 via the Hunig's base acylation procedure of Intermediate 74 using Z-Leu-ONp.

$^1$H NMR (400 MHz, CDCl$_3$, mixture of rotomers) δ: 7.43–7.26 (m, 5H), 6.84–6.75 (m, 3H), 5.61 (dd 1H), 5.16–5.04 (m, 2H), 4.63–4.55 (m, 1H), 3.90–3.34 (c, 12H), 1.80–1.68 (m, 1H), 1.64–1.40 (m, 2H), 1.36–1.24 (m, 1H), 1.14 (d, 3H), 1.05–0.92 (m, 6H) 0.74 (d, 3H), 0.65–0.59 (m, 2H), 0.37–0.32 (m, 2H). LRMS (Electrospray, positive): Da/e 553.7 (m+1).

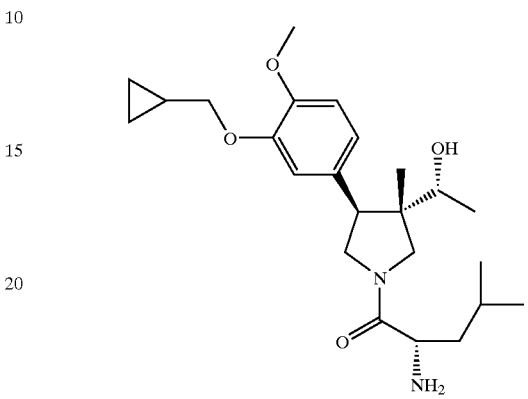

EXAMPLE 133

$R^1$=$CH_2C_3H_5$; $R^3$=(S)—COCH($CH_2$CH($CH_3$)$CH_3$)$NH_2$

1-{3-((1R)-1-Hydroxyethyl)(3S,4S)-4-[3-(cyclopropylmethoxy)-4-methoxyphenyl]-3-methylpyrrolidinyl}(2S)-2-amino-4-methylpentan-1-one Prepared from Example 132 via the debenzylation method of Intermediate 31.

$^1$H NMR (Methanol-d$_4$, 400 MHz, mixture of rotomers) δ: 6.96–6.86 (m, 3H), 4.33–4.28 (m, 1H), 4.03–3.28 (c, 11H), 1.87–1.65 (m, 3H), 1.29–1.18 (m, 1H), 1.14–0.96 (m, 9H), 0.76 (d, 3H), 0.61–0.55 (m, 2H), 0.36–0.29 (m, 2H). LRMS (Electrospray, positive): Da/e 419.5 (m+1).

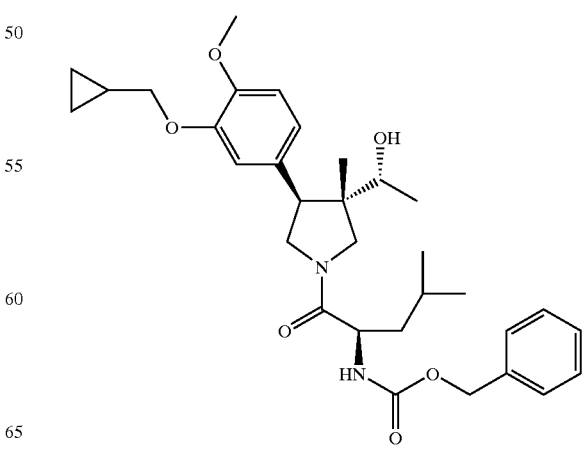

EXAMPLE 134

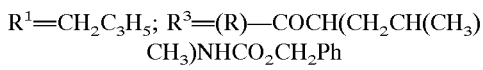

N-((1R)-2-{3-((1R)-1-Hydroxyethyl)(3S,4S)-4-[3-(cyclopropylmethoxy)-4-methoxyphenyl]-3-methylpyrrolidinyl}-1-(2-methylpropyl)-2-oxoethyl)(phenylmethoxy)carboxamide Prepared from Intermediate 67 via the Hunig's base acylation method of Intermediate 74 using Z-D-Leu-ONp.

$^1$H NMR (400 MHz, CDCl$_3$, mixture of rotomers) δ: 7.40–7.28 (m, 5H), 6.85–6.70 (m, 3H), 5.57 (dd 1H), 5.14–5.04 (m, 2H), 4.58–4.49 (m, 1H), 4.11–3.19 (c, 11H), 1.78–1.66 (m, 1H), 1.60–1.22 (m, 3H), 1.15 (dd, 3H), 1.03–0.85 (m, 6H) 0.72 (d, 3H), 0.65–0.57 (m, 2H), 0.38–0.30 (m, 2H). LRMS (Electrospray, positive): Da/e 553.7 (m+1).

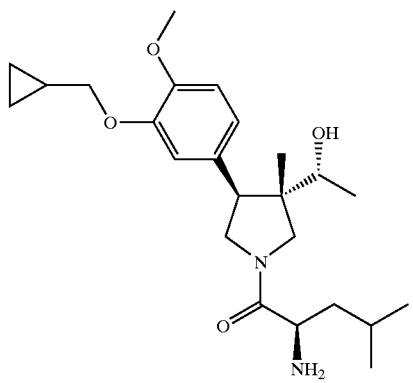

EXAMPLE 135

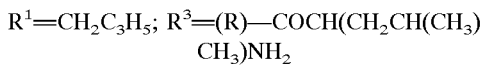

(2R)-1-{3-((1R)-1-Hydroxyethyl)(3S,4S)-4-[3-(cyclopropylmethoxy)-4-methoxyphenyl]-3-methylpyrrolidinyl}-2-amino-4-methylpentan-1-one Prepared from Example 134 via the debenzylation method of Intermediate 31.

$^1$H NMR (Methanol-d$_4$, 400 MHz, mixture of rotomers) δ: 6.97–6.91 (m, 2H), 6.88–6.83 (m, 1H), 4.29–3.25 (c, 11H), 1.85–1.59 (m, 3H), 1.30–1.19 (m, 1H), 1.10 (dd, 3H), 1.06–0.93 (m, 6H), 0.77 (dd, 3H), 0.62–0.55 (m, 2H), 0.36–0.29 (m, 2H). LRMS (Electrospray, positive): Da/e 419.5 (m+1).

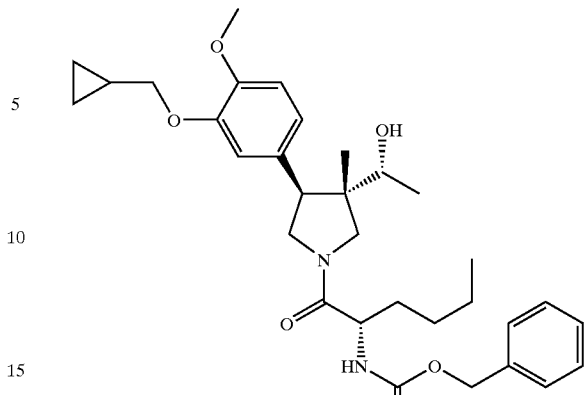

EXAMPLE 136

N-(2-{3-((1R)-1-Hydroxyethyl)(3S,4S)-4-[3-(cyclopropylmethoxy)-4-methoxyphenyl]-3-methylpyrrolidinyl}(1S)-1-butyl-2-oxoethyl)(phenylmethoxy)carboxamide Prepared from Intermediate 67 via the acylation method of Example 7 using Z-NLeu-ONp.

$^1$H NMR (400 MHz, CDCl$_3$, mixture of rotomers) δ: 7.40–7.25 (m, 5H), 6.85–6.75 (m, 3H), 5.69 (dd 1H), 5.14–5.05 (m, 2H), 4.56–4.50 (m, 1H), 3.87–3.34 (c, 11H), 1.80–1.54 (m, 2H), 1.43–1.24 (m, 5H), 1.14 (m, 3H), 0.96–0.85 (m, 3H) 0.74 (s, 3H), 0.65–0.61 (m, 2H), 0.37–0.32 (m, 2H). LRMS (Electrospray, positive): Da/e 553.8 (m+1).

EXAMPLE 137

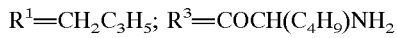

1-{3-((1R)-1-Hydroxyethyl)(3S,4S)-4-[3-(cyclopropylmethoxy)-4-methoxyphenyl]-3-methylpyrrolidinyl}(2S)-2-aminohexan-1-one Prepared from Example 136 via the debenzylation method of Intermediate 31.

$^1$H NMR (400 MHz, CDCl$_3$, mixture of rotomers) δ: 6.93–6.85 (m, 3H), 4.33–4.25 (m, 1H), 4.02–3.47 (c, 11H), 1.96–1.79 (m, 2H), 1.51–1.35 (m, 4H), 1.30–1.19 (m, 1H), 1.11 (dd, 3H), 1.03–0.93 (m, 3H) 0.77 (d, 3H), 0.62–0.56 (m, 2H), 0.35–0.30 (m, 2H). LRMS (Electrospray, positive): Da/e 419.5 (m+1).

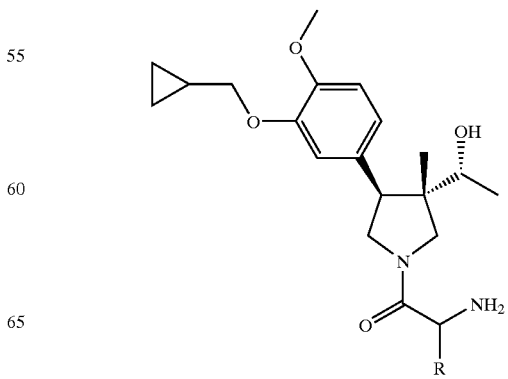

EXAMPLE 138

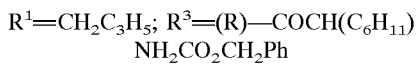

N-((1R)-2-{3-((1R)-1-Hydroxyethyl)(3S,4S)-4-[3-(cyclopropylmethoxy)-4-methoxyphenyl]-3-methylpyrrolidinyl}-(1R)-cyclohexyl-2-oxoethyl)(phenylmethoxy)carboxamide EDCI/HOBT Coupling Procedure A reaction vial equipped with a stir vane was charged with N-carboxybenzyl-D-cyclohexylglycine (23.8 mg, 0.0819 mmol), dry $CH_2Cl_2$ (350 ul), EDCI (15.7 mg, 0.0819 mmol), and hydroxybenzotriazole (HOBT) (12.5 mg, 0.0819 mmol). This mixture was allowed to stir at room temperature for 1 hour, and Intermediate 67 (25 mg, 0.0819 mmol) was added in one portion. After stirring at room temperature for 48 hours, the reaction mixture was diluted with $CH_2Cl_2$ (5 mL), washed with 1N HCl (2×20 mL), saturated $NaHCO_3$ solution (1×20 ml), dried ($Na_2SO_4$), and concentrated to 27 mg (57%) of a white foam.

$^1$H NMR (400 MHz, $CDCl_3$, mixture of rotomers) δ: 7.39–7.29 (m, 5H), 6.86–6.78 (m, 2H), 6.75–6.68 (m, 1H), 5.54 (dd, 1H), 4.37–3.25 (c, 12H), 1.81.1.56 (m, 5H), 1.36–0.95 (m, 10H), 0.71 (d, 3H), 0.66–0.59 (m, 2H), 0.39–0.31 (m, 2H). LRMS (Electrospray, positive): Da/e 580.2 (m+1).

EXAMPLE 139

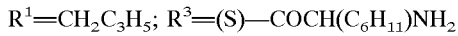

(2R)-1-{3-((1R)-1-Hydroxyethyl)(3S,4S)-4-[3-(cyclopropylmethoxy)-4-methoxyphenyl]-3-methylpyrrolidinyl}-2-amino-2-cyclohexylethan-1-one Prepared from Example 138 via the debenzylation procedure of Intermediate 31.

$^1$H NMR (Methanol-$d_4$, 400 MHz, mixture of rotomers) δ: 6.95–6.78 (m, 3H), 4.10–3.20 (c, 12H), 1.96–1.62 (m, 5H), 1.39–1.02 (m, 10H), 0.75 (d, 3H), 0.62–0.51 (m, 2H), 0.35–0.23 (m, 2H). LRMS (Electrospray, positive): Da/e 445.5 (m+1).

EXAMPLE 140

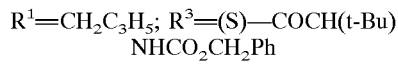

N-((1R)-2-{3-((1R)-1-Hydroxyethyl)(3S,4S)-4-[3-(cyclopropylmethoxy)-4-methoxyphenyl]-3-methylpyrrolidinyl}-(1S)-cyclohexyl-2-oxoethyl)(phenylmethoxy)carboxamide Prepared from Intermediate 67 via the EDCI/HOBT coupling procedure of Example 138 using N-carboxybenzyl-L-t-butylglycine.

$^1$H NMR (400 MHz, $CDCl_3$, mixture of rotomers) δ: 7.39–7.29 (m, 5H), 6.84–6.76 (m, 3H), 5.59–5.53 (m, 1H), 5.14–5.02 (m, 2H), 4.34 (dd, 1H), 3.87–3.33 (c, 10H), 1.34–1.24 (m, 1H), 1.14 (dd, 3H), 0.74 (d, 3H), 0.66–0.59 (m, 2H), 0.39–0.31 (m, 2H). LRMS (Electrospray, positive): Da/e 554.2 (m+1).

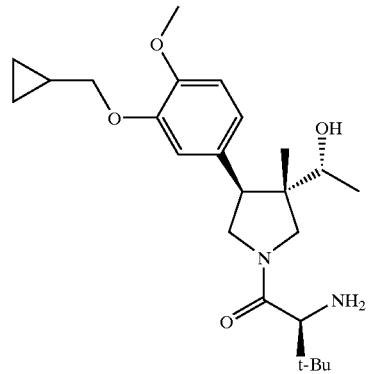

EXAMPLE 141

1-{3-((1R)-1-Hydroxyethyl)(3S,4S)-4-[3-(cyclopropylmethoxy)-4-methoxyphenyl]-3-methylpyrrolidinyl}(2S)-2-amino-3,3-dimethylbutan-1-one Prepared from Example 140 via the debenzylation procedure of Intermediate 31.

$^1$H NMR (Methanol-$d_4$, 400 MHz, mixture of rotomers) δ: 6.98–6.86 (m, 3H), 4.16–3.33 (c, 12H), 1.29–1.20 (m, 1H), 1.15–0.97 (m, 12H), 0.75 (d, 3H), 0.62–0.56 (m, 2H), 0.36–0.30 (m, 2H). LRMS (Electrospray, positive): Da/e 419.5 (m+1).

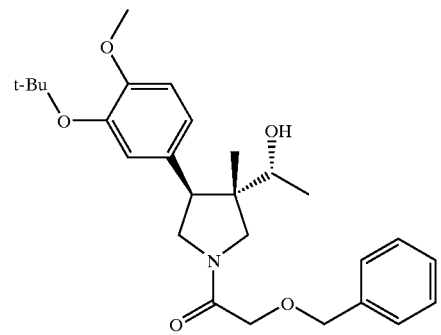

EXAMPLE 142

1-{(3R)-3-((1R)-1-Hydroxyethyl)-4-[3-(tert-butoxy)-4-methoxyphenyl]-3-methylpyrrolidinyl}-2-(phenylmethoxy)ethan-1-one Intermediate 73 (775 mg, 2.53 mmol) was coupled with benzyloxyacetyl chloride (497 μL, 3.16 mmol) by the Hunig's base procedure of Intermediate 74 to give Example 134 as a brown foam (978 mg, 85%).

$^1$H-NMR (400 MHz, $CDCl_3$) δ: 7.41–7.30 (m, 5H), 6.90 (m, 2H), 6.81 (d, 1H), 4.64 (dd, 2H), 4.15 (dd, 2H), 3.95 (dd, 1H), 3.80 (s, 3H), 3.62 (dd, 1H), 3.57 (m, 2H), 3.44 (d, 1H), 3.21 (d, 1H), 1.33 (s, 9H), 1.16 and 1.11 (two doublets, 3H, rotomers), 0.73 (d, 3H, rotomers).

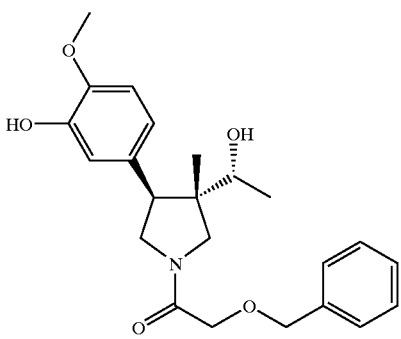

EXAMPLE 143

R¹=H; R³=COCH₂OCH₂Ph

1-[(3R)-3-((1R)-1-Hydroxyethyl)-4-(3-hydroxy-4-methoxyphenyl)-3-methylpyrrolidinyl]-2-(phenylmethoxy)ethan-1-one To a stirred solution of Example 142 (750 mg, 1.65 mmol) in CH₂Cl₂ (6.6 mL) at 0° C. under a drying tube was added trifluoroacetic acid (763 μL, 9.9 mmol). Cooling was removed from the reaction, and it was allowed to warm to room temperature, then stirred for 3.5 hours. The reaction was concentrated by rotary evaporation to remove excess trifluoroacetic acid, then was diluted with CH₂Cl₂ (30 mL), and washed with 10% Na₂CO₃ (2×30 mL). The organic layers were dried (MgSO₄), filtered, and concentrated in vacuo to provide Example 143. Flash chromatography in EtOAc gave, after pooling and concentration in vacuo of product containing fractions, Example 143 as a white foam (650 mg, 98%).

¹H-NMR (400 MHz, CDCl₃) δ: 7.42 (m, 5H), 6.83–6.70 (m, 3H), 4.64 (s, 2H), 4.16 (s, 2H), 3.93 (dd, 1H), 3.85 (s, 3H), 3.78 (d, 1H), 3.74 (dd, 2H), 3.67–3.52 (m, 4H), 3.44 (d, 1H), 3.20 (d, 1H), 1.16 and 1.10 (doublets, 3H, rotomers), 0.73 (s, 3H).

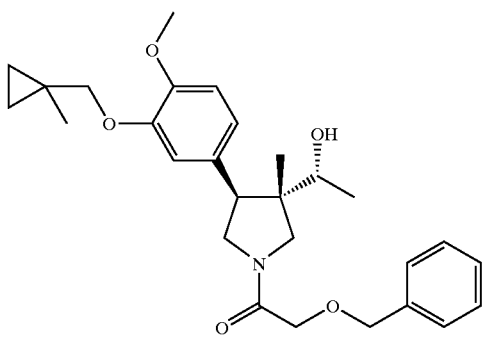

EXAMPLE 144

R¹=CH₂C(CH₃)(CH₂CH₂); R³=COCH₂OCH₂Ph

2-Benzyloxy-1-(3-((1R)-1-hydroxyethyl)-(3S,4S)-4-[4-methoxy-3-(1-methylcyclopropylmethoxy)phenyl]-3-methylpyrrolidin-1-yl)ethanone
Solid Phase Mitsunobu Procedure To a stirred solution of Example 143 (40 mg, 0.1 mmol) in THF (1.5 mL) at room temperature in a capped conical reaction vial was added PS-triphenylphosphine (1.65 mmol/g, 182 mg, 0.3 mmol). After allowing the suspension to slowly stir for 5 minutes to permit gel swelling, 1-methylcyclopropaneMethanol (29 μL, 0.3 mmol) was added, and the reaction cooled to 0° C. The suspension then was treated with DIAC (59 μL, 0.3 mmol), and the reaction warmed to 65° C. After stirring slowly overnight, the reaction was cooled to room temperature and filtered through a polystyrene frit with THF (30 mL). The filtrate was concentrated in vacuo and flash chromatographed on a 15 mm×61" column with 1/1/0.1 EtOAc/hexane/Methanol and product containing fractions pooled and concentrated in vacuo to provide Example 144 as a yellow oil (40 mg, 86%).

¹H-NMR (400 MHz, CDCl₃) δ: 7.42–7.25 (m, 5H), 6.83–6.77 (m, 3H), 4.63 (s, 2H), 4.15 (dd, 2H), 3.96–3.20 (m, 6H, rotomers), 3.81 (s, 3H), 1.74 (m, 1H), 1.24 (s, 3H), 1.17 and 1.10 (doublets, 3H, rotomers), 0.72 (d, 3H, rotomers), 0.53 (m, 2H), 0.41 (m, 2H).

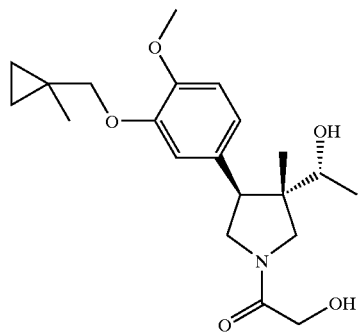

EXAMPLE 145

R¹=CH₂C(CH₃)(CH₂CH₂); R³=COCH₂OH 1-((3R)-3-((1R)-1-Hydroxyethyl)-4-{4-methoxy-3-[(methylcyclopropyl)methoxy]phenyl}-3-methylpyrrolidinyl)-2-hydroxyethan-1-one The crude product of Example 144 (40 mg, 0.086 mmol) was subjected to the debenzylation procedure of Intermediate 31 to give Example 145 as a clear oil (32.5 mg, 100%).

¹H-NMR (CDCl₃/CD₃OD, 400 MHz) δ: 6.87–6.79 (m, 3H), 3.97–3.18 (m, 7H, rotomers), 3.83 (s, 3H), 1.23 (s, 3H), 1.14 and 1.11 (doublets, 3H, rotomers), 0.77 (s, 3H), 0.56 (m, 2H), 0.42 (m, 2H). LRMS (Electrospray, positive): Da/e 378.2 (m+1).

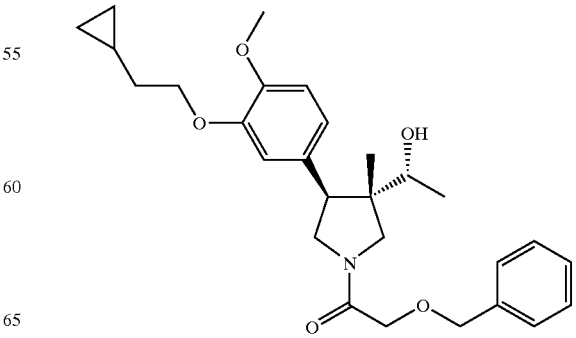

EXAMPLE 146

R$^1$=CH$_2$CH$_2$C$_3$H$_5$; R$^3$=COCH$_2$OCH$_2$Ph

2-Benzyloxy-1-[(3S,4S)-4-[3-(2-cyclopropylethoxy)-4-methoxyphenyl]-3-((1R)-1-hydroxyethyl)-3-methylpyrrolidin-1-yl]ethanone Example 143 was subjected to the procedure of Example 144 using 2-cyclopropylethanol (26 mg, 0.3 mmol) to provide Example 146 (41 mg, 88%).

$^1$H-NMR (400 MHz, CDCl$_3$) δ: 7.41–7.25 (m, 5H), 6.82–6.74 (m, 3H), 4.63 (s, 2H), 4.15 (dd, 2H), 4.04 (dd, 2H), 3.98–3.20 (m, 5H, rotomers), 3.81 (s, 3H), 1.82 and 1.79 (m, 1H, rotomers), 1.72 (dd, 2H), 1.40–1.20 (m, 1H), 1.18 and 1.12 (d, 3H, rotomers), 0.82 (m, 1H), 0.74 (s, 3H), 0.46 (m, 2H), 0.12 (m, 2H).

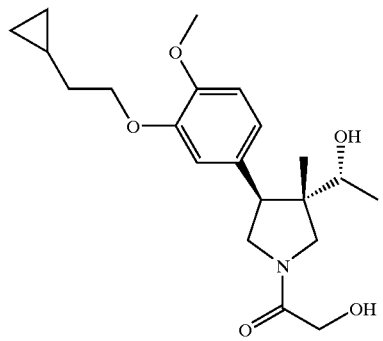

EXAMPLE 147

R$^1$=CH$_2$CH$_2$C$_3$H$_5$; R$^3$=COCH$_2$OH

1-{(3R)-3-((1R)-1-Hydroxyethyl)-4-[3-(2-cyclopropylethoxy)-4-methoxyphenyl]-3-methylpyrrolidinyl}-2-hydroxyethan-1-one Example 146 was subjected to the debenzylation procedure of Intermediate 31 to provide Example 147 as a clear oil (27.4 mg, 82%).

$^1$H-NMR (CDCl$_3$/CD$_3$OD, 400 MHz) δ: 6.91–6.80 (m, 3H), 4.19 (m, 2H), 4.10 (m, 2H), 3.97–3.15 (m, 5H, rotomers), 3.82 (s, 3H), 1.73 (dd, 2H), 1.25 (m, 1H), 1.14 and 1.12 (doublets, 3H, rotomers), 0.85 (m, 1H), 0.78 (s, 3H), 0.46 (m, 2H), 0.14 (m, 2H). LRMS (Electrospray, positive): Da/e 378.5 (m+1).

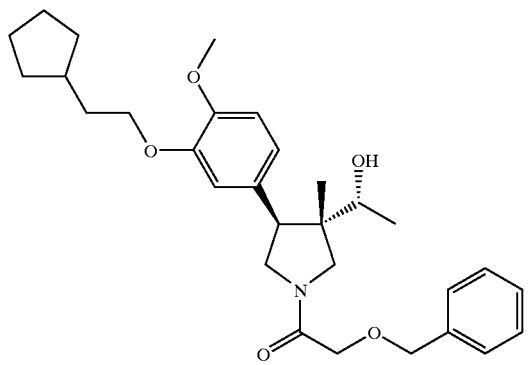

EXAMPLE 148

R$^1$=CH$_2$CH$_2$C$_5$H$_9$; R$^3$=COCH$_2$OH

1-{(3R)-3-((1R)-1-Hydroxyethyl)-4-[3-(2-cyclopentylethoxy)-4-methoxyphenyl]-3-methylpyrrolidinyl}-2-hydroxyethan-1-one Prepared using the procedure of Example 144 using Example 143 and 2-cyclopentylethanol (34 mg, 0.3 mmol) to provide Example 148 (41 mg, 100%).

$^1$H-NMR (400 MHz, CDCl$_3$) δ: 7.41–7.25 (m, 5H), 6.82–6.74 (m, 3H), 4.63 (s, 2H), 4.15 (dd, 2H), 3.99 (dd, 2H), 3.98–3.20 (m, 5H, rotomers), 3.81 (s, 3H), 2.00–1.20 (m, 11H), 1.18 and 1.12 (d, 3H, rotomers), 0.74 (s, 3H).

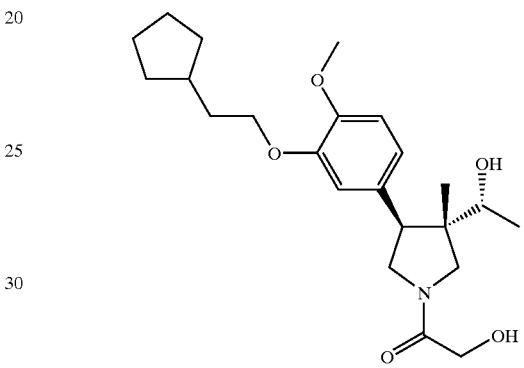

EXAMPLE 149

1-[(3S,4S)-4-[3-(2-cyclopentylethoxy)-4-methoxyphenyl]-3-((1R)-1-hydroxyethyl)-3-methylpyrrolidin-1-yl]-2-hydroxyethanone Example 148 was subjected to the debenzylation procedure of Intermediate 31 to afford the product as as a clear oil (34.7 mg, 86%).

$^1$H-NMR (CDCl$_3$/CD$_3$OD, 400 MHz) δ: 6.87–6.80 (m, 3H), 4.18 (m, 2H), 4.03 (m, 2H), 3.99–3.11 (m, 5H, rotomers), 3.84 (s, 3H), 2.01–1.15 (m, 11H), 1.14 and 1.11 (doublets, 3H, rotomers), 0.77 (s, 3H). LRMS (Electrospray, positive): Da/e 406.4 (m+1).

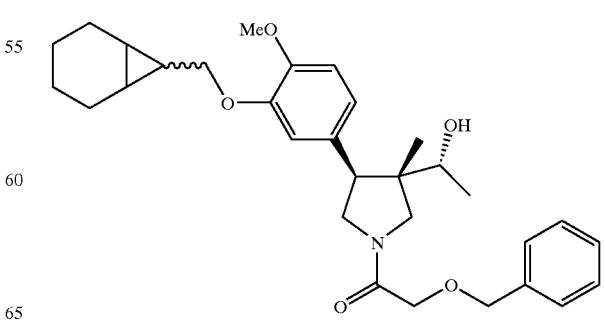

EXAMPLE 150

2-Benzyloxy-1-[4-(S)-[3-(bicyclo[4.1.0]hept-7-yl-methoxy)-4-methoxyphenyl]-3-(S)-(1-(R)-hydroxy-ethyl)-3-methylpyrrolidin-1-yl]ethanone Prepared from 143 by the Mitsunobu reaction of Example 144 using bicyclo[4.1.0]hept-7-yl-Methanol to afford an 80:20 mixture of cis and trans isomers (34% yield).

$^1$H NMR (CDCl$_3$, 400 MHz) δ: 7.42–7.23 (m, 5H), 6.85–6.72 (m, 3H), 5.06–4.89 (m, 1H), 4.67 (s, 2H), 4.15 (s, 2H), 4.07–3.56 (m, 9H), 2.09–1.56 (m, 8H), 1.36–0.87 (m, 8H), 0.73 (m, 3H). LRMS (Electrospray, positive): Da/e 508.6 (m+1).

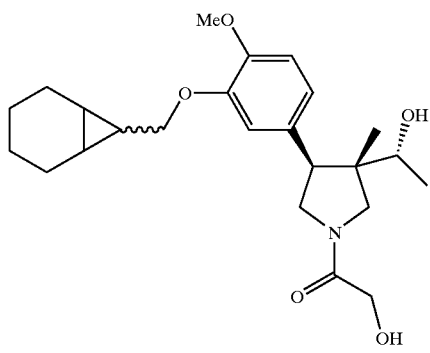

EXAMPLE 151

1-[4-(S)-[3-(Bicyclo[4.1.0]hept-7-ylmethoxy)-4-methoxyphenyl]-3-(S)-(1-(R)-hydroxyethyl)-3-methylpyrrolidin-1-yl]-2-hydroxyethanone Example 150 (15 mg, 30 mmol) was dissolved in 95% ethanol (1 mL) and the solution was treated with Pearlman's catalyst (20% Pd(OH)$_2$ on carbon, 15 mg). The reaction mixture was hydrogenolyzed at 1 atmosphere (or at 50 psi) of hydrogen for 16 hours. The reaction mixture was filtered to remove the catalyst, then the solvent was removed with a stream of nitrogen. The product was purified by chromatography on silica gel if necessary using EtOAc/hexanes/Methanol (1:1:0.2). (76% yield).

$^1$H NMR (CDCl$_3$, 400 MHz) δ: 6.73–6.66(m,3H), 4.04–3.99 (m,2H), 3.94–3.87 (m, 4H), 3.83–3.20 (m, 7H), 3.15–2.73 (m, 1H), 1.78–1.47 (m, 5H), 1.14–0.69 (10H), 0.63–0.60 (3H). LRMS (Electrospray, positive): Da/e 418.3 (m+1).

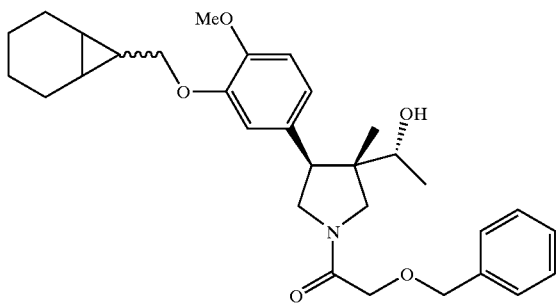

EXAMPLE 152

2-Benzyloxy-1-[4-(S)-[3-(bicyclo[3.1.0]hex-6-yl-methoxy)-4-methoxyphenyl]-3-(S)-(1-(R)-hydroxy-ethyl)-3-methylpyrrolidin-1-yl]ethanone Prepared from 143 by the Mitsunobu method of Example 144 using bicyclo[3.1.0]hex-6-yl-Methanol. The product was an inseparable mixture of isomers at the alcohol side chain (32% yield).

$^1$H NMR (CDCl$_3$, 400 MHz) δ: 7.45–7.29 (m, 5H), 6.84–6.72 (m, 3H), 5.02–4.94 (m,1H), 4.66 (s, 2H), 4.16 (s, 2H), 4.08–3.44 (m, 8H), 1.96–1.51 (m, 4H), 1.26 (d, 6H), 1.18–1.08 (dd, 5H), 0.72 (m, 3H). LRMS (Electrospray, positive): Da/e 494.4 (m+1).

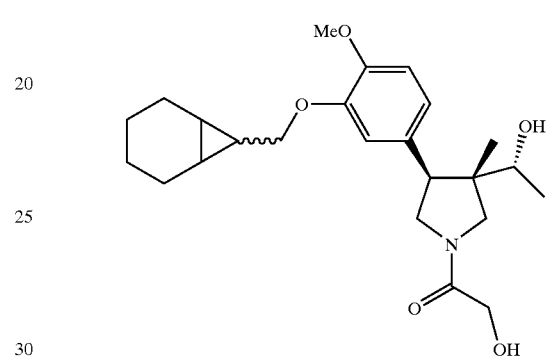

EXAMPLE 153

1-[4-(S)-[3-(Bicyclo[3.1.0]hex-6-ylmethoxy)-4-methoxyphenyl]-3-(S)-(1-(R)-hydroxyethyl)-3-methylpyrrolidin-1-yl]-2-hydroxyethanone Prepared from Example 152 by the dibenzylation method of Example 151(90% yield).

$^1$ H NMR (CD$_3$OD, 400 MHz) δ: 6.87–6.79 (m, 3H), 4.97–4.90 (m, 1H), 4.19–4.14 (m, 2H),3.99–3.36 (m, 7H), 3.30–2.89 (m, 1H), 1.92–1.52 (m, 4H), 1.28 (d, 6H), 1.16–1.06 (m, 6H), 0.77 (m, 3H). LRMS (Electrospray, positive): Da/e 404.3(m+1).

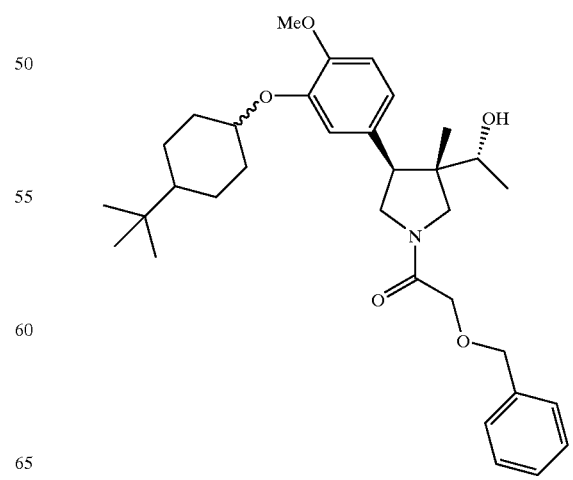

EXAMPLE 154

2-Benzyloxy-1-[4-(S)-[3-(4-tert-butylcyclohexyloxy)-4-methoxyphenyl]-3-(S)-(1-(R)-hydroxyethyl)-3-methylpyrrolidin-1-yl]ethanone Prepared by the Mitsunobu method of Example 144 using Example 143 and 4-tert-butyl-cyclohexanol (17% yield).

$^1$H NMR (CDCl$_3$, 400 MHz) δ: 7.43–7.28 (m, 5H), 6.85–6.73 (m, 3H), 6.37 (brd s, 1H), 5.02–4.93 (m, 2H), 4.67 (s, 2H), 4.13 (m, 2H), 3.89–3.43 (m, 7H), 2.19–1.36 (m, 8H), 1.26 (d, 9H), 1.18–1.08 (dd, 1H), 0.92–0.81 (m, 6H). LRMS (Electrospray, positive): Da/e 538.8 (m+1).

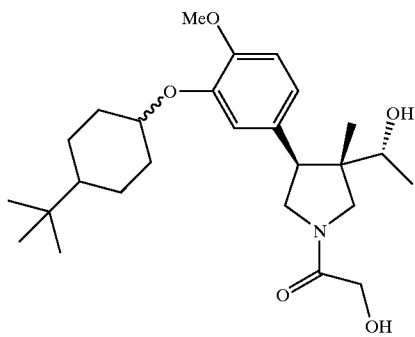

EXAMPLE 155

1-[4-(S)-[3-(4-tert-Butylcyclohexyloxy)-4-methoxyphenyl]-3-(S)-(1-(R)-hydroxyethyl)-3-methylpyrrolidin-1-yl]-2-hydroxyethanone Prepared from Example 154 by the dibenzylation procedure of Example 151 (89% yield).

$^1$H NMR (CD$_3$OD, 400 MHz) δ: 6.82–6.74 (m, 3H), 4.91–4.85 (m, 3H), 3.82–3.78 (m, 4H), 3.76–3.30 (m, 4H), 2.14–1.34 (m, 2H), 1.22–1.18 (m, 10H), 1.08–0.99 (m, 3H), 0.86–0.78 (m, 9H), 0.79–0.75 (m, 3H). LRMS (Electrospray, positive): Da/e 448.8(m+1).

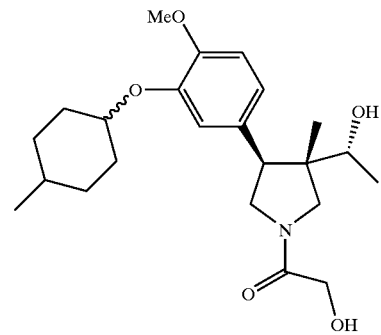

EXAMPLE 156

2-Benzyloxy-1-{3-(S)-(1-(R)-hydroxyethyl)-4-(S)-[4-methoxy-3-(4-methylcyclohexyloxy)phenyl]-3-methylpyrrolidin-1-yl}ethanone Prepared from Example 143 by the Mitsunobu procedure using 4-methylcyclohexanol (mixture of isomers) (10% yield).

$^1$H NMR (CDCl$_3$, 400 MHz) δ: 7.42–7.28 (m, 5H), 6.83–6.74 (m, 3H), 4.67 (s, 2H), 4.40–4.36 (m, 1H), 4.15–4.12 (m, 2H), 3.97–3.44 (m, 8H), 1.98–1.91 (m, 2H), 1.60–0.85 (m, 15H), 0.74–0.71 (d, 3H). LRMS (Electrospray, positive): Da/e 496.7 (m+1).

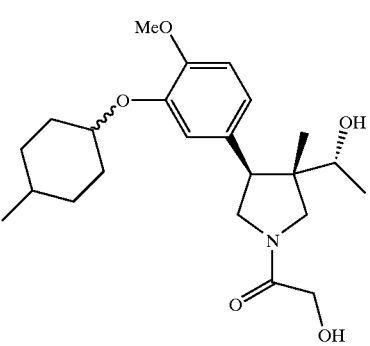

EXAMPLE 157

2-Hydroxy-1-{3-(S)-(1-(R)-hydroxyethyl)-4-(S)-[4-methoxy-3-(4-methylcyclohexyloxy)phenyl]-3-methylpyrrolidin-1-yl}ethanone Prepared from Example 156 by the debenzylation procedure of Example 151 (quantitative yield).

$^1$H NMR (CD$_3$OD, 400 MHz) δ: 6.87–6.79 (m, 3H), 4.18–4.11 (m, 2H), 3.98–3.70 (m, 1H), 3.69–3.36 (m, 10H), 3.09–2.89 (m, 1H), 1.99–1.92 (m, 1H), 1.61–1.43 (m, 6H), 1.28–1.25 (m, 2H), 1.14–1.10 (m, 3H), 0.97–0.86 (m, 3H), 0.78–0.76 (m, 3H). LRMS (Electrospray, positive): Da/e 406.6 (m+1).

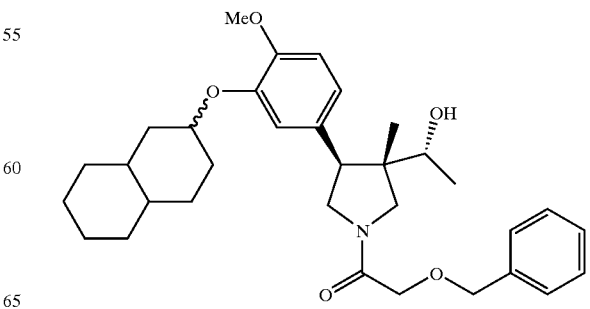

EXAMPLE 158

2-Benzyloxy-1-[4-(S)-[3-(decahydronaphthalen-2-yloxy)-4-methoxyphenyl]-3-(S)-(1-(R)-hydroxyethyl)-3-methylpyrrolidin-1-yl]ethanone Prepared from Example 143 by the Mitsunobu procedure using decahydronaphthalen-2-ol (mixture of isomers) (10% yield).

$^{1}$H NMR (CDCl$_{3}$, 400 MHz) δ: 7.42–7.29 (m, 5H), 6.85–6.74 (m, 3H), 5.03–4.95 (m, 1H), 4.68 (s, 2H), 3.98–3.45 (m, 7H), 1.90–1.10 (m, 22 H), 0.75–0.72 (m, 3H) LRMS (Electrospray, positive): Da/e 536.7 (m+1).

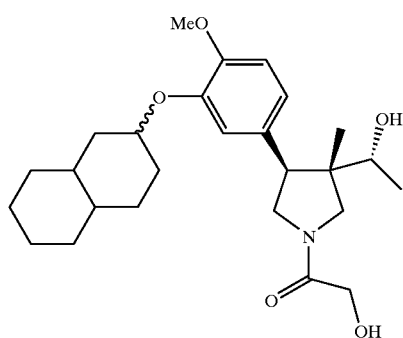

EXAMPLE 159

1-[4-(S)-[3-(Decahydronaphthalen-2-yloxy)-4-methoxyphenyl]-3-(S)-(1-(R)-hydroxyethyl)-3-methylpyrrolidin-1-yl]-2-hydroxyethanone Prepared from Example 158 by the debenzylation procedure of Example 151 (quantitative yield).

$^{1}$H NMR (CDCl$_{3}$, 400 MHz) δ: 6.85–6.79 (m, 3H), 5.02–4.94 (m, 1H), 4.23–4.12 (m, 2H), 4.03–3.48 (m, 10H), 3.08–2.89 (m, 1H), 1.89–1.80 (m, 2H), 1.78–1.13 (m, 17H), 0.77–0.75 (m, 3H) LRMS (Electrospray, positive): Da/e 446.1 (m+1).

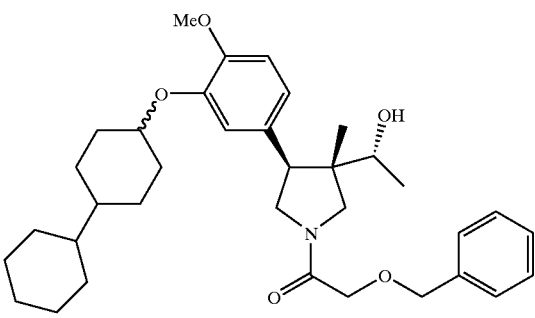

EXAMPLE 160

2-Benzyloxy-1-[4-(S)-[3-(bicyclohexyl-4-yloxy)-4-methoxyphenyl]-3-(S)-(1-(R)-hydroxyethyl)-3-methylpyrrolidin-1-yl]ethanone Prepared from Example 143 by the Mitsunobu procedure using bicyclohexyl-4-ol (mixture of isomers) (12% yield).

$^{1}$H NMR (CDCl$_{3}$, 400 MHz) δ: 7.42–7.29 (m, 5H), 6.84–6.74 (m, 3H), 5.03–4.95 (m, 1H), 4.68 (s, 2H), 4.17–4.11 (m, 2H), 3.98–3.45 (m, 7H), 1.90–1.10 (m, 26H), 0.75–0.72 (m, 3H). LRMS (Electrospray, positive): Da/e 564.8 (m+1).

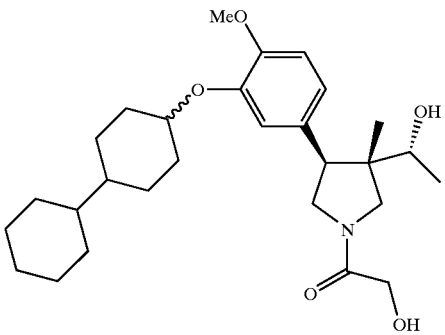

EXAMPLE 161

1-[4-(S)-[3-(Bicyclohexyl-4-yloxy)-4-methoxyphenyl]-3-(S)-(1-(R)-hydroxyethyl)-3-methylpyrrolidin-1-yl]-2-hydroxyethanone Prepared from Example 160 by the debenzylation procedure of Example 151 (quantitative yield).

$^{1}$H NMR (CDCl$_{3}$, 400 MHz) δ: 6.85–6.79 (m, 3H), 5.02–4.93 (m, 1H), 4.20–4.15 (m, 2H), 4.07–3.47 (m, 8H), 3.07–2.88 (m, 1H), 2.17–1.94 (m, 2H), 1,82–0.82 (m, 23H), 0.77–0.74 (brd s, 3H). LRMS (Electrospray, positive): Da/e 474.6 (m+1).

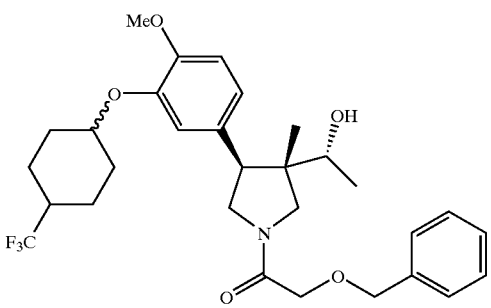

EXAMPLE 162

2-Benzyloxy-1-{3-(S)-(1-(R)-hydroxyethyl)-4-(S)-[4-methoxy-3-(4-trifluoromethylcyclohexyloxy)phenyl]-3-methylpyrrolidin-1-yl}ethanone Prepared from Example 143 by the Mitsunobu procedure using 4-trifluoromethylcyclohexanol (mixture of isomers) (40% yield).

$^{1}$H NMR (CDCl$_{3}$, 400 MHz) δ: 7.46–7.24 (m, 5H), 6.88–6.77 (m, 3H), 4.72–4.61 (brd s, 2H), 5.03–4.89 (brd m, 1H), 4.19–3.18 (m, 10H), 2.26–0.80 (m, 14H), 0.75–0.68 (brd, 3H). LRMS (Electrospray, positive): Da/e 550.7 (m+1).

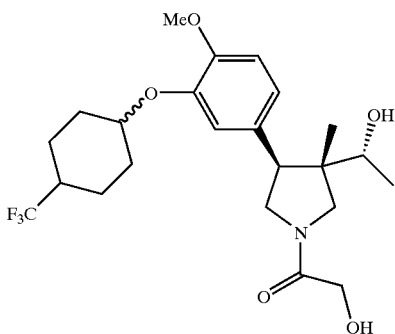

EXAMPLE 163

2-Hydroxy-1-{3-(S)-(1-(R)-hydroxyethyl)-4-(S)-[4-methoxy-3-(4-trifluoromethylcyclohexyloxy)phenyl]-3-methylpyrrolidin-1-yl}ethanone Prepared from Example 162 by the debenzylation procedure of Example 151 (quantitative yield).

$^1$H NMR (CDCl$_3$, 400 MHz) δ: 6.85–6.83 (m, 3H), 5.03–4.90 (m, 1H), 4.26–4.15 (m, 2H), 4.13–3.95 (m, 2H), 3.89–3.37 (m, 7H), 3.10–2.90 (m, 1H), 2.26–2.18 (m, 2H), 2.08–2.01 (m, 3H), 1.55–0.86 (m, 7H), 0.75 (s, 3H). LRMS (Electrospray, positive): Da/e 460.3(m+1).

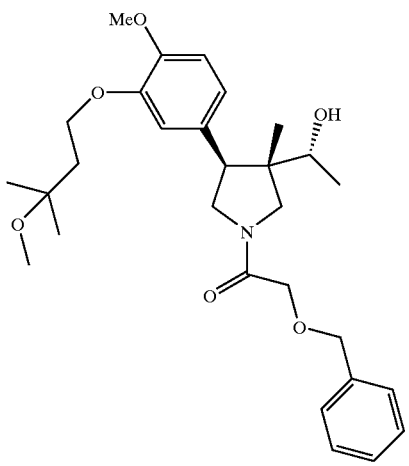

EXAMPLE 164

2-Benzyloxy-1-{3-(S)-(1-(R)-hydroxyethyl)-4-(S)-[4-methoxy-3-(3-methoxy-3-methylbutoxy)phenyl]-3-methylpyrrolidin-1-yl}ethanone Prepared from Example 143 by the Mitsunobu procedure using 3-methoxy-3-methylbutanol (78% yield).

$^1$H NMR (CDCl$_3$, 400 MHz) δ: 7.42–7.29 (m, 5H), 6.85–6.72 (m, 3H), 4.67 (s, 2H), 4.17–4.13 (m, 3H), 3.97–3.45 (m, 9H), 3.23 (d, 4H), 2.07–2.01 (m, 2H), 1.23 (s, 6H), 1.16–1.09 (dd, 4H), 0.72 (d, 3H). LRMS (Electrospray, positive): Da/e 500.6 (m+1).

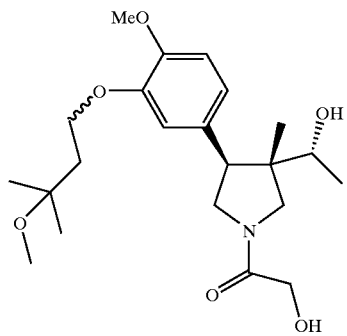

EXAMPLE 165

2-Hydroxy-1-{3-(S)-(1-(R)-hydroxyethyl)-4-(S)-[4-methoxy-3-(3-methoxy-3-methylbutoxy)phenyl]-3-methylpyrrolidin-1-yl}ethanone Prepared from Example 164 by the debenzylation method of Example 151 (97% yield).

$^1$H NMR (CDCl$_3$, 400 MHz) δ: 6.83–6.72 (m, 3H), 4.19–4.11 (m, 4H), 4.01–3.79 (m, 1H), 3.83 (s, 3H), 3.72–3.46 (m, 7H), 3.22 (s, 3H), 2.05–1.99 (m, 2H), 1.22 (brd s, 7H), 1.16–1.11 (m, 3H), 0.73 (brd s, 3H). LRMS (Electrospray, positive): Da/e 410.2 (m+1).

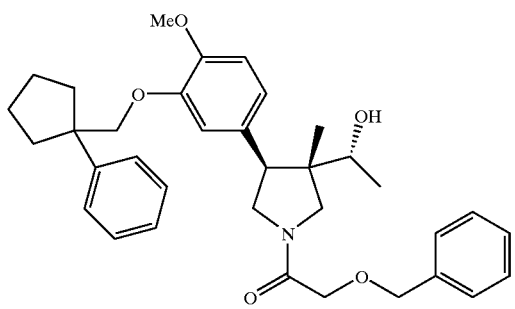

EXAMPLE 166

2-Benzyloxy-1-{3-(S)-(1-(R)-hydroxyethyl)-4-(S)-[4-methoxy-3-(1-phenylcyclopentylmethoxy)phenyl]-3-methylpyrrolidin-1-yl}ethanone Prepared from Example 143 by the Mitsunobu procedure using (1-phenylcyclopentyl)Methanol (25% yield)

$^1$H NMR (CDCl$_3$, 400 MHz) δ: 7.46–7.13 (m, 10H), 6.78–6.37 (m, 3H), 5.01–4.93 (m, 1H), 4.66 (s, 2H), 4.15–4.10 (m, 2H), 3.92–3.41 (m, 7H), 2.24–2.15 (m, 1H), 2.04–1.97 (m, 2H), 1.84–1.70 (m, 4H), 1.26 (d, 6H), 1.13–1.05 (dd, 3H), 0.87–0.85 (m, 1H), 0.65 (2H). LRMS (Electrospray, positive): Da/e 558.5 (m+1).

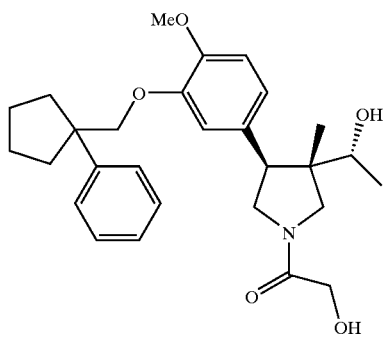

EXAMPLE 167

2-Hydroxy-1-{3-(S)-(1-(R)-hydroxyethyl)-4-(S)-[4-methoxy-3-(1-phenylcyclopentylmethoxy)phenyl]-3-methylpyrrolidin-1-yl}ethanone Prepared from Example 166 by the debenzylation procedure of Example 151 (26% yield).

$^1$H NMR (CDCl$_3$, 400 MHz) δ: 7.46–7.43 (m, 2H), 7.34–7.27 (m, 2H), 7.23–7.18 (m, 1H), 6.81–6.71 (m, 3H), 6.53–6.48 (m, 1H), 4.15–4.09 (m, 2H), 3.93–3.88 (m, 2H), 3.78–3.46 (m, 7H), 2.25–0.68 (m, 17H). LRMS (Electrospray, positive): Da/e 468.7 (m+1).

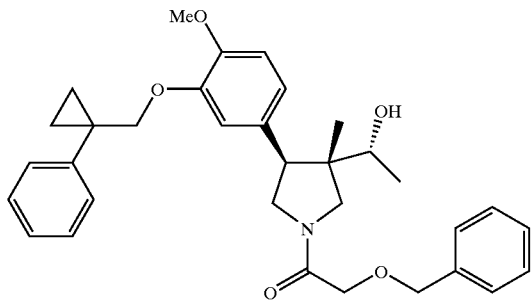

EXAMPLE 168

2-Benzyloxy-1-{3-(S)-(1-(R)-hydroxyethyl)-4-(S)-[4-methoxy-3-(1-phenylcyclopropylmethoxy)phenyl]-3-methylpyrrolidin-1-yl}ethanone Prepared from Example 143 by the Mitsunobu procedure using (1-phenylcyclopropyl)Methanol (90% yield).

$^1$H NMR (CDCl$_3$, 400 HMz) δ: 7.46–7.16 (m, 10H), 6.79–6.72 (m, 2H), 6.64–6.59 (m, 1H), 4.66 (s, 2H), 4.14–4.12 (m, 2H), 4.10–4.02 (m, 2H), 3.91–3.42 (m, 9H), 1.28–1.25 (m, 1H), 1.14–1.06 (m, 3H), 1.04–0.95 (m, 4H), 0.66 (s, 3H). LRMS (Electrospray, positive): Da/e 530.7 (m+1).

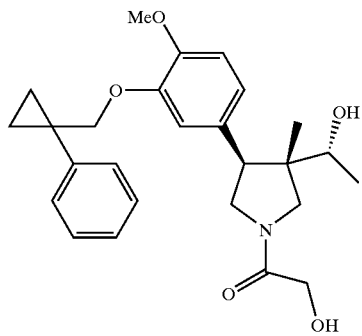

EXAMPLE 169

2-Hydroxy-1-{3-(S)-(1-(R)-hydroxyethyl)-4-(S)-[4-methoxy-3-(1-phenylcyclopropylmethoxy)phenyl]-3-methylpyrrolidin-1-yl}ethanone Prepared from Example 168 by the debenzylation procedure of Example 151 (44% yield).

$^1$H NMR (CDCl$_3$, 400 HMz) δ: 7.47–7.21 (m, 5H), 6.84–6.60 (m, 3H), 4.15–4.04 (m, 4H), 3.99–3.46 (m, 8H), 3.05–2.99 (m, 1H), 2.11–2.04 (m, 1H), 1.74–1.59 (m, 2H), 1.29–0.96 (m, 4H), 0.88–0.68 (m, 4H). LRMS (Electrospray, positive): Da/e 440.1(m+1).

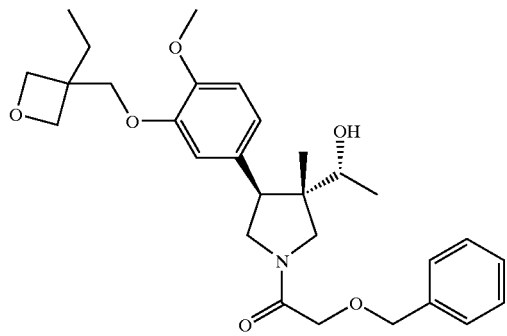

EXAMPLE 170

R$^1$=CH$_2$C(CH$_2$CH$_3$)(CH$_2$OCH$_2$);
R$^3$=COCH$_2$OCH$_2$Ph

2-Benzyloxy-1-[(3S,4S)-4-3-(3-ethyloxetan-3-yl-methoxy)-4-methoxyphenyl]-3-((1R)-1-hydroxyethyl)-3-methylpyrrolidin-1-yl]ethanone Prepared from Example 143 according to the procedure in Example 144 using 3-ethyl-3-oxetaneMethanol (34 mL, 0.3 mmol) to yield Example 150 (44 mg, 88%).

$^1$H-NMR (400 HMz, CDCl$_3$) δ: 7.41–7.25 (m, 5H), 6.84–6.80 (m, 3H), 4.64 (s, 2H), 4.58 (dd, 2H), 4.49 (d, 2H), 4.17–4.11 (m, 3H), 3.99 (dd, 2H), 3.98–3.20 (m, 5H, rotomers), 3.80 (s, 3H), 1.91 (dd, 2H), 1.80 (d, 1H), 1.24 (dd, 1H), 1.17 and 1.13 (doublets, 3H, rotomers), 0.94 (t, 3H), 0.73 (s, 3H).

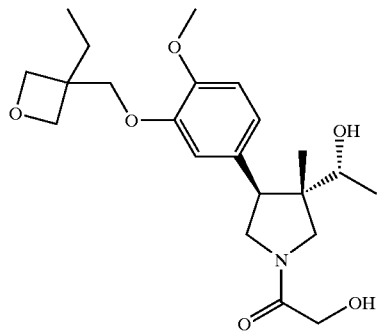

EXAMPLE 171

R¹=CH₂C(CH₂CH3)(CH₂OCH₂); R³=COCH₂OH 1-((3R)-3-((1R)-1-Hydroxyethyl)-4-{3-[(3-ethyloxetan-3-yl)methoxy]-4-methoxyphenyl}-3-methylpyrrolidinyl)-2-hydroxyethan-1-one Example 170 was deprotected using the debenzylation of Intermediate 31 to provide Example 171 as a clear oil (28.6 mg, 80%).

¹H-NMR (CDCl₃/CD₃OD, 400 HMz) δ: 6.91–6.83 (m, 3H), 4.64 (d, 1H), 4.19 (m, 2H), 4.12 (m, 1H), 4.00–3.14 (m, 12H), 3.83 (s, 3H), 1.15 (m, 3H), 0.96 (m, 3H), 0.78 (s, 3H). LRMS (Electrospray, positive): Da/e 408.5 (m+1).

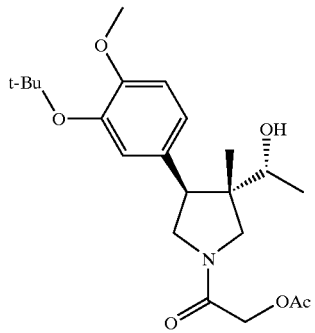

EXAMPLE 172

R¹=t-Bu; R³=COCH₂OAc (2-{3-((1R)-1-Hydroxyethyl)(3S,4S)-4-[3-(tert-butoxy)-4-methoxyphenyl]-3-methylpyrrolidinyl}-2-oxoethyl acetate Prepared from Intermediate 73 via the Hunig's base coupling procedure of Intermediate 74 using acetoxyacetyl chloride.

¹H NMR (400 HMz, CDCl₃, mixture of rotamers) δ: 6.94–6.81 (m, 3H), 4.72–4.58 (m, 2H), 3.80 (m, 3H), 3.97–3.17 (m, 6H), 2.19 (s, 3H), 1.33 (d, 9H), 1.15 (t, 3H), 0.76 (d, 3H).

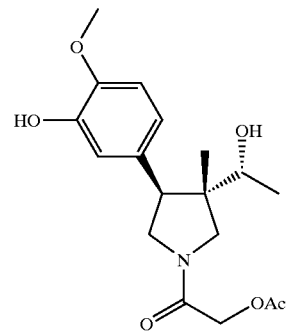

EXAMPLE 173

R¹=H; R³=COCH₂OAc

2-[3-((1R)-1-Hydroxyethyl)(3S,4S)-4-(3-hydroxy-4-methoxyphenyl)-3-methylpyrrolidinyl]-2-oxoethyl acetate Example 172 was deprotected by the TFA method of Example 143 to afford Example 173 as a tan foam (173 mg, 80%).

¹H NMR (400 HMz, CDCl₃, mixture of rotamers) δ: 6.86–6.70 (m, 3H), 5.64 (br s, 1H), 4.72–4.62 (m, 2H), 3.88 (m, 3H), 3.95–3.18 (c, 6H), 2.20 (d, 3H), 1.15 (t, 3H), 0.77 (d, 3H). LRMS (Electrospray, positive): Da/e 352.2 (m+1).

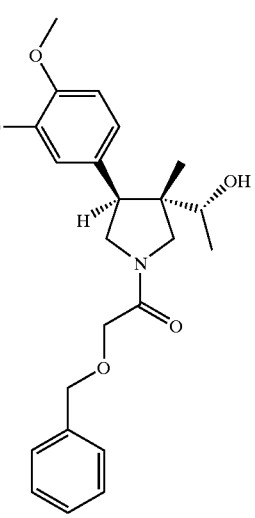

EXAMPLE 174

R¹=4-Ph-Ph-CH₂CH₂; R³=C(=O)CH₂OCH₂Ph

2-Benzyloxy-1-[(3S,4S)-4-[3-(2-biphenyl-4-ylethoxy)-4-methoxyphenyl]-3-((R)-1-hydroxy-ethyl)-3-methylpyrrolidin-1-yl]ethanone Example 143 (60 mg, 0.15 mmol) was subjected to the Mitsunobu procedure of Example 144 using 4-hydroxyethylbiphenyl (90 mg, 0.45 mmol) and used without further purification or characterization (73 mg, 84%).

EXAMPLE 175

R¹=4-Ph-Ph-CH₂CH₂; R³=C(=O)CH₂OH

1-[(3S,4S)-4-[3-(2-Biphenyl-4-ylethoxy)-4-methoxyphenyl]-3-((R)-1-hydroxyethyl)-3-methylpyrrolidin-1-yl]-2-hydroxyethanone Example 174 was subjected to the debenzylation procedure of Intermediate 31 to afford Example 175.

1H NMR (300 HMz, CDCl₃, mixture of rotomers) δ: 7.58 (br t, 7.4 Hz, 3 H), 7.47–7.27 (m, 6H), 6.86–6.77 (m, 3H), 4.24 (dt, J=3.0, 7.4 Hz, 2H), 4.11 (br t, J=4.1 Hz, 2 H), 4.01–3.47 (m, 5.5H, rotomers), 3.87 (s, 3H), 3.20 (t, J=7.4 Hz, 2H), 3.03 (d, J=9.8 Hz, 0.5 H, rotamer), 1.36/1.32 (2d, J=3.6/3.7 Hz, 1H), 1.16/1.13 (2D, J=6.5/6.4 Hz, 3H), 0.74 (s, 3H). LRMS (Electrospray, positive): m/e 490 (m+H)⁺.

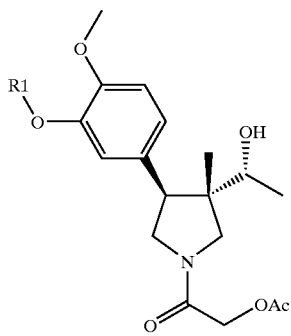

EXAMPLE 176

R¹=CH₂C≡CPh; R³=COCH₂OAc

2-{3-((1R)-1-Hydroxyethyl)(3S,4S)-4-[4-methoxy-3-(3-phenylprop-2-ynyloxy)phenyl]-3-methylpyrrolidinyl}-2-oxoethyl acetate A round bottom flask equipped with a stir bar and condenser was charged with the compound of Example 173 (270 mg, 0.769 mmol), acetone (5 mL), CsCO₃ (376 mg, 1.15 mmol), and Intermediate 90 (242 mg, 1.15 mmol) under a nitrogen atmosphere. The mixture was refluxed for 4 hours, then allowed to cool to room temperature. The acetone was removed under reduced pressure, and the residue taken up in EtOAc/water. The resulting mixture was extracted with EtOAc (2×100 mL), dried (Na₂SO₄), and concentrated. Biotage purification (40 M cartridge, 1:1:0.1 EtOAc:hexane:-MeOH) afforded 146 mg of Example 176 as a white foam (41%).

¹H NMR (400 HMz, CDCl₃, mixture of rotomers) δ: 7.41–7.26 (m, 5H), 7.05 (dd, 1H), 6.85 (d, 2H), 5.05–4.95 (m, 2H), 4.70–4.58 (m, 2H), 3.88 (d, 3H), 3.95–3.13 (c, 6H), 2.19 (s, 3H), 0.97–0.92 (dd, 3H), 0.71 (d, 3H). LRMS (Electrospray, positive): Da/e 466.4 (m+1).

EXAMPLE 177

R¹=CH₂C≡C-4-FPh; R³=COCH₂OAc 2-(3-((1R)-1-Hydroxyethyl)(3S,4S)-4-{3-[3-(4-fluorophenyl)prop-2-ynyloxy]-4-methoxyphenyl}-3-methylpyrrolidinyl)-2-oxoethyl acetate Prepared from Example 173 by the method of Example 176 using Intermediate 91 as the alkylating agent.

¹H NMR (400 HMz, CDCl₃, mixture of rotomers) δ: 7.40–7.36 (m, 2H), 7.04–6.97 (m, 3H), 6.86–6.85 (m, 2H), 4.98–4.97 (m, 2H), 4.71–4.59 (m, 2H), 3.88 (d, 3H), 3.96–3.16 (c, 6H), 2.20–2.18 (m, 3H), 1.01 (t, 3H), 0.72 (d, 3H). LRMS (Electrospray, positive): Da/e 484.8 (m+1).

EXAMPLE 178

R¹=CH(C₃H₅)C₃H₅; R³=COCH₂OAc

2-{3-((1R)-1-Hydroxyethyl)(3S,4S)-4-[3-(dicyclopropylmethoxy)-4-methoxyphenyl]-3-methylpyrrolidinyl}-2-oxoethyl acetate Prepared from Example 173 by the Mitsunobu method of Example 144 using dicyclopropylcarbinol.

¹H NMR (400 HMz, CDCl₃, mixture of rotomers) δ: 7.26–6.78 (m, 3H), 4.74–4.60 (m, 2H), 3.96–3.46 (m, 9H), 3.21–3.10 (m, 2H), 2.20 (s, 3H), 1.26 (d, 1H), 1.19–1.11 (m, 4H), 0.75 (d, 3H), 0.55–0.41 (m, 4H), 0.33–0.24 (m, 4H). LRMS (Electrospray, positive): Da/e 446.5 (m+1).

EXAMPLE 179

R¹=3-(4-chlorophenyl)(1,2,4-oxadiazol-5-yl)methyl; R³=CoCH₂OAc

2-[3-((1R)-1-Hydroxyethyl)(3S,4S)-4-(3-{[3-(4-chlorophenyl)(1,2,4-oxadiazol-5-yl)]methoxy}-4-methoxyphenyl)-3-methylpyrrolidinyl]-2-oxoethyl acetate Prepared from Example 173 via the CsCO₃ method of Example 176 using Intermediate 87.

¹H NMR (400 HMz, CDCl₃, mixture of rotomers) δ: 8.02 (d, 2H), 7.46 (d, 2H), 6.95–6.85 (m, 3H), 5.40 (d, 2H), 4.70–4.58 (m, 2H), 3.94 (d, 3H), 3.95–3.12 (c, 6H), 2.19 (s, 3H), 1.04–1.00 (dd, 3H), 0.64 (d, 3H). LRMS (Electrospray, positive): Da/e 544.4 (m+1).

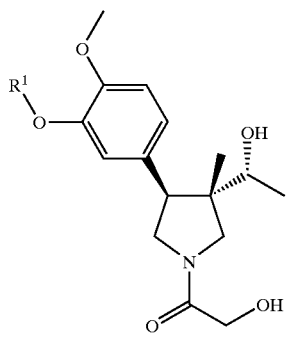

EXAMPLE 180

R¹=CH₂C≡CPh; R³=COCH₂OH

1-{3-((1R)-1-Hydroxyethyl)(3S,4S)-4-[4-methoxy-3-(3-phenylprop-2-ynyloxy)phenyl]-3-methylpyrrolidinyl}-2-hydroxyethan-1-one Prepared from Example 176 via the LiOH hydrolysis procedure of Intermediate 5.

¹H NMR (400 HMz, CDCl₃, mixture of rotomers) δ: 7.40–7.26 (m, 5H), 7.07–7.06 (m, 1H), 6.85–6.84 (m, 2H), 5.05–4.94 (m, 2H), 3.89 (s, 3H), 4.13–2.99 (c, 8H), 0.98–0.92 (dd, 3H), 0.71 (s, 3H). LRMS (Electrospray, positive): Da/e 424.6 (m+1).

EXAMPLE 181

R¹=CH₂C≡C-4-FPh; R³=COCH₂OH 1-(3-((1R)-1-Hydroxyethyl)(3S,4S)-4-{3-[3-(4-fluorophenyl)prop-2-ynyloxy]-4-methoxyphenyl}-3-methylpyrrolidinyl)-2-hydroxyethan-1-one Prepared from Example 177 via the LiOH hydrolysis procedure of Intermediate 5.

¹H NMR (400 HMz, CDCl₃, mixture of rotomers) δ: 7.39–7.36 (m, 2H), 7.03–6.98 (m, 3H), 6.85 (s, 2H), 5.02–4.93 (m, 2H), 3.89 (s, 3H), 4.15–3.01 (c, 8H), 1.04–0.99 (dd, 3H), 0.72 (s, 3H). LRMS (Electrospray, positive): Da/e 442.7 (m+1).

EXAMPLE 182

R¹=C₃H₅CHC₃H₅; R³=COCH₂OH

1-{3-((1R)-1-Hydroxyethyl)(3S,4S)-4-[3-(dicyclopropylmethoxy)-4-methoxyphenyl]-3-methylpyrrolidinyl}-2-hydroxyethan-1-one Prepared from Example 178 by the LiOH hydrolysis procedure of Intermediate 5.

¹H NMR (400 HMz, CDCl₃, mixture of rotomers) δ: 6.90–6.78 (m, 3H), 4.17–3.44 (c, 11H), 3.15–3.03 (m, 2H), 1.32–1.20 (m, 1H), 1.19–1.09 (m, 4H), 0.75 (d, 3H), 0.54–0.39 (m, 4H), 0.34–0.23 (m, 4H). LRMS (Electrospray, positive): Da/e 404.5 (m+1).

EXAMPLE 183

R¹=3-(4-chlorophenyl)(1,2,4-oxadiazol-5-yl)methyl; R³=COCH₂OH

1-[3-((1R)-1-Hydroxyethyl)(3S,4S)-4-(3-{[3-(4-chlorophenyl)(1,2,4-oxadiazol-5-yl)]methoxy}-4-methoxyphenyl)-3-methylpyrrolidinyl]-2-hydroxyethan-1-one Prepared from Example 179 via the LiOH hydrolysis procedure of Intermediate 5.

¹H NMR (400 HMz, CDCl₃, mixture of rotomers) δ: 8.03 (d, 2H), 7.47 (d, 2H), 6.95–6.86 (m, 3H), 5.40 (s, 2H), 3.88 (s, 3H), 4.12–2.98 (c, 8H), 1.05–0.99 (dd, 3H), 0.64 (d, 3H). LRMS (Electrospray, positive): Da/e 502.4 (m+1).

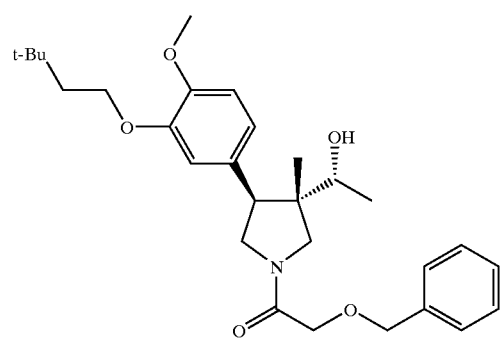

EXAMPLE 184

R¹=CH₂CH₂t-Bu; R³=COCH₂OCH₂Ph

1-{3-((1R)-1-Hydroxyethyl)(3S,4S)-4-[3-(3,3-dimethylbutoxy)-4-methoxyphenyl]-3-methylpyrrolidinyl}-2-(phenylmethoxy)ethan-1-one Prepared from Example 143 via the Mitsunobu method of Example 144 using 3,3-dimethyl-1-butanol.

¹H NMR (400 HMz, CDCl₃, mixture of rotomers) δ: 7.41–7.31 (m, 5H), 6.80–6.75 (m, 3H), 4.70–4.63 (m, 2H), 4.15–3.21 (c, 13H), 1.80–1.73 (m, 2H), 1.17–1.10 (m, 2H), 0.98 (s, 9H), 0.74 (d, 3H). LRMS (Electrospray, positive): Da/e 484.6 (m+1).

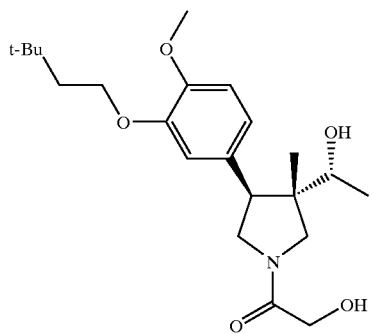

EXAMPLE 185

R¹=CH₂CH₂t-Bu; R³=COCH₂OH

1-{3-((1R)-1-Hydroxyethyl)(3S,4S)-4-[3-(3,3-dim-ethylbutoxy)-4-methoxyphenyl]-3-methylpyrrolidinyl}-2-hydroxyethan-1-one Prepared from Example 184 via the debenzylation method of Intermediate 31.

¹H NMR (400 HMz, CDCl₃, mixture of rotomers) δ: 6.88–6.71 (m, 3H), 4.38–2.99 (c, 13H), 1.82–1.73 (m, 2H), 1.19–1.08 (m, 3H), 0.97 (s, 9H), 0.80–0.69 (m, 3H). LRMS (Electrospray, positive): Da/e 394.4 (m+1).

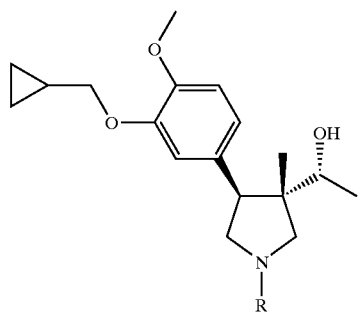

EXAMPLE 186

R¹=CH₂C₃H₅; R³=COCH₂OCH₂Ph

1-{3-((1R)-1-Hydroxyethyl)(3S,4S)-4-[3-(cyclopropylmethoxy)-4-methoxyphenyl]-3-methylpyrrolidinyl}-2-(phenylmethoxy)ethan-1-one Prepared from Intermediate 67 via the Hunig's base coupling method of Intermediate 74 using benzyloxy-acetyl chloride.

¹H NMR (400 HMz, CDCl₃, mixture of rotomers) δ: 7.40–7.29 (m, 5H), 6.82–6.74 (m, 3H), 4.66 (s, 2H), 4.15–3.20 (c, 11H), 1.71–1.57 (br s, 1H), 1.35–1.23 (m, 1H), 1.16–1.07 (dd, 3H), 0.71 (s, 3H), 0.62 (d, 2H), 0.34 (d, 2H). LRMS (Electrospray, positive): Da/e 454.6 (m+1).

EXAMPLE 187

R¹=CH₂C₃H₅; R³=COCH₂OH

1-{3-((1R)-1-Hydroxyethyl)(3S,4S)-4-[3-(cyclopropylmethoxy)-4-methoxyphenyl]-3-methylpyrrolidinyl}-2-hydroxyethan-1-one Prepared from Example 186 via the debenzylation method of Intermediate 31.

¹H NMR (Methanol-d₄, 400 HMz) δ: 6.95–6.84 (m, 3H), 4.31–4.22 (m, 2H), 3.91–3.23 (c, 11H), 1.30–1.19 (m, 1H), 0.74 (s, 3H), 0.62–56 (m, 2H), 0.35–0.28 (m, 2H). LRMS (Electrospray, positive): Da/e 364.2 (m+1).

EXAMPLE 188

R¹=CH₂C₃H₅; R³=COCH₂NHCO₂CH₂Ph

N-(2-{3-((1R)-1-Hydroxyethyl)(3S,4S)-4-[3-(cyclopropylmethoxy)-4-methoxyphenyl]-3-methylpyrrolidinyl}-2-oxoethyl)(phenylmethoxy)carboxamide Prepared from Intermediate 67 via the acylation procedure of Example 7 using Z-Gly-ONp.

¹H NMR (400 HMz, CDCl₃, mixture of rotomers) δ: 7.45–7.30 (m, 5H), 6.85–6.76 (m, 3H), 5.81 (br s, 1H), 5.13 (s, 2H), 4.10–3.43 (c, 12H), 3.17 (d, 1H), 1.68 (br s, 1H), 1.36–1.26 (m, 1H), 1.14 (t, 3H), 0.73 (d, 3H), 0.66–0.60 (m, 2H), 0.38–0.31 (m, 2H).

EXAMPLE 189

R¹=CH₂C₃H₅; R³=COCH₂NH₂

1-{3-((1R)-1-Hydroxyethyl)(3S,4S)-4-[3-(cyclopropylmethoxy)-4-methoxyphenyl]-3-methylpyrrolidinyl}-2-aminoethan-1-one Prepared from Example 188 via the debenzylation procedure of Intermediate 31.

¹H NMR (Methanol-d₄, 400 HMz, mixture of rotomers) δ: 6.96–6.81 (m, 3H), 4.00–3.27 (c, 13H), 1.29–1.18 (m, 1H), 1.13–1.07 (m, 3H), 0.75 (m, 3H), 0.62–54 (m, 2H), 0.35–0.28 (m, 2H). LRMS (Electrospray, positive): Da/e 363.2 (m+1).

EXAMPLE 190

R¹=CH₂C₃H₅; R³=COC(CH₃)₂OCOCH₃

2-{3-((1R)-1-Hydroxyethyl)(3S,4S)-4-[3-(cyclopropylmethoxy)-4-methoxyphenyl]-3-methylpyrrolidinyl}-1,1-dimethyl-2-oxoethyl acetate Prepared from Intermediate 67 via the Hunig's base coupling procedure of Intermediate 74 using 2-acetoxy-isobutyryl chloride.

¹H NMR (400 HMz, CDCl₃, mixture of rotomers) δ: 6.87–6.70 (m, 3H), 3.93–3.32 (c, 11H), 2.08 (d, 3H), 1.81–1.65 (br m, 1H), 1.65–1.53 (m, 6H), 1.35–1.23 (m, 1H), 1.19–1.11 (t, 3H), 0.68 (d, 3H), 0.65–0.57 (m, 2H), 0.37–0.30 (m, 2H).

EXAMPLE 191

R¹=CH₂C₃H₅; R³=COC(CH₃)₂OH

1-{3-((1R)-1-Hydroxyethyl)(3S,4S)-4-[3-(cyclopropylmethoxy),-4-methoxyphenyl]-3-methylpyrrolidinyl}-2-hydroxy-2-methylpropan-1-one Prepared from Example 190 via the LiOH hydrolysis procedure of Intermediate 5.

¹H NMR (400 HMz, CDCl₃, mixture of rotomers) δ: 6.84–6.75 (m, 3H), 4.43 (br s, 1H), 4.01–3.41 (c, 11H), 1.52–1.41 (m, 6H), 1.32–1.17 (m, 1H), 1.16–1.08 (t, 3H), 0.73 (d, 3H), 0.63–0.57 (m, 2H), 0.37–0.29 (m, 2H). LRMS (Electrospray, positive):. Da/e 392.5 (m+1).

EXAMPLE 192

$R^1$=CH$_2$C$_3$H$_5$; $R^3$=(S)—COCH(CH$_3$)OAc

2-{3-((1R)-1-Hydroxyethyl)(3S,4S)-4-[3-(cyclopropylmethoxy)-4-methoxyphenyl]-3-methylpyrrolidinyl}(1S)-1-methyl-2-oxoethyl acetate Prepared from Intermediate 67 via the Hunig's base coupling procedure of Intermediate 74 using (S)-2-acetoxypropionyl chloride.

$^1$H NMR (400 HMz, CDCl$_3$, mixture of rotomers) δ: 6.83–6.76 (m, 3H), 5.25–5.17 (m, 1H), 4.08–3.35 (c, 12H), 2.15–2.09 (m, 3H), 1.50–1.44 (m, 3H), 1.35–1.23 (m, 1H), 1.15 (d, 3H), 0.79–0.71 (m, 3H), 0.65–0.60 (m, 2H), 0.37–0.30 (m, 2H).

EXAMPLE 193

$R^1$=CH$_2$C$_3$H$_5$; $R^3$=(S)—COCH(CH$_3$)OH

1-{3-((1R)-1-Hydroxyethyl)(3S,4S)-4-[3-(cyclopropylmethoxy)-4-methoxyphenyl]-3-methylpyrrolidinyl}(2S)-2-hydroxypropan-1-one Prepared from Example 192 via the LiOH hydrolysis procedure of Intermediate 5.

$^1$H NMR (4.00 HMz, CDCl$_3$, mixture of rotomers) δ: 6.84–6.73 (m, 3H), 4.39–4.28 (m, 1H), 3.88–3.48 (c, 10H), 3.29 (dd, 1H), 1.40–1.20 (m, 4H), 1.12 (t, 3H), 0.73 (d, 3H), 0.64–0.55 (m, 2H), 0.37–0.29 (m, 2H). LRMS (Electrospray, positive): Da/e 378.7 (m+1).

EXAMPLE 194

$R^1$=CH$_2$C$_3$H$_5$; $R^3$=COCH(Ph)OAc

2-{3-((1R)-1-Hydroxyethyl)(3S,4S)-4-[3-(cyclopropylmethoxy)-4-methoxyphenyl]-3-methylpyrrolidinyl}-2-oxo-1-phenylethyl acetate Prepared from Intermediate 67 via the Hunig's base coupling procedure of Intermediate 74 using O-acetylmandelic acid chloride.

$^1$H NMR (400 HMz, CDCl$_3$, mixture of rotomers and diastereomers) δ: 7.57–7.35 (m, 5H), 6.84–6.51 (m, 3H), 6.11–6.04 (m, 1H), 4.08–3.05 (c, 11H), 2.21–2.14 (m, 3H), 1.36–1.20 (m, 1H), 1.14–1.06 (dd, 3H), 0.78 and 0.48 (s and d, 3H), 0.67–0.57 (m, 2H), 0.37–0.28 (m, 2H). LRMS (Electrospray, positive): Da/e 482.6 (m+1).

EXAMPLE 195

$R^1$=CH$_2$C$_3$H$_5$; $R^3$=COCH(Ph)OH

1-{3-((1R)-1-Hydroxyethyl)(3S,4S)-4-[3-(cyclopropylmethoxy)-4-methoxyphenyl]-3-methylpyrrolidinyl}-2-hydroxy-2-phenylethan-1-one Prepared from Example 194 via the LiOH hydrolysis procedure of Intermediate 5.

$^1$H NMR (400 HMz, CDCl$_3$, mixture of rotomers and diastereomers) δ: 7.40–7.28 (m, 5H), 6.81–6.42 (m, 3H), 5.13–4.61 (m, 1H), 4.07–3.29 (c, 10H), 3.21–2.79 (m, 1H), 1.36–1.20 (m, 1H), 1.15–0.97 (dd, 3H), 0.73 and 0.47 (d and s, 3H), 0.65–0.56 (m, 2H), 0.37–0.28 (m, 2H). LRMS (Electrospray, positive): Da/e 440.2 (m+1).

EXAMPLE 196

$R^1$=CH$_2$C$_3$H$_5$; $R^3$=COCH(4-FPh)OAc

2-{3-((1R)-1-Hydroxyethyl)(3S,4S)-4-[3-(cyclopropylmethoxy)-4-methoxyphenyl]-3-methylpyrrolidinyl}-1-(4-fluorophenyl)-2-oxoethyl acetate Prepared from Intermediate 67 via the Hunig's base coupling procedure of Intermediate 74 using (chlorocarbonyl)(4-fluorophenyl)methyl acetate.

$^1$H NMR (400 HMz, CDCl$_3$, mixture of rotomers and diastereomers) δ: 7.60–7.46 (m, 2H), 7.15–7.03 (m, 2H), 6.85–6.54 (m, 3H), 6.09–5.99 (m, 1H), 4.07–2.87 (c, 11H), 2.19–2.12 (m, 3H), 1.33–1.20 (m, 1H), 1.15–1.03 (dd, 3H), 0.78 and 0.52 (d and d, 3H), 0.65–0.57 (m, 2H), 0.38–0.27 (m, 2H). LRMS (Electrospray, positive): Da/e 501.0 (m+1).

EXAMPLE 197

$R^1$=CH$_2$C$_3$H$_5$; $R^3$=COCH(4-FPh)OH

1-{3-((1R)-1-Hydroxyethyl)(3S,4S)-4-[3-(cyclopropylmethoxy)-4-methoxyphenyl]-3-methylpyrrolidinyl}-2-(4-fluorophenyl)-2-hydroxyethan-1-one Prepared from Example 196 via the LiOH hydrolysis procedure of Intermediate 5.

$^1$H NMR (400 HMz, CDCl$_3$, mixture of rotomers and diastereomers) δ: 7.60–7.25 (m, 2H), 7.12–7.00 (m, 2H), 6.84–6.48 (m, 3H), 5.11–4.59 (m, 1H), 4.04–2.79 (c, 11H), 1.35–1.23 (m, 1H), 1.15–1.00 (dd, 3H), 0.75 and 0.48 (d and s, 3H), 0.66–0.60 (m, 2H), 0.37–0.30 (m, 2H) LRMS (Electrospray, positive): Da/e 458.2 (m+1).

EXAMPLE 198

$R^1$=CH$_2$C$_3$H$_5$; $R^3$=COC(CH$_2$CH$_2$)OAc ({3-((1R)-1-Hydroxyethyl)(3S,4S)-4-[3-(cyclopropylmethoxy)-4-methoxyphenyl]-3-methylpyrrolidinyl}-carbonyl)cyclopropyl acetate Prepared from Intermediate 67 via the Hunig's base coupling procedure of Intermediate 74 using (chlorocarbonyl)cyclopropyl acetate.

$^1$H NMR (400 HMz, CDCl$_3$) δ: 6.85–6.72 (m, 3H), 4.06–3.31 (c, 11H), 2.10 (s, 3H), 1.74–1.62 (m, 1H), 1.59–1.47 (m, 1H), 1.35–1.19 (m, 2H), 1.14 (d, 3H), 1.02–0.93 (m, 1H), 0.71 (s, 3H), 0.65–0.59 (m, 2H) 0.37–0.30 (m, 2H). LRMS (Electrospray, positive): Da/e 432.5 (m+1).

EXAMPLE 199

$R^1$=CH$_2$C$_3$H$_5$; $R^3$=COC(CH$_2$CH$_2$)OH 3-((1R)-1-Hydroxyethyl)(3S,4S)-4-[3-(cyclopropylmethoxy)-4-methoxyphenyl]-3-methylpyrrolidinyl hydroxycyclopropyl ketone Prepared from Example 198 via the LiOH hydrolysis procedure of Intermediate 5.

$^1$H NMR (400 HMz, CDCl$_3$) δ: 6.88–6.78 (m, 3H), 4.42–3.30 (c, 11H), 1.42–1.22 (m, 3H), 1.16 (d, 3H), 1.11–0.88 (m, 3H), 0.74 (d, 3H), 0.66–0.59 (m, 2H), 0.39–0.31 (m, 2H). LRMS (Electrospray, positive): Da/e 390.5 (m+1).

EXAMPLE 200

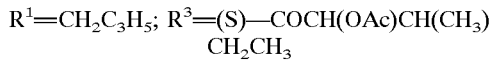

2-{3-((1R)-1-Hydroxyethyl)(3S,4S)-4-[3-(cyclopropylmethoxy)-4-methoxyphenyl]-3-methylpyrrolidinyl}(1S)-1-(methylpropyl)-2-oxoethyl acetate Prepared from Intermediate 67 via the Hunig's base coupling procedure of Intermediate 74 using (1S)-1-(chlorocarbonyl)-2-methylbutyl acetate.

$^1$H NMR (400 HMz, CDCl$_3$, mixture of rotomers and diastereomers) δ: 6.85–6.72 (m, 3H), 4.84 (dd, 1H), 3.89–3.31 (c, 11H), 2.12 (d, 3H), 2.09–1.95 (m, 1H), 1.75–1.62 (m, 1H), 1.35–1.19 (m, 2H), 1.15 (t, 3H), 1.00–0.86 (m, 6H), 0.75 (d, 3H), 0.65–0.56 (m, 2H), 0.37–0.30 (m, 2H). LRMS (Electrospray, positive): Da/e 462.5 (m+1).

EXAMPLE 201

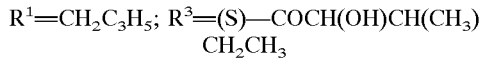

1-{3-((1R)-1-Hydroxyethyl)(3S,4S)-4-[3-(cyclopropylmethoxy)-4-methoxyphenyl]-3-methylpyrrolidinyl}(2S)-2-hydroxy-3-methylpentan-1-one Prepared from Example 200 via the LiOH hydrolysis procedure of Intermediate 5.

$^1$H NMR (400 HMz, CDCl$_3$, mixture of rotomers and diastereomers) δ: 6.85–6.76 (m, 3H), 4.18–4.11 (m, 1H), 3.94–3.26 (c, 11H), 1.75–1.66 (m, 1H), 1.54–1.19 (m, 4H), 1.15 (dd, 3H), 1.07 (m, 3H), 0.94–0.85 (m, 3H), 0.76 (d, 3H), 0.66–0.60 (m, 2H), 0.38–0.32 (m, 2H). LRMS (Electrospray, positive): Da/e 420.5 (m+1).

EXAMPLE 202

R$^1$=CH$_2$C$_3$H$_5$; R$^3$=(S)—COCH(OAc)CH$_2$CH(CH$_3$)$_2$

2-{3-((1R)-1-Hydroxyethyl)(3S,4S)-4-[3-(cyclopropylmethoxy)-4-methoxyphenyl]-3-methylpyrrolidinyl}(1S)-1-(2-methylpropyl)-2-oxoethyl acetate Prepared from Intermediate 67 via the Hunig's base coupling procedure of Intermediate 74 using (1S)-1-(chlorocarbonyl)-3-methylbutyl acetate.

$^1$H NMR (400 HMz, CDCl$_3$, mixture of rotomers) δ: 6.84–6.74 (m, 3H), 5.19–5.10 (m, 1H), 4.15–2.95 (c, 11H), 2.13 (d, 3H), 1.95–1.72 (m, 2H), 1.58–1.39 (m, 2H), 1.34–1.23 (m, 1H), 1.18–1.12 (m, 3H), 1.00–0.88 (m, 6H), 0.75 (d, 3H), 0.68–0.57 (m, 2H), 0.37–0.30 (m, 2H). LRMS (Electrospray, positive).: Da/e 462.5 (m+1)

EXAMPLE 203

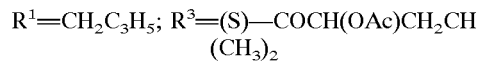

1-{3-((1R)-1-Hydroxyethyl)(3S,4S)-4-[3-(cyclopropylmethoxy)-4-methoxyphenyl]-3-methylpyrrolidinyl}(2S)-2-hydroxy-4-methylpentan-1-one Prepared from Example 202 via the LiOH hydrolysis procedure of Intermediate 5.

$^1$H NMR (400 HMz, CDCl$_3$, mixture of rotomers) δ: 6.86–6.77 (m, 3H), 4.32–4.25 (m, 1H), 3.88–2.97 (c, 11H), 2.05–1.93 (m, 1H), 1.73–1.21 (m, 5H), 1.14 (dd, 3H), 1.02–0.93 (m, 6H), 0.76 (d, 3H), 0.66–0.60 (m, 2H), 0.38–0.32 (m, 2H). LRMS (Electrospray, positive): Da/e 420.3 (m+1).

EXAMPLE 204

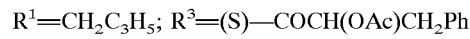

2-{3-((1R)-1-Hydroxyethyl)(3S,4S)-4-[3-(cyclopropylmethoxy)-4-methoxyphenyl]-3-methylpyrrolidinyl}(1S)-2-oxo-1-benzylethyl acetate Prepared from Intermediate 67 via the Hunig's base coupling procedure using (1S)-1-(chlorocarbonyl)-2-phenylethyl acetate.

$^1$H NMR (400 HMz, CDCl$_3$, mixture of rotomers) δ: 7.40–7.26 (m, 5H), 6.82–6.70 and 6.52–6.47 (m and m, 3H), 5.30–5.18 (m, 1H), 3.90–2.79 (c, 13H), 2.11 (d, 3H), 1.35–1.25 (m, 1H), 1.05 (dd, 3H), 0.66 and 0.33 (s and s, 3H), 0.68–0.60 (m, 2H), 0.39–0.32 (m, 2H). LRMS (Electrospray, positive): Da/e 497.0 (m+1).

EXAMPLE 205

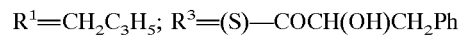

1-{3-((1R)-1-Hydroxyethyl)(3S,4S)-4-[3-(cyclopropylmethoxy)-4-methoxyphenyl]-3-methylpyrrolidinyl}(2S)-2-hydroxy-3-phenylpropan-1-one Prepared from Example 204 (20 mg, 0.040 mmol) by the LiOH hydrolysis procedure of Intermediate 5 to afford 14.5 mg (79%) of Example 205 as a colorless film.

$^1$H NMR (400 HMz, CDCl$_3$, mixture of rotomers) δ: 7.40–7.26 (m, 5H), 6.82–6.75 and 6.56–6.53 (m and m, 3H), 4.51–4.43 (m, 1H), 3.90–2.70 (c, 13H), 1.35–1.25 (m, 1H), 1.09 (dd, 3H), 0.69 and 0.52 (s and s, 3H), 0.68–0.60 (m, 2H), 0.39–0.32 (m, 2H). LRMS (Electrospray, positive): Da/e 454.3 (m+1).

EXAMPLE 206

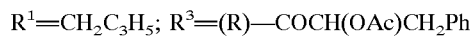

(1R)-2-{3-((1R)-1-Hydroxyethyl)(3S,4S)-4-[3-(cyclo-propylmethoxy)-4-methoxyphenyl]-3-methylpyrrolidinyl}-2-oxo-1-benzylethyl acetate Prepared from Intermediate 67 via the Hunig's base coupling procedure of Intermediate 74 using (1R)-1-(chlorocarbonyl)-2-phenylethyl acetate.

$^1$H NMR (400 HMz, CDCl$_3$, mixture of rotomers) δ: 7.37–7.22 (m, 5H), 6.82–6.72, 6.64, 6.45 (m, d, and dd, 3H), 5.27 and 5.18 (dd, t, 1H), 3.99–2.56 (c, 13H), 2.12 (s, 3H) 1.34–1.24 (m, 1H), 1.13–1.02 (dd, 3H), 0.68 and 0.34 (s and s, 3H), 0.65–0.58 (m, 2H), 0.37–0.30 (m, 2H). LRMS (Electrospray, positive): Da/e 496.6 (m+1).

EXAMPLE 207

R¹=CH₂C₃H₅; R³=(R)—COCH(OH)CH₂Ph ((2R)-1-{3-((1R)-1-Hydroxyethyl)(3S,4S)-4-[3-(cyclopropylmethoxy)-4-methoxyphenyl]-3-methylpyrrolidinyl}-2-hydroxy-3-phenylpropan-1-one Prepared from Example 206 via the lithium peroxide method of Intermediate 43.

¹H NMR (400 HMz, CDCl₃, mixture of rotomers) δ: 7.35–7.18 (m, 5H), 6.84–6.67 (m, 3H), 4.48–4.40 (m, 1H), 4.04–2.70 (c, 13H), 1.34–1.24 (m, 1H), 1.08 (dd, 3H), 0.71 and 0.49 (s and s, 3H), 0.65–0.58 (m, 2H), 0.38–0.31 (m, 2H). LRMS (Electrospray, positive): Da/e 454.5 (m+1).

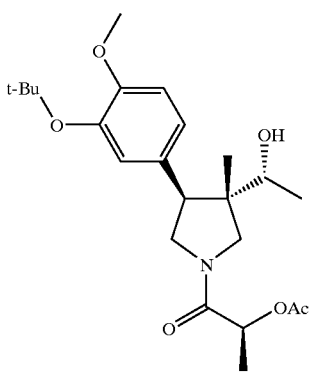

EXAMPLE 208

R¹=t-Bu; R³=(S)—COCH(OAc)CH₃

2-{3-((1R)-1-Hydroxyethyl)(3S,4S)-4-[3-(tert-butoxy)-4-methoxyphenyl]-3-methylpyrrolidinyl}(1S)-1-methyl-2-oxoethyl acetate Prepared from Intermediate 73 via the Hunig's base coupling procedure of Intermediate 74 using (S)-2-acetoxypropionyl chloride.

¹H NMR (400 HMz, CDCl₃, mixture of rotomers) δ: 6.95–6.81 (m, 3H), 5.24–5.11 (m, 1H), 3.80 (m, 3H), 4.08–3.38 (m, 6H), 2.15–2.12 (d, 3H), 1.49–1.46 (dd, 3H), 1.33 (d, 9H), 1.14 (d, 3H), 0.76 (d, 3H). LRMS (Electrospray, positive): Da/e 422.4 (m+1).

EXAMPLE 209

R¹=H; R³=(S)—COCH(OAc)CH₃

2-(3-((1R)-1-Hydroxyethyl)(3S,4S)-4-(3-hydroxy-4-methoxyphenyl)-3-methylpyrrolidinyl](1S)-1-methyl-2-oxoethyl acetate Prepared from Example 208 via the TFA deprotection method of Example 143.

¹H NMR (400 HMz, CDCl₃, mixture of rotomers) δ: 6.88–6.70 (m, 3H), 5.73–5.69 (br d, 1H), 5.25–5.19 (m, 1H), 3.88 (d, 3H), 4.06–3.38 (m, 6H), 2.12 (d, 3H), 1.49–1.46 (d, 3H), 1.16–1.14 (dd, 3H), 0.75 (d, 3H). LRMS (Electrospray, positive): Da/e 366.3 (m+1).

EXAMPLE 210

R¹=CH₂C≡CPh; R³=(S)—COCH(OAc)CH₃

2-{3-((1R)-1-Hydroxyethyl)(3S,4S)-4-[4-methoxy-3-(3-phenylprop-2-ynyloxy)phenyl]-3-methylpyrrolidinyl}-(1S)-1-methyl-2-oxoethyl acetate Prepared from Example 209 via the Cs₂CO₃ method of Example 176 using Intermediate 90.

¹H NMR (400 HMz, CDCl₃, mixture of rotomers) δ: 7.39–7.26 (m, 5H), 7.05 (d, 1H), 6.85 (s, 2H), 5.23–5.17 (m, 1H), 5.05–4.95 (m, 2H), 3.86 (s, 3H), 4.07–3.36 (d, 6H), 2.15–2.12 (d, 3H), 1.47–1.40 (t, 3H), 1.36–1.33 (m, 1H), 0.99–0.95 (m, 3H), 0.75–0.71 (d, 3H). LRMS (Electrospray, positive): Da/e (m+1).

EXAMPLE 211

R¹=CH₂C≡CPh; R³=(S)—COCH(OH)CH₃

1-{3-((1R)-1-Hydroxyethyl)(3S,4S)-4-[4-methoxy-3-(3-phenylprop-2-ynyloxy)phenyl]-3-methylpyrrolidinyl}-(2S)-2-hydroxypropan-1-one Prepared from Example 210 via the O-acetate deprotection method of Example 95.

¹H NMR (400 HMz, CDCl₃, mixture of rotomers) δ: 7.41–7.26 (m, 5H), 7.07 (d, 1H), 6.86 (s, 2H), 5.05–4.94 (m, 1H), 4.36–4.30 (m, 1H), 3.89 (s, 3H), 3.91–3.48 (c, 5H), 3.28 (dd, 1H), 1.37–1.32 (m, 3H) 0.99–0.92 (dd, 3H), 0.73–0.70 (d.3H). LRMS (Electrospray, positive): Da/e 438.2 (m+1).

EXAMPLE 212

R¹=CH₂C≡C-4-FPh; R³=(S)—COCH(OAc)CH₃

2-(3-((1R)-1-Hydroxyethyl)(3S,4S)-4-{3-[3-(4-fluorophenyl)prop-2-ynyloxy]-4-methoxyphenyl}-3-methylpyrrolidinyl)-2-oxoethyl acetate Prepared from Example 209 via the Cs₂CO₃ method of Example 176 using Intermediate 91.

¹H NMR (400 MHz, CDCl₃, mixture of rotomers) δ: 7.40–7.36 (m, 2H), 7.03–6.96 (m, 3H), 5.22–5.20 (q, 1H), 4.98–4.96 (m, 2H), 4.07–3.53 (c, 6H), 3.88–3.86 (m, 3H), 2.14–2.11 (d, 3H), 1.47–1.42 (t, 3H), 1.06–1.01 (m, 3H), 0.75–0.72 (d, 3H). LRMS (Electrospray, positive): Da/e 498.5 (m+1).

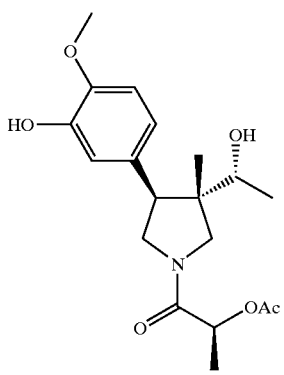

EXAMPLE 213

R¹=CH₂C≡C-4-FPh; R³=(S)—COCH(OH)CH₃

1-(3-((1R)-1-Hydroxyethyl)(3S,4S)-4-{3-[3-(4-fluorophenyl)prop-2-ynyloxy]-4-methoxyphenyl}-3-methylpyrrolidinyl)(2S)-2-hydroxypropan-1-one Prepared from Example 212 via the O-acetate deprotection method of Example 95.

¹H NMR (400 HMz, CDCl₃, mixture of rotomers) δ: 7.40–7.26 (m, 2H), 7.04–6.98 (m, 3H), 6.86 (s, 2H), 5.03–4.97 (m, 2H), 4.40–4.30 (m, 1H), 3.89 (s, 3H), 3.94–3.52 (c, 5H), 3.29 (dd, 1H), 1.39–1.28 (d, 3H), 1.04–1.00 (m, 3H), 0.74–0.72 (d, 3H). LRMS (Electrospray, positive): Da/e 456.5 (m+1).

EXAMPLE 214

R¹=CH₂C≡C-4-CF₃Ph; R³=(S)—COCH(OAc)CH₃

2-[3-((1R)-1-Hydroxyethyl)(3S,4S)-4-(4-methoxy-3-{3-[4-(trifluoromethyl)phenyl]prop-2-ynyloxy}phenyl)-3-methylpyrrolidinyl](1S)-1-methyl-2-oxoethyl acetate Prepared from Example 209 via the Cs₂CO₃ method of Example 176 using Intermediate 92.

¹H NMR (400 HMz, CDCl₃, mixture of rotomers) δ: 7.57–7.45 (m, 4H), 7.01 (d, 1H), 6.88–6.83 (m, 2H), 5.22–5.17 (m, 1H), 5.00 (s, 2H), 4.07–3.35 (c, 6H), 3.88 (d, 3H), 2.13–2.11 (d, 3H), 1.47–1.42 (dd, 3H), 1.12 (d, 3H), 0.75–0.71 (d, 3H). LRMS (Electrospray, positive): Da/e 548.8 (m+1).

EXAMPLE 215

R¹=CH₂C≡C-4-CF₃Ph; R³=(S)—COCH(OH)CH₃

1-[3-((1R)-1-Hydroxyethyl)(3S,4S)-4-(4-methoxy-3-{3-[4-(trifluoromethyl)phenyl]prop-2-ynyloxy}phenyl)-3-methylpyrrolidinyl](2S)-2-hydroxypropan-1-one Prepared from Example 214 via the O-acetate deprotection method of Example 95.

¹H NMR (400 HMz, CDCl₃, mixture of rotomers) δ: 7.56 (d, 2H), 7.50 (d, 2H), 7.03 (s, 1H), 6.87 (s, 2H), 5.01 (s, 2H), 4.36–4.33 (m, 1H), 3.89 (s, 3H), 3.91–3.49 (c, 5H), 3.30 (dd, 1H), 1.37–1.35 (dd, 3H), 1.04–1.01 (t, 3H), 0.74–0.71 (d, 3H). LRMS (Electrospray, positive): Da/e 505.9 (m+1).

EXAMPLE 216

R¹=3-(4-chlorophenyl)(1,2,4-oxadiazol-5-yl)methyl; R³=(S)—COCH(OAc)CH₃

2-[3-((1R)-1-Hydroxyethyl)(3S,4S)-4-(3-{[3-(4-chlorophenyl)(1,2,4-oxadiazol-5-yl)]methoxy}-4-methoxyphenyl)-3-methylpyrrolidinyl](1S)-1-methyl-2-oxoethyl acetate Prepared from Example 209 via the Cs₂CO₃ method of Example 176 using Intermediate 87.

¹H NMR (400 HMz, CDCl₃, mixture of rotomers) δ: 8.01 (d, 2H), 7.46 (d, 1H), 6.96–6.85 (m, 3H), 5.45–5.36 (m, 2H), 5.21–5.14 (m, 1H), 4.02–3.36 (c, 6H), 3.84 (m, 3H), 2.11 (d, 3H), 1.47–1.42 (m, 3H), 1.04–1.02 (d, 3H), 0.67–0.65 (d, 3H). LRMS (Electrospray, positive): Da/e 558.2 (m+1).

EXAMPLE 217

R¹=3-(4-chlorophenyl)(1,2,4-oxadiazol-5-yl)methyl; R³=(S)—COCH(OH)CH₃

1-[3-((1R)-1-Hydroxyethyl)(3S,4S)-4-(3-{[3-(4-chlorophenyl)(1,2,4-oxadiazol-5-yl)]methoxy}-4-methoxyphenyl)-3-methylpyrrolidinyl](2S)-2-hydroxypropan-1-one Prepared from Example 216 via the O-acetate deprotection method of Example 95.

¹H NMR (400 HMz, CDCl₃, mixture of rotomers) δ: 8.06–8.00 (m, 2H), 7.49–7.45 (m, 2H), 6.97–6.86 (m, 3H), 5.41 (m, 2H), 4.35–4.32 (m, 1H), 3.88 (s, 3H) 3.86–3.19 (c, 6H), 1.38–1.32 (m, 3H), 1.05–1.00 (dd, 3H), 0.66–0.63 (d, 3H) LRMS (Electrospray, positive): Da/e 516.4 (m+1).

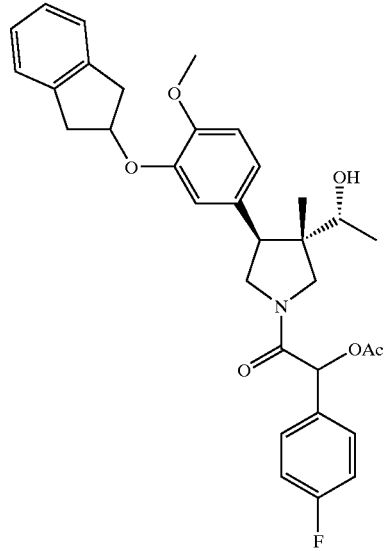

EXAMPLE 218

R¹=2-indanyl; R³=COCH(OAc)4-FPh

2-[3-((1R)-1-Hydroxyethyl)(3S,4S)-4-(3-indan-2-yloxy-4-methoxyphenyl)-3-methylpyrrolidinyl]-1-(4-fluorophenyl)-2-oxoethyl acetate Intermediate 51 (72.8 mg, 0.198 mmol) was acylated by the K₂CO₃ procedure of Example 7 with 2-acetoxyfluoromandelic acid chloride (120 mg, 0.297 mmol, 1.5 eq) to give a clear, colorless oil (84.2 mg, 75%).

¹H NMR (400 HMz, CDCl₃, mixture of rotomers) δ: 7.53–7.47 (m, 2H), 7.26–7.03 (m, 6H), 6.87–6.59 (m, 3H), 6.09–6.04 (m, 1H), 5.28–5.01 (m, 1H), 4.14–3.03 (c, 13H), 2.16 (s, 3H), 1.27–1.06 (m, 3H), 0.82–0.80 (d, 1.5H), 0.55–0.52 (d, 1.5H).

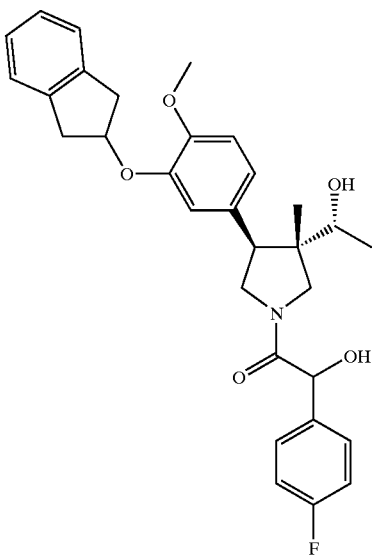

EXAMPLE 219

R¹=2-indanyl; R³=COCH(OH)4-FPh

1-[3-((1R)-1-Hydroxyethyl)(3S,4S)-4-(3-indan-2-yloxy-4-methoxyphenyl)-3-methylpyrrolidinyl]-2-(4-fluorophenyl)-2-hydroxyethan-1-one Example 218 (19 mg, 0.034 mmol, 1 eq) was subjected to the LiOH hydrolysis procedure of Intermediate 5 to yield a white powder (6.1 mg, 35%).

¹H NMR (400 HMz, CDCl₃, mixture of rotamers) δ: 6.97–6.80 (c, 7H), 4.19 (m, 2H), 4.13 (t, 2H), 3.82 (s, 3H), 3.72 (s, 3H), 3.83–3.48 (c, 4H), 3.25 (dd, 1H), 2.27 (quintet, 2H), 1.70 (s, 1H), 1.56 (br d, 1H), 1.13 (t, 3H), 0.73 (s, 3H) LRMS (Electrospray, positive): Da/e 520.4 (m+1).

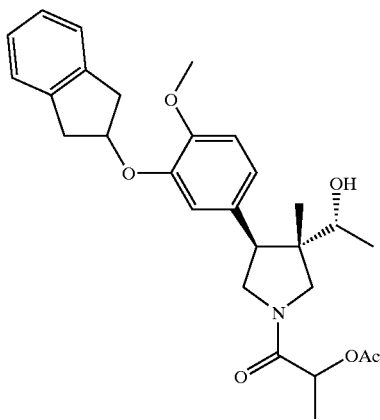

EXAMPLE 220

R¹=2-indanyl; R³=COCH(OAc)CH₃

2-[3-((1R)-1-Hydroxyethyl)(3S,4S)-4-(3-indan-2-yloxy-4-methoxyphenyl)-3-methylpyrrolidinyl]-1-methyl-2-oxoethyl acetate Intermediate 51 (27 mg, 0.074 mmol) was acylated by the K₂CO₃ procedure of Example 7 using (+)-2-acetoxypropionyl chloride (12.1 μL, 0.110 mmol, 1.5 eq) to yield a clear, colorless oil (16.7 mg, 47%).

¹H NMR (400 HMz, CDCl₃, mixture of rotomers) δ: 7.27–7.17 (m, 4H), 6.85–6.83 (m, 3H), 5.30–5.17 (m, 2H), 4.13–3.19 (c, 9H), 2.14 (s, 3H), 1.72 (br s, 1H), 1.51–1.47 (m, 4H), 1.19–1.17 (d, 3H), 0.82–0.78 (d, 3H).

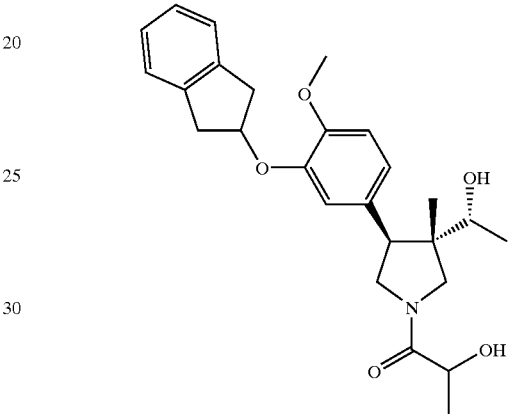

EXAMPLE 221

R¹=2-indanyl; R³=COCH(OH)CH₃

1-[3-((1R)-1-Hydroxyethyl)(3S,4S)-4-(3-indan-2-yloxy-4-methoxyphenyl)-3-methylpyrrolidinyl]-2-hydroxypropan-1-one Example 220 (16.7 mg, 0.0347 mmol, 1 eq) was subjected to the LiOH hydrolysis procedure of Intermediate 5 to yield a white solid (4.7 mg, 31%).

¹H NMR (400 HMz, CDCl₃, mixture of rotomers) δ: 7.27–7.17 (m, 4H), 6.85–6.84 (m, 3H), 5.19–5.15 (m, 1H), 4.39–4.35 (m, 1H), 3.90–3.18 (c, 14H), 1.57–1.37 (m, 3H), 1.28–1.15 (m, 3H), 0.80–0.78 (d, 3H). LRMS (Electrospray, positive): Da/e 440.4 (m+1).

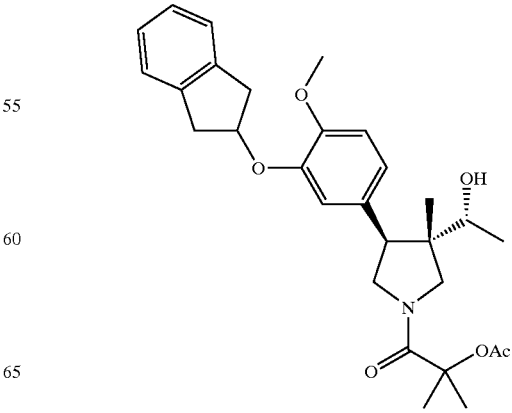

EXAMPLE 222

R¹=2-indanyl; R³=COC(CH₃)(OAc)CH₃

2-[3-((1R)-1-Hydroxyethyl)(3S,4S)-4-(3-indan-2-yloxy-4-methoxyphenyl)-3-methylpyrrolidinyl]-1,1-dimethyl-2-oxoethyl acetate Intermediate 51 (40 mg, 0.11 mmol) was acylated by the K₂CO₃ procedure of Example 7 using 2-acetoxy-2-methyl-propionyl chloride (31 µL, 0.22 mmol, 2 eq) to yield a clear, colorless oil (22 mg, 40%).

¹H NMR (400 HMz, CDCl₃, mixture of rotomers) δ: 7.26–7.16 (m, 4H), 6.85–6.77 (m, 3H), 4.17 (m, 1H), 3.95–3.19 (c, 14H), 2.10 (s, 3H), 1.65–1.57 (m, 6H), 1.20–1.17 (m, 3H), 0.73 (s, 3H).

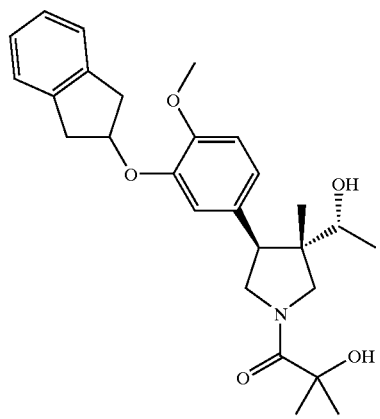

EXAMPLE 223

R¹=2-indanyl; R³=COC(CH₃)(OH)CH₃

1-[3-((1R)-1-Hydroxyethyl)(3S,4S)-4-(3-indan-2-yloxy-4-methoxyphenyl)-3-methylpyrrolidinyl]-2-hydroxy-2-methylpropan-1-one Example 222 (22 mg, 0.044 mmol) was subjected to the LiOH hydrolysis procedure of Intermediate 5 to yield product as a white solid (4.3 mg, 22%).

¹H NMR (400 HMz, CDCl₃, mixture of rotomers) δ: 7.26–7.17 (m, 4H), 6.83 (m, 3H), 5.18–5.17 (m, 1H), 4.45–4.44 (m, 1H), 3.89–3.19 (c, 14H), 1.53–1.48 (m, 6H), 1.19–1.17 (m, 3H), 0.79–0.78 (d, 3H). LRMS (Electrospray, positive): Da/e 454.4 (m+1).

EXAMPLE 224

R¹=t-Bu; R³=CO₂CH₃

Methyl (3R)-3-((1R)-1-hydroxyethyl)-4-[3-(tert-butoxy)-4-methoxyphenyl]-3-methylpyrrolidine-carboxylate Intermediate 73 (6.5 µL, 0.084 mmol) was acylated by the Hunig's base method of Intermediate 74 with methyl chloroformate to provide Example 224 as a yellow oil (19 mg, 94%).

¹H-NMR (400 HMz, CDCl₃) δ: 6.96 (d, 1H), 6.84 (s, 1H), 6.83 (d, 1H), 3.80 (s, 3H), 3.77–3.58 (m, 4H), 3.06 (d, 1H), 1.36 (s, 9H), 1.16 (d, 3H), 0.76 (s, 3H).

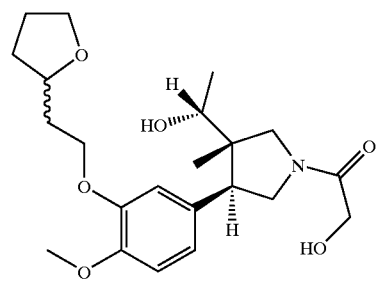

EXAMPLE 225

2-Hydroxy-1-((3S,4S)-3-((R)-1-hydroxyethyl)-4-{4-methoxy-3-[2-(tetrahydrofuran-2-yl)ethoxy]phenyl}-3-methylpyrrolidin-1-yl)ethanone Prepared from Example 143 by the Mitsunobu procedure of Example 144 using 2-tetrahydrofuran-2-ylethanol followed by debenzylation via the method of Intermediate 31.

¹H NMR data δ: 6.75–6.87 (m, 3H); 4.16–4.20 (m, 2H) 4.15 (s, 3H); 3.49–4.13 (m, 11H); 3.05 (d, 1H); 1.97–2.10 (m, 2H)1.88–1.96 (t, 2H); 1.56–1.63 (m, 2H); 1.3–1.17 (t, 3H); 0.75 (s, 3H).

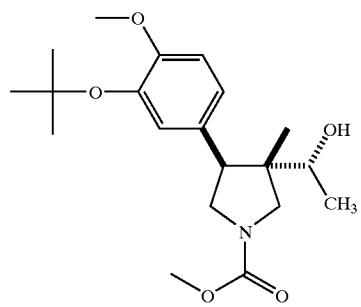

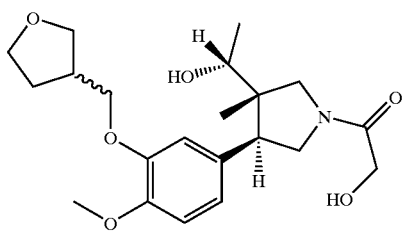

EXAMPLE 226

2-Hydroxy-1-{(3S,4S)-3-((R)-1-hydroxy-ethyl)-4-[4-methoxy-3-(tetrahydrofuran-3-ylmethoxy)phenyl]-3-methylpyrrolidin-1-yl}ethanone Prepared from Example 143 by the Mitsunobu method of Example 144 using tetrahydrofuran-3-ylMethanol followed by the debenzylation procedure of Intermediate 31.

¹H NMR data δ: 6.79–6.82 (m, 3H); 4.13–4.16 (m, 2H); 3.48–3.98 (m, 11H); 3.84 (s, 3H); 3.05 (d, 1H); 2.80 (bt; 1H); 2.07–2.15 (M, 2H); 1.72–1.79 (m, 1H); 1.16 (t, 3H); 0.76 (s, 3H).

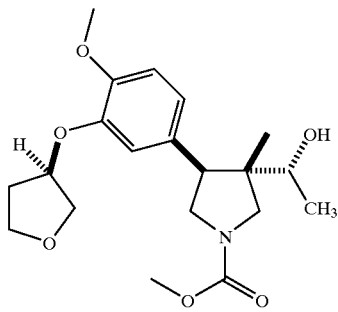

EXAMPLE 227

R¹=(S)—CH(CH₂OCH₂CH₂); R³=CO₂CH₃

Methyl (3R)-3-((1R)-1-hydroxyethyl)-4-[3-((3S)-oxolan-3-yloxy)-4-methoxyphenyl]-3-methylpyrrolidinecarboxylate Prepared from Intermediate 74 (146 mg, 0.47 mmol) by the solid phase Mitsunobu procedure of Example 144 using (S)-(+)-3-hydroxytetrahydrofuran (38 μL), 0.47 mmol) to afford Example 227 as a clear oil (95 mg, 53%).

¹H-NMR (400 HMz, CDCl₃) δ: 6.82 (m, 2H), 6.78 (m, 1H), 4.95 (m, 1H), 4.03–3.20 (m, 10H), 3.82 (s, 3H), 3.66 (s, 3H), 2.17 (m, 2H), 1.17 (t, 3H), 0.73 (s, 3H). LRMS (Electrospray, positive): Da/e 379.8 (m+1).

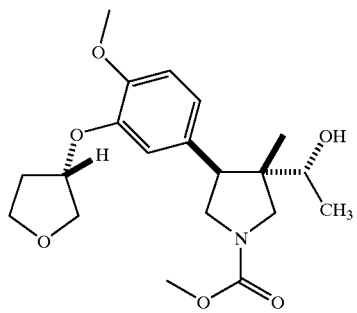

EXAMPLE 228

R¹=(R)—CH(CH₂OCH₂CH₂); R³=CO₂CH₃

Methyl (3R)-3-((1R)-1-hydroxyethyl)-4-[3-((3R)-oxolan-3-yloxy)-4-methoxyphenyl]-3-methylpyrrolidinecarboxylate Prepared from Intermediate 74 using the solid phase Mitsunobu reaction of Example 144 and (R)-(–)-3-hydroxytetrahydrofuran (46 μL), 0.57 mmol) to give Example 228 as a clear oil (27 mg, 37%).

¹H-NMR (400 HMz, CDCl₃) δ: 6.82 (m, 2H), 6.78 (m, 1H), 4.95 (m, 1H), 4.03–3.20 (m, 10H), 3.82 (s, 3H), 3.66 (s, 3H), 2.17 (m, 2H), 1.17 (t, 3H), 0.73 (s, 3H). LRMS (Electrospray, positive): Da/e 380.3 (m+1).

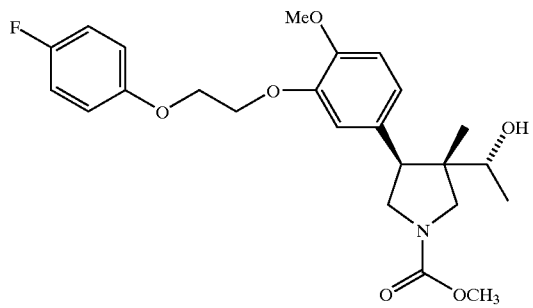

EXAMPLE 229

R¹=CH₂CH₂O-4-FPh; R³=CO₂CH₃

Methyl 3-((1R)-1-hydroxyethyl)(3S,4S)-4-{3-[2-(4-fluorophenoxy)ethoxy]-4-methoxyphenyl}-3-methylpyrrolidinecarboxylate Prepared by the K₂CO₃ etherification procedure of Example 43 using Intermediate 74 (21.2 mg, 0.0685 mmol, 1 eq) and 4-fluorophenoxyethyl bromide (60 mg, 0.27 mmol, 4.0 eq), yielding a clear, colorless oil (15.2 mg, 49.7%).

¹H NMR (400 HMz, CDCl₃) δ: 6.99–6.83 (c, 7H), 4.35 (t, 2H), 4.29 (t, 2H), 3.83 (s, 3H), 3.72 (s, 3H), 3.83–3.48 (c, 4H), 3.25 (dd, 1H), 1.64 (s, 1H), 1.42 (br d, 1H), 1.13 (t, 3H), 0.73(s, 3H).

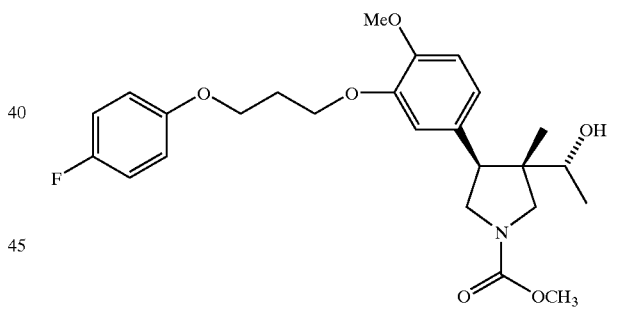

EXAMPLE 230

R¹=CH₂CH₂CH₂O-4-FPh; R³=CO₂CH₃

Methyl 3-((1R)-1-hydroxyethyl)(3S,4S)-4-{3-[3-(4-fluorophenoxy)propoxy]-4-methoxyphenyl}-3-methylpyrrolidinecarboxylate Prepared from Intermediate 74 (25.2 mg, 0.0815 mmol, 1 eq) by the K₂CO₃ etherification procedure of Example 43 using 1-(3-chloropropoxy)-4-fluorobenzene (62 mg, 0.33 mmol, 4.0 eq) to yield Example 230 as a clear, colorless oil (19.0 mg, 50.5%).

¹H NMR (400 HMz, CDCl₃) δ: 6.97–6.80 (c, 7H), 4.19 (m, 2H), 4.13 (t, 2H), 3.82 (s, 3H), 3.72 (s, 3H), 3.83–3.48 (c, 4H), 3.25 (dd, 1H), 2.27 (quintet, 2H), 1.70 (s, 1H), 1.56 (br d, 1H), 1.13 (t, 3H) 0.73(s, 3H).

EXAMPLE 231

R$^1$=CH$_2$C≡CH; R$^3$=CO$_2$CH$_3$

Methyl 3-((1R)-1-hydroxyethyl)(3S,4S)-4-(4-methoxy-3-prop-2-ynyloxyphenyl)-3-methylpyrrolidinecarboxylate Prepared from Intermediate 74 via the K$_2$CO$_3$ etherification procedure of Example 43 using propargyl bromide.

$^1$H NMR (400 HMz, CDCl$_3$) δ: 6.97 (s, 1H), 6.87–6.82 (m, 2H), 4.76 (s, 2H), 3.86 (s, 3H), 3.73 (s, 3H), 3.90–3.55 (m, 5H), 3.27 (dd, 1H), 2.48 (s, 1H) 1.49–1.46 (m, 1H), 1.14 (t, 3H), 0.75 (s, 3H). LRMS (Electrospray, positive): Da/e 348.1 (m+1).

EXAMPLE 232

R$^1$=CH$_2$C≡CCH$_3$; R$^3$=CO$_2$CH$_3$

Methyl 3-((1R)-1-hydroxyethyl)(3S,4S)-4-(3-but-2-ynyloxy-4-methoxyphenyl)-3-methylpyrrolidinecarboxylate Prepared from Intermediate 74 via the K$_2$CO$_3$ etherification procedure of Example 43 using 1-bromo-2-butyne.

$^1$H NMR (400 HMz, CDCl$_3$) δ: 6.96 (s, 1H), 6.85–6.82 (m, 2H), 4.72–4.71 (m, 2H), 3.86 (s, 3H), 3.72 (s, 3H), 3.90–3.55 (m, 5H), 3.27 (dd, 1H), 2.48 (s, 1H), 1.81 (s, 3H), 1.52–1.48 (m, 1H), 1.14 (t, 3H), 0.77 (s,3H). LRMS (Electrospray, positive): Da/e 362.2 (m+1).

EXAMPLE 233

R$^1$=CH$_2$C≡CPh; R$^3$=CO$_2$CH$_3$

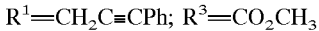

Methyl 3-((1R)-1-hydroxyethyl)(3S,4S)-4-[4-methoxy-3-(3-phenylprop-2-ynyloxy)phenyl]-3-methylpyrrolidinecarboxylate Prepared from Intermediate 74 by the Mitsunobu reaction of Example 144 using 3-phenyl-2-propyn-1-ol.

$^1$H NMR (400 HMz, CDCl$_3$, mixture of rotomers) δ: 7.41–7.38 (m, 2H), 7.32–7.27 (m, 3H), 7.07 (d, 1H), 6.84 (s, 2H), 5.00–4.94 (m, 2H), 3.88 (s, 3H), 3.72 (s, 3H), 3.80–3.69 (m, 3H), 3.57–3.50 (m, 2H), 3.23 (dd, 1H), 1.35–1.32 (m, 1H), 0.98–0.94 (dd, 3H), 0.70(d, 3H). LRMS (Electrospray, positive): Da/e 424.2 (m+1).

EXAMPLE 234

R$^1$=CH$_2$C≡C-4-FPh; R$^3$=CO$_2$CH$_3$

Methyl 3-((1R)-1-hydroxyethyl)(3S,4S)-4-{3-[3-(4-fluorophenyl)prop-2-ynyloxy]-4-methoxyphenyl}-3-methylpyrrolidinecarboxylate Prepared from Intermediate 74 via the solid phase Mitsunobu procedure of Example 144 using. Intermediate 89.

$^1$H NMR (400 HMz, CDCl$_3$, mixture of rotomers) δ: 7.40–7.36 (m, 2H), 7.04–6.97 (m, 3H), 6.85 (s, 2H), 4.97 (s, 2H), 3.88 (s, 3H), 3.72 (s, 3H), 3.86–3.65 (m, 3H), 3.58–3.48 (m, 2H), 3.24 (dd, 1H), 1.013 (t, 3H), 1.14 (t, 3H), 0.71 (d, 3H). LRMS (Electrospray, positive) Da/e 442.5 (m+1).

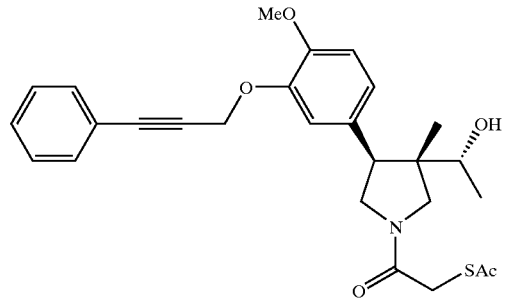

EXAMPLE 235

R$^1$=CH$_2$C≡CPh; R$^3$=COCH$_2$SAc

1-{3-((1R)-1-Hydroxyethyl)(3S,4S)-4-[4-methoxy-3-(3-phenylprop-2-ynyloxy)phenyl]-3-methylpyrrolidinyl}-2-acetylthioethan-1-one Prepared from Example 118 (30 mg, 0.082 mmol, 1.0 eq) by the Cs$_2$CO$_3$ procedure of Example 176 using phenylpropargyl mesylate (17.4 mg, 0.082 mmol, 1.0 eq, yielding a clear, colorless oil (13.2 mg, 33%).

$^1$H NMR (400 HMz, CDCl$_3$, mixture of rotomers) δ: 7.45–6.86 (m, 8H), 4.13–3.49 (c, 12H), 2.31 (s, 3H), 1.60 (s, 1H), 1.28–1.24 (dd, 1H), 1.15–1.08 (dd, 3H), 0.73 (s, 3H)

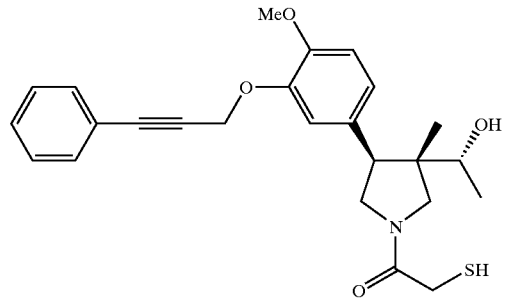

EXAMPLE 236

R$^1$=CH$_2$C≡CPh; R$^3$=COCH$_2$SH

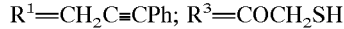

1-{3-((1R)-1-Hydroxyethyl)(3S,4S)-4-[4-methoxy-3-(3-phenylprop-2-ynyloxy)phenyl]-3-methylpyrrolidinyl}-2-sulfanylethan-1-one Prepared from Example 235 (13.2 mg, 0.0274 mmol) by the LiOH hydrolysis procedure of Intermediate 5 to give a clear, colorless oil (10.5 mg, 87%).

$^1$H NMR (CD$_3$OH, 400 HMz, mixture of rotomers) δ: 7.41–7.20 (m, 5H), 6.91–6.75(m, 3H), 4.01–3.29 (c, 12H), 3.21 (s, 1H), 1.88 (s, 1H), 1.38–1.21 (m, 1H), 1.07–1.03 (m, 3H), 0.73–0.72 (m, 3H). LRMS (Electrospray, positive): Da/e 440.4 (m+1).

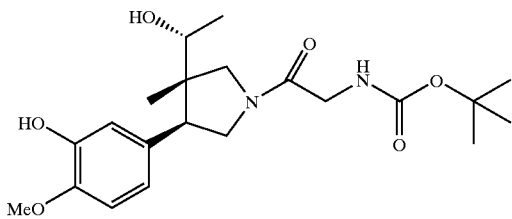

Intermediate 93

{2-[(3S,4S)-3-((R)-1-Hydroxyethyl)-4-(3-hydroxy-4-methoxyphenyl)-3-methylpyrrolidin-1-yl]-2-oxo-ethyl)carbamic acid tert-butyl ester To a flask containing a solution of Intermediate 70 (67.2 mg, 0.27 mmol) in dioxane (2.0 mL) was added a 1.0 M solution of aqueous $K_2CO_3$ (1.0 mL, 1.0 mmol). A solution of N-Boc-glycine p-nitrophenyl ester (236 mg, 0.79 mmol) in dioxane (100 mL) was added via syringe to the mixture. The mixture was stirred at room temperature for 30 minutes. The reaction was diluted with EtOAc (100 mL), then washed with aqueous $NaHCO_3$ (3×50 mL) and with brine (50 mL), dried over $Na_2SO_4$, filtered, and concentrated in vacuo to yield a yellow powder (43 mg. 84% yield).

$^1$H NMR ($CDCl_3$, 300 HMz, mixture of rotomers) δ: 6.88–6.77 (m, 2H, aromatic), 6.75–6.65 (m, 1H, aromatic), 5.56 (br, s, 1H, NH), 4.07–3.83 (m, 3H), 3.89 (s, 3H, OMe), 3.82–3.68 (m, 2H), 3.67–3.52 (m, 2H), 3.46 (d, 1H, J=11.5 Hz), 3.19 (d, 1H, J=11.5 Hz), 1.46 (s, 9H), 1.16–1.05 (m, 3H), 0.74 (d, 3H). LRMS (Electrospray, positive): Da/e 353.151 (m+1).

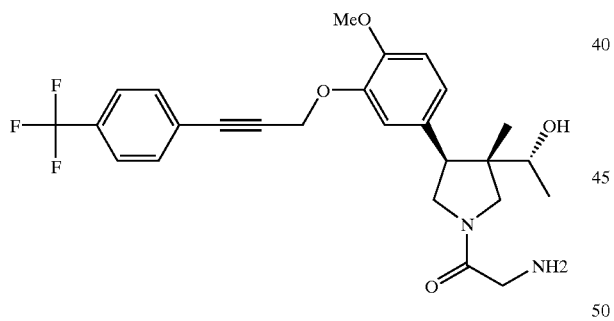

EXAMPLE 237

2-Amino-1-((3S,4S)-3-((R)-1-hydroxyethyl)-4-{4-methoxy-3-[3-(4-trifluoromethylphenyl)-prop-2-ynyloxy]phenyl}-3-methylpyrrolidin-1-yl)ethanone Prepared from Intermediate 93 by the $Cs_2CO_3$ method of Example 176 from the procedure of Example 109 to provide the product as an amber oil (12.7 mg, 4.1% yield).

$^1$H NMR ($CDCl_3$, 300 HMz, mixture of rotomers) δ: 7.55–7.4 (m, 4H, aromatic), 7.93 (s, 1H, aromatic), 6.85–6.7 (m, 2H, aromatic), 4.96 (s, 2H), 4.38 (br. s, 2H), 4.0–3.4 (m, 7H), 3.83 (d, 3H, OMe), 3.2 (dd, 1H), 1.0–0.88 (m, 3H), 0.65 (m, 3H). LRMS (Electrospray, positive): Da/e 491.20 (m+1).

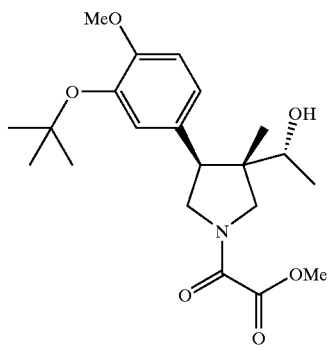

EXAMPLE 238

$R^1$=t-Bu; $R^3$=$COCO_2CH_3$

Methyl 2-{3-((1R)-1-hydroxyethyl)(3S,4S)-4-[3-(tert-butoxy)-4-methoxyphenyl]-3-methylpyrrolidi-nyl}-2-oxoacetate Prepared from Intermediate 73 via the Hunig's base coupling procedure of Intermediate 74 using methyl oxalyl chloride.

$^1$H NMR (400 HMz, $CDCl_3$, mixture of rotomers) δ: 6.93–6.81 (m, 3H), 4.01–3.44 (c, 12H), 1.32 (s, 9H), 1.16–1.12 (dd, 3H), 0.77–0.74 (d, 3H). LRMS (Electrospray, positive): Da/e 394.0 (m+1).

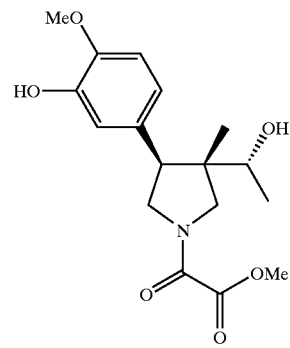

EXAMPLE 239

$R^1$=H; $R^3$=$COCO_2CH_3$

Methyl 2-[3-((1R)-1-hydroxyethyl)(3S,4S)-4-(3-hydroxy-4-methoxyphenyl)-3-methylpyrrolidinyl]-2-oxoacetate Prepared from Example 238 via the TFA deprotection method of Example 143.

$^1$H NMR (400 HMz, $CDCl_3$, mixture of rotomers) δ: 6.85–6.70 (m, 3H), 5.60–5.56 (br m, 1H), 4.00–3.46 (c, 12H), 1.17–1.13 (dd, 3H), 0.79–0.76 (d and d, 3H). LRMS (Electrospray, positive): Da/e 338.1 (m+1).

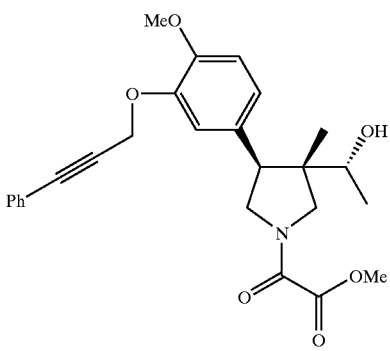

EXAMPLE 240

R¹=CH₂C≡CPh; R³=COCO₂CH₃

Methyl 2-{3-((1R)-1-hydroxyethyl)(3S,4S)-4-[4-methoxy-3-(3-phenylprop-2-ynyloxy)phenyl]-3-methylpyrrolidinyl}-2-oxoacetate Prepared from Example 239 via the Mitsunobu method of Example 144 using 3-phenyl-2-propyn-1-ol.

¹H NMR (400 HMz, CDCl₃, mixture of rotomers) δ: 7.41–7.26 (m, 5H), 7.07 (s, 1H), 6.86–6.85 (m, 2H) 5.05–4.95 (m, 2H), 4.06–3.43 (c, 12H), 0.98–0.91 (dd, 3H), 0.74–0.71 (d, 3H) LRMS (Electrospray, positive): Da/e 452.7 (m+1).

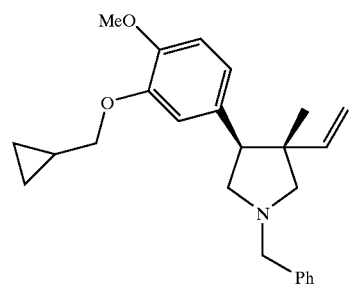

Intermediate 94

1-Benzyl-4-(3-cyclopropylmethoxy-4-methoxyphenyl)-3-methyl-3-vinylpyrrolidine

A round bottom flask equipped with a stir bar and rubber septum was charged with dry diethyl ether (10 mL) and methyltriphenylphosphonium bromide (1.88 g, 5.27 mmol) under a nitrogen atmosphere. Butyllithium (2.32 mL, 5.80 mmol, 2.5 M in hexanes) then was added by syringe resulting in an orange/yellow suspension that was stirred at room temperature for 3 hours. A Et₂O solution of Intermediate 65 (2.0 g, 5.27 mmol in 10 mL of ether) then was added, discharging the color immediately. After stirring at room temperature for two hours, the reaction mixture was quenched with saturated NH₄Cl solution, extracted with EtOAc (2×50 mL), dried (Na₂SO₄), and concentrated. Column chromatography (Biotage system, 40M cartridge, 25% EtOAc/hexane) afforded 850 mg (43%) of an orange oil).

¹H NMR (400 HMz, CDCl₃) δ: 7.42–7.23 (m, 5H), 6.80–6.68 (m, 3H), 6.05 (dd, 1H), 4.95 (dd, 1H), 4.87 (dd, 1H), 4.87 (dd, 1H), 3.86–3.79 (m, 6H), 3.71 (dd, 2H), 3.22 (t, 1H), 3.04–2.96 (m, 2H), 2.81 (d, 1H), 2.52 (d, 1H), 1.37–1.26 (m, 1H), 0.77 (s, 3H), 0.66–0.60 (m, 2H), 0.37–0.32 (m, 2H).

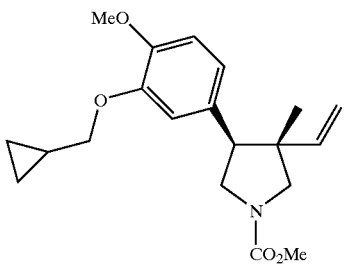

Intermediate 95

4-(3-Cyclopropylmethoxy-4-methoxyphenyl)-3-methyl-3-vinylpyrrolidine-1-carboxylic acid methyl ester A solution of Intermediate 94 (480 mg, 1.27 mmol) in 10 mL of acetonitrile was treated with methyl chloroformate (491 μL, 6.36 mmol), and the mixture was refluxed for 6 hours. The reaction mixture then was concentrated under reduced pressure, and the residue purified by chromatography (Biotage system, 40s cartridge, 10% EtOAc/hexane to 20% EtOAc/hexane) to give 237 mg of a yellow oil (54%).

¹H NMR (400 HMz, CDCl₃) δ: 6.81 (d, 1H), 6.72–6.67 (m, 2H), 5.87 (dd, 1H), 5.09 (d, 1H), 4.95 (dd, 1H), 3.85 (s, 3H), 3.84–3.68 (m, 7H), 3.52–3.32 (m, 2H), 3.14 (t, 1H), 1.35–1.25 (m, 1H), 0.35 (s, 3H), 0.66–0.60 (m, 2H), 0.37–0.32 (m, 2H).

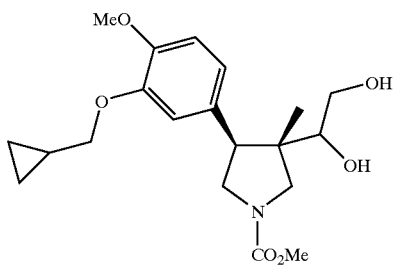

EXAMPLE 241

R¹=CH₂C₃H₅; R³=CO₂CH₃; R₄=H; R₅=CH₂OH; R₆=H 4-(3-Cyclopropylmethoxy-4-methoxyphenyl)-3-(1,2-dihydroxyethyl)-3-methylpyrrolidine-1-carboxylic acid methyl ester A reaction vial equipped with a stir vane was charged with Intermediate 95 (46 mg, 0.133 mmol), acetone (250 ul), water (500 ul), and N-methyl morpholine N-oxide (17.1 mg, 0.146 mmol). To this mixture was added osmium tetroxide in t-butanol (50 μ, 0.004 mmol, 2.5 wt % solution). The resulting mixture was stirred at room temperature for 24 hours. The reaction mixture then was diluted with 10% aqueous sodium thiosulfate solution (5 mL), filtered through GF/F filter paper. The filtrate was extracted with EtOAc (2×10 mL), dried (Na$_2$SO$_4$), and concentrated. Biotage purification (12S cartridge, 1:1:1 EtOAc/hexane/MeOH) afforded 18 mg of Example 241 (36%).

$^1$H NMR (400 HMz, CDCl$_3$) δ: 6.81 (d, 1H), 3.86 (s, 3H), 3.85–3.36 (c, 15H), 3.23 (dd, 1H), 1.35–1.27 (m, 1H), 0.75 (s, 3H), 0.66–0.59 (m, 2H), 0.38–0.32 (m, 2H). LRMS (Electrospray, positive): Da/e 380.2 (m+1).

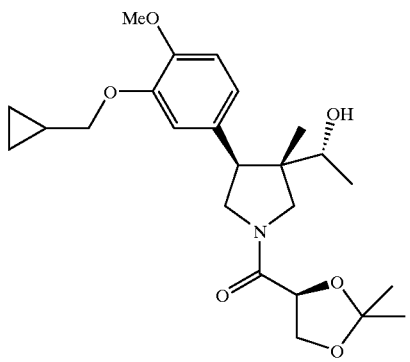

EXAMPLE 242

R$^1$=CH$_2$C$_3$H$_5$; R$^3$=(S)—COCH(CH$_2$OC(CH$_3$)(CH$_3$)O)

[4-(S)-(3-Cyclopropylmethoxy-4-methoxyphenyl)-3-(S)-(1-(R)-hydroxyethyl)-3-methylpyrrolidin-1-yl]-(2,2-dimethyl-[1,3]dioxolan-4-(S)-yl)methanone Intermediate 67 was acylated by the Hunig's base procedure of Intermediate 74 using 2,2-dimethyl-[1,3]dioxolane-4-(S)-carbonyl chloride to afford Example 242 (22%).

$^1$H NMR (CDCl$_3$, 400 HMz) δ: 6.83–6.78, m, 4H), 4.71–4.65 (m, 1H), 4.37–4.32 (m, 1H), 4.23–4.15 (m, 1H), 3.95–3.44 (m, 10H), 1.72–1.15 (m, 10H), 0.76 (s, 3H), 0.67–0.62 (m, 2H), 0.38–0.33 (m, 2H). LRMS (Electrospray, positive): Da/e 434.4 (m+1).

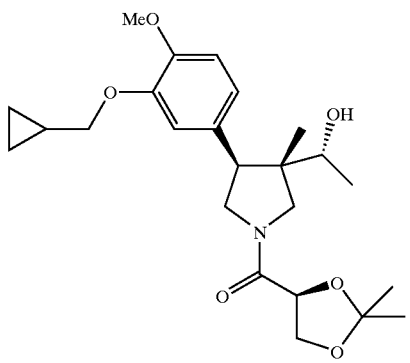

EXAMPLE 243

R$^1$=CH$_2$C$_3$H$_5$; R$^3$=(S)—COCH(OH)CH$_2$OH

1-[4-(S)-(3-Cyclopropylmethoxy-4-methoxyphenyl)-3-(S)-(1-(R)-hydroxyethyl)-3-methylpyrrolidin-1-yl]-2-(S)-3-dihydroxypropan-1-one Example 242 (9 mg, 20 μmol) was dissolved in a solution of acetic acid/water (3:1, 0.9 mL). The reaction mixture was stirred at room temperature for 72 hours. The solution was neutralized by pouring into an NaHCO$_3$ solution. The solution was concentrated to dryness, then the solids were extracted five times with CH$_2$Cl$_2$. The combined organics were dried over Na$_2$SO$_4$ and concentrated in vacuo (5.1 mg, 62%).

$^1$H NMR (CDCl$_3$, 400 HMz) δ: 6.84–6.76,m, 3H), 4.40–4.37 (m, 1H), 3.89–3.32 (m, 11H), 2.33–1.95 (m, 1H), 1.34–1.12 (m, 7H), 0.89–0.81 (m, 1H), 0.78–0.73 (m, 3H), 0.66–0.61 (m, 2H), 0.37–0.32 (m, 2H). LRMS (Electrospray, positive): Da/e 394.0 (m+1).

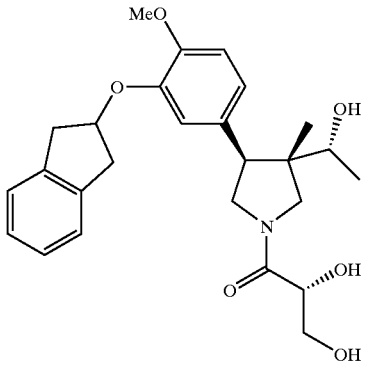

EXAMPLE 244

R$^1$=2-indanyl; R$^3$=(R)—COCH(OH)CH$_2$OH (R)-2,3-Dihydroxy-1-{(3S,4S)-3-((R)-1-hydroxyethyl)-4-[3-(indan-2-ylmethoxy)-4-methoxyphenyl]-3-methylpyrrolidin-1-yl}propan-1-one Prepared from Intermediate 96 by the procedure described in Example 75 and deprotected as in Example 243.

$^1$H NMR (CDCl$_3$, 300 HMz, mixture of rotomers) δ: 7.26–7.16 (m, 4H, aromatic), 6.83–6.82 (br. s, 3H, aromatic), 5.19–5.15 (m, 1H), 4.45–4.32 (m, 1H), 4.10–3.50 (m, 8H), 3.80 (d, 3H, OMe), 3.45–3.12 (m, 5H), 1.27–1.25 (m, 1H), 1.20–1.15 (m, 3H), 0.79–0.77 (m, 3H). LRMS (Electrospray, positive): Da/e 470.58 (m+1)

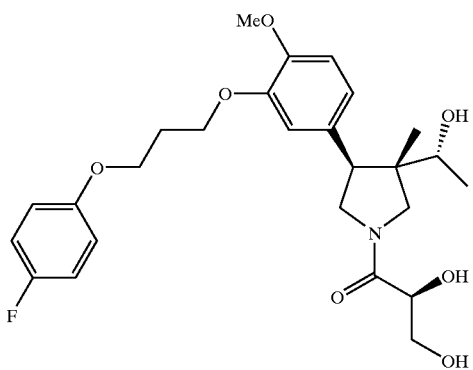

EXAMPLE 245

R[1]=4-F-Ph—OCH$_2$CH$_2$CH$_2$; R[3]=(R)—COCH(OH)CH$_2$OH)

(S)-1-[(3S,4S)-4-(3-[3-(4-Fluorophenoxy)propoxy]-4-methoxyphenyl}-3-((R)-1-hydroxyethyl)-3-methylpyrrolidin-1-yl]-2,3-dihydroxypropan-1-one Prepared by the procedure set forth in Example 243.
$^1$H NMR (CDCl$_3$, 300 HMz, mixture of rotomers) δ: 6.99–6.92 (m, 2H, aromatic), 6.87–6.79 (m, 5H, aromatic), 4.39 (s, 1H), 4.22–4.12 (m, 4H), 4.0 (d, 1H), 3.89–3.56 (m, 7H), 3.83 (s, 3H, OMe), 3.4–3.32 (dd, 1H), 2.32–2.24 (m, 2H) 1.17–1.12 (m, 3H), 0.74 (d, 3H). LRMS (Electrospray, positive): Da/e 492.25 (m+1).

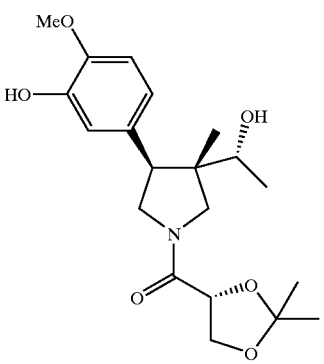

Intermediate 96

1-((R)-2,2-Dimethyl-1,3-dioxolan-4-yl)-1-[(3S,4S)-3-((R)-1-hydroxyethyl)-4-(3-hydroxy-4-methoxyphenyl)-3-methylpyrrolidin-1-yl)methanone A round bottom flask equipped with a stir bar and rubber septum was charged with 5-[4-(1-hydroxy-ethyl)-4-methylpyrrolidin-3-yl)-2-methoxyphenol (2.4 g, 9.55 mmol), dry CH$_2$Cl$_2$ (50 mls), and DIEA (3.49 mls, 20.1 mmol) under a nitrogen atmosphere. The mixture was chilled to 0° C. and (S)-2.2-dimethyl-[1,3]dioxolane-4-carbonyl chloride (3.14 g, 19.1 mmol) in 15 ml of CH$_2$Cl$_2$ was added dropwise by syringe. The reaction mixture was allowed to gradually warm to room temperature over a 16-hour period. The mixture then was diluted with 50 ml of CH$_2$Cl$_2$, washed with 1N HCl (2×50 ml), saturated aqueous NaHCO$_3$ (1×50 ml), dried over Na$_2$SO$_4$, and concentrated to 3.9 g of a tan foam. The material was taken up in 100 ml CH$_3$OH and chilled to 0° C. Three equivalents of aqueous 1N LiOH then were added (29 ml, 29.0 mmol), the mixture was stirred at 0° C. for 2 hours, then warmed to room temperature for 2 hours. The reaction mixture next was concentrated under reduced pressure with the bath temperature at 30° C. to remove CH$_3$OH. The remaining aqueous material was neutralized with saturated NH$_4$Cl to pH 7 and extracted with EtOAc (2×100 ml). The extracts were dried over Na$_2$SO$_4$ and concentrated to 2.74 g of a tan foam (76%).

$^1$H NMR (CDCl$_3$, 400 HMz, mixture of rotomers) δ: 6.90–6.70 (m, 3H), 5.66 (br, s, 1H), 4.68 (t, 1H), 4.34 (t, 1H), 4.23–4.09 (m, 6H), 3.89 (s, 3H), 3.94–3.42 (m, 5H), 1.49–1.37 (m, 6H), 1.17 (d, 3H), 0.76 (s, 3H). LRMS (Electrospray, positive): Da/e 378.3 (m–1).

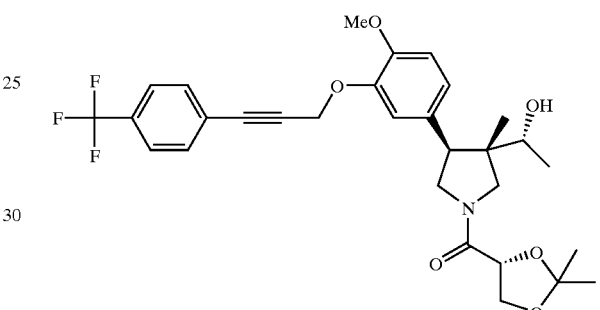

EXAMPLE 246

R[1]=F$_3$C-Ph-C≡CCH$_2$; R[3]=CO-2,2-dimethyl-1,3-dioxolan-4-yl 1-((R)-2,2-Dimethyl-1,3-dioxolan-4-yl)-1-((3S,4S)-3-((R)-1-hydroxyethyl)-4-{4-methoxy-3-[3-(4-trifluoro-methylphenyl)prop-2-ynyloxy]phenyl}-3-methylpyrrolidin-1-yl)methanone To a flask containing anhydrous Cs$_2$CO$_3$ (67 mg, 0.206 mmol, 1.1 eq) under a nitrogen blanket was added a solution of Intermediate 96 (71 mg, 0.187 mmol, 1.0 eq) in anhydrous acetone (1 mL). Intermediate 92 (52.1 mg, 0.187 mmol, 1.0 eq) was added to the mixture via syringe. The reaction mixture then was heated and stirred at 65° C. for 4 hours. The reaction mixture was cooled to room temperature and diluted with water (50 mL). The aqueous solution was extracted with EtOAc (3×30 mL), and the combined organics were washed with brine (50 mL), then dried over Na$_2$SO$_4$, filtered, and concentrated in vacuo to yield a white foamy product (104 mg).

$^1$H NMR (CDCl$_3$, 300 HMz, mixture of rotomers) δ: 7.5–7.35 (m, 4H, aromatic), 6.96 (d, 1H, aromatic), 6.85–6.75 (m, 2H, aromatic), 4.92 (d, 2H, CH$_2$), 4.65–4.50 (m, 1H), 4.35–4.20 (m, 1H), 4.15–4.00 (m, 1H), 3.85–3.40 (m, 5H), 3.8 (d, 3H, OMe), 3.35–3.30 (dd, 1H), 1.45–1.25 (2d, 6H, Me), 1.0–0.9(m, 3H), 0.63 (d, 3H). LRMS (Electrospray, positive): Da/e 562.25 (m+1).

EXAMPLE 247

R$^1$=F$_3$C-Ph-C≡—CCH$_2$; R$^3$=CO—CH(OH)CH$_2$OH

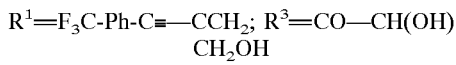

(R)-2,3-Dihydroxy-1-((3S,4S)-3-((R)-1-hydroxyethyl)-4-{4-methoxy-3-[3-(4-trifluoromethylphenyl)prop-2-ynyloxy]phenyl}-3-methylpyrrolidin-1-yl)propan-1-one To a reaction vial containing Example 246 (104 mg, 0.185 mmol) was added acetic acid (3.0 mL) and water (1.0 mL). The vial then was sealed, heated to 50° C., and stirred for 2 hours. The reaction mixture was concentrated in vacuo and purified by reversed-phase HPLC on a C18 column (Luna 10: C18, 250×10 mm). Gradient elution of 50–100% acetonitrile-water (0.05% TFA) yielded product as amber oil (27.8 mg, 28.5% yield).

$^1$H NMR (CDCl$_3$, 300 HMz, mixture of rotomers) δ: 7.6–7.45 (m, 4H, aromatic), 7.69 (d, 1H, aromatic), 6.9–6.82 (m, 2H, aromatic), 5.0 (m, 2H), 4.4–4.32 (m, 1H), 4.1–3.2 (m, 7H), 3.89 (d, 3H, OMe), 1.05 (s, 3H), 0.72 (m, 3H). LRMS (Electrospray, positive): Da/e 522.15 (m+1).

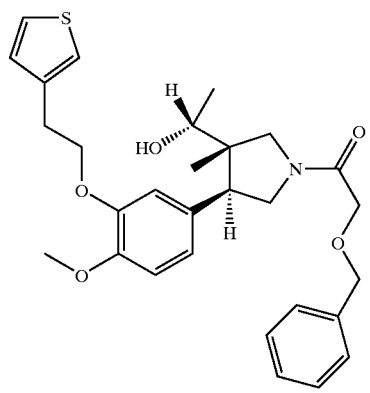

EXAMPLE 248

R$^1$=3-thienyl-CH$_2$CH$_2$; R$^3$=COCH$_2$OCH$_2$Ph

2-Benzyloxy-1-{(3S,4S)-3-((R)-1-hydroxyethyl)-4-[4-methoxy-3-(2-thiophen-3-yl-ethoxy)phenyl]-3-methylpyrrolidin-1-yl}ethanone Prepared by alkylation of Example 143 by the K$_2$CO$_3$ procedure of Example 7 using 2-(3-thienyl)ethyl bromide.

$^1$H NMR data δ: 7.27–7.38 (m, 6H); 7.05–7.07 (m, 1H); 7.12–7.13 (m, 1H); 6.74–6.84 (m, 3H); 6.05 (s, 2H); 4.15–4.22 (m, 4H); 3.44–3.93 (m, 6.5H); 3.86 (s, 3H); 3.14–3.24 (m, 2.5H); 1.13 (dd, 3H); 0.72 (s, 3H).

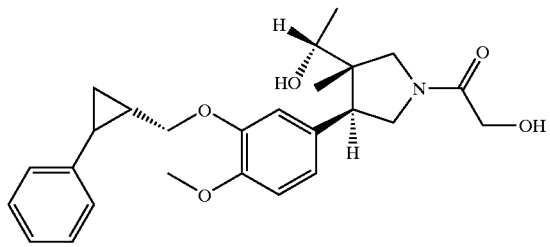

EXAMPLE 249

R$^1$=Ph(cyclo-C$_3$H$_4$)CH$_2$; R$^3$=COCH$_2$OH

2-Hydroxy-1-{(3S,4S)-3-((R)-1-hydroxyethyl)-4-[4-methoxy-3-((R)-2-phenylcyclopropylmethoxy)phenyl]-3-methylpyrrolidin-1-yl}ethanone Prepared by alkylation of Example 143 by the Mitsunobu procedure of Example 144 using 2-phenylcyclopropanol and removal of the benzyl group by the debenzylation procedure of Intermediate 31.

$^1$H NMR data δ: 7.17–7.30 (m, 5H); 6.72–6.85 (m, 3H); 4.00–4.14 (m, 2H); 3.49–3.98 (m, 8.5H); 3.86 (s, 3H); 3.05 (d, 0.5H); 2.86–2.93 (m, 1H); 2.51–2.60 (m, 1H); 2.27–2.34 (m, 1H); 1.02–1.05 (dd, 3H); 0.74 (sd, 3H).

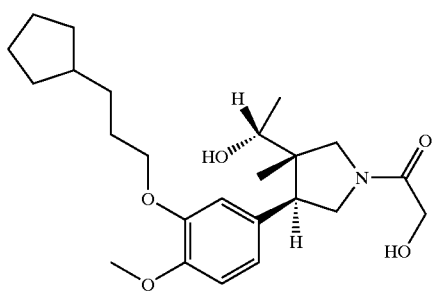

EXAMPLE 250

R$^1$=C$_5$H$_9$CH$_2$CH$_2$CH$_2$; R$^3$=COCH$_2$OH

1-[(3S,4S)-4-[3-(3-Cyclopentylpropoxy)-4-methoxyphenyl]-3-((R)-1-hydroxyethyl)-3-methylpyrrolidin-1-yl]-2-hydroxyethanone Prepared from Example 143 by the Mitsunobu procedure of Example 144 using 3-cyclopentylpropan-1-ol and removal of the benzyl group by the debenzylation procedure of Intermediate 31.

$^1$H NMR data δ: 6.75–6.83 (m, 3H); 4.12–4.15 (m, 2H); 3.96–4.01 (m, 2.5H); 3.86 (s, 3H); 3.79–3.86 (m, 1H); 3.59–3.70 (m, 4H); 3.06 (d, 0.5H); 1.75–1.88 (m, 5H); 1.44–1.61 (m, 6H); 1.16 (t, 5H); 0.77 (sd, 3H).

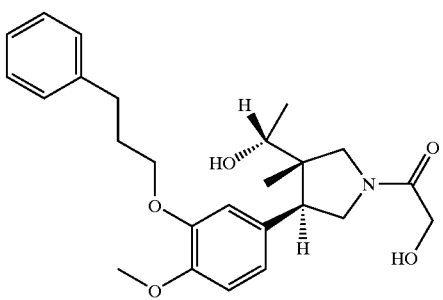

EXAMPLE 251

R[1]=PhCH$_2$CH$_2$CH$_2$; R[3]=COCH$_2$OH

2-Hydroxy-1-{(3S,4S)-3-((R)-1-hydroxyethyl)-4-[4-methoxy-3-(3-phenylpropoxy)phenyl]-3-methylpyrrolidin-1-yl}ethanone Prepared from Example 143 by the K$_2$CO$_3$ procedure of Example 7 using 3-phenylpropyl chloride and removal of the benzyl group by the debenzylation procedure by Intermediate 31.

$^1$H NMR data δ: 7.16–7.31 (m, 5H); 6.74–6.85 (m, 3H); 4.13–4.15 (m, 2H); 3.94–4.04 (m, 2H); 3.86 (s, 3H); 3.76–3.83 (m, 1H); 3.47–3.70 (m, 4H); 3.04–3.07 (m, 3H); 2.80–2.85 (t, 2H); 2.10–2.20 (quint, 2H); 1.14 (t, 3H); 0.74 (s, 3H).

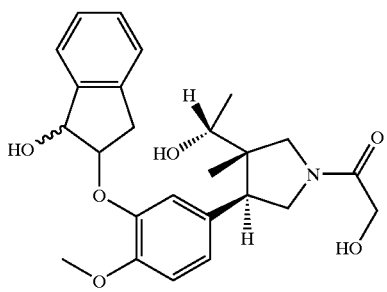

EXAMPLE 252

R[1]=1-hydroxyindan-2-yl; R[3]=COCH$_2$OH

2-Hydroxy-1-{(3S,4S)-3-((R)-1-hydroxyethyl)-4-[3-(1-hydroxyindan-2-yloxy)-4-methoxyphenyl]-3-methylpyrrolidin-1-yl}ethanone Prepared from Example 143 by the K$_2$CO$_3$ procedure of Example 7 using indene oxide and removal of the benzyl group by the debenzylation procedure of Intermediate 31.

$^1$H NMR data δ: 7.48–7.51 (m, 1H); 7.24–7.32 (m, 3H); 6.85–6.96 (m, 3H); 5.11–5.14 (m, 1H); 4.84–4.89 (m, 1H); 3.98–4.15 (m, 3H); 3.84–3.86 (m, 1H); 3.83 (s, 3H); 3.50–3.78 (m, 4.5H); 3.16–3.32 (m, 2H); 3.06 (d, 0.5H); 1.15–1.20 (m, 3H); 0.77 (s, 3H).

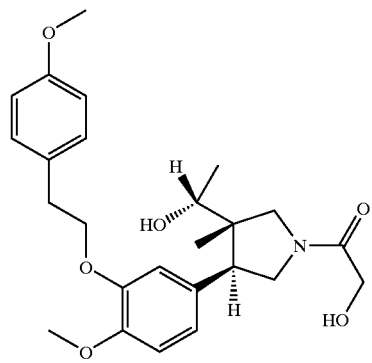

EXAMPLE 253

R[1]=4-CH$_3$OPhCH$_2$CH$_2$; R[3]=COCH$_2$OH

2-Hydroxy-1-((3S,4S)-3-((R)-1-hydroxyethyl)-4-{4-methoxy-3-[2-(4-methoxyphenyl)ethoxy]phenyl}-3-methylpyrrolidin-1-yl)ethanone Prepared from Example 143 by the K$_2$CO$_3$ procedure of Example 7 using 1-(2-chloroethyl)-4-methoxybenzene and removal of the benzyl group by the debenzylation procedure of Intermediate 31.

$^1$H NMR data δ: 7.20–7.23 (d, 2H); 6.74–6.88 (m, 5H); 4.10–4.18 (m, 4H); 3.72–3.91 (m, 2H); 3.86 (s, 3H); 3.80 (s, 3H); 3.48–3.64 (m, 4H); 3.02–3.11 (m, 2H); 1.12–1.17 (m, 3H); 0.74 (s, 3H).

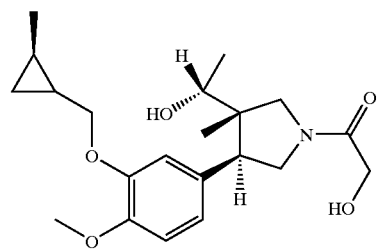

EXAMPLE 254

R[1]=CH$_3$(cyclo-C$_3$H$_4$)CH$_2$; R[3]=COCH$_2$OH

2-Hydroxy-1-{(3S,4S)-3-((R)-1-hydroxyethyl)-4-[4-methoxy-3-((R)-2-methylcyclopropylmethoxy)phenyl]-3-methylpyrrolidin-1-yl}ethanone Prepared from Example 143 by the K$_2$CO$_3$ procedure of Example 7 using 1-(2-chloroethyl)-4-methoxybenzene and removal of the benzyl group by the debenzylation procedure of Intermediate 31.

$^1$H NMR data δ: 6.77–6.84 (m, 3H); 4.15–4.18 (m, 2H); 3.78–3.99 (m, 4H); 3.86 (s, 3H); 3.49–3.71 (m, 3.5H); 3.08 (d, 0.5H); 1.14–1.19 (m, 3H); 1.07 (sd, 3H); 0.92–1.03 (m, 1H); 0.76–0.77 (m, 4H); 0.50–0.52 (m, 1H); 0.37–0.41 (m, 1H).

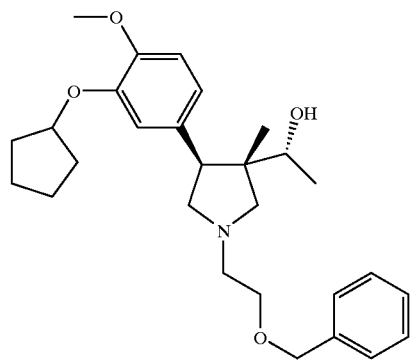

EXAMPLE 255

1-(R)-[1-(2-Benzyloxyethyl)-4-(S)-(3-cyclopenty-loxy-4-methoxyphenyl)-3-(S)-methylpyrrolidin-3-yl]-ethanol Intermediate 68 (86.4 mg, 0.27 mmol) was dissolved in 1,2-dichloroethane (1 mL) and the solution was treated with benzyloxyacetaldehyde (38 μL, 0.27 mmol), followed by sodium triacetoxyborohydride (81 mg, 0.38 mmol). The reaction was stirred for 18 hours at room temperature. Additional sodium triacetoxyborohydride (40 mg, 0.19 mmol) was added and stirring continued for 8 hours. The reaction mixture was diluted with 1.0 M NaOH (0.5 mL) and stirred vigorously for 15 minutes. The layers were separated, the aqueous phase was washed with $CH_2Cl_2$, and the organic layers were combined. After washing with 6% $NaHCO_3$, the organics were dried with $Na_2SO_4$, then concentrated in vacuo. The crude material (129 mg) was chromatographed on silica gel with $CHCl_3$/95% ethanol/conc. $NH_4OH$ (170: 15:1), providing Example 255 (27 mg, 22%).

$^1$H NMR (CDCl$_3$, 400 HMz) δ: 7.36–7.26 (m, 5H), 6.81–6.73 (m, 3H), 4.79–4.73 (m, 1H), 4.54 (s, 1H), 3.82 (s, 3H), 3.71–3.54 (m, 4H), 3.40–3.35 (m, 1H), 3.24–3.21 (m, 1H), 2.80–2.67 (m, 2H), 2.63–2.56 (m, 1H), 2.16–2.09 (m, 1H), 1.95–1.88 (m, 8H), 1.65–1.57 (m, 2H), 1.22–1.10 (m, 3H), 0.49 (m, 3H). LRMS (Electrospray, positive): 454.5 Da/e (m+1).

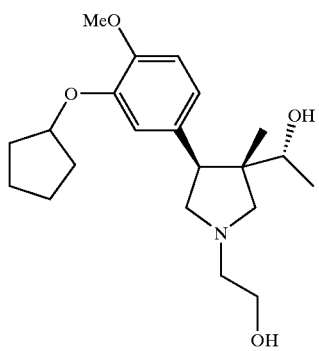

EXAMPLE 256

1-(R)-[4-(S)-(3-Cyclopentyloxy-4-methoxyphenyl)-1-(2-hydroxyethyl)-3-(S)-methylpyrrolidin-3-yl]ethanol Example 255 (25 mg, 55 mmol) was subjected to the debenzylation procedure of Intermediate 31 to afford Example 256 (7.4 mg, 28%) as the TFA salt after HPLC purification.

$^1$H NMR (CDCl$_3$, 400 HMz) δ: 6.84–6.65 (m, 3H), 5.40–4.90 (brd, 2H), 4.74 (brd s, 1H), 4.26–3.21 (m, 11H), 1.97–1.73 (m, 6H), 1.66–1.56 (m, 3H), 1.33–0.77 (m, 4H), 0.69 (s, 3H). LRMS (Electrospray, positive): 364.4 Da/e (m+1).

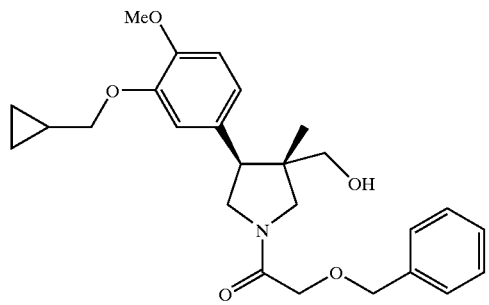

EXAMPLE 257

2-Benzyloxy-1-[4-(S)-(3-cyclopropylmethoxy-4-methoxyphenyl)-3-(S)-hydroxymethyl-3-methylpyrrolidin-1-yl]ethanone

[4-(S)-(3-Cyclopropylmethoxy-4-methoxyphenyl)-3-(S)-methylpyrrolidin-3-yl]methanol (100 mg, 0.34 mmol) was dissolved in $CH_2C_2$ (1.7 mL), and the solution was cooled to 0° C. DIEA (144 μL, 0.82 mmol) was added, followed by benzyloxyacetyl chloride (114 μL, 0.72 mmol). The reaction was allowed to warm to room temperature slowly and stirred for 18 hours. Water was added (0.25 mL) and the reaction was stirred for 1.5 hours. $CH_2C_2$ was added and the mixture was washed once with water, twice with 1N HCl, once with water, twice with 6% $NaHCO_3$, then dried over $Na_2SO_4$ and concentrated in vacuo. The residue was dissolved in THF (1 mL) and cooled to 0° C. A solution of LiOH in water (1.36M, 1 mL, 1.36 mmol) was added and the hydrolysis was allowed to proceed at 0° C. for 4 hours. The reaction mixture was quenched with saturated $NH_4Cl$, and the THF was removed by concentration in vacuo. The residue was resuspended in $CH_2C_2$, and washed twice with 6%. $NaHCO_3$, dried over $Na_2SO_4$ and concentrated in vacuo.

$^1$H NMR (CDCl$_3$, 400 HMz) δ: 7.40–7.28 (m, 5H), 6.83–6.79 (m, 1H), 6.73–6.66 (m, 2H), 4.66 (s, 2H), 4.16–4.13 (m, 2H), 3.86 (s, 3H), 3.83–3.78 (m, 3H), 3.63–3.26 (brd m, 4H), 3.06–3.00 (m, 1H), 2.50–2.45 (brd m, 1H), 1.34–1.12 (m, 1H), 1.03–0.99 (m, 2H), 0.73 (s, 3H), 0.66–0.61 (m, 2H), 0.36–0.32 (m, 2H) LRMS (Electrospray, positive): Da/e 440.3 (m+1).

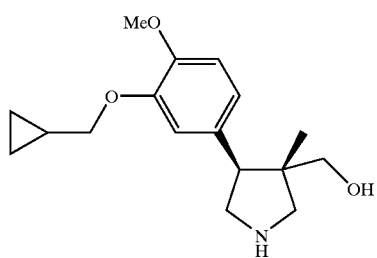

Intermediate 97

[4-(S)-(3-Cyclopropylmethoxy-4-methoxyphenyl)-3-(S)-methylpyrrolidin-3-yl]methanol

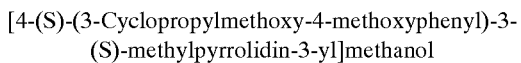

Intermediate 65 (0.99 g, 2.6 mmol) was dissolved in ethanol (95%, 10 mL) and the solution was treated with Pearlman's catalyst (20% Pd(OH)$_2$ on carbon, 250 mg). The mixture was hydrogenated at 1 atmosphere of H$_2$ for 16 hours. Additional catalyst (250 mg) was added and the reaction continued for an additional 24 hours. The catalyst was removed by filtration and the reaction mixture was concentrated in vacuo (0.68 g, 89%).

$^1$H NMR (CDCl$_3$, 400 HMz) δ: 6.84–6.73 (m, 3H), 3.87–3.83 (m, 4H), 3.59–3.47 (m, 3H), 3.30–3.20 (m, 3H), 2.85 (d, J=10.6, 1H), 2.35–2.12 (brd m, 1H), 1.35–1.27 (m, 1H), 0.64–0.60 (m, 4H), 0.37–0.31 (m, 2H), 0.36–0.32 (m, 2H). LRMS (Electrospray, positive): Da/e 377.3 (m+1).

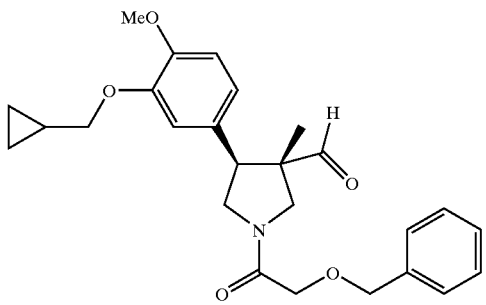

EXAMPLE 258

1-(2-Benzyloxyacetyl)-4-(S)-(3-cyclopropylmethoxy-4-methoxyphenyl)-3-(S)-methylpyrrolidine-3-carbaldehyde

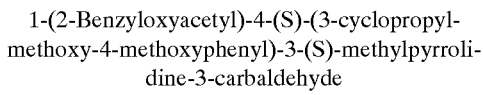

Oxalyl chloride (2.0 M in CH$_2$Cl$_2$, 0.175 mL, 0.35 mmol) was added to CH$_2$Cl$_2$ (0.52 mL). The resulting solution was cooled to −60° C. A solution of DMSO (47 mL, 0.66 mmol) dissolved in CH$_2$Cl$_2$ (0.18 mL) then was added dropwise. The solution was stirred for 5 minutes and Example 257 (dissolved in 1.0 mL CH$_2$Cl$_2$) added to a Swern oxidation mixture. After the reaction had been stirred for 30 minutes at −60° C., Et$_3$N (0.25 mL) was added and the reaction mixture was warmed to room temperature. After 30 minutes, water was added and the solution was stirred vigorously for 15 minutes. The layers were separated, the aqueous phase washed once with CH$_2$Cl$_2$. The combined organic layers were washed with saturated NaCl, dried over Na$_2$SO$_4$, and concentrated in vacuo. The crude material was chromatographed on SiO$_2$ using EtOAc/hexanes (2:1), (76 mg, 50%).

$^1$H NMR (CDCl$_3$, 400 HMz) δ: 9.62–9.57 (m, 1H), 7.41–7.30 (m, 5H), 6.84–6.78 (m, 1H), 6.68–6.56 (m, 2H), 4.68–4.63 (m, 2H), 4.20–4.10 (m, 2H), 4.05–3.32 (m, 5H), 3.87 (s, 3H), 1.57–1.55 (m, 2H), 1.33–1.24 (m, 1H), 0.92–0.88 (m, 3H), 0.67–0.60 (m, 2H), 0.37–0.31 (m, 2H).

EXAMPLE 259

1-((R)-2,2-Dimethyl-1,3-dioxolan-4-yl)-1-[(3S,4S)-3-((R)-1-hydroxyethyl)-4-(3-hydroxy-4-methoxyphenyl)-3-methylpyrrolidin-1-yl]methanone

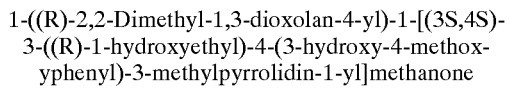

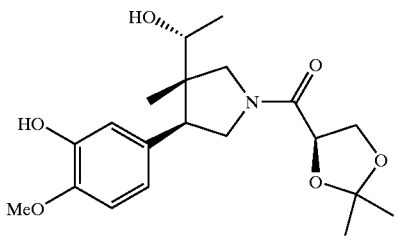

To a stirred solution of Intermediate 70 (73.5 mg, 0.293 mmol, 1.0 eq) in CH$_2$Cl$_2$ (3 mL) at room temperature under a nitrogen blanket was added Et$_3$N (65.2 mg, 0.645 mmol), followed by 2,2-dimethyl-1,3-dioxolane-(4R)-carbonyl chloride (53.2 mg, 0.322 mmol). The reaction was stirred at room temperature overnight. The reaction mixture then was poured into 50 mL EtOAc, washed with brine, dried with Na$_2$SO$_4$, and concentrated in vacuo to give a foamy product (94 mg, 85% yield). The crude product was hydrolyzed by LiOH via Intermediate 5 to yield Example 259.

$^1$H NMR (CDCl$_3$, 300 HMz) δ: 6.97–6.58 (m, 3H, aromatic), 4.68 (t, 1H, J=6.4 Hz), 4.44–4.34 (m, 1H), 4.24–3.95 (m, 1H), 3.94–3.50 (m, 5H), 3.87 (d, 3H, OMe), 3.42 (d, 1H, J=12.4 Hz), 3.35 (d, 1H, J=12.4 Hz), 1.4 (m, 6H), 1.15 (m, 3H), 0.75 (m, 3H).

EXAMPLE 260

1-((R)-2,2-Dimethyl-1,3-dioxolan-4-yl-)-1-{(3S,4S)-3-((R)-1-hydroxyethyl)-4-[4-methoxy-3-(3-phenyl-prop-2-ynyloxy)phenyl]-3-methylpyrrolidin-1-yl}methanone

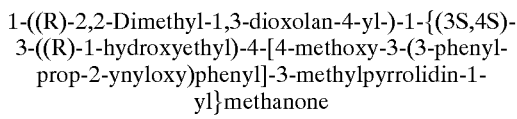

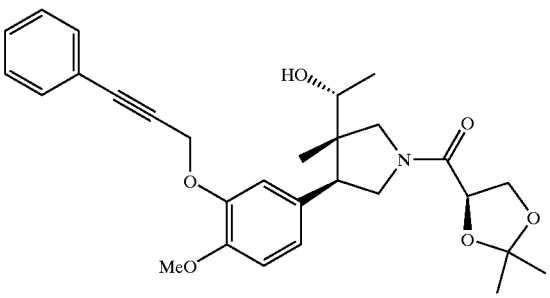

Prepared from Example 259 (126 mg, 0.332 mmol, 1.0 eq) and Intermediate 90 (69.8 mg, 0.332 mmol, 1.0 eq) by the method of Example 176 to yield a white foamy product (160 mg).

$^1$H NMR (CDCl$_3$, 300 HMz, mixture of rotamers) δ: 7.42–7.25 (m, 5H, aromatic), 7.08 (d, 1H, aromatic), 6.86 (d, 2H, aromatic), 5.0 (d, 2H, CH$_2$), 4.72–4.60 (m, 1H), 4.45–4.32 (m, 1H), 4.22–4.10 (m, 1H), 3.95–3.70 (m, 3H), 3.89 (s, 3H, OMe), 3.70–3.45 (m, 2H), 3.44–3.29 (m, 1H), 1.5–1.38 (2d, 6H, Me), 1.02–0.75–0.65(m, 3H), 0.63 (d, 3H). LRMS (Electrospray, positive): Da/e 494.55 (m+1).

EXAMPLE 261

(R)-2,3-Dihydroxy-1-{(3S,4S)-3-((R)-1-hydroxyethyl)-4-[4-methoxy-3-(3-phenylprop-2-ynyloxy)phenyl]-3-methylpyrrolidin-1-yl}propan-1-one

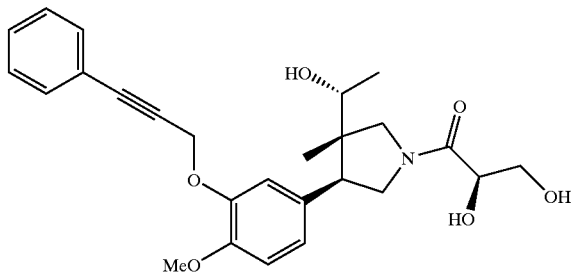

To a reaction vial containing Example 260 (160 mg, 0.323 mmol) was added acetic acid (3.0 mL) and water (1.0 mL). The vial was sealed, heated to 50° C., and stirred for 2 hours. The reaction was concentrated in vacuo and purified by reversed-phase HPLC on a C18 column (Luna 10μ, C18, 250×10 mm). Gradient elution of 50–100% acetonitrile-water (0.05% TFA) provided Example 261 as white foamy solid (52.2 mg, 35.6% yield).

$^1$H NMR (CDCl$_3$, 300 HMz, mixture of rotamers) δ: 7.5–7.21 (m, 5H, aromatic), 7.05 (m, 1H, aromatic), 6.9–6.75 (m, 2H, aromatic), 5.0 (d, 2H), 4.31 (s, 1H), 4.01–3.2 (m, 9H), 3.88 (s, 3H, OMe), 1.01–0.9 (m, 3H), 0.7 (s, 3H). LRMS (Electrospray, positive): Da/e 454.20 (m+1).

EXAMPLE 262

1-((S)-2,2-Dimethyl-1,3-dioxolan-4-yl)-1-[(3S,4S)-3-((R)-1-hydroxyethyl)-4-(3-hydroxy-4-methoxyphenyl)-3-methylpyrrolidin-1-yl]methanone

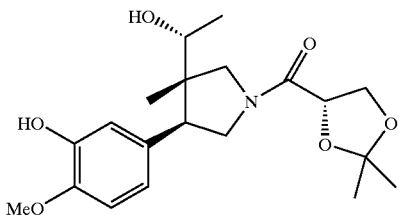

To a stirred solution of Intermediate 70 (73.5 mg, 0.293 mmol, 1.0 eq) in CH$_2$Cl$_2$ (3 mL) at room temperature under a nitrogen blanket was added Et$_3$N (65.2 mg, 0.645 mmol), followed by 2,2-dimethyl-1,3-dioxolane-(4S)-carbonyl chloride (53.2 mg, 0.322 mmol). The reaction was stirred at room temperature overnight, then poured into 50 mL EtoAc, washed with brine, dried with Na$_2$SO$_4$, and concentrated in vacuo. to give a foamy product (94 mg, 85% yield). The crude product was hydrolyzed by LiOH via Intermediate 5 to yield Example 262.

$^1$H NMR (CDCl$_3$, 300 HMz) δ: 6.93–6.65 (m, 3H, aromatic), 5.68 (s, 1H), 4.67 (m, 1H), 4.34 (m, 1H), 4.21 (m, 1H), 3.94–3.40 (m, 5H), 3.89 (s, 3H, OMe), 1.4 (m, 6H), 1.16 (m, 3H), 0.76 (m, 3H).

EXAMPLE 263

1-((S)-2,2-Dimethyl-1,3-dioxolan-4-yl)-1-{(3S,4S)-3-((R)-1-hydroxyethyl)-4-[4-methoxy-3-(3-phenylprop-2-ynyloxy)phenyl]-3-methylpyrrolidin-1-yl}methanone

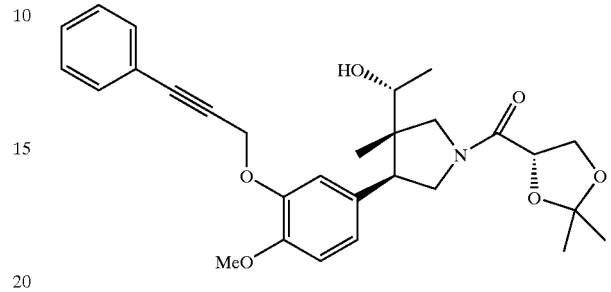

Prepared from Example 262 (126 mg, 0.332 mmol, 1.0 eq) and Intermediate 90 (69.8 mg, 0.332 mmol, 1.0 eq) by the method of Example 176 to yield a white foamy product (160 mg,).

$^1$H NMR (CDCl$_3$, 300 HMz, mixture of rotamers) δ: 7.52–7.15 (m, 5H, aromatic), 7.08 (d, 1H, aromatic), 6.86 (d, 2H, aromatic), 5.98 (m, 2H, CH$_2$), 4.64 (m, 1H), 4.35–4.32 (m, 1H), 4.22–4.10 (m, 1H), 3.97–3.36 (m, 5H), 3.89 (s, 3H, OMe), 1.5–1.38 (2d, 6H, Me), 1.02–0.75 (m, 3H), 0.74 (s, 3H). LRMS (Electrospray, positive): Da/e 494.55 (m+1).

EXAMPLE 264

(S)-2,3-Dihydroxy-1-{(3S,4S)-3-((R)-1-hydroxyethyl)-4-[4-methoxy-3-(3-phenylprop-2-ynyloxy)phenyl]-3-methylpyrrolidin-1-yl}propan-1-one

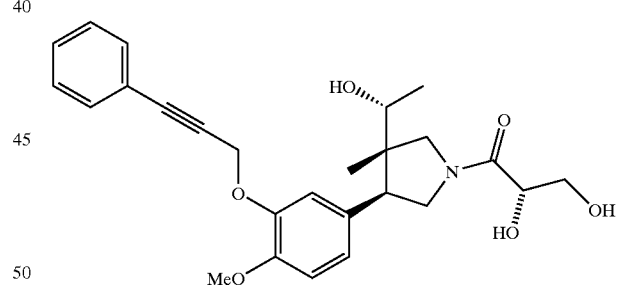

To a reaction vial containing Example 263 (160 mg, 0.323 mmol) was added acetic acid (3.0 mL) and water (1.0 mL). The vial was sealed, heated to 50° C. and stirred for 2 hours. The reaction was concentrated in vacuo and purified by reversed-phase HPLC on a C18 column (Luna 10μ, C18, 250×10 mm). Gradient elution of 50–100% acetonitrile-water (0.05% TFA) gave product as white foamy solid (52.2 mg, 35.6% yield).

$^1$H NMR (CDCl$_3$, 300 HMz, mixture of rotamers) δ: 7.44–7.18 (m, 5H, aromatic), 7.08 (s, 1H, aromatic), 6.86 (s, 2H, aromatic), 4.6 (s, 2H, CH$_2$), 4.4–4.3 (m, 1H), 4.01–4.62 (m, 7H), 3.89 (s, 3H, OMe), 3.59–3.46 (m, 1H), 3.32–3.29 (m, 1H), 2.4 (m, 1H), 0.95 (m, 3H), 0.72 (d, 3H). LRMS (Electrospray, positive): Da/e 454.20 (m+1). [α]$_D$=14.6° (c=1.00, EtOH).

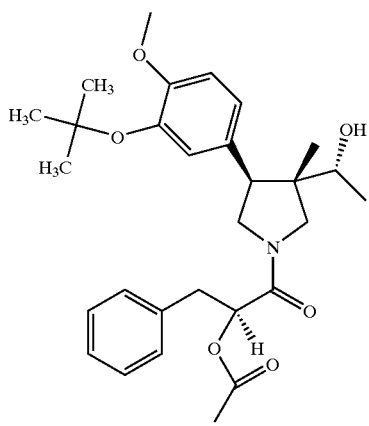

EXAMPLE 265

R₁=t-Bu; R₃=(S)—COCH(OAc)CH₂Ph

Prepared from Intermediate 73 by acylation with acetic acid (S)-1-chlorocarbonyl-2-phenylethyl ester according to procedure of F. Babudri et al., *Tetrahedron*, 8, 2431–2440 (1999).

LRMS (Electrospray, positive): m/z 498 (m+1).

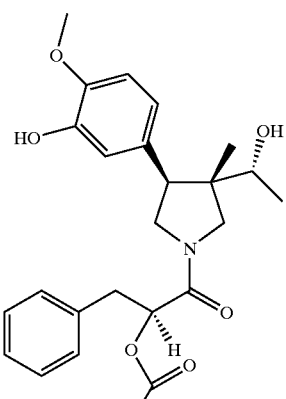

EXAMPLE 266

R₁=H; R₃=(S)—COCH(OAc)CH₂Ph

Prepared from Example 265 by the TFA method of Example 143 to afford Example 266.

LRMS (Electrospray, positive): m/z 442 (m+1).

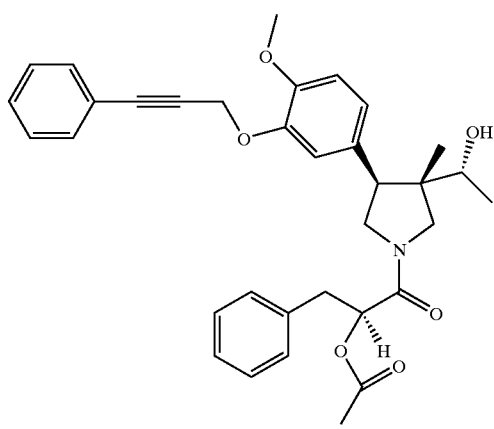

EXAMPLE 267

Acetic acid (S)-1-benzyl-2-{(3S,4S)-3-((R)-1-hydroxy-ethyl)-4-[4-methoxy-3-(3-phenylprop-2-ynyloxy)phenyl]-3-methylpyrrolidin-1-yl}-2-oxo-ethyl ester R¹=PhC≡CCH₂; R₃=(S)—COCH(OAc)CH₂Ph Example 266 (88 mg, 0.2 mmol) and Intermediate 90 (50 mg, 0.24 mmol) were subjected to the Cs₂CO₃ procedure of Example 176, and the crude residue (110 mg) was used without further purification.

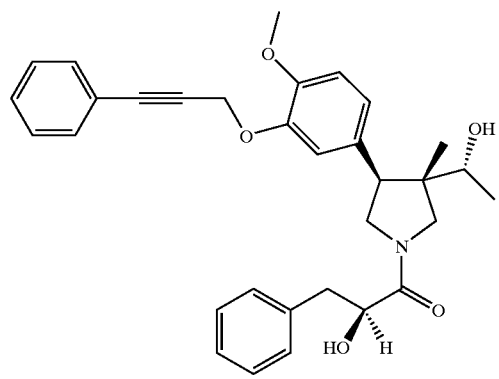

EXAMPLE 268

(S)-2-Hydroxy-1-{(3S,4S)-3-((R)-1-hydroxyethyl)-4-[4-methoxy-3-(3-phenylprop-2-ynyloxy)phenyl]-3-methylpyrrolidin-1-yl}-3-phenylpropan-1-one R¹=PhC≡CCH₂; R₃=(S)—COCH(OH)CH₂Ph Example 267 (110 mg crude, 0.2 mmol theoretical) was subjected to the O-Acetate deprotection procedure and purified by HPLC (20×50 mm YMC CombiPrep C18 column, 20 mL/min, 10–95% acetonitrile/water in 7 min) to yield Example 268 (38 mg, 75%).

¹H NMR (300 HMz, CDCl₃, mixture of rotamers) δ: 7.50–7.16 (m, 10H), 7.10–6.52 (m, 3H), 5.05–4.92 (m, 2H), 4.52–4.36 (m, 1H), 3.88 (s, 3H), 3.87–2.72 (m, 9H), 1.48/1.29 (2d, J=4.3/4.6 Hz, 1H), 0.93/0.88 (2d, J=6.4 Hz, 3H), 0.66/0.51 (2s, 3H). LRMS (Electrospray, positive): m/e 514 (m+H)⁺.

The compounds of structural formula (II) were tested for an ability to inhibit PDE4. The ability of a compound to inhibit PDE4 activity is related to the IC₅₀ value for the compound, i.e., the concentration of inhibitor required for 50% inhibition of enzyme activity. The IC₅₀ value for compounds of structural formula (II) were determined using recombinant human PDE4.

The in vitro phosphodiesterase activity inhibitory $IC_{50}$ values, and the resulting calculated $K_i$ values of compounds set forth in the examples were determined by measuring the inhibition of cAMP hydrolysis as a function of the concentration of the test compound over the range of 0 to 1 mM. The $K_i$ values of the compounds tested in the aforementioned assay ranged from about 0.0003 μM to about 100 μM.

The compounds of the present invention typically exhibit an $IC_{50}$ value against recombinant human PDE4 of less than about 50 μM, and preferably less than about 25 μM, and more preferably less than about 15 μm. The compounds of the present invention typically exhibit an $IC_{50}$ value against recombinant human PDE4 of less than about 1 μM, and often less than about 0.05 μM. To achieve the full advantage of the present invention, a present PDE4 inhibitor has an $IC_{50}$ of about 700 pM (picomolar) to about 15 μM.

The $IC_{50}$ values for the compounds were determined from concentration-response curves typically using concentrations ranging from 0.1 pM to 500 μM. Tests against other PDE enzymes using standard methodology, as described in Loughney et al., *J. Biol. Chem.*, 271, pp. 796–806 (1996), also showed that compounds of the present invention are highly selective for the cAMP-specific PDE4 enzyme.

In particular, a compound of the present invention, i.e., Sample 66, has an $IC_{50}$ vs. human recombinant PDE4B of 0.015 μM, but has an $IC_{50}$ vs. PDE1A of 80 μM, vs. PDE1B of 100 μM, vs. PDE1C of 12 μM, vs. PDE2 of 450 μM, vs. PDE3A of 40 μM, vs. PDE5 of 270 μM, and vs. PDE7 of 36 μM. This illustrates the selectivity of the present compound with respect to inhibiting PDE4.

The compounds of structural formula (II) also were tested for an ability to reduce TNFα secretion in human peripheral blood lymphocytes. The ability to reduce TNFα secretion is related to the $EC_{50}$ values (i.e., the effective concentration of the compound capable of inhibiting 50% of the total TNFα).

The in situ inhibition of TNFα release derived from endotoxin treated isolated human peripheral blood lymphocytes resulted in $EC_{50}$ values of compounds set forth in the examples were determined as a function of the concentration of the test compound over a range of 0 to 100 μM. The $EC_{50}$ values of the compounds tested in the aforementioned assay ranged from about 0.0002 μM to about 20 μM.

The compounds of the present invention typically exhibit an $EC_{50}$ value of less than about 50 μM, and preferably less than about 25 μM, and more preferably less than about 15 μM. The compounds of the present invention typically exhibit a PBL/TNFα $EC_{50}$ value of less than about 1 μM, and often less than about 0.05 μM. To achieve the full advantage of the present invention, a present PDE4 inhibitor has an $EC_{50}$ value of about 1000 pM (picomolar) to about 20 μM.

The production of recombinant human PDEs and the $IC_{50}$ and $EC_{50}$ determinations can be accomplished by well-known methods in the art. Exemplary methods are described as follows:

Expression of Human PDEs

Expression in Baculovirus-Infected *Spodoptera fugiperda* (Sf9) Cells

Baculovirus transfer plasmids were constructed using either pBlueBacIII (Invitrogen) or pFastBac (BRL-Gibco). The structure of all plasmids was verified by sequencing across the vector junctions and by fully sequencing all regions generated by PCR. Plasmid pBB-PDE1A3/6 contained the complete open reading frame of PDE1A3 (Loughney et al., *J. Biol. Chem.*, 271, pp. 796–806 (1996)) in pBlueBacIII. Plasmid Hcam3aBB contained the complete open reading frame of PDE1C3 (Loughney et al. (1996)) in pBlueBacIII. Plasmid pBB-PDE3A contained the complete open reading frame of PDE3A (Meacci et al., *Proc. Natl. Acad. Sci., USA*, 89, pp. 3721–3725 (1992)) in pBlueBacIII.

Recombinant virus stocks were produced using either the MaxBac system (Invitrogen) or the FastBac system (Gibco-BRL) according to the manufacturer's protocols. In both cases, expression of recombinant human PDEs in the resultant viruses was driven off the viral polyhedron promoter. When using the MaxBac® system, virus was plaque purified twice in order to insure that no wild type (occ+) virus contaminated the preparation. Protein expression was carried out as follows. Sf9 cells were grown at 27° C. in Grace's Insect culture medium (Gibco-BRL) supplemented with 10% fetal bovine serum, 0.33% TC yeastolate, 0.33% lactalbumin hydrolysate, 4.2 mM $NaHCO_3$, 10 μg/mL gentamycin, 100 units/mL penicillin, and 100 μg/mL streptomycin. Exponentially growing cells were infected at a multiplicity of approximately 2 to 3 virus particles per cell and incubated for 48 hours. Cells were collected by centrifugation, washed with nonsupplemented Grace's medium, and quick-frozen for storage.

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

Calmodulin Purification

Calmodulin used for activation of the PDE1 enzymes was purified from bovine testes essentially as described by Dedman et al., *Methods in Enzymology*, 102, pp. 1–8 (1983) using the Pharmacia Phenyl-Sepharose® procedure.

Immobilization of Calmodulin on Agarose

Calmodulin was immobilized on BioRad AffiGel® 15 per manufacturer's instructions.

Human Phosphodiesterase Preparations

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5′-nucleotidase. Hence, the amount of [32P]phosphate liberated is proportional to enzyme activity. The assay was performed at 30° C. in a 100 μL reaction mixture containing (final concentrations) 40 mM Tris HCl (pH 8.0), 1 μM $ZnSO_4$, 5 mM $MgC_2$, and 0.1 mg/mL bovine serum albumin (BSA). Alternatively, in assays assessing PDE1-specific activity, incubation mixtures further incorporated the use of 0.1 mM $CaCl_2$ and 10 μg/mL calmodulin. PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) μg of Crotalus atrox venom then was added, and the incubation was continued for 3 minutes (15 minutes total). The reaction was stopped by addition of 200 μL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Inhibitor analyses were performed similarly to the method described in Loughney et al., *J. Biol. Chem.*, 271, pp. 796–806 (1996), except both cGMP and cAMP were used, and substrate concentrations were kept below 32 nM, which is far below the Km of the tested PDEs.

Purification of PDE1A3 from SF9 Cells

Cell pellets (5 g) were mixed with 10 mL of Lysis Buffer (50 mM MOPS pH 7.5, 2 mM dithiothreitol (DTT), 2 mM benzamidine HCl, 5 μM $ZnSO_4$, 0.1 mM $CaCl_2$, 20 μg/mL calpain inhibitors I and II, and 5 μg/mL each of leupeptin, pepstatin, and aprotinin) at room temperature. The cells were lysed by passage through a French® pressure cell (SLM-Aminco®, Spectronic Instruments, Inc., Rochester N.Y.). The resultant lysate was centrifuged in a Beckman ultracentrifuge using a type T180 rotor at 45,000 rpm for 1 hr. The supernatant was recovered and filtered through a 0.2 μm filter. This filtrate was applied to a 2.6×90 cm column of SEPHACRYL® S-300 equilibrated in Column Buffer-A (Lysis Buffer containing 100 mM NaCl, and 2 mM $MgCl_2$). The column flow rate was adjusted to 1 mL/min and fractions of 7 mL were collected. Active fractions were pooled and supplemented with 0.16 mg of calmodulin. The enzyme was applied overnight at a flow rate of 0.2 mL/min to an ACC-1 agarose immunoaffinity column as described in Hansen et al., *Methods in Enzymology* 159, pp. 453–557 (1988). The column was washed with 5 volumes of Column Buffer B (Column Buffer A without NaCl) and followed by 5 volumes of Column Buffer C (Column Buffer A containing 250 mM NaCl). The column was eluted with Column Buffer D (50 mM MOPS pH 7.5, 1 mM EDTA, 1 mM EGTA, 1 mM DTT, 1 mM benzamidine HCl, 100 mM NaCl, 20 μg/mL calpain inhibitors I and II, and 5 μg/mL each of leupeptin, pepstatin, and aprotinin) by applying one column volume at 0.1 mL/min, stopping flow for 1 hour, and then continuing elution at the same flow rate. Fractions of 0.5 mL were collected. Fractions displaying activity were pooled, and first dialyzed against dialysis buffer containing 25 mM MOPS pH 7.5, 100 mM NaCl, 10 μM $ZnSO_4$, 1 mM $CaCl_2$, 1 mM DTT, and 1 mM benzamidine HCl. A subsequent dialysis against dialysis buffer containing 50% glycerol was performed prior to quick-freezing the sample with dry ice and storage at −70° C. The resultant preparations were about 10 to 15% pure by SDS-PAGE. These preparations had specific activities of about 5 to 20 μmol cAMP hydrolyzed per minute per milligram protein.

Purification of PDE1B from *S. cerevisiae*

Yeast cells (50 g) were thawed by mixing with 100 mL glass beads (0.5 mM, acid washed) and 200 mL Buffer A at room temperature. Buffer A consisted of 50 mM MOPS pH 7.5, 1 mM DTT, 2 mM benzamidine HCl, 0.01 mM $ZnSO_4$, 5 mM $MgCl_2$, 20 μg/mL calpain inhibitors I and II, and 5 μg/mL each of leupeptin, pepstatin, and aprotinin. The mixture was cooled to 4° C., transferred to a Bead-Beater®, and the cells lysed by rapid mixing for 6 cycles of 30 seconds each. The homogenate was centrifuged for 15 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE1B was precipitated by the addition of solid ammonium sulfate (0.33 g/mL supernatant) while stirring in an ice bath and maintaining the pH between 7.0 and 7.5. This mixture then was centrifuged for 22 minutes in a Beckman J2 centrifuge using a JA-10 rotor at 9,000 rpm (12,000×g). The supernatant was discarded and the pellet was dissolved in 100 mL of buffer B (50 mM MOPS pH 7.5, 1 mM DTT, 1 mM benzamidine HCl, 0.01 mM $ZnSO_4$, 2 mM $MgCl_2$, 2 mM $CaCl_2$, and 5 μg/mL each of leupeptin, pepstatin, and aprotinin). The pH and conductivity were corrected to 7.5 and 15–20 milli-Siemens (mS), respectively. This solution was loaded onto a 20 mL column of calmodulin-Agarose. that had been equilibrated with 10 column volumes of Buffer B at a rate of 1 mL/min. The flow-through was reapplied to the column at least 5 times. The column was washed with 5 volumes of Buffer B, 5 volumes of buffer B containing 250 mM NaCl, and 2 volumes of Buffer B without NaCl again. Elution was accomplished by applying one volume of Buffer C (50 mM MOPS pH 7.5, 1 mM EDTA, 1 mM EGTA, 1 mM DTT, 1 mM benzamidine HCl) at 0.33 mL/min, then stopping flow for 1 hour before continuing the elution. Fractions of about 4 mL were collected and assayed for PDE activity. Active fractions were pooled and concentrated to a volume of 5 mL, using an Amicon ultrafiltration system. The concentrate was then applied to a 320 mL Sephacryl® S-300 column (1.6×150 cm) that had been equilibrated with at least 2 volumes of Buffer D (25 mM MOPS pH 7.5, 1 mM DTT, 1 mM benzamidine HCl, 0.01 mM $ZnSO_4$, 2 mM CaCl, and 100 mM NaCl). The column was developed at a flow rate of 1 mL/min (11 cm/hr), and 5 mL fractions were collected. The activity peak was pooled and dialyzed overnight against Buffer D containing 50% glycerol. The purified enzyme was frozen on dry ice and stored at −70° C. The resultant preparations were about >90% pure by SDS-PAGE. These preparations had specific activities of about 10 to 30 μmol cGMP hydrolyzed per minute per milligram protein.

Purification of PDE1C3 from Sf9 Cells

Cell pellets (5 g) were thawed on ice with 20 mL of Lysis Buffer (50 mM MOPS pH 7.4, 10 μM $ZnSO_4$, 0.1 mM $CaC_2$, 1 mM DTT, 2 mM benzamidine HCl, 5 μg/mL each of pepstatin, leupeptin, and aprotinin). Cells were lysed by passage through a French® pressure cell (SLM-Aminco®, Spectronic Instruments) while temperatures were maintained below 10° C. The resultant cell homogenate was centrifuged at 36,000 rpm at 4° C. for 45 min in a Beckman ultracentrifuge using a Type TI45 rotor. The supernatant was discarded and the resultant pellet was resuspended with 40 mL of Solubilization Buffer (Lysis Buffer containing 1 M NaCl, 0.1 M $MgCl_2$, 1 mM $CaCl_2$, 20 μg/mL calmodulin, and 1% Sulfobetaine SB12 (Z3-12) by sonicating using a VibraCell tuner with a microtip for 3×30 seconds. This was performed in a crushed ice/salt mix for cooling. Following sonication, the mixture was slowly mixed for 30 minutes at 4° C. to finish solubilizing membrane bound proteins. This mixture was centrifuged in a Beckman ultracentrifuge using a type TI45 rotor at 36,000 rpm for 45 minutes. The supernatant was diluted with Lysis Buffer containing 10 µg/mL calpain inhibitors I and II. The precipitated protein was centrifuged for 20 minutes at 9,000 rpm in a Beckman JA-10 rotor. The recovered supernatant then was subjected to Mimetic Blue® AP Agarose Chromatography.

To run the Mimetic Blue® AP Agarose Column, the resin initially was shielded by the application of 10 bed volumes of 1% polyvinylpyrrolidone (i.e., MW of 40,000) to block nonspecific binding sites. The loosely bound PVP-40 was removed by washing with 10 bed volumes of 2 M NaCl, and 10 mM sodium citrate pH 3.4. Just prior to addition of the solubilized PCE1C3 sample, the column was equilibrated with 5 bed volumes of Column Buffer A (50 mM MOPS pH 7.4, 10 µM $ZnSO_4$, 5 mM $MgCl_2$, 0.1 mM $CaCl_2$, 1 mM DTT, 2 mM benzamidine HCl).

The solubilized sample was applied to the column at a flow rate of 2 mL/min with recycling such that the total sample was applied 4 to 5 times in 12 hours. After loading was completed, the column was washed with 10 column volumes of Column Buffer A, followed by 5 column volumes of Column Buffer B (Column Buffer A containing 20 mM 5'-AMP), and followed by 5 column volumes of Column Buffer C (50 mM MOPS pH 7.4, 10 µM $ZnSO_4$, 0.1 mM $CaCl_2$, 1 mM DTT, and 2 mM benzamidine HCl). The enzyme was eluted into three successive pools. The first pool consisted of enzyme from a 5-bed volume wash with Column Buffer C containing 1 mM cAMP. The second pool consisted of enzyme from a 10-bed volume wash with Column Buffer C containing 1 M NaCl. The final pool of enzyme consisted of a 5-bed volume wash with Column Buffer C containing 1 M NaCl and 20 mM cAMP.

The active pools of enzyme were collected and the cyclic nucleotide removed via conventional gel filtration chromatography or chromatography on hydroxyapatite resins. Following removal of cyclic nucleotides, the enzyme pools were dialyzed against Dialysis Buffer containing 25 mM MOPS pH 7.4, 10 µM $ZnSO_4$, 500 mM NaCl, 1 mM $CaCl_2$, 1 mM DTT, 1 mM benzamidine HCl, followed by dialysis against Dialysis buffer containing 50% glycerol. The enzyme was quick-frozen with the aid of dry ice and stored at −70° C.

The resultant preparations were about >90% pure by SDS-PAGE. These preparations had specific activities of about 0.1 to 1.0 µmol cAMP hydrolyzed per minute per milligram protein.

Purification of PDE2 from *S. cerevisiae*

Frozen yeast cell pellets from strain YI34 (10 g, stored at −70° C.) were allowed to thaw on ice in 25 mL of Lysis Buffer (50 mM MOPS, pH 7.2, 1 mM EDTA, 1 mM EGTA, 0.1 mM DTT, 0.1 mM 4-(2-amino-ethyl)benzenesulfonyl fluoride (AEBSF), 1 µg/mL of pepstatin, leupeptin, aprotinin, calpain inhibitors I and II, and 2 mM benzamidine). Cells were lysed by three passages through a French® pressure cell (SLM-Aminco®, Spectronic Instruments). The lysate was centrifuged at 36,000 rpm in a Beckman Ultracentrifuge rotor Type 45Ti for 60 minutes at 4° C. The. supernatant was separated from sediment and passed through a 15 mL Epoxy-cGMP Sepharose resin at 4° C. two times at about 0.5 mL/min. The column subsequently was washed with 45 mL of Wash Buffer 1 (50 mM MOPS, pH 7.2, 0.1 mM EDTA, 0.1 mM DTT). Following this wash, the column was washed with 45 mL of Wash Buffer 2 (Wash Buffer 1 containing 0.5 M NaCl). Following this salt wash, the column was washed with 15 mL of Wash Buffer 3 (Wash Buffer 1 containing 0.25 M NaCl). The column was transferred to room temperature and allowed to warm. Approximately 25 mL of Elution Buffer (Wash Buffer 3 containing 10 mM cGMP, maintained at room temperature) was applied to the column and the effluent was collected in 2 mL fractions. Small aliquots of each of the fractions were diluted 20-fold in PBS containing 5 mM $MgCl_2$ to allow hydrolysis of the competing ligand and to aid detection of PDE2 activity. Active fractions were passed through a Pharmacia PD-10® gel filtration column to exchange into Wash Buffer 3. This exchanged pool was diluted 50% v/v with sterile 80% glycerol and stored at −20° C. The resultant preparations were greater than 85% pure as judged by SDS-PAGE with subsequent staining of protein by Coomassie R-250. These preparations had specific activities of about 150 to 250 µmol cGMP hydrolyzed per minute per milligram protein.

Preparation of PDE3A from Sf9 Cells

Cells (2×1010) were suspended in Lysis Buffer containing 50 mM MOPS pH 7.5, 2 mM DTT, 2 mM benzamidine HCl, 5 µM $ZnSO_4$, 0.1 mM $CaCl_2$, 20 µg/mL calpain inhibitors I and II, and 5 µg/mL each of leupeptin, pepstatin, and aprotinin. The mixture was sonicated twice for 30 seconds and the cells were lysed in a French® pressure cell (SLM-Aminco®, Spectronic Instruments) at 4° C. The lysate was centrifuged 100,000×g for 45 minutes. The pellet was washed once in Lysis Buffer and suspended in 46 mL Lysis Buffer with a Dounce homogenizer. Aliquots were stored at −70° C. These preparations had specific activities of about 1 to 2 nmol cAMP hydrolyzed per minute per milligram protein.

Human PDE4A, 4B, 4C, 4D Preparations

Preparation of PDE4A from *S. cerevisiae*

Yeast cells (50 g of yeast strain YI26 harboring HDUN1.46) were thawed at room temperature by mixing with 50 mL of Lysis Buffer (50 mM MOPS pH 7.5, 10 µM $ZnSO_4$, 2 mM $MgCl_2$, 14.2 mM 2-mercapto-ethanol, 5 µg/mL each of pepstatin, leupeptin, aprotinin, 20 µg/mL each of calpain inhibitors I and II, and 2 mM benzamidine HCl). Cells were lysed in a French® pressure cell (SLM-Aminco®, Spectronic Instruments) at 10° C. The extract was centrifuged in a Beckman JA-10 rotor at 9,000 rpm for 22 minutes at 4° C. The supernatant was removed and centrifuged in a Beckman TI45 rotor at 36,000 rpm for 45 minutes at 4° C.

PDE4A was precipitated from the high-speed supernatant by the addition of solid ammonium sulfate (0.26 g/mL supernatant) while stirring in an ice bath and maintaining the pH between 7.0 and 7.5. The precipitated proteins containing PDE4A were collected via centrifugation in a Beckman JA-10 rotor at 9,000 rpm for 22 minutes. The precipitate was resuspended in 50 mL of Buffer G (50 mM MOPS pH 7.5, 10 µM $ZnSO_4$, 5 mM $MgCl_2$, 100 mM NaCl, 14.2 mM 2-mercaptoethanol, 2 mM benzamidine HCl, 5 ug/mL each of leupeptin, pepstatin, and aprotinin, and 20 µg/mL each of calpain inhibitors I and II) and passed through a 0.45 µm filter.

The resuspended sample (50 to 100 mL) was loaded onto a 5×100 cm column of Pharmacia SEPHACRYL® S-300 equilibrated in Buffer G. Enzyme activity was eluted at a flow rate of 2 mL/min and pooled for later fractionation.

The PDE4A isolated from gel filtration chromatography was applied to a 1.6×20 cm column of Sigma Cibacron Blue Agarose-type 300 (10 mL) equilibrated in Buffer A (50 mM MOPS pH 7.5, 1.0 µM ZnSO$_4$, 5 mM MgCl$_2$, 14.2 mM 2-mercaptoethanol, and 100 mM benzamidine HCl). The column was washed in succession with 50 to 100 mL of Buffer A, 20 to 30 mL of Buffer A containing 20 mM 5'-AMP, 50 to 100 mL of Buffer A containing 1.5 M NaCl, and 10 to 20 mL of Buffer C (50 mM Tris HCl pH 8, 10 µM ZnSO$_4$, 14.2 mM 2-mercaptoethanol, and 2 mM benzamidine HCl). The enzyme was eluted with 20 to 30 mL of Buffer C containing 20 mM cAMP.

The PDE activity peak was pooled, and precipitated with ammonium sulfate (0.33 g/mL enzyme pool) to remove excess cyclic nucleotide. The precipitated proteins were resuspended in Buffer X (25 mM MOPS pH 7.5, 5 µM ZnSO$_4$, 50 mM NaCl, 1 mM DTT, and 1 mM benzamidine HCl), and desalted via gel filtration on a Pharmacia PD-10® column per manufacturer's instructions. The enzyme was quick-frozen in a dry ice/ethanol bath and stored at –70° C.

The resultant preparations were about >80% pure by SDS-PAGE. These preparations had specific activities of about 10 to 40 µmol cAMP hydrolyzed per minute per milligram protein.

Preparation of PDE4B from *S. cerevisiae*

Yeast cells (150 g of yeast strain YI23 harboring HDUN2.32) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 µg/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 seconds each. The homogenate was centrifuged for 22 minutes in a Beckman J2-21M centrifuge using a JA-10 rotor at 9,000 rpm and 4° C. The supernatant was recovered and centrifuged in a Beckman XL-80 ultra-centrifuge using a TI45 rotor at 36,000 rpm for 45 minutes at 4° C. The supernatant was recovered and PDE4B was precipitated by the addition of solid ammonium sulfate (0.26 g/mL supernatant) while stirring in an ice bath and maintaining the pH between 7.0 and 7.5. This mixture was then centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM MgCl$_2$, 1 mM DTT, 1 mM benzamidine HCl, and 5 µg/mL each of leupeptin, pepstatin, and aprotinin). The pH and conductivity were corrected to 7.5 and 15–20 mS, respectively.

The resuspended sample was loaded onto a 1.6×200 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE activity peak was pooled, and precipitated with ammonium sulfate (0.4 g/mL enzyme pool) to remove excess cyclic nucleotide. The precipitated proteins were resuspended in Buffer X (25 mM MOPS pH 7.5, 5 µM ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at –70° C.

The resultant preparations were about >90% pure by SDS-PAGE. These preparations had specific activities of about 10 to 50 µmol cAMP hydrolyzed per minute per milligram protein.

Preparation of PDE4C from *S. cerevisiae*

Yeast cells (150 g of yeast strain YI30 harboring HDUN3.48) were thawed by mixing with 100 mL glass beads (0.5 mM, acid washed) and 150 mL Lysis Buffer (50 mM MOPS pH 7.2, 2 mM EDTA, 2 mM. EGTA, 1 mM DTT, 2 mM benzamidine HCl, 5 µg/mL each of pepstatin, leupeptin, aprotinin, calpain inhibitors I and II) at room temperature. The mixture was cooled to 4° C., transferred to a BEAD-BEATER®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultra-centrifuge using a TI45 rotor at 36,000 rpm for 45 minutes at 4° C.

The supernatant was recovered and PDE4C was precipitated by the addition of solid ammonium sulfate (0.26 g/mL supernatant) while stirring in an ice bath and maintaining the pH between 7.0. and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM MgCl$_2$, 1 mM DTT, 2 mM benzamidine HCl, and 5 µg/mL each of leupeptin, pepstatin, and aprotinin). The pH and conductivity were corrected to 7.5 and 15–20 mS, respectively.

The resuspended sample was loaded onto a 1.6×20 cm column. (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and then 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE4C activity peak was pooled, and precipitated with ammonium sulfate (0.4 g/mL enzyme pool) to remove excess cyclic nucleotide. The precipitated proteins were resuspended in Buffer X (25 mM MOPS pH 7.2, 5 µM ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at –70° C.

The resultant preparations were about >80% pure by SDS-PAGE. These preparations had specific activities of about 10 to 20 µmol cAMP hydrolyzed per minute per milligram protein.

Preparation of PDE4D from *S. cerevisiae*

Yeast cells (100 g of yeast strain YI29 harboring HDUN4.11) were thawed by mixing with 150 mL glass beads (0.5 mM, acid washed) and 150 mL Lysis Buffer (50 mM MOPS pH 7.2, 10 µM ZnSO$_4$, 2 mM MgCl$_2$, 14.2 mM 2-mercaptoethanol, 2 mM benzamidine HCl, 5 µg/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4D was precipitated by the addition of solid ammonium sulfate (0.33 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 100 mL of Buffer A (50 mM MOPS pH 7.5, 10 $\mu$M $ZnSO_4$, 5 mM $MgCl_2$, 14.2 mM 2-mercaptoethanol, 100 mM benzamidine HCl, and 5 $\mu$g/mL each of leupeptin, pepstatin, aprotinin, calpain inhibitor I and II). The pH and conductivity were corrected to 7.5 and 15–20 mS, respectively.

At a flow rate of 0.67 mL/min, the resuspended sample was loaded onto a 1.6×20 cm column (10 mL) of Sigma Cibacron Blue Agarose-type 300 equilibrated in Buffer A. The column was washed in succession with 50 to 100 mL of Buffer A, 20 to 30 mL of Buffer A containing 20 mM 5'-AMP, 50 to 100 mL of Buffer A containing 1.5 M NaCl, and then 10 to 20 mL of Buffer C (50 mM Tris HCl pH 8, 10 $\mu$M $ZnSO_4$, 14.2 mM 2-mercaptoethanol, 2 mM benzamidine HCl). The enzyme was eluted with 20 to 30 mL of Buffer C containing 20 mM cAMP.

The PDE4D activity peak was pooled and precipitated with ammonium sulfate (0.4 g/mL enzyme pool) to remove excess cyclic nucleotide. The precipitated proteins were resuspended in Buffer X (25 mM MOPS pH 7.2, 5 $\mu$M $ZnSO_4$, 50 mM, NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme preparation was quick-frozen in a dry ice/ethanol bath and stored at −70° C.

The resultant preparations were about >80% pure by SDS-PAGE. These preparations had specific activities of about 20 to 50 $\mu$mol cAMP hydrolyzed per minute per milligram protein.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 $\mu$M $ZnSO_4$). Cells were lysed in a Microfluidizer® (Microfluidics Corp.) using nitrogen at 20,000 psi. The lysate was centrifuged and filtered through 0.45 $\mu$m disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 MM $MgCl_2$, 0.25 mM DTT, 10 $\mu$M $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 $\mu$M $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60%. ammonium sulfate, and resuspended in Buffer C (20 mM Bis-Tris Propane, pH 6.8, 125 mM NaCl, 0.5 mM DTT, and 10 $\mu$M $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 $\mu$mol cGMP hydrolyzed per minute per milligram protein.

Preparation of PDE7 from *S. cerevisiae*

Cell pellets (126 g) were thawed and resuspended at room temperature. for about 30 minutes with an equal volume of Lysis Buffer (50 mM Tris HCl, pH 8, 1 mM EDTA, 1 mM DTT, 50 mM NaCl, 2 mM benzamidine HCl, and 5 $\mu$g/mL each of pepstatin, leupeptin, and aprotinin). The cells were lysed at 0–4° C. with the aid of glass beads (125 mL) in a Bead-Beater® for 6×30 second cycles. The lysate was centrifuged and filtered through 0.45 $\mu$m disposable filters. The filtered extract (178 mL) was distributed into 4 mL aliquots, quick-frozen with dry ice, and stored in a freezer at −70° C. These preparations were stable to several cycles of freezing and thawing and had specific activities of about 50 to 100 pmol cAMP hydrolyzed per minute per milligram protein.

Lipopolysaccharide-Stimulated TNFα Release from Human Peripheral Blood Lymphocytes To assess the ability of a compound to reduce TNFα secretion in human peripheral blood lymphocytes (PBL), the following tests were performed. Previous studies have demonstrated that incubation of human PBL with cAMP-elevating agents, such as prostaglandin E21, forskolin, 8-bromo-cAMP, or dibutryl-cAMP, inhibits the secretion of TNFα by the cells when stimulated by lipopolysaccharide (LPS; endotoxin). Accordingly, preliminary experiments have been performed to demonstrate that selective PDE4 inhibitors, such as rolipram, inhibit LPS-induced TNFα secretion from human lymphocytes in a dose-dependent fashion. Hence, TNFα secretion from human PBL was used as a standard for the ability of a compound to elevate intracellular cAMP concentrations and/or to inhibit PDE4 activity within the cell.

Heparinized blood (approximately 30 mL) drawn from human volunteers was mixed 1:1 with Dulbecco's modified phosphate-buffered saline. This mixture was mixed 1:1 with HISTOPAQUE® and centrifuged at 1,500 rpm at room temperature without braking in the swinging bucket of a Beckman model TJ6 centrifuge. Erythrocytes were centrifuged to the bottom of the tubes, and serum remained at the surface of the tubes. A layer containing lymphocytes sedimented between the serum and HISTOPAQUE® layers, and was removed by aspiration to a fresh tube. The cells were quantified and adjusted to 3×10$^6$ cells/mL and a 100 $\mu$L aliquot is placed into the wells of a 96 well plate. Test compounds and RPMI media (Gibco/BRL Life Sciences) are added to each of the wells 15 minutes prior to addition of bacterial LPS (25 mg/mL). The mixture was allowed to incubate for 20 hours at 37° C. in a humidified chamber. The cells then were separated by centrifuging at 800 rpm for 5 minutes at room temperature. An aliquot of 180 $\mu$L of supernatant was transferred to a new plate for determination of TNFα concentration. TNFα protein in the cell supernatant fluids was measured using a commercially available enzyme-linked immunosorbent assay (ELISA) (CYTO-SCREEN® Immunoassay Kit from Biosource International).

The cell-based assay provided the following results for various pyrrolidine compounds of the present invention. The $EC_{50}$ values (i.e., effective concentration of the compound capable of inhibiting 50% of the total TNFα) illustrate the ability of the present compounds to inhibit LPS-stimulated TNFα release from human PBL.

The table below illustrates the ability of compounds of formula (II) to inhibit PDE4 activity and TNFα release in vitro. In the following table, the $IC_{50}$ values were determined against human recombinant PDE4.

| Sample Number[1] | Stereochemistry | PDE4 $IC_{50}$ (M × $10^{-9}$) | PBL/TNFα $EC_{50}$ (M × $10^{-9}$) |
|---|---|---|---|
| 1 | Absolute, as drawn | 87.0 | 1,205.8 |
| 2 | Absolute, as drawn | 260.0 | 1,900.0 |
| 3 | Relative stereochemistry as drawn; racemic | 180.0 | 3,261.7 |
| 4 | Relative, stereochemistry as drawn; racemic | 190.0 | 3,611.5 |
| 5 | Relative, stereochemistry as drawn; racemic | 75.0 | 1,551.3 |
| 6 | Relative, stereochemistry as drawn; racemic | 75.0 | 3,657.5 |
| 7 | Absolute, as drawn | 5,800.0 | |
| 8 | Absolute, as drawn | 784.0 | 909.6 |
| 9 | Absolute, as drawn | 13,000.0 | |
| 10 | Absolute, as drawn | 7,900.0 | |
| 11 | Absolute, as drawn | 3,700.0 | |
| 12 | Absolute, as drawn | 2,600.0 | |
| 13 | Absolute, as drawn | 1,000.0 | 2,339.5 |
| 14 | Absolute, as drawn | 900.0 | 2,981.5 |
| 15 | Relative stereochemistry as drawn; racemic, mixture of ether isomers | 4.3 | 108.8 |
| 16 | Relative stereochemistry as drawn; racemic, mixture of ether isomers | 7.3 | 46.4 |
| 17 | Absolute, as drawn | 2,211.6 | 3,447.3 |
| 18 | Absolute, as drawn | 1,027.3 | 5,101.6 |
| 19 | Absolute, as drawn | 1,974.0 | 1,951.1 |
| 20 | Absolute, as drawn | 536.0 | 170.0 |
| 21 | Absolute, as drawn | 16.2 | 278.0 |
| 22 | Absolute, as drawn | 520.4 | 164.0 |
| 23 | Absolute, as drawn | 1,592.2 | |
| 24 | Absolute, as drawn; mixture of ether isomers | 1.6 | 40.0 |
| 25 | Absolute, as drawn; mixture of ether isomers | 2.8 | 12.2 |
| 26 | Absolute, as drawn; mixture of ether isomers | 35.0 | 106.0 |
| 27 | Absolute, as drawn; mixture of ether isomers | 1.8 | 36.0 |
| 28 | Absolute, as drawn | 23.0 | 241.0 |
| 29 | Absolute, as drawn | 4.9 | 78.0 |
| 30 | Absolute, as drawn | 100.0 | 440.0 |
| 31 | Absolute, as drawn | 3.6 | 35.0 |
| 32 | Absolute, as drawn | 1,000.0 | 801.0 |
| 33 | Absolute, as drawn | 2,100.0 | |
| 34 | Absolute, as drawn | 402.6 | 250.0 |
| 35 | Absolute, as drawn | 35.6 | 20.3 |
| 36 | Absolute, as drawn | 187.2 | 1,600.0 |
| 37 | Absolute, as drawn | .768 | 72.0 |
| 38 | Absolute, as drawn | 5.9 | 36.0 |
| 39 | Absolute, as drawn | 2.7 | 48.1 |
| 40 | Absolute, as drawn | 98.4 | 139.1 |
| 41 | Absolute, as drawn | 27.0 | 266.9 |
| 42 | Absolute, as drawn | 7.5 | 171.7 |
| 43 | Absolute, as drawn | 12.5 | 145.8 |
| 44 | Absolute, as drawn | 41.2 | 238.0 |
| 45 | Absolute, as drawn | 247.6 | 694.0 |
| 46 | Absolute, as drawn | 1,805.9 | 13,317.0 |
| 47 | Absolute, as drawn | 2,727.4 | 20,000.0 |
| 48 | Absolute, as drawn | 89.7 | 446.0 |
| 49 | Absolute, as drawn | 14.3 | 26.2 |
| 50 | Absolute, as drawn | 44.8 | 151.2 |
| 51 | Absolute, as drawn | 44.7 | 72.6 |
| 52 | Absolute, as drawn | 26.7 | |
| 53 | Absolute, as drawn; mixture of tetrahydrofuryl isomers | 116.3 | 112.6 |
| 54 | Absolute, as drawn; mixture of 2,2-dimethyl-4-oxo-4-pyrrolidin-1-yl-butyric acid and 3,3-dimethyl-4-oxo-4-pyrrolidin-1-yl-butyric acid amides | 464.7 | |
| 55 | Absolute, as drawn | 1,842.1 | |
| 56 | Absolute, as drawn | 4.0 | |
| 57 | Absolute, as drawn | 95.6 | |
| 58 | Absolute, as drawn | | |
| 59 | Racemic; relative stereochemistry as shown | 58.0 | 170.0 |
| 60 | Racemic; relative stereochemistry as shown | 74.0 | 44.0 |
| 61 | Racemic; relative stereochemistry as shown | 18.3 | 57.8 |
| 62 | Racemic, relative stereochemistry as shown | 6.8 | 10.2 |
| 63 | Racemic, relative stereochemistry as shown, nonbornyl residue racemic | 51.4 | 267.4 |
| 64 | Racemic, relative stereochemistry as shown, nonbornyl residue racemic | 8.5 | 36.2 |
| 65 | Racemic, relative stereochemistry as shown | 220.0 | 181.0 |
| 66 | Absolute stereochemistry as shown | 14.0 | 71.6 |
| 67 | Absolute stereochemistry as shown | 514.7 | 603.3 |
| 68 | Absolute stereochemistry as shown | 61.1 | 169.9 |
| 69 | Absolute stereochemistry as shown | 13.3 | 57.0 |
| 70 | Absolute stereochemistry as shown; single undefined alcohol isomer 1 | 498.5 | 547.2 |
| 71 | Absolute stereochemistry as shown; single undefined alcohol isomer 2 | 1,707.2 | |
| 72 | Absolute, as drawn | 2,452.6 | |
| 73 | Absolute, as drawn | 9,131.0 | |
| 74 | Absolute, as drawn | 352.3 | 557.3 |
| 75 | Absolute, as drawn | 45.1 | 121.0 |
| 76 | Absolute, as drawn | 36.6 | 173.0 |
| 77 | Absolute, as drawn | 188.7 | 580.0 |
| 78 | Absolute, as drawn | 760.1 | 1,288.6 |
| 79 | Absolute, as drawn | 1,639.0 | 2,366.6 |
| 80 | Absolute, as drawn | 300.0 | 272.4 |
| 81 | Absolute, as drawn | 700.0 | 624.8 |
| 82 | Absolute, as drawn | 389.8 | 490.0 |
| 83 | Absolute, as drawn | 172.0 | 51.0 |
| 84 | Absolute, as drawn | 21.7 | 40.0 |
| 85 | Absolute, as drawn | 3,576.8 | |
| 86 | Absolute, as drawn | 6,077.6 | |
| 87 | Absolute, as drawn | 896.6 | 934.4 |
| 88 | Absolute, as drawn | 953.4 | 629.5 |
| 89 | Absolute, as drawn | 699.0 | 860.0 |
| 90 | Absolute, as drawn | 69.4 | 61.0 |
| 91 | Absolute, as drawn | 150.0 | 44.0 |
| 92 | Absolute, as drawn | 439.4 | |
| 93 | Absolute, as drawn | 33.1 | 7.8 |

-continued

| Sample Number[1] | Stereochemistry | PDE4 IC$_{50}$ (M × 10$^{-9}$) | PBL/TNFα EC$_{50}$ (M × 10$^{-9}$) |
|---|---|---|---|
| 94 | Absolute stereochemistry as shown | 238.2 | 1,800.0 |

[1]See Appendix A for structure of each sample

The data presented above shows that the present compounds are potent inhibitors of PDE4, e.g., the compounds have an IC$_{50}$ vs. human recombinant PDE4 of about 700 pM to about 15 μM. Preferred compounds have an IC$_{50}$ of about 100 nM or less, and especially preferred compounds have an IC$_{50}$ of about 50 nM or less.

Similarly, preferred compounds have a PBL/TNFα EC$_{50}$ about 500 nM or less, and preferably about 200 nM or less. More preferred compounds have a PBL/TNFα EC$_{50}$ of about 100 nM or less.

To achieve the full advantages of the present invention, the compounds have an IC$_{50}$ vs. human recombinant PDE4 of about 100 nM or less and a PBL/TNFα EC$_{50}$ of about 500 nM or less. More preferably, the compounds have an IC$_{50}$ of about 50 nM or less and a PBL/TNFα EC$_{50}$ of about 100 nM or less.

Animal Models

Assay for Inhibition of Serum TNFα Levels in Mammals (Mouse/TNFα ED$_{50}$ (mg/kg))

In order to assess the ability of a compound to reduce serum TNFα levels in mammals, the following protocol was employed. Those skilled in the art appreciate that previous studies have demonstrated that incubation of LPS-activated human monocytes with agents that can elevate cAMP, like PGE2, forskolin, and the dbcAMP, inhibited secretion of TNFα. PDE4 inhibitors like rolipram, which also elevate cAMP, have been found to inhibit serum TNFα as well. Rolipram has also been found to inhibit secretion of TNFα from LPS-activated mouse macrophages. Accordingly, in vivo efficacy of a PDE4 reducing compound was shown by dosing with compound and measuring reduction of serum TNFα levels in LPS-injected mice. Female C3H mice, 20–25 gm body. weight, were fasted overnight and dosed intraperitoneally with test compound in appropriate vehicle 60 minutes before LPS injection. Five μg of LPS was then injected intraperitoneally into the mice. Ninety minutes after LPS injection, mice were bled from the heart. Blood was allowed to clot overnight at 4° C. Samples were centrifuged for 10 minutes in a microcentrifuge and the serum removed and stored at −20° C. until analysis. Serum levels of TNFα were subsequently measured using a commercially available ELISA kit (Genzyme) following the protocol enclosed in the kit. The percent of inhibition of serum TNFα levels caused by the compound was determined relative to serum TNFα levels in control mice receiving vehicle alone.

Combined Mouse endotoxin-stimulated TNFα Release and Locomotor Activity Assay (ED$_{50}$ (mg/kq))

The purpose of this study was to determine the efficacy of PDE4 inhibitors in vivo in an LPS mouse model together with a determination with respect to central nervous system (CNS) side-effects manifested by a decrease in spontaneous mobility.

The test animals were female Balb/c mice, having an average weight of about 20 g. The PDE4 inhibitors, formulated in 30% Cremophor® EL, were administered via intraperitoneal (i.p.) injections at doses of 0.1, 1.0, 10.0, and 100 mg/kg. Individual dose volumes (about 150 μL) were adjusted based on the body weights measured. One hour later, 5 mg/kg LPS in a final volume of 200 μL was injected via the tail vein to each animal. Ninety minutes following the LPS treatment, the animals were bled and serum samples were collected before being stored at −70° C. until assayed.

For efficacy determination, the serum samples were diluted two-fold and TNFα levels were determined using the CYTOSCREEN® Immunoassay Kit (Biosource International). The data were averaged between triplicate sample subjects for each of the tested compounds.

Movement of the X-Y plane, or rearing up on the hind legs, was quantified by counting the number of "light-beam" crosses per unit of time. A decrease in the number of activity events is directly proportional to the mobility or immobilization of the animal. The quantitative scoring correlated well with the subjective measurements described above.

The following table summarizes the Mouse/TNFα ED$_{50}$ (mg/kg) results obtained by the above-described method:

| Sample Number[1] | Mouse/TNFα ED$_{50}$ (mg/kg) | ED$_{50}$ (mg/kg)[3] |
|---|---|---|
| 29 | — | 9.8 |
| 31 | 3 | 83 |
| 61 | 0.2 | >50 |
| 62 | 0.08 | >50 |
| 66 | 5 | >50 |
| 67 | — | >50 |
| 68 | 12 | 20 |
| 69 | 7 | <0.5 |

[3]effective dose, in mg/kg, that decreases spontaneous mobility 50% of control.

It also was determined that compounds of formula (II) have fewer central nervous system side effects compared to rolipram and to compounds disclosed in Feldman et al. U.S. Pat. No. 5,665,754. It also was found that central nervous system activity is related to the absolute stereochemistry of the present compounds.

It is known that stereoisomers of drugs can have substantially different biological activities, e.g., potency, selectivity, absorption, distribution metabolism, execution, and side effect profiles. In the present invention, the enantiomers and diastereomers represented by compounds (A)–(D) in the following table were tested for effects on in vitro PDE activity, cell-based LPS/TNFα release from human peripheral blood lymphocytes (PBLs), mouse mobility, and ferret emesis.

As shown in the following table, compounds (C) and (A) (i.e., Samples 66 and 69, respectively) show similar inhibition of PDE4 and LPS-stimulated TNFα release, but substantially different behavioral profiles. Compounds (C) and (A), which exhibit less CNS activity, are derived from the predominant product of the [3+2] azomethine ylide cyclization to the chiral α,β-unsaturated amide. Thus, the absolute stereochemistry of a PDE4 inhibitor of the present invention contributes significantly to the behavioral profile of the compound.

| Examples | Compound | PDE4 IC$_{50}$ (nM) | Mouse/TNFα ED$_{50}$ (mg/kg) | CNS Side Effects[1] |
|---|---|---|---|---|
| (A) | | 13.3 | 7 | Severe |
| (C) | | 14.0 | 5 | No effect |
| (B) | | 61.1 | 12 | No effect |
| (D) | | 514.7 | — | No effect |
| Sample No. 62 | | 6.8 | 0.08 | Little to no effect (at 50 mg/kg) |

-continued

| Examples | Compound | PDE4 IC$_{50}$ (nM) | Mouse/TNFα ED$_{50}$ (mg/kg) | CNS Side Effects[1] |
|---|---|---|---|---|
| Sample No. 61 | (structure) | 18.3 | 0.2 | Little to no effect (at 50 mg/kg) |

[1] CNS side effects were determined by a subjective assessment of mouse immobility following injection of compounds i.p. at 1, 10, and 100 mg/kg doses. Mobility (or lack thereof) assessment was scored by observing the following: reduced exploratory behavior, fattened posture, prone positioning, ruffled fur, etc. No apparent effects were noted over the 60 minutes time frame of assessment with Examples 8(C), 8(D), and 8(B). However, mice were affected at all doses when given Example 8(A). Furthermore, at the highest dose of Example 8(A), mice became moribund and died within 10 minutes of treatment.

The data presented above show that compounds of formula (II) are potent and selective inhibitors of PDE4. As an important added advantage, the compounds of formula (II) also reduced or eliminated the adverse CNS side effects associated with prior PDE4 inhibitors. Compounds of formula (II) were further tested for emetogenic properties in animal models to further illustrate the efficacy of the compounds. The method and results of the emetogenic test are set forth below.

Emetic Modeling in the Ferret Following Oral and Intravenous Dosing With PDE4-Selective Inhibitors This study was conducted to investigate the emetogenic properties of PDE4 inhibitors in vivo. The ferret previously has been established as a valuable tool for assessing emesis following exposure to test compounds. Previous studies indicated that the emetic response of a ferret to many PDE4 inhibitors is predictive of the disposition of humans toward the same test compounds. Therefore, lack of and/or decrease in emetic potential of test compounds in ferrets predicts a favorable nonemetic effect in humans. Emesis is a complex physiological response to noxious agents that can be intiated. peripherally or centrally. Hence, PDE4-selective agents were tested when administered both intravenously or orally.

The test animals were adult, castrated, and descented male ferrets (species=*Mustela putorius furo*, Strain=*Sable*) ranging in weight from about 1 to 1.5 kg. The tests were performed in quadruplicate on animals that were naive to PDE4 inhibitors. The PDE4 inhibitors were formulated in 10% Polyoxyl-35 castor oil (CREMOPHOR® EL, available from BASF Corporation, Parsippany, N.J.) in phosphate buffered saline (PBS), and were administered via i.v. injections into an indwelling catheter surgically positioned in the right. external jugular vein at a rate of 0.66 mL per kg body weight. PDE4 inhibitors for oral consumption were formulated in 30%. CREMOPHOR® EL in PBS, and administered by intubating animals with a 16-gauge feeding needle into the stomach. The animals received the PDE4 inhibitors in a volume of 1.33 mL per kg body weight.

All animals were fasted for 8 to 12 hours prior to administration of PDE4 inhibitors. Following administration of a PDE4 inhibitor, emetic and behavioral responses were quantified for three hours post dosing. The total number of emetic responses and vomiting episodes were quantified during the observation interval. In addition, latency time to first emetic episode, duration of emesis episodes, and gross behavioral changes including ataxia, profuse and viscous salivation, mouth clawing, hyperventilation, backward walking, flattened body posture, hyperactivity, lip licking, and general appearance were recorded.

For comparative purposes, the emetogenic effect of Samples 66 and 69 were tested intravenously at 1.0, 2.5, 5.0, and 10 mg/kg and orally at 2.5, 10, 17, and 25 mg/kg. The results are summarized in the following table:

COMPARATIVE RESULTS

| Compound (A) (Sample 69) | Number of Emetic Events | | | |
|---|---|---|---|---|
| Oral (mg/kg) | Vomits | Retches | Total | Responders |
| 2.5 | 0 | 0 | 0 | 0/4 |
| 10.0 | 5 | 27 | 32 | 3/4 |
| 17.0 | 7 | 51 | 58 | 3/4 |
| 25.0 | 26 | 88 | 114 | 4/4 |
| Intravenous (mg/kg) | Vomits | Retches | Total | Responders |
| 1.0 | 0 | 0 | 0 | 0/4 |
| 2.5 | 0 | 3 | 3 | 1/4 |
| 5.0[1] | 0 | 300 | 300 | 2/2 |
| 10.0 | — | — | — | — |

| Compound (C) (Sample 66) | Number of Emetic Events | | | |
|---|---|---|---|---|
| Oral (mg/kg) | Vomits | Retches | Total | Responders |
| 2.5 | 0 | 0 | 0 | 0/4 |
| 10.0 | 8 | 14 | 22 | 2/4 |
| 17.0 | 1 | 17 | 18 | 2/3 |
| 25.0 | 12 | 61 | 73 | 4/4 |
| Intravenous (mg/kg) | Vomits | Retches | Total | Responders |
| 1.0 | 0 | 0 | 0 | 0/4 |
| 2.5 | 0 | 0 | 0 | 0/4 |

-continued

COMPARATIVE RESULTS

| 5.0[1] | 0 | 10 | 10 | 2/4 |
| 10.0 | 4 | 27 | 31 | 4/4 |

[1] Only two ferrets were dosed intravenously with 5 mg/kg compound (A) because of the severity of the responses. Therefore, 10 mg/kg Example 8(A) was not administered intravenously.

In general, both compounds (C) and (A), delivered either orally or via intravenous injection, produced a clear dose response in terms of emetic behavior. Compound (A) produced a much stronger emetic response than compound (C). This was readily apparent when the responses to oral dosing was compared. For example, at a dose of 25 mg/kg body weight, compound (A) produced more retching and vomiting episodes than the same oral dose of compound (C). In addition, the number of retches and vomiting events per episode was much greater for compound (A) than compound (C) in this dose group. A similar trend was apparent at oral dosages of 17 and 11 mg/kg body weight, with compound (A) exhibiting a stronger response than compound (C). There were no apparent differences observed between the lowest dosed groups for both molecules. In these cases, some minor lip licking/mouth pawing was evident with both compounds, but no emetic responses were observed.

The results of oral dosing contrast markedly with that of intravenous dosing. At an intravenous dose of 5 mg/kg body weight of compound (A), one of the tested animals died almost immediately after dosing (within 5 minutes), whereas the second animal was clearly distressed, but recovered after 3 hours. The distress can be attributed either to an acute toxicity event or to an exaggerated pharmacological response to centrally mediated emesis. It also was noted that the distressed and labored breathing in these dosed animals was difficult to distinguish from extreme retching behavior. The effects were not nearly as severe with intravenous administration of compound (C) as shown in the above table. Although all animals exhibited emetic behavior at the 10 mg/kg body weight dose with compound (C), none displayed the distress associated with the 5 mg/kg dose of compound (A). With the exception of the 5 mg/kg body weight dose of compound (A), all of the animals recovered from their treatment and appeared normal.

Obviously, many modifications and variations of the invention as hereinbefore set forth can be made without departing from the spirit and scope thereof and, therefore, only such limitations should be imposed as are indicated by the appended claims.

Sample No. 1

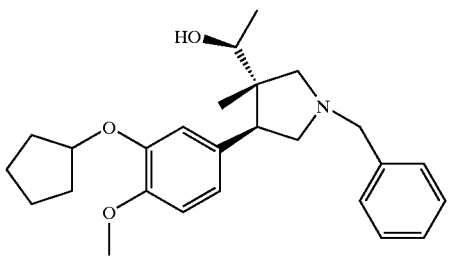

Sample No. 2

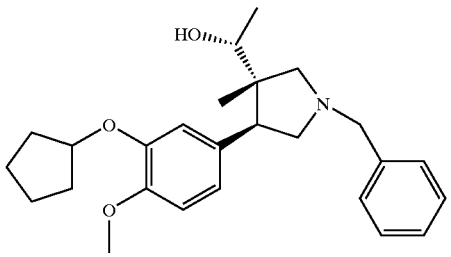

Sample No. 3

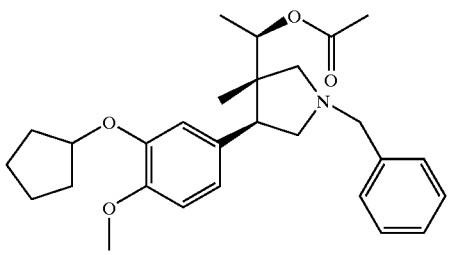

| Assay | Example 101 | Example 264 | Example 109 | Example 268 | Example 195 |
|---|---|---|---|---|---|
| PDE4B $IC_{50}$ ($\mu M$) | 0.011 | 0.003 | 0.02 | 0.015 | 0.007 |
| Cell based $EC_{50}$ ($\mu M$) | 0.03 | 0.010 | 0.03 | 0.006 | 0.03 |
| Mouse LPS Challenge $ED_{50}$ (mg/kg) | 3 | 1 | 5 | 5 | 9 |
| Mouse Inhibition of Spontaneous Mobility $ED_{50}$ (mg/kg) | 100 | <100 | 100 | 100 | 100 |

The results summarized in the above tables show that the compounds of the present invention are useful for selectively inhibiting PDE4 activity in a mammal, without exhibiting the adverse CNS and emetic effects associated with prior PDE4 inhibitors.

-continued
Sample No. 4
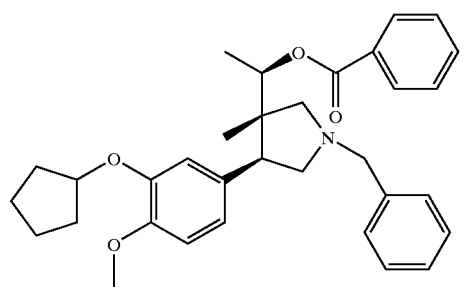
Sample No. 5
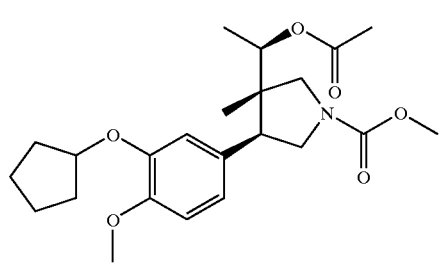
Sample No. 6
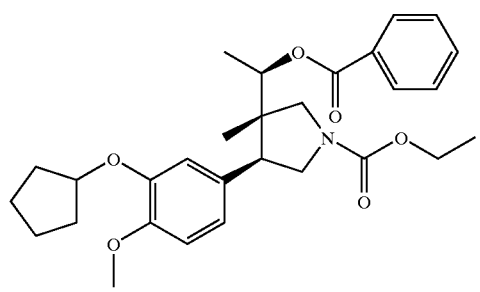
Sample No. 7
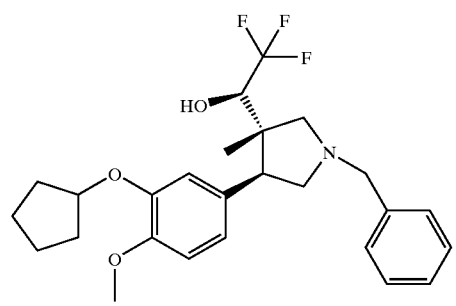
Sample No. 8
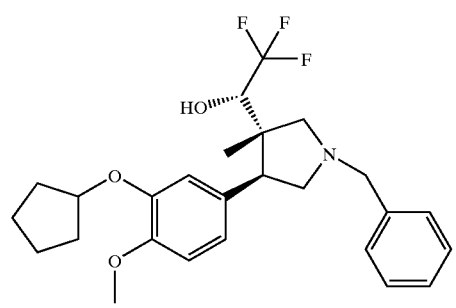
-continued
Sample No. 9
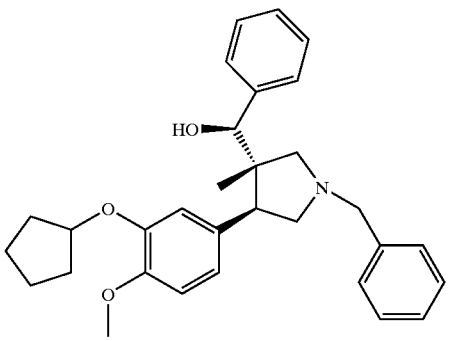
Sample No. 10
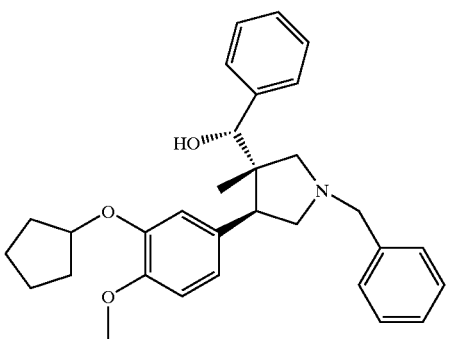
Sample No. 11
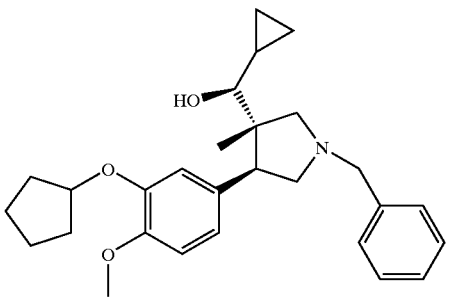
Sample No. 12
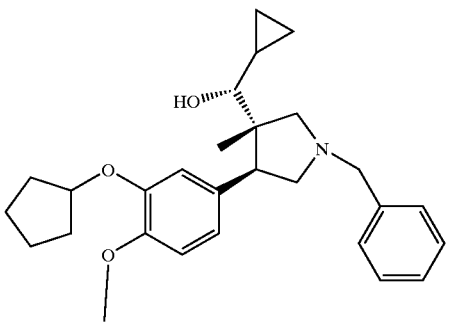

-continued

Sample No. 13

Sample No. 14

Sample No. 15

Sample No. 16

Sample No. 17

-continued

Sample No. 18

Sample No. 19

Sample No. 20

Sample No. 21

Sample No. 22

-continued
Sample No. 23
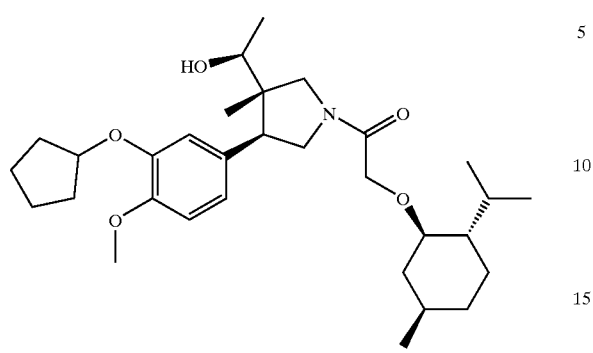
Sample No. 24
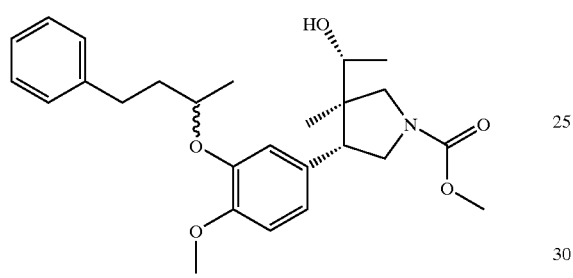
Sample No. 25
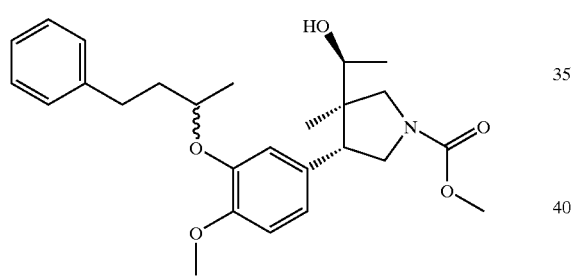
Sample No. 26
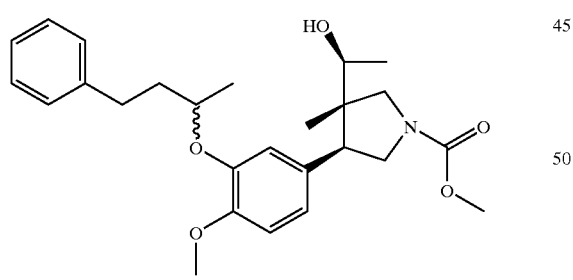
Sample No. 27
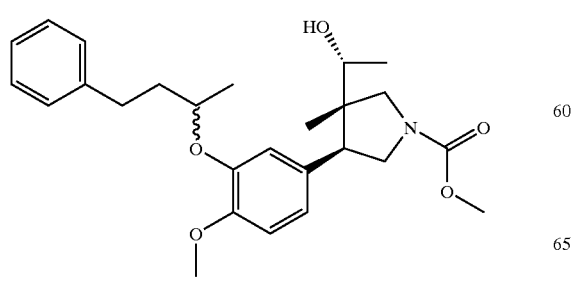
-continued
Sample No. 28
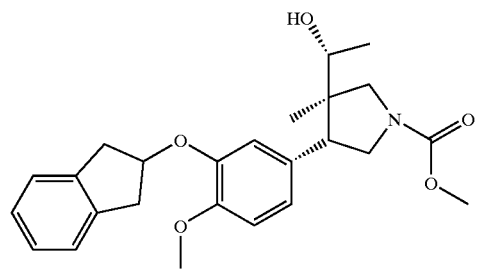
Sample No. 29
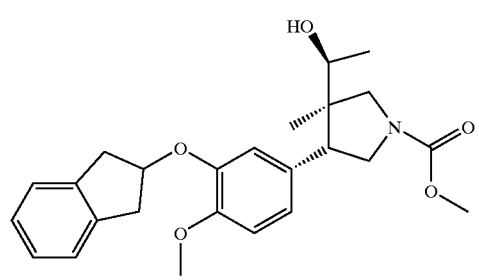
Sample No. 30
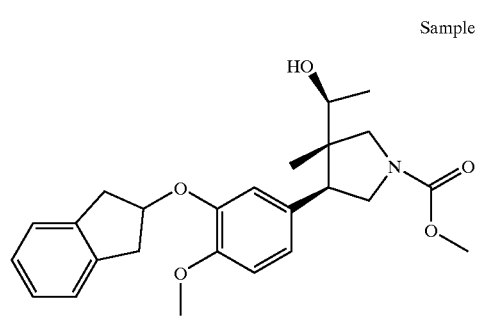
Sample No. 31
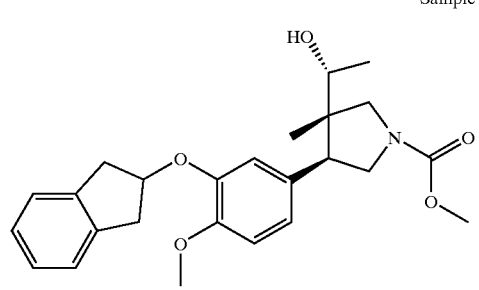
Sample No. 32
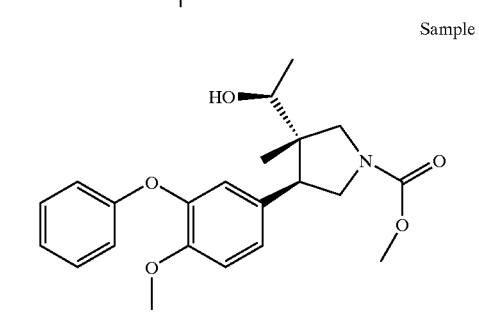

Sample No. 33
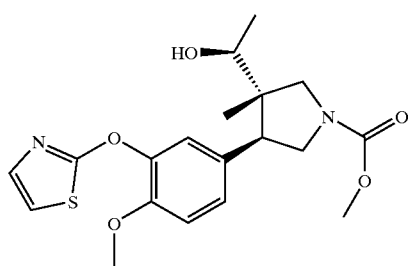
Sample No. 34
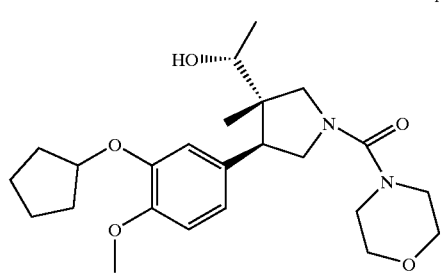
Sample No. 35
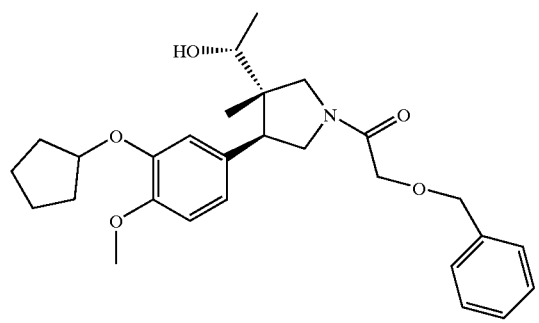
Sample No. 36
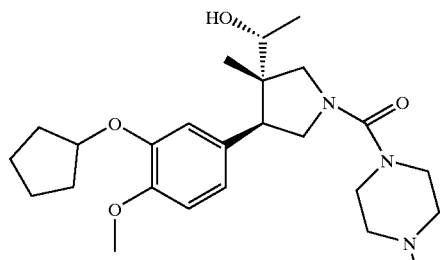
Sample No. 37
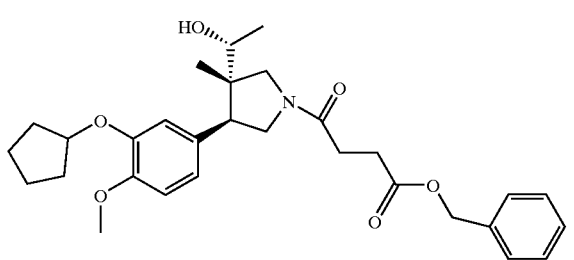
Sample No. 38
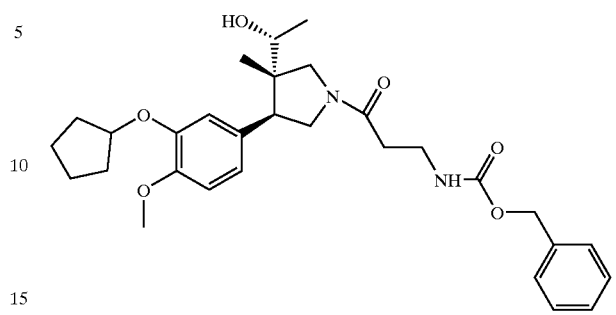
Sample No. 39
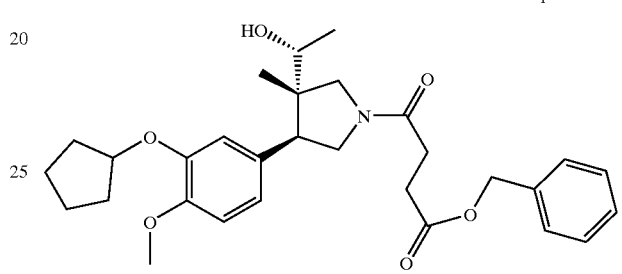
Sample No. 40
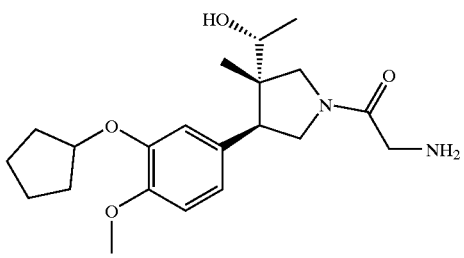
Sample No. 41
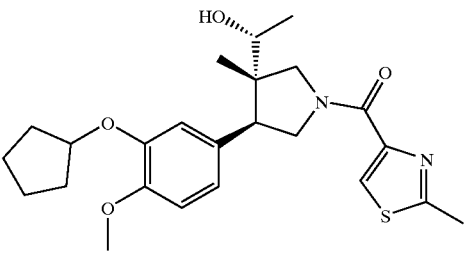
Sample No. 42
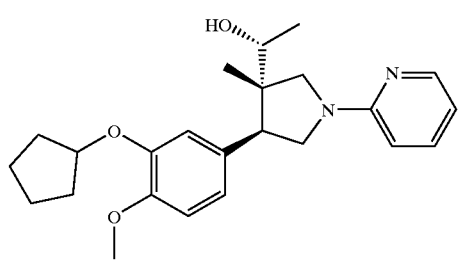

-continued
Sample No. 43
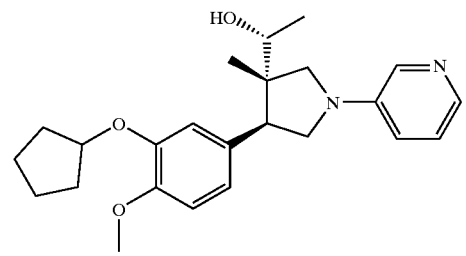
Sample No. 44
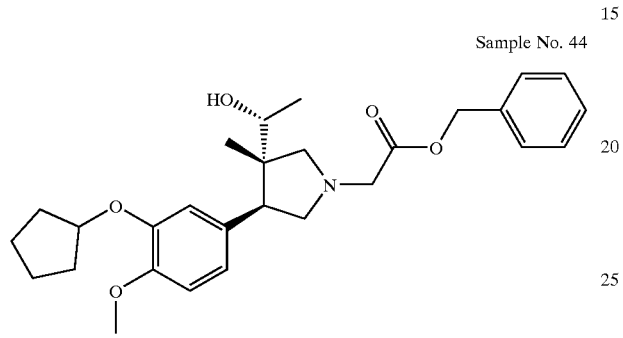
Sample No. 45
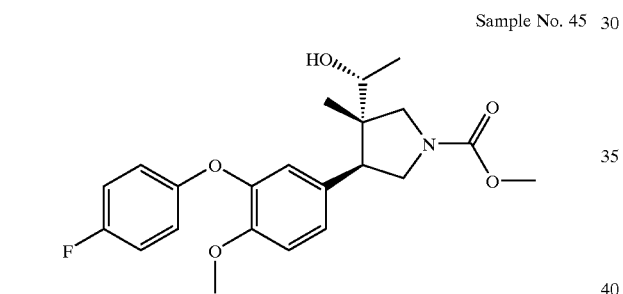
Sample No. 46
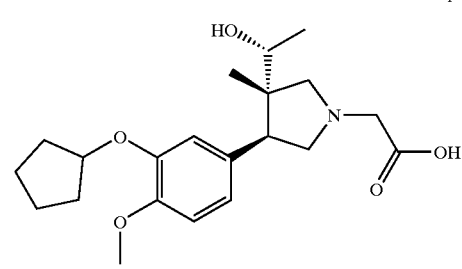
Sample No. 47
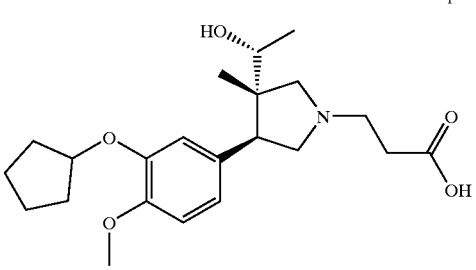
-continued
Sample No. 48
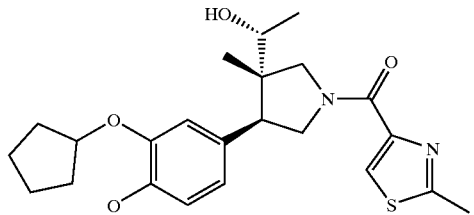
Sample No. 49
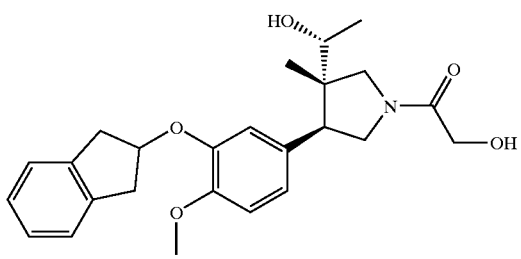
Sample No. 50
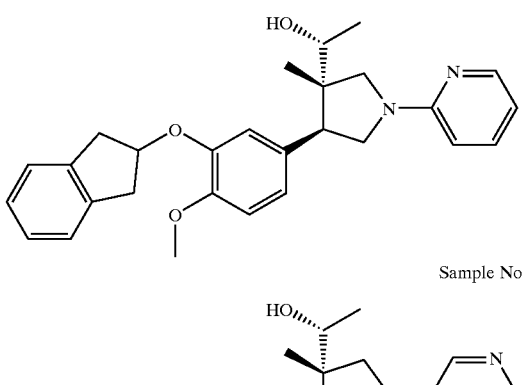
Sample No. 51
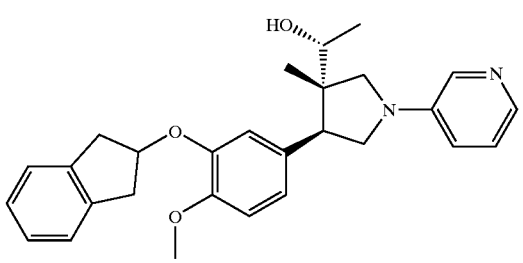
Sample No. 52
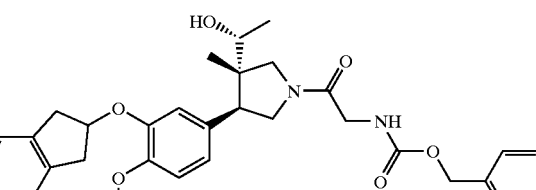
Sample No. 53
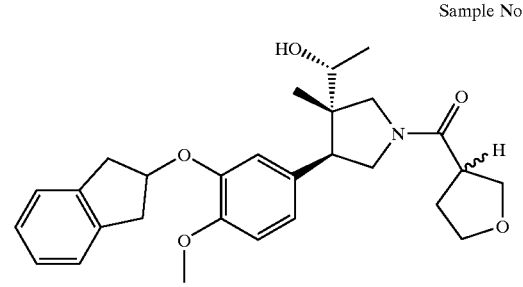

Sample No. 54
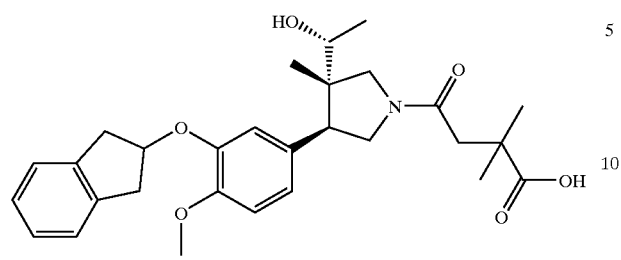
Sample No. 55
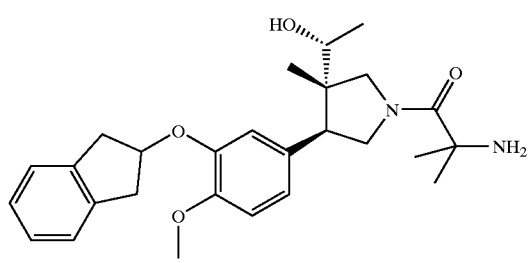
Sample No. 56
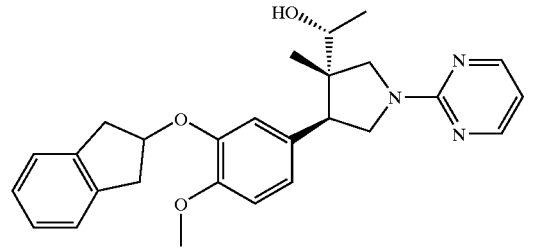
Sample No. 57
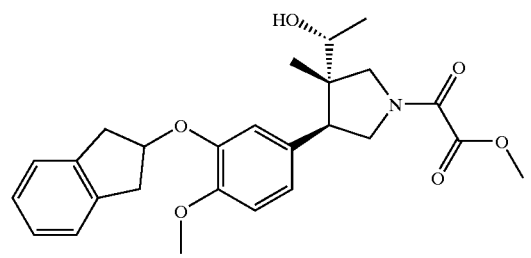
Sample No. 58
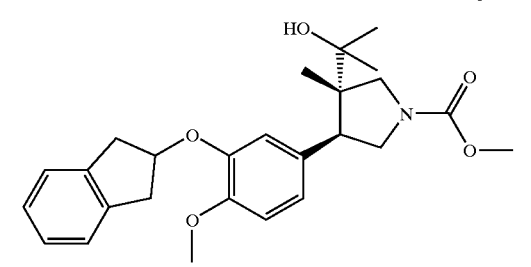
Sample No. 59
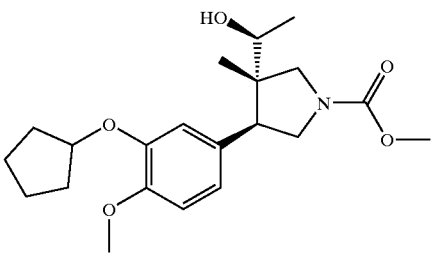
Sample No. 60
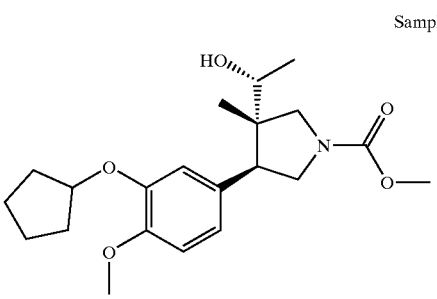
Sample No. 61
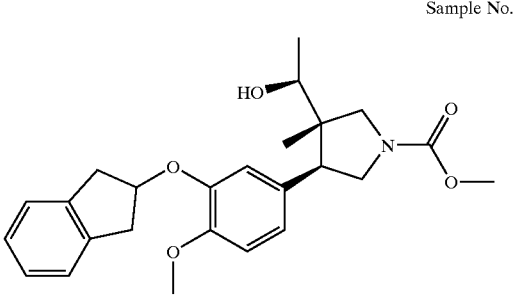
Sample No. 62
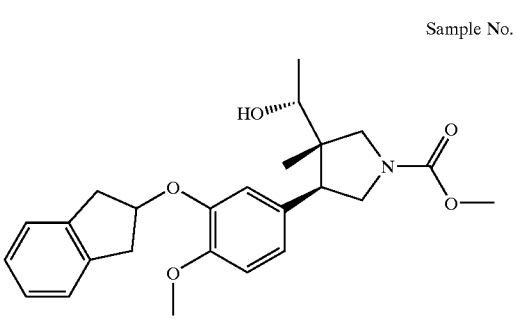
Sample No. 63
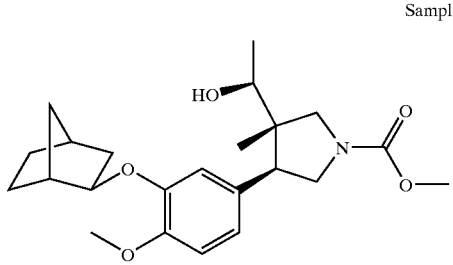

Sample No. 64
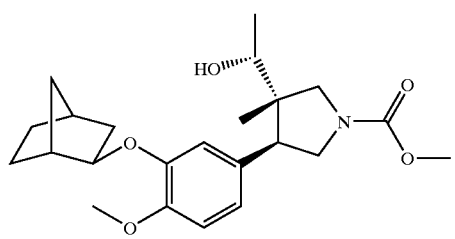
Sample No. 65
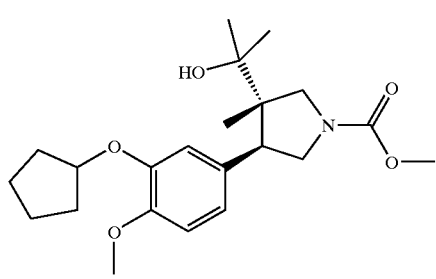
Sample No. 66
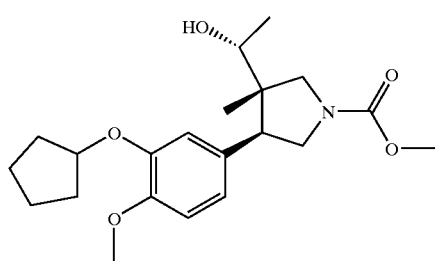
Sample No. 67
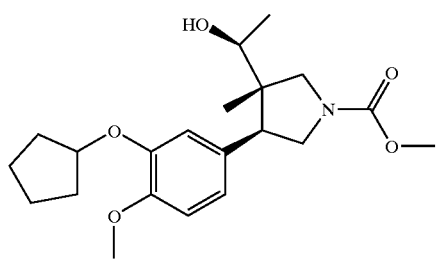
Sample No. 68
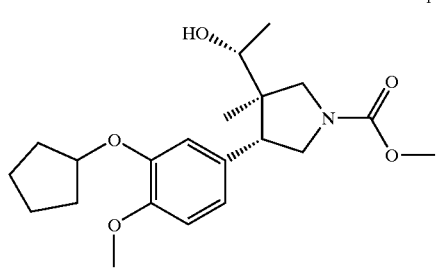
Sample No. 69
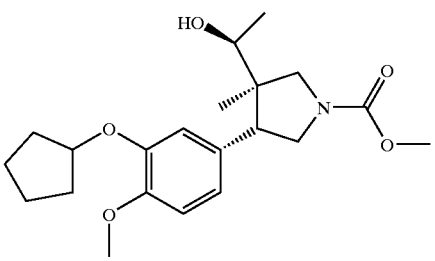
Sample No. 70
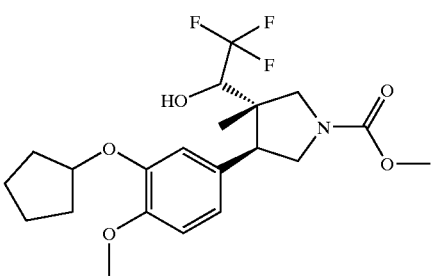
Sample No. 71
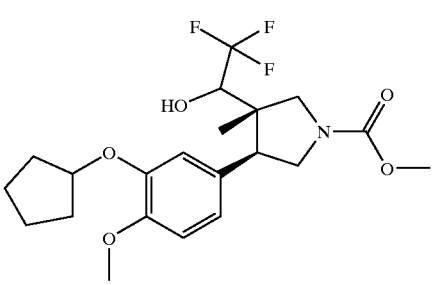
Sample No. 72
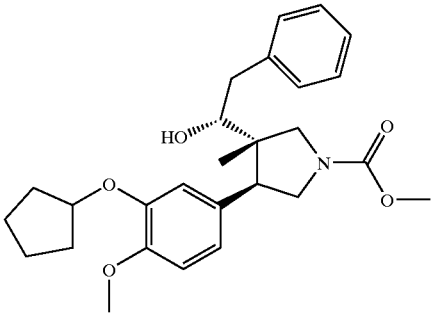
Sample No. 73
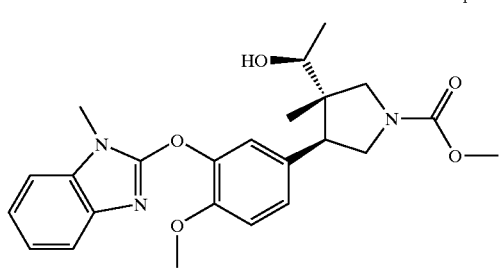

Sample No. 74
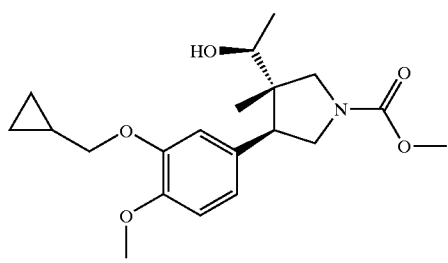
Sample No. 75
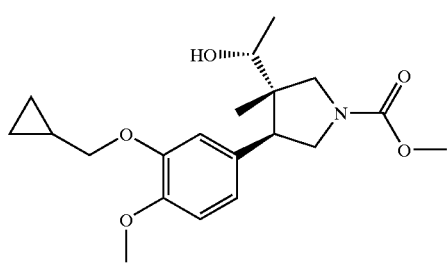
Sample No. 76
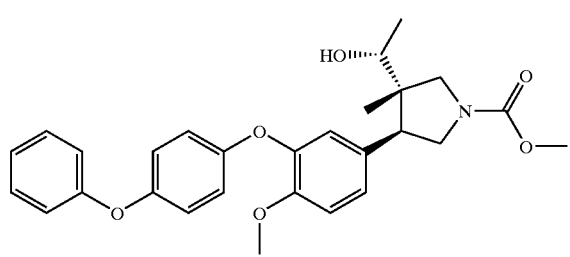
Sample No. 77
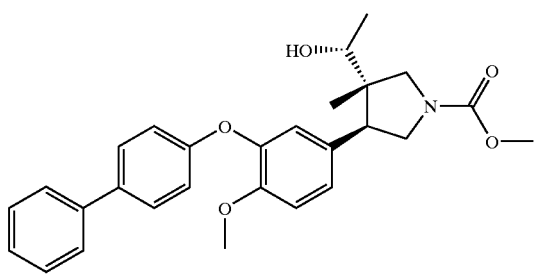
Sample No. 78
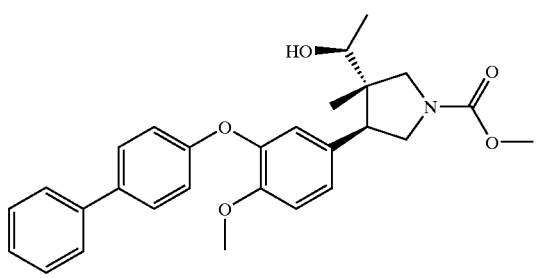
Sample No. 79
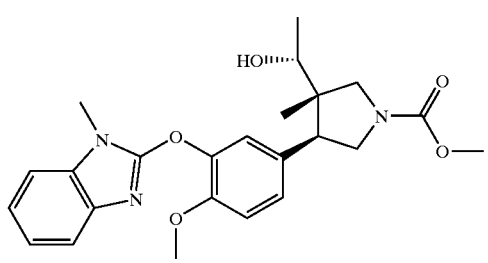
Sample No. 80
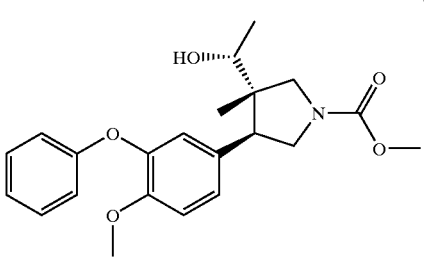
Sample No. 81
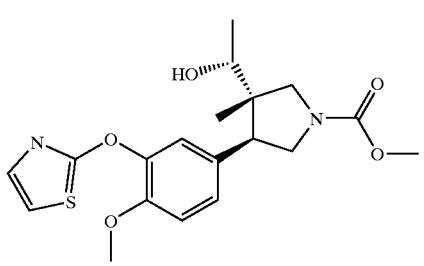
Sample No. 82
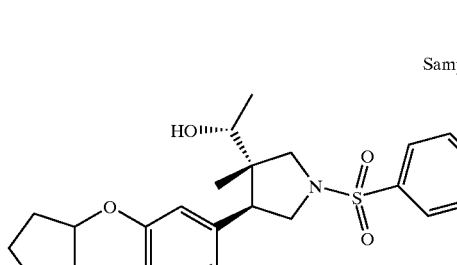
Sample No. 83
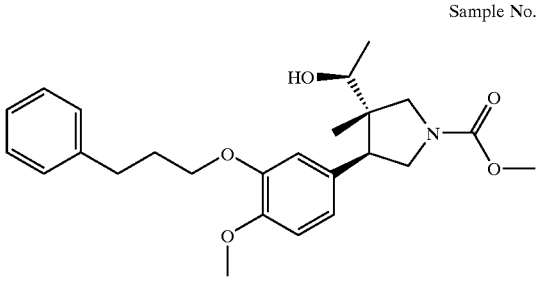

Sample No. 84
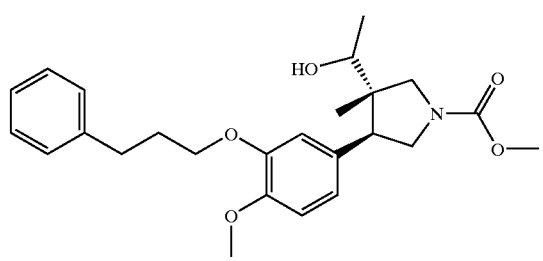
Sample No. 85
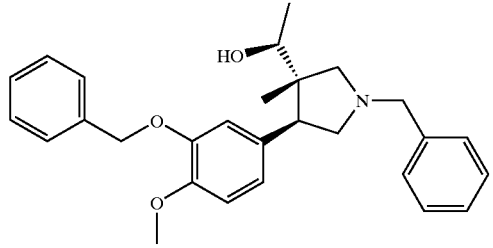
Sample No. 86
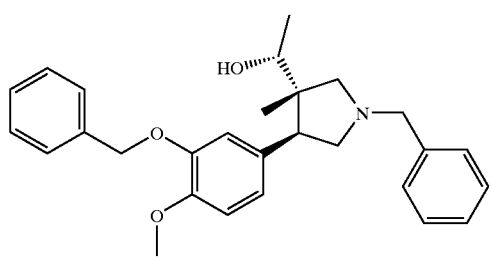
Sample No. 87
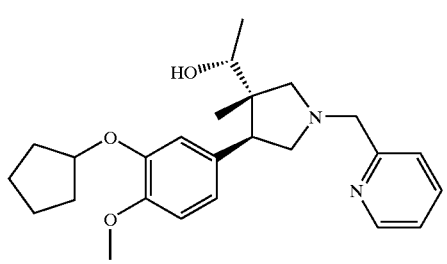
Sample No. 88
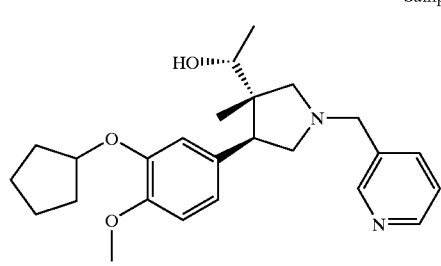
Sample No. 89
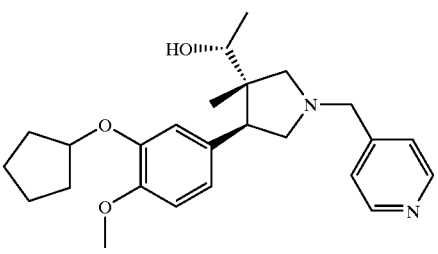
Sample No. 90
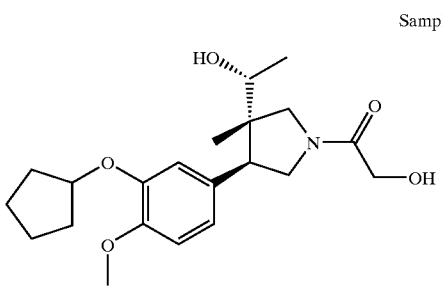
Sample No. 91
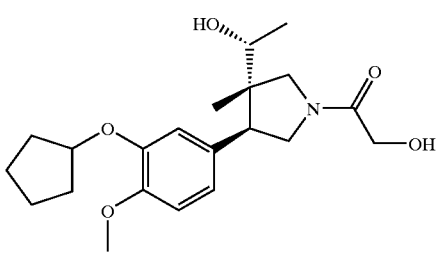
Sample 92
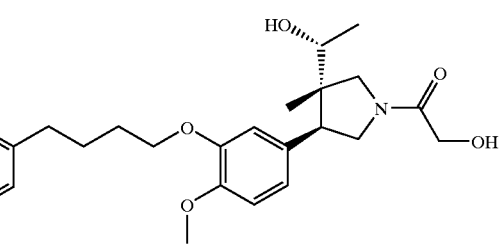
Sample No. 93
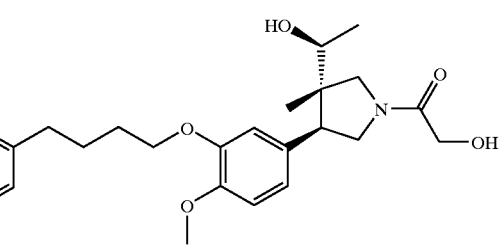

Sample No. 94

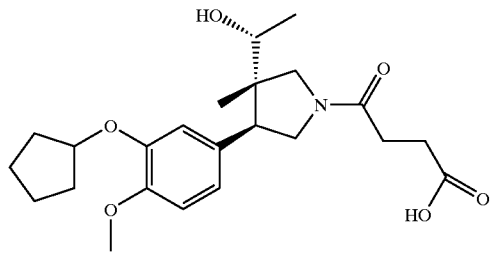

What is claimed is:

1. A method of treating a mammal for rheumatoid arthritis, osteoarthritis, gouty arthritis, or spondylitis comprising administering to said mammal an effective amount of a pharmaceutical composition comprising (a) a compound of

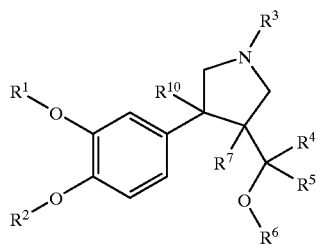

wherein $R^1$ is selected from the group consisting of hydrogen, lower alkyl, bridged alkyl, aryl, cycloalkyl, a 4-, 5-, or 6-membered saturated heterocycle, heteroaryl, $C_{1-4}$alkylenearyl, $C_{1-4}$alkyleneOaryl, $C_{1-4}$alkyleneheteroaryl, $C_{1-4}$alkyleneHet, $C_{2-4}$alkylenearylOaryl, $C_{1-4}$alkylene bridged alkyl, $C_{1-4}$alkylenecycloalkyl, substituted or unsubstituted propargyl, substituted or unsubstituted allyl, and halocycloalkyl;

$R^2$ is selected from the group consisting of hydrogen, methyl, and halo-substituted methyl;

$R^3$ is selected from the group consisting of $C(=O)OR^7$, $C(=O)R^7$, $NHC(=O)OR^7$, $C_{1-3}$alkyleneC$(=O)OR^8$, $C_{1-3}$alkyleneC$(=O)R^8$, $C(=NH)NR^8R^9$, $C(=O)NR^8R^9$, $C(=O)C(=O)$— $NR^8R^9$, $C(=O)C(=O)$ $OR^8$, $C_{1-4}$alkyleneOR$^8$, aryl, $C_{1-3}$alkylenearyl, $C_{1-3}$alkyleneheteroaryl, SO$_2$heteroaryl, Het, and heteroaryl;

$R^4$ is selected from the group consisting of hydrogen, lower alkyl, haloalkyl, cycloalkyl, and aryl;

$R^5$ is selected from the group consisting of hydrogen, lower alkyl, alkynyl, haloalkyl, hydroxyalkyl, cycloalkyl, and aryl;

$R^6$ is selected from the group consisting of hydrogen, lower alkyl, and $C(=O)R^7$;

$R^7$ is selected from the group consisting of lower alkyl, branched or unbranched, $C_{1-4}$alkylenearyl, cycloalkyl, Het, $C_{1-4}$alkylenecycloalkyl, heteroaryl, and aryl, each optionally substituted with one or more of OC$(=O)R^8$, $C(=O)OR^8$, $OR^8$, $NR^8R^9$, or $SR^8$;

$R^8$ and $R^9$, same or different, are selected from the group consisting of hydrogen, lower alkyl, cycloalkyl, aryl, heteroaryl, $C(=O)Oalkyl$, $C(=O)Oaryl$, $C(=O)alkyl$, alkylSO$_2$, haloalkylSO$_2$, $C(=O)C_{1-3}$alkylenearyl, $C(=O)OC_{1-4}$alkylenearyl, $C_{1-4}$alkylenearyl, and Het, or $R^8$ and $R^9$ together form a 4-membered to 7-membered ring;

$R^{10}$ is selected from the group consisting of hydrogen, alkyl, haloalkyl, cycloalkyl, aryl, $C(=O)$-alkyl, $C(=O)cycloalkyl$, $C(=O)aryl$, $C(=O)Oalkyl$, $C(=O)$-Ocycloalkyl, $C(=O)aryl$, CH$_2$OH, CH$_2$Oalkyl, CHO, CN, NO$_2$, and SO$_2R^{11}$;

$R^{11}$ is selected from the group consisting of alkyl, cycloalkyl, trifluoromethyl, aryl, aralkyl, and NR$^8R^9$; or a salt or solvate thereof; and (b) a pharmaceutically acceptable carrier.

2. A method of treating a mammal for thyroid-associated ophthalmopathy, Behcet disease, asthma, chronic bronchitis, allergic rhinitis, adult respiratory distress syndrome, chronic pulmonary inflammatory disease, chronic obstructive pulmonary disease, silicosis, or pulmonary sarcoidosis comprising administering to said mammal an effective amount of a pharmaceutical composition comprising (a) a compound having a formula

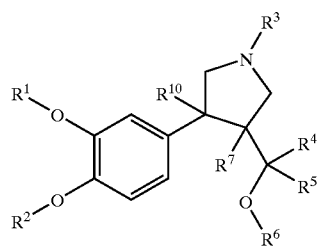

wherein $R^1$ is selected from the group consisting of hydrogen, lower alkyl, bridged alkyl, aryl, cycloalkyl, a 4-, 5-, or 6-membered saturated heterocycle, heteroaryl, $C_{1-4}$alkylenearyl, $C_{1-4}$alkyleneOaryl, $C_{1-4}$alkyleneheteroaryl, $C_{1-4}$alkyleneHet, $C_{2-4}$alkylenearylOaryl, $C_{1-4}$alkylene bridged alkyl, $C_{1-4}$alkylenecycloalkyl, substituted or unsubstituted propargyl, substituted or unsubstituted allyl, and halocycloalkyl;

$R^2$ is selected from the group consisting of hydrogen, methyl, and halo-substituted methyl;

$R^3$ is selected from the group consisting of $C(=O)OR^7$, $C(=O)R^7$, $NHC(=O)OR^7$, $C_{1-3}$alkyleneC$(=O)OR^8$, $C_{1-3}$alkyleneC$(=O)R^8$, $C(=NH)NR^8R^9$, $C(=O)NR^8R^9$, $C(=O)C(=O)$—$NR^8R^9$, $C(=O)C(=O)OR^8$, $C_{1-4}$alkyleneOR$^8$, aryl, $C_{1-3}$alkylenearyl, $C_{1-3}$alkyleneheteroaryl, SO$_2$heteroaryl, Het, and heteroaryl;

$R^4$ is selected from the group consisting of hydrogen, lower alkyl, haloalkyl, cycloalkyl, and aryl;

$R^5$ is selected from the group consisting of hydrogen, lower alkyl, alkynyl, haloalkyl, hydroxyalkyl, cycloalkyl, and aryl;

$R^6$ is selected from the group consisting of hydrogen, lower alkyl, and $C(=O)R^7$;

$R^7$ is selected from the group consisting of lower alkyl, branched or unbranched, $C_{1-4}$alkylenearyl, cycloalkyl, Het, $C_{1-4}$alkylenecycloalkyl, heteroaryl, and aryl, each optionally substituted with one or more of OC$(=O)R^8$, $C(=O)OR^8$, $OR^8$, $NR^8R^9$, or $SR^8$;

$R^8$ and $R^9$, same or different, are selected from the group consisting of hydrogen, lower alkyl, cycloalkyl, aryl, heteroaryl, C(=O)Oalkyl, C(=O)Oaryl, C(=O)alkyl, alkylSO$_2$, haloalkylSO$_2$, C(=O)C$_{1-3}$alkylenearyl, C(=O)OC$_{1-4}$alkylenearyl, C$_{1-4}$alkylenearyl, and Het, or $R^8$ and $R^9$ together form a 4-membered to 7-membered ring;

$R^{10}$ is selected from the group consisting of hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, and SO$_2$R$^{11}$;

$R^{11}$ is selected from the group consisting of alkyl, cycloalkyl, trifluoromethyl, aryl, aralkyl, and NR$^8$R$^9$; or a salt or solvate thereof; and (b) a pharmaceutically acceptable carrier.

\* \* \* \* \*